(12) United States Patent
Ali et al.

(10) Patent No.: US 12,274,699 B2
(45) Date of Patent: Apr. 15, 2025

(54) METHODS OF TREATING CHOLANGIOCARCINOMA

(71) Applicant: Foundation Medicine, Inc., Cambridge, MA (US)

(72) Inventors: Siraj Mahamed Ali, Cambridge, MA (US); Matthew J. Hawryluk, Newton, MA (US); Jie He, Newton, MA (US); Doron Lipson, Chestnut Hill, MA (US); Vincent A. Miller, West Orange, NJ (US); Jeffrey S. Ross, Lebanon Springs, NY (US); Philip James Stephens, Lexington, MA (US)

(73) Assignee: Foundation Medicine, Inc., Boston, MA (US)

( * ) Notice: Subject to any disclaimer, the term of this patent is extended or adjusted under 35 U.S.C. 154(b) by 0 days.

(21) Appl. No.: 18/346,029

(22) Filed: Jun. 30, 2023

(65) Prior Publication Data
US 2023/0372338 A1 Nov. 23, 2023

Related U.S. Application Data

(60) Continuation of application No. 17/204,830, filed on Mar. 17, 2021, now Pat. No. 11,771,698, which is a division of application No. 14/761,518, filed as application No. PCT/US2014/012136 on Jan. 17, 2014, now Pat. No. 10,980,804.

(60) Provisional application No. 61/756,372, filed on Jan. 24, 2013, provisional application No. 61/754,509, filed on Jan. 18, 2013.

(51) Int. Cl.
| | | |
|---|---|---|
| A61K 31/517 | (2006.01) |
| A61K 31/19 | (2006.01) |
| A61K 31/404 | (2006.01) |
| A61K 31/435 | (2006.01) |
| A61K 31/4412 | (2006.01) |
| A61K 31/4439 | (2006.01) |
| A61K 31/47 | (2006.01) |
| A61K 31/496 | (2006.01) |
| A61K 31/498 | (2006.01) |
| A61K 31/5025 | (2006.01) |
| A61K 31/506 | (2006.01) |
| A61K 31/519 | (2006.01) |
| A61K 31/53 | (2006.01) |
| A61K 31/5383 | (2006.01) |
| A61K 31/553 | (2006.01) |
| A61K 45/06 | (2006.01) |
| C07K 14/705 | (2006.01) |
| C07K 14/71 | (2006.01) |
| C07K 16/40 | (2006.01) |
| C12N 9/12 | (2006.01) |
| C12N 15/113 | (2010.01) |
| C12Q 1/6883 | (2018.01) |
| C12Q 1/6886 | (2018.01) |
| G01N 33/573 | (2006.01) |

(52) U.S. Cl.
CPC ........ *A61K 31/5025* (2013.01); *A61K 31/404* (2013.01); *A61K 31/435* (2013.01); *A61K 31/4412* (2013.01); *A61K 31/4439* (2013.01); *A61K 31/47* (2013.01); *A61K 31/496* (2013.01); *A61K 31/498* (2013.01); *A61K 31/506* (2013.01); *A61K 31/517* (2013.01); *A61K 31/519* (2013.01); *A61K 31/53* (2013.01); *A61K 31/5383* (2013.01); *A61K 31/553* (2013.01); *A61K 45/06* (2013.01); *C07K 14/705* (2013.01); *C07K 14/71* (2013.01); *C07K 16/40* (2013.01); *C12N 9/12* (2013.01); *C12N 15/1137* (2013.01); *C12Q 1/6883* (2013.01); *C12Q 1/6886* (2013.01); *C12Y 207/10001* (2013.01); *G01N 33/573* (2013.01); *C07K 2319/00* (2013.01); *C12N 2310/11* (2013.01); *C12N 2310/12* (2013.01); *C12N 2310/14* (2013.01); *C12Q 2600/156* (2013.01); *C12Q 2600/158* (2013.01); *G01N 2333/912* (2013.01); *G01N 2500/04* (2013.01)

(58) Field of Classification Search
CPC ..... A61K 31/517; A61K 31/498; A61K 31/19
USPC .................................. 514/266.23, 248, 561
See application file for complete search history.

(56) References Cited

U.S. PATENT DOCUMENTS

| | | |
|---|---|---|
| 3,687,808 A | 8/1972 | Merigan et al. |
| 3,773,919 A | 11/1973 | Boswell et al. |
| 4,366,241 A | 12/1982 | Tom et al. |
| 4,376,110 A | 3/1983 | David et al. |
| 4,458,066 A | 7/1984 | Caruthers et al. |
| 4,469,863 A | 9/1984 | Ts'o et al. |
| 4,476,301 A | 10/1984 | Imbach et al. |
| 4,517,288 A | 5/1985 | Giegel et al. |
| 4,676,980 A | 6/1987 | Segal et al. |
| 4,816,567 A | 3/1989 | Cabilly et al. |
| 4,837,168 A | 6/1989 | de Jaeger et al. |

(Continued)

FOREIGN PATENT DOCUMENTS

| | | |
|---|---|---|
| CA | 2880013 A1 | 1/2014 |
| CN | 113186287 A | 7/2021 |

(Continued)

OTHER PUBLICATIONS

Adnane et al., (1991). "BEK and FLG, two receptors to members of the FGF family, are amplified in subsets of human breast cancers," Oncogene, 6(4):659-63.

(Continued)

*Primary Examiner* — Raymond J Henley, III
(74) *Attorney, Agent, or Firm* — MORRISON & FOERSTER LLP

(57) ABSTRACT

Methods and compositions for treating cholangiocarcinoma.

24 Claims, 27 Drawing Sheets
Specification includes a Sequence Listing.

(56) References Cited

U.S. PATENT DOCUMENTS

| | | |
|---|---|---|
| 4,845,205 A | 7/1989 | Dinh et al. |
| 4,868,103 A | 9/1989 | Stavrianopoulos et al. |
| 4,873,316 A | 10/1989 | Meade et al. |
| 4,981,957 A | 1/1991 | Lebleu et al. |
| 4,987,071 A | 1/1991 | Cech et al. |
| 5,023,243 A | 6/1991 | Tullis |
| 5,034,506 A | 7/1991 | Summerton et al. |
| 5,093,246 A | 3/1992 | Cech et al. |
| 5,116,742 A | 5/1992 | Cech et al. |
| 5,118,800 A | 6/1992 | Smith et al. |
| 5,134,066 A | 7/1992 | Rogers et al. |
| 5,166,315 A | 11/1992 | Summerton et al. |
| 5,175,273 A | 12/1992 | Bischofberger et al. |
| 5,177,195 A | 1/1993 | Gregory et al. |
| 5,185,444 A | 2/1993 | Summerton et al. |
| 5,188,897 A | 2/1993 | Suhadolnik et al. |
| 5,214,134 A | 5/1993 | Weis et al. |
| 5,216,141 A | 6/1993 | Benner |
| 5,223,409 A | 6/1993 | Ladner et al. |
| 5,225,539 A | 7/1993 | Winter |
| 5,235,033 A | 8/1993 | Summerton et al. |
| 5,264,423 A | 11/1993 | Cohen et al. |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann et al. |
| 5,321,131 A | 6/1994 | Agrawal et al. |
| 5,359,044 A | 10/1994 | Cook et al. |
| 5,367,066 A | 11/1994 | Urdea et al. |
| 5,393,878 A | 2/1995 | Leumann et al. |
| 5,399,676 A | 3/1995 | Froehler |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,224 A | 2/1996 | Bittner et al. |
| 5,500,362 A | 3/1996 | Robinson et al. |
| 5,502,177 A | 3/1996 | Matteucci et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,307 A | 7/1996 | Cook et al. |
| 5,541,316 A | 7/1996 | Engelskirchen et al. |
| 5,545,806 A | 8/1996 | Lonberg et al. |
| 5,547,835 A | 8/1996 | Koster |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,567,811 A | 10/1996 | Misiura et al. |
| 5,569,825 A | 10/1996 | Lonberg et al. |
| 5,571,799 A | 11/1996 | Tkachuk et al. |
| 5,571,894 A | 11/1996 | Wels et al. |
| 5,576,427 A | 11/1996 | Cook et al. |
| 5,587,361 A | 12/1996 | Cook et al. |
| 5,587,458 A | 12/1996 | King et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer |
| 5,597,909 A | 1/1997 | Urdea et al. |
| 5,602,240 A | 2/1997 | De Mesmaeker et al. |
| 5,605,798 A | 2/1997 | Koster |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,070 A | 4/1997 | Cook et al. |
| 5,624,821 A | 4/1997 | Winter et al. |
| 5,625,050 A | 4/1997 | Beaton et al. |
| 5,625,126 A | 4/1997 | Lonberg et al. |
| 5,627,053 A | 5/1997 | Usman et al. |
| 5,631,169 A | 5/1997 | Lakowicz et al. |
| 5,633,360 A | 5/1997 | Bischofberger et al. |
| 5,633,425 A | 5/1997 | Lonberg et al. |
| 5,639,873 A | 6/1997 | Barascut et al. |
| 5,646,265 A | 7/1997 | McGee |
| 5,648,260 A | 7/1997 | Winter et al. |
| 5,658,873 A | 8/1997 | Bertsch-Frank et al. |
| 5,661,016 A | 8/1997 | Lonberg et al. |
| 5,663,312 A | 9/1997 | Chaturvedula |
| 5,670,633 A | 9/1997 | Cook et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,714,331 A | 2/1998 | Buchardt et al. |
| 5,719,262 A | 2/1998 | Buchardt et al. |
| 5,731,168 A | 3/1998 | Carter et al. |
| 5,750,373 A | 5/1998 | Garrard et al. |
| 5,750,692 A | 5/1998 | Cook et al. |
| 5,770,429 A | 6/1998 | Lonberg et al. |
| 5,776,688 A | 7/1998 | Bittner et al. |
| 5,821,337 A | 10/1998 | Carter et al. |
| 5,869,046 A | 2/1999 | Presta et al. |
| 5,876,930 A | 3/1999 | Livak et al. |
| 6,015,886 A | 1/2000 | Dale et al. |
| 6,028,188 A | 2/2000 | Arnold et al. |
| 6,075,181 A | 6/2000 | Kucherlapati et al. |
| 6,124,445 A | 9/2000 | Imbach et al. |
| 6,147,200 A | 11/2000 | Manoharan et al. |
| 6,150,584 A | 11/2000 | Kucherlapati et al. |
| 6,160,109 A | 12/2000 | Just et al. |
| 6,166,197 A | 12/2000 | Cook et al. |
| 6,169,170 B1 | 1/2001 | Gryaznov et al. |
| 6,172,209 B1 | 1/2001 | Manoharan et al. |
| 6,194,551 B1 | 2/2001 | Idusogie et al. |
| 6,222,025 B1 | 4/2001 | Cook et al. |
| 6,235,887 B1 | 5/2001 | Froehler et al. |
| 6,239,265 B1 | 5/2001 | Cook |
| 6,248,516 B1 | 6/2001 | Winter et al. |
| 6,268,490 B1 | 7/2001 | Imanishi et al. |
| 6,277,569 B1 | 8/2001 | Bittner et al. |
| 6,277,603 B1 | 8/2001 | Cook |
| 6,326,199 B1 | 12/2001 | Cook et al. |
| 6,346,614 B1 | 2/2002 | Metelev et al. |
| 6,380,368 B1 | 4/2002 | Froehler et al. |
| 6,444,423 B1 | 9/2002 | Meade et al. |
| 6,455,258 B2 | 9/2002 | Bastian et al. |
| 6,528,640 B1 | 3/2003 | Beigelman et al. |
| 6,531,590 B1 | 3/2003 | Manoharan et al. |
| 6,534,639 B1 | 3/2003 | Manoharan et al. |
| 6,602,684 B1 | 8/2003 | Umaña et al. |
| 6,608,035 B1 | 8/2003 | Agrawal et al. |
| 6,617,438 B1 | 9/2003 | Beigelman et al. |
| 6,639,062 B2 | 10/2003 | Manoharan et al. |
| 6,670,461 B1 | 12/2003 | Wengel et al. |
| 6,683,167 B2 | 1/2004 | Metelev et al. |
| 6,737,056 B1 | 5/2004 | Presta |
| 6,794,499 B2 | 9/2004 | Wengel et al. |
| 6,858,715 B2 | 2/2005 | Ravikumar et al. |
| 6,867,294 B1 | 3/2005 | Sanghvi et al. |
| 6,878,805 B2 | 4/2005 | Manoharan et al. |
| 6,982,321 B2 | 1/2006 | Winter |
| 6,998,484 B2 | 2/2006 | Koch et al. |
| 7,015,315 B1 | 3/2006 | Cook et al. |
| 7,041,816 B2 | 5/2006 | Ravikumar et al. |

(56) References Cited

U.S. PATENT DOCUMENTS

| | | |
|---|---|---|
| 7,041,870 B2 | 5/2006 | Tomizuka et al. |
| 7,045,610 B2 | 5/2006 | Dempcy et al. |
| 7,053,207 B2 | 5/2006 | Wengel |
| 7,084,125 B2 | 8/2006 | Wengel |
| 7,087,409 B2 | 8/2006 | Barbas et al. |
| RE39,464 E | 1/2007 | Cook et al. |
| 7,189,826 B2 | 3/2007 | Rodman |
| 7,244,567 B2 | 7/2007 | Chen et al. |
| 7,273,933 B1 | 9/2007 | Krotz et al. |
| 7,321,029 B2 | 1/2008 | Gryaznov et al. |
| 7,332,581 B2 | 2/2008 | Presta |
| 7,371,826 B2 | 5/2008 | Presta |
| 7,399,845 B2 | 7/2008 | Seth et al. |
| 7,427,672 B2 | 9/2008 | Imanishi et al. |
| 7,495,088 B1 | 2/2009 | Brakel et al. |
| 7,521,541 B2 | 4/2009 | Eigenbrot et al. |
| 7,527,791 B2 | 5/2009 | Adams et al. |
| 8,377,921 B2 | 2/2013 | Michellys et al. |
| 9,340,830 B2 | 5/2016 | Lipson et al. |
| 10,000,814 B2 | 6/2018 | Cronin et al. |
| 10,980,804 B2 | 4/2021 | Ali et al. |
| 11,098,368 B2 | 8/2021 | Cronin et al. |
| 11,230,589 B2 | 1/2022 | Lipson et al. |
| 11,578,372 B2 | 2/2023 | Hawryluk et al. |
| 2002/0164328 A1 | 11/2002 | Shinkawa et al. |
| 2002/0197679 A1 | 12/2002 | Tang et al. |
| 2003/0115614 A1 | 6/2003 | Kanda et al. |
| 2003/0143204 A1 | 7/2003 | Lewis et al. |
| 2003/0157108 A1 | 8/2003 | Presta |
| 2003/0166282 A1 | 9/2003 | Brown et al. |
| 2003/0224432 A1 | 12/2003 | Myers et al. |
| 2004/0038278 A1 | 2/2004 | Tzertzinis et al. |
| 2004/0086884 A1 | 5/2004 | Beach et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2005/0014934 A1 | 1/2005 | Hinton et al. |
| 2005/0079574 A1 | 4/2005 | Bond |
| 2005/0119455 A1 | 6/2005 | Fuh et al. |
| 2005/0123546 A1 | 6/2005 | Umana et al. |
| 2005/0266000 A1 | 12/2005 | Bond et al. |
| 2005/0287541 A1 | 12/2005 | Nakagawara et al. |
| 2006/0025576 A1 | 2/2006 | Miller et al. |
| 2006/0246497 A1 | 11/2006 | Huang et al. |
| 2006/0275779 A1 | 12/2006 | Li et al. |
| 2007/0010657 A1 | 1/2007 | Klocke et al. |
| 2007/0059710 A1 | 3/2007 | Luke et al. |
| 2007/0061900 A1 | 3/2007 | Murphy et al. |
| 2007/0087362 A1 | 4/2007 | Church et al. |
| 2007/0117126 A1 | 5/2007 | Sidhu et al. |
| 2007/0160598 A1 | 7/2007 | Dennis et al. |
| 2007/0194225 A1 | 8/2007 | Zorn |
| 2007/0237764 A1 | 10/2007 | Birtalan et al. |
| 2007/0248605 A1 | 10/2007 | Hestir et al. |
| 2007/0292936 A1 | 12/2007 | Barthelemy et al. |
| 2008/0051462 A1 | 2/2008 | Fritz et al. |
| 2008/0069820 A1 | 3/2008 | Fuh et al. |
| 2008/0131375 A1 | 6/2008 | Gordon et al. |
| 2008/0171689 A1 | 7/2008 | Williams |
| 2008/0226664 A1 | 9/2008 | Old et al. |
| 2009/0002360 A1 | 1/2009 | Chen et al. |
| 2009/0130101 A1 | 5/2009 | Cohen |
| 2009/0156475 A1 | 6/2009 | Rikova et al. |
| 2009/0209496 A1 | 8/2009 | Chaplin et al. |
| 2010/0029498 A1 | 2/2010 | Gnirke et al. |
| 2011/0118298 A1 | 5/2011 | Fritz et al. |
| 2011/0150893 A1 | 6/2011 | Cho et al. |
| 2011/0183924 A1 | 7/2011 | Mintz et al. |
| 2012/0039805 A1 | 2/2012 | Lisanti et al. |
| 2012/0208706 A1 | 8/2012 | Downing et al. |
| 2013/0034559 A1 | 2/2013 | Queva et al. |
| 2013/0096021 A1 | 4/2013 | Chinnaiyan et al. |
| 2014/0336236 A1 | 11/2014 | Cronin et al. |
| 2015/0073036 A1 | 3/2015 | Hawryluk et al. |
| 2015/0366866 A1 | 12/2015 | Ali et al. |
| 2016/0009785 A1 | 1/2016 | Lipson et al. |
| 2016/0010068 A1 | 1/2016 | Bastian et al. |
| 2016/0272725 A1 | 9/2016 | Stransky et al. |
| 2018/0030548 A1 | 2/2018 | Nanda et al. |
| 2018/0045727 A1 | 2/2018 | Spetzler et al. |
| 2018/0346992 A1 | 12/2018 | Cronin et al. |
| 2019/0367613 A1 | 12/2019 | Harvey et al. |
| 2020/0299775 A1 | 9/2020 | Hawryluk et al. |
| 2021/0283134 A1 | 9/2021 | Ali et al. |
| 2022/0002818 A1 | 1/2022 | Cronin et al. |
| 2022/0169703 A1 | 6/2022 | Lipson et al. |
| 2022/0243280 A1 | 8/2022 | Darcy et al. |

FOREIGN PATENT DOCUMENTS

| | | |
|---|---|---|
| EP | 171496 A2 | 2/1986 |
| EP | 173494 A2 | 3/1986 |
| EP | 184187 A2 | 6/1986 |
| EP | 264166 A1 | 4/1988 |
| EP | 404097 A2 | 12/1990 |
| EP | 125023 B1 | 6/1991 |
| EP | 430402 A2 | 6/1991 |
| EP | 698096 B1 | 2/1996 |
| EP | 2057465 A2 | 5/2009 |
| EP | 2877854 B1 | 9/2022 |
| WO | WO-1986001533 A1 | 3/1986 |
| WO | WO-1987002671 A1 | 10/1987 |
| WO | WO-1988009810 A1 | 12/1988 |
| WO | WO-1989010134 A1 | 11/1989 |
| WO | WO-1990002809 A1 | 3/1990 |
| WO | WO-1992001047 A1 | 7/1991 |
| WO | WO-1991017271 A1 | 11/1991 |
| WO | WO-1992009690 A2 | 6/1992 |
| WO | WO-1992015679 A1 | 9/1992 |
| WO | WO-1992018619 A1 | 10/1992 |
| WO | WO-1992020791 A1 | 11/1992 |
| WO | WO-1993001161 A1 | 1/1993 |
| WO | WO-1993001288 A1 | 1/1993 |
| WO | WO-1993008829 A1 | 5/1993 |
| WO | WO-1993016185 A2 | 8/1993 |
| WO | WO-1994016101 A2 | 7/1994 |
| WO | WO-1994021822 A1 | 9/1994 |
| WO | WO-1994026889 A2 | 11/1994 |
| WO | WO-1994029351 A2 | 12/1994 |
| WO | WO-1996029431 A2 | 9/1996 |
| WO | WO-1997030087 A1 | 8/1997 |
| WO | WO-1998058964 A1 | 12/1998 |
| WO | WO-1999022764 A1 | 5/1999 |
| WO | WO-1999051642 A1 | 10/1999 |
| WO | WO-2000061739 A1 | 10/2000 |
| WO | WO-2001027081 A1 | 4/2001 |
| WO | WO-2001029246 A1 | 4/2001 |
| WO | WO-2002031140 A1 | 4/2002 |
| WO | WO-2003011878 A2 | 2/2003 |
| WO | WO-2003031568 A2 | 4/2003 |
| WO | WO-2003084570 A1 | 10/2003 |
| WO | WO-2003085107 A1 | 10/2003 |
| WO | WO-2003085119 A1 | 10/2003 |
| WO | WO-2004013099 A1 | 2/2004 |
| WO | WO-2004056312 A2 | 7/2004 |
| WO | WO-2005016894 A1 | 2/2005 |
| WO | WO-2005035586 A1 | 4/2005 |
| WO | WO-2005035778 A1 | 4/2005 |
| WO | WO-2005053742 A1 | 6/2005 |
| WO | WO-2005100402 A1 | 10/2005 |
| WO | WO-2006029879 A2 | 3/2006 |
| WO | WO-2006121168 A1 | 11/2006 |
| WO | WO-2007005874 A2 | 1/2007 |
| WO | WO-2007060402 A1 | 5/2007 |
| WO | WO-2008021290 A2 | 2/2008 |
| WO | WO-2008077546 A1 | 7/2008 |
| WO | WO-2009089004 A1 | 7/2009 |
| WO | WO-2009101611 A1 | 8/2009 |
| WO | WO-2009114335 A2 | 9/2009 |
| WO | WO-2010027827 A2 | 3/2010 |
| WO | WO-2010077634 A1 | 7/2010 |
| WO | WO-2010081817 A1 | 7/2010 |

(56) References Cited

FOREIGN PATENT DOCUMENTS

| WO | WO-2011005861 A1 | 1/2011 |
|---|---|---|
| WO | WO-2011066342 A2 | 6/2011 |
| WO | WO-2011066389 A1 | 6/2011 |
| WO | WO-2011135376 A1 | 11/2011 |
| WO | WO-2012092426 A1 | 7/2012 |
| WO | WO-2013059740 A1 | 4/2013 |
| WO | WO-2013076186 A1 | 5/2013 |
| WO | WO-2013087716 A2 | 6/2013 |
| WO | WO-2014018673 A2 | 1/2014 |
| WO | WO-2014036387 A2 | 3/2014 |
| WO | WO-2014071358 A2 | 5/2014 |
| WO | WO-2014071419 A2 | 5/2014 |
| WO | WO-2014113729 A2 | 7/2014 |
| WO | WO-2014130975 A1 | 8/2014 |
| WO | WO-2015016718 A1 | 2/2015 |
| WO | WO-2016196671 A1 | 12/2016 |
| WO | WO-2019158512 A1 | 8/2019 |

OTHER PUBLICATIONS

Akslen et al., (2005). "BRAF and NRAS mutations are frequent in nodular melanoma but are not associated with tumor cell proliferation or patient survival," J Invest Dermatol, 125(2):312-7.
Al-Ahmadie et al., (2011). "Somatic mutation of fibroblast growth factor receptor-3 (FGFR3) defines a 20 distinct morphological subtype of high-grade urothelial carcinoma," J Pathol, 224(2):270-9, 20 pages.
Alazzouzi et al., (2005). "SMAD4 as a prognostic marker in colorectal cancer," Clinical cancer research, 11(7):2606-11.
Albanese et al., (2010). "Dual targeting of CDK and tropomyosin receptor kinase families by the oral inhibitor PHA-848125, an agent with broad-spectrum antitumor efficacy", Mol Cancer Ther 9(8):2243-54.
Alberti et al., (2003). "RET and NTRK1 proto-oncogenes in human diseases," J Cell Physiol, 195:168-186.
Albertson (1984). "Localization of the ribosomal genes in Caenorhabditis elegans chromosomes by in situ hybridization using biotin-labeled probes," EMBO J., 3:1227-1234.
Almagro et al., (2008). "Humanization of antibodies," Front. Biosci., 13:1619-1633.
Alonso et al, (1994). "Biodegradable microspheres as controlled-release tetanus toxoid delivery systems," Vaccine, 12(4):299-306.
Altorki et al., (2010). "Phase II Proof-of-Concept Study of Pazopanib Monotherapy in Treatment-Naive Patience With State I/II Respectable Non-Small-Cell Lung Cancer" Journal of Clinical Oncology, 28(19):3131-3137.
Altschul et al., (1990). "Basic local alignment search tool," J. Mol Biol., 215:403-410.
Altschul et al., (1997). "Gapped BLAST and PSI-BLAST: a new generation of protein database search programs," Nucleic Acids Res., 25(17):3389-3402.
Amatu et al., (2016). "NTRK gene fusions as novel targets of cancer therapy across multiple tumour types" ESMO Open, 1:e000023, 9 pages.
Andoniou et al., (1994). "Tumour induction by activated abl involves tyrosine phosphorylation of the product of the cbl oncogene," EMBO J, 13(19):4515-23.
Arbitrario et al., (2010). "SNS-314, a pan-Aurora kinase inhibitor, shows potent anti-tumor activity and dosing flexibility in vivo," Cancer Chemother Pharmacol., 65(4):707-717. Abstract Only.
Ardini et al., (2014). "The TPM3-NTRK1 rearrangement is a recurring event in colorectal carcinoma and is associated with tumor sensitivity to TRKA kinase inhibition," Mol Oncol., 8:1495-507.
Avet-Loiseau et al., (1998). "High Incidence of Translocations t(11;14)(q13;q32) and t(4;14)(p16;q32) in Patients with Plasma Cell Malignancies" Cancer Research, 58:5640-5645.
Baca et al., (1997). "Antibody humanization using monovalent phage display," J. Biol. Chem., 272(16):10678-10684.

Bacher et al., (2010). "Mutations of the TET2 and CBL 20 genes: novel molecular markers in myeloid malignancies," Ann Hematol, 89(7):643-52.
Bai et al., (2010). "GP369, an FGFR2-IIIb-Specific Antibody, Exhibits Potent antitumor Activity against Human Cancers Driven by Activated FGFR2 Signaling" Cancer Research, 70(19):7630-39.
Banerji et al., (1983). "A lymphocyte-specific cellular enhancer is located downstream of the joining region in immunoglobulin heavy chain genes," Cell, 33(3):729-740.
Baraniskin et al., (2011). "A Prognostic value of reduced SMAD4 expression in patients with metastatic colorectal cancer under oxaliplatin-containing chemotherapy: a translational study of the AIO colorectal study group," Clinical colorectal cancer, 10(1):24-29. Abstract Only.
Barringer et al., (1990). "Blunt-end and single-strand ligations by *Escherichia coli* ligase: influence on an in vitro amplification scheme," Gene, 89(1):117-122.
Bartel et al., (1993). "Isolation of new ribozymes from a large pool of random sequences," Science, 261(5127):1411-1418.
Beaucage et al., (1981). "Deoxynucleoside phosphoramidites—A new class of key intermediates for deoxypolynucleotide synthesis," Tetrahedron Letters, 22(20):1859-1862.
Beidler et al., (1988). "Cloning and high level expression of a chimeric antibody with specificity for human carcinoembryonic antigen," J. Immunol., 141(11):4053-4060.
Beimfohr et al., (1999). "NTRK1 re-arrangement in papillary thyroid carcinomas of children after the Chernobyl reactor accident," Int J Cancer, 80(6):842-7.
Bender et al., (2019). "Refractory and metastatic infantile fibrosarcoma harboring LMNA-NTRK1 fusion shows complete and durable response to crizotinib," Cold Spring Harb Mol Case Stud., 5:a00376, 9 pages.
Bernt et al., (2011). "A role for DOT1L in MLL-rearranged leukemias," Epigenomics, 3(6):667-70.
Bernt et al., (2011). "MLL-rearranged leukemia is dependent on aberrant H3K79 methylation by DOT1L," Cancer Cell, 20(1):66-78.
Better et al. (1988). "*Escherichia coli* secretion of an active chimeric antibody fragment," Science, 240(4855):1041-1043.
Bhatia et al., (2011). "Immunobiology of Merkel cell carcinoma: implications for immunotherapy of a polyomavirus-associated cancer," Curr. Oncol. Rep., 13(6):488-497.
Billy et al., (2001). "Specific interference with gene expression induced by long, double-stranded RNA in mouse embryonal teratocarcinoma cell lines," Proc. Natl. Sci. USA, 98(25):14428-14433.
Birch et al., (2011). "Chromosome 3 Anomalies Investigated by Genome Wide SNP Analysis of Benign, Low Malignant Potential and Low Grade Ovarian Serous Tumours," PLoS One, 6:e28250, 20 pages.
Boerner et al., (1991). "Production of antigen-specific human monoclonal antibodies from in vitro-primed human splenocytes," J. Immunol., 147(1):86-95.
Borrow et al., (1996). "The translocation t(8;16)(p11;p13) of acute myeloid leukaemia fuses a putative 25 acetyltransferase to the CREB-binding protein," Nat Genet, 14(1):33-41.
Bouhana et al., (2012). "Abstract 1798: Identification of pan-Trk inhibitors for the treatment of Trk-driven cancers," Cancer Res, 72(8 Suppl):1798, 2 pages.
Bown, (2001). "Neuroblastoma tumour genetics: clinical and biological aspects," J Clin Pathol, 54(12):897-910.
Brambilla et al., (2001). "The new World Health Organization classification of lung tumours," Eur Respir J, 18:1059-1068.
Branton et al., (2008). "The potential and challenges of nanopore sequencing," Nat Biotechnol., 26(10):1146-1153.
Brave et al., (2011). "Assessing the Activity of Cediranib, a VEGFR-2/3 Tyrosine Kinase Inhibitor, against VEGFR-1 and Members of the Structurally Related PDGFR Family" Molecular Cancer Therapeutics, 10(5):861-873.
Brennan et al., (1985). "Preparation of bispecific antibodies by chemical recombination of monoclonal immunoglobulin G1 fragments," Science, 229(4708):81-83.

(56) References Cited

OTHER PUBLICATIONS

Brenner et al., (2011). "Mechanistic rationale for inhibition of poly(ADP-ribose) polymerase in ETS gene fusion-positive prostate cancer," Cancer Cell, 19(5):664-78.
Brodeur et al., (2009). "Trk receptor expression and inhibition in neuroblastomas," Clin Cancer Res, 15(10):3244-50.
Bruggemann et al., (1987). "Comparison of the effector functions of human immunoglobulins using a matched set of chimeric antibodies," J. Exp. Meet., 166(5):1351-1361.
Butler et al., (2008). "ALLPATHS: de novo assembly of whole-genome shotgun microreads," Genome Res., 18(5):810-820.
Butti et al., (1995). "A sequence 10 analysis of the genomic regions involved in the rearrangements between TPM3 and NTRK1 genes producing TRK oncogenes in papillary thyroid carcinomas," Genomics, 28(1):15-24.
Byrne et al., (1989). "Multiplex gene regulation: a two-tiered approach to transgene regulation in transgenic mice," Proc. Natl. Acad Sci. USA, 86(14):5473-5477.
Byron et al., (2008). "Inhibition of Activated Fibroblast Growth Factor Receptor 2 in Endometrial Cancer Cells Induces Cell Death Despite PTEN Abrogation" Cancer Research, 68(17):6902-10005.
Calame et al., (1988). "Transcriptional controlling elements in the immunoglobulin and T cell receptor loci," Adv. Immunol., 43:235-275.
Camidge et al., (2010). "Optimizing the detection of lung cancer patients harboring anaplastic lymphoma kinase (ALK) gene rearrangements potentially suitable for ALK inhibitor treatment," Clin Cancer Res, 16(22):5581-5590.
Camper et al., (1989). "Postnatal repression of the alpha-fetoprotein gene is enhancer independent," Genes Dev., 3(4):537-546.
Caneiro et al., (2015). "FGFR3-TACC3: A novel gene fusion in cervical cancer," Gynecologic Oncology Reports, 13:53-56.
Capelletti et al., (2014). "Identification of Recurrent FGFR3-TACC3 Fusion Oncogenes from Lung Adenocarcinoma," Clin Cancer Res, 20:6551-6558.
Cappellen et al., (1999). "Frequent activating mutations of FGFR3 in human bladder and cervix carcinomas," Nature Genetics, 23:18-20.
Carboni et al., (2009). "BMS-754807, a small molecule inhibitor of insulin-like growth factor-1R/IR," Mol Cancer Ther., 8(12):3341-3349.
Carell et al., (1994). "A Solution-Phase Screening Procedure for the Isolation of Active Compounds from a Library of Molecules," Angew. Chem. Int. Ed. Engl., 33(20):2061-2064.
Carrell et al., (1994). "A Novel Procedure for the Synthesis of Libraries Containing Small Organic Molecules," Angew. Chem. Int. Ed. Engl., 33(20):2059-2061.
Carrillo de Santa Pau et al., (2009). "Prognostic significance of the expression of vascular endothelial growth factors A, B, C, and D and their receptors R1, R2, and R3 in patients with nonsmall cell lung cancer," Cancer, 115(8):1701-1712.
Carter et al., (1992). "Humanization of an anti-p185HER2 antibody for human cancer therapy," Proc. Natl. Acad. Sci. USA, 89(10):4285-4289.
Carver et al., (2009). "Aberrant ERG expression cooperates with loss of PTEN to promote cancer progression in the prostate," Nat Genet, 41(5):619-24, 14 pages.
Chan et al., (2008). "A phase I trial of CEP-701 + gemcitabine in patients with advanced adenocarcinoma of the pancreas," Invest New Drugs, 26(3):241-7.
Chase et al., (2012). "Ponatinib as targeted therapy for FGFR1 fusions associated with the 8p11 myeloproliferative syndrome," Haematologica, 98:103-6.
Chen et al., (2005). "FGFR3 as a therapeutic target of the small molecule inhibitor PKC412 in hematopoietic malignancies," Oncogene, 24:8259-8267.
Chen et al., (1999). "Selection and analysis of an optimized anti-VEGF antibody: crystal structure of an affinity-matured Fab in complex with antigen," J Mol Biol., 293(4):865-881.
Chi et al., (2012). "ETV6-NTRK3 as a therapeutic target of small molecule inhibitor PKC412," Biochem Biophys Res Commun., 429(1-2):87-92. Abstract Only.
Chiorean et al, (2003). "Imatinib Mesylate (STI-571), a c-Abl Kinase Inhibitor, Indirectly Blocks Receptor Tyrosine Kinase Activation and Induces Apoptosis in a Human Cholangiocarcinoma Cell Line," Gastroenterology, 24(4):1.
Cho et al., (2007). "Enhanced Expression of Keratinocyte Growth Factor and Its Receptor Correlates with Venous Invasion in Pancreatic Cancer," The American Journal of Pathology, 170(6):1964-74.
Cho et al., (1993). "An unnatural biopolymer," Science, 261(5126):1303-1305.
Chowdhury (2008). "Engineering hot spots for affinity enhancement of antibodies," Methods Mol. Biol., 207:179-196.
Chu et al., (2008). "Potent RNAi by short RNA triggers," RNA, 14(9):1714-1719.
Clackson et al., (1991). "Making antibody fragments using phage display libraries," Nature, 352(6336):624-628.
Clark et al., (2007). "Diversity of TMPRSS2-ERG fusion transcripts in the human prostate," Oncogene, 26(18):2667-73.
Clark et al., (2009). "ETS gene fusions in prostate cancer," Nat Rev Urol., 6(8):429-39.
Clemens et al., (2000). "Use of double-stranded RNA interference in *Drosophila* cell lines to dissect signal transduction pathways," Proc. Natl. Acad. Sci. USA, 97(12):6499-6503.
ClinicalTrials.gov, (2017). "Identifier No. NCT02568267, "Basket Study of Entrectinib (RXDX-101) for the Treatment of Patients With Solid Tumors Harboring NTRK 1/2/3/ (Trk A/B/C), ROS1, or ALK Gene Rearrangements (Fusions) (STARTRK-2), available online at <https://clinicaltrials.gov/ct2/show/NCT02568267?term=NTRK1+fusion+lung&rank=1>, 5 pages.
ClinicalTrials.gov, (2017). "Identifier No. NCT0257643.1, Study of LOXO-101 in Subjects With NTRK Fusion Positive Solid Tumors (NAVIGATE)," available online at <https://clinicaltrials.gov/ct2/show/NCT02576431?term=NTRK1+fusion+lung&rank=2>, 4 pages.
Clynes et al., (1998). "Fc receptors are required in passive and active immunity to melanoma," Proc. Nat'l Acad. Sci. USA, 95:652-656.
Cocco et al., (2018). "NTRK fusion-positive cancers and TRK inhibitor therapy," Nat Rev Clin Oncol., 15:731-747, 34 pages.
Cocco et al., (2019). "Resistance to TRK inhibition mediated by convergent MAPK pathway activation," Nat Med., 25(9):1422-1427. Abstract Only.
Cohen et al., (1996). "Emerging technologies for sequencing antisense oligonucleotides: capillary electrophoresis and mass spectrometry," Adv Chromatogr., 36:127-162.
Cohen et al., (2009). "A phase I dose-escalation study of danusertib (PHA-739358) administered as a 24-hour infusion with and without granulocyte colony-stimulating factor in a 14-day cycle in patients with advanced solid tumors," Clin Cancer Res, 15(21):6694-701.
Cole et al., (2010). "Inhibition of FGFR2 and FGFR1 increases cisplatin sensitivity in ovarian cancer," Cancer Biology & Therapy, 10(5):495-504.
Cole et al., (1985). "The EBV-Hybridoma Technique and its Application to Human Lung Cancer," Monoclonal Antibodies and Cancer Therapy, pp. 77-96.
Cortes et al., (2012). "Abstract No. 163: A Pivotal PhaM 2 Trial of Ponatinib in Patients with Chronic Myeloid Leukemia (CML) and Philadelphia Chromosome-Positive Acute Lymphoblastic Leukemia (Ph+ALL) Reslltllnt or Intole111nt to Dasatinib or Nilotinib, or with the T315I BCR-ABL Mutation: 1Z-Month Follow-up of the PACE Trial," ASH Annual Meeting and Exposition (Dec. 9, 2012), 2 pages.
Costa et al., (2016). "FGFR3-TACC3 fusion in solid tumors: mini review," Oncotarget, 7(34):555924-55938.
Cragg et al., (2003). "Complement-mediated lysis by anti-CD20 mAb correlates with segregation into lipid rafts," Blood, 101(3):1045-1052.
Cronin et al. (2004). "Measurement of gene expression in archival paraffin-embedded tissues: development and performance of a 92-gene reverse transcriptase-polymerase chain reaction assay," Am J Pathol., 164(1):35-42.

(56) References Cited

OTHER PUBLICATIONS

Cui et al., (2011). "Structure Based Drug Design of Crizotinib (PF-02341066), a Potent and Selective Dual Inhibitor of Mesenchymal—Epithelial Transition Factor (c-MET) Kinase and Anaplastic Lymphoma Kinase (Alk)," J Med Chem, 54:6342-6363.

Cull et al., (1992). "Screening for receptor ligands using large libraries of peptides linked to the C terminus of the lac repressor," Proc Natl Acad Sci USA, 89(5):1865-1869.

Cunningham et al., (1989). "High-resolution epitope mapping of hGH-receptor interactions by alanine-scanning mutagenesis," Science, 244(4908):1081-1085.

Curran et al., (2012). "Crizotinib: in locally advanced or metastatic non-small cell lung cancer," Drugs, 72(1):99-107.

Cwirla et al., (1990). "Peptides on phage: a vast library of peptides for identifying ligands," Proc. Natl. Acad. Sci., 87(16):6378-6382.

Daigle et al., (2011). "Selective killing of mixed lineage leukemia cells by a potent small-molecule DOT1L inhibitor," Cancer Cell, 20(1):53-65.

Dall'Acqua et al., (2005). "Antibody humanization by framework shuffling," Methods, 36(1):43-60.

Daugrois et al., (2021). "Gene Expression Signature Associated with Clinical Outcome in ALK-Positive Anaplastic Large Cell Lymphoma," Cancers, 13(21):5523.

Davies et al., (2012). "Identifying and targeting ROS1 gene fusions in non-small cell lung cancer," Clin Cancer Res., 18(17):4570-4579.

De Braekeleer et al., (2012). "MLL-ELL fusion gene 15 in two infants with acute monoblastic leukemia and myeloid sarcoma," Leukemia Lymphoma, 53(6):1222-4.

Degrassi et al., (2010). "Efficacy of PHA-848125, a cyclin-dependent kinase inhibitor, on the K-Ras(G12D) LA2 lung adenocarcinoma transgenic mouse model: evaluation by multimodality imaging," Mol Cancer Ther, 9(3):673-81.

Deinhardt et al., (2014). "Trk receptors," Handb Exp Pharmacol., 220:103-19.

Demetri et al., (2018). "Efficacy and safety of entrectinib in patients with NTRK fusion-positive (NTRK-fp) Tumors: Pooled analysis of STARTRK-2, STARTRK-1 and ALKA-372-001," ESMO, 29(S8), 1 page.

Devlin et al., (1990). "Random peptide libraries: a source of specific protein binding molecules," Science, 249(4967):404-406.

DeWitt et al., (1993). "'Diversomers": an approach to nonpeptide, nonoligomeric chemical diversity," Proc. Natl. Acad Sci. U.S.A., 90(15):6909-6913.

Dhami et al., (2018). "Comprehensive genomic profiling aids in treatment of metastatic endometrial cancer," Cold Spring Harb Mol Case Stud, 4:a002089, 14 pages.

Di Martino et al., (2012). "A Decade of FGF Receptor Research in Bladder Cancer: Past, Present, and Future Challenges," Adv Urol, 2012:429213, 10 pages.

Diep et al., (2012). "Down-regulation of Yes Associated Protein 1 expression reduces cell proliferation and clonogenicity of pancreatic cancer cells," PloS one, 7(3):e32783, 9 pages.

Doebele et al., (2015). "An Oncogenic NTRK Fusion in a Patient with Soft-Tissue Sarcoma with Response to the Tropomyosin-Related Kinase Inhibitor LOXO-101," Cancer Discovery, 5:1049-1057.

Doebele et al., (2013). "Abstract No. 8023; NTRK1 Gene Fusions as a Novel Oncogene Target in Lung Cancer,", 2013 ASCO Annual Meeting (May 31-Jun. 4, 2013), 2 pages.

Doebele et al., (2013). "Poster: NTRK1 Gene Fusions as a Novel Oncogene Target in Lung Cancer", 2013 ASCO Annual Meeting, (May 31-Jun. 4, 2013), 1 page.

Doebele et al., (2012). "Mechanisms of resistance to crizotinib in patients with ALK gene rearranged non-small cell lung cancer," Clin Cancer Res, 18:1472-1482.

Doebele et al., (2018). "Abstract No. 0A02.01, Efficacy and Safety of Entrectinib in Locally Advanced or Metastatic ROS1-Positive Non-Small Cell Lung Cancer (NSCLC)," IASLC 19th World Conference on Lung Cancer, 1 page.

Doebele et al., (2019). "Time-to-treatment discontinuation (TTD) and real-world progression-free survival (rwPFS) as endpoints for comparative efficacy analysis between entrectinib trial and crizotinib real-world ROS1 fusion-positive (ROS1+) Nsclc patients," 2019 ASCO Annual Meeting I; ASCO Abstract 9070.

Dong et al., (2012). "Inactivation of MYO5B Promotes Invasion and Motility in Gastric Cancer Cells," Digestive diseases and sciences, 57:1247-52.

Donnem et al., (2011). "Prognostic impact of angiogenic markers in non-small-cell lung cancer is related to tumor size," Clin Lung Cancer, 12:106-15.

Drilon et al., (2017). "Safety and Antitumor Activity of the Multitargeted Pan-TRK, ROS1, and ALK Inhibitor Entrectinib: Combined Results from Two Phase I Trials (ALKA-372-001 and STARTRK-1)," Cancer Discov., 7(4):400-409.

Drilon et al., (2018). "Efficacy of Larotrectinib in TRK Fusion-Positive Cancers in Adults and Children," N Engl J Med., 378(8):731-739.

Duijkers et al., (2012). "High anaplastic 25 lymphoma kinase immunohistochemical staining in neuroblastoma and ganglioneuroblastoma is an independent predictor of poor outcome," Am J Pathol, 180(3):1223-31.

Duncan et al., (1988). "The binding site for C1q on IgG," Nature, 322(6166):738-740.

Edgar, (2006). "From cell structure to transcription: Hippo forges a new path," Cell, 124(2):267-73.

Edlund et al., (1985). "Cell-specific expression of the rat insulin gene: evidence for role of two distinct 5' flanking elements," Science, 230(4728):912-916.

Edwards et al., (2005). "Mass-spectrometry DNA sequencing," Mut. Res., 573(1-2):3-12. Abstract Only.

Elbashir et al., (2001). "Duplexes of 21-nucleotide RNAs mediate RNA interference in cultured mammalian cells," Nature, 411(6836):494-498.

Elbashir et al., (2001). "Functional anatomy of siRNAs for mediating efficient RNAi in *Drosophila melanogaster* embryo lysate," EMBO, 20(23):6877-6888.

Eldridge et al., (1991). "Biodegradable microspheres as a vaccine delivery system," Molec. Immunol., 28:287-294.

Elmen et al., (2005). "Locked nucleic acid (LNA) mediated improvements in siRNA stability and functionality," Nucleic Acids Research, 33(1):439-447.

El-Osta et al., (2011). "BRAF mutations in advanced cancers: clinical 5 characteristics and outcomes," PLoS One, 6(10):e25806, 13 pages.

Emens, (2008). "Cancer vaccines: on the threshold of success," Expert Opin Emerg Drugs, 13(2):295-308, 22 pages.

Erb et al., (1994). "Recursive deconvolution of combinatorial chemical libraries," Proc. Natl. Acad Sci. USA, 91(24):11422-11426.

Eswarakumar et al., (2005). "Cellular signaling by fibroblast growth factor receptors," Cytokine Growth Factor Rev, 16(2): 139-49. Abstract Only.

Extended European Search Report received for European Patent Application No. 21179077.9 mailed on Dec. 10, 2021, 7 pages.

Falk et al., (2011). "An efficient high-throughput screening method for MYST family acetyltransferases, a new class of epigenetic drug targets," J Biomol Screen, 16(10):1196-205.

Fang et al., (2016). "Detection of a novel RET gene fusion in a non-small cell lung cancer patient using AMP chemistry," J Thoracic Oncol., 11:S21-S22.

Fang et al., (2019). "MPRIP-ALK, a Novel ALK Rearrangement That Responds to ALK Inhibition in NSCLC," J Thorac Oncol., 14:e148-e151.

Farago et al., (2015). "Durable Clinical Response to Entrectinib in NTRK1-Rearranged Non-Small Cell Lung Cancer" Journal of Thoracic Oncology, 10(12):1670-1674.

Faria et al., (2001). "Phosphoramidate oligonucleotides as potent antisense molecules in cells and in vivo," Nature Biotech., 19(1):40-44.

Felici et al., (1991). "Selection of antibody ligands from a large library of oligopeptides expressed on a multivalent exposition vector," J. Mol. Biol., 222(2):301-310.

(56) References Cited

OTHER PUBLICATIONS

Fellouse et al., (2004). "Synthetic antibodies from a four-amino-acid code: a dominant role for tyrosine in antigen recognition," Proc. Natl. Acad. Sci. USA, 101(34):12467-12472.
Feng et al., (2002). "Methylation of H3-lysine 79 is mediated by a new family of HMTases without a SET domain," Curr Biol., 12(12):1052-8.
Feng et al., (2011). "RNAi-mediated silencing of VEGF-C inhibits non-small cell lung cancer progression by simultaneously down-regulating the CXCR4, CCR7, VEGFR-2 and VEGFR-3-dependent axes-induced ERK, p38 and AKT signalling pathways," Eur J Cancer, 47:2353-63.
Fletcher et al., (2011). "ENMD-2076 is an orally active kinase inhibitor with antiangiogenic and antiproliferative mechanisms of action," Mol Cancer Ther., 10(1):126-137.
Fodor et al., (1993). "Multiplexed biochemical assays with biological chips," Nature, 364(6437):555-556.
Fountzilas et al., (2008). "Gemcitabine combined with gefitinib in patients with inoperable or metastatic pancreatic cancer: a phase II Study of the Hellenic Cooperative Oncology Group with biomarker evaluation," Cancer Invest, 26(8):784-93.
Frampton et al., (2013). "Development and validation of a clinical cancer genomic profiling test based on massively parallel DNA sequencing," Nature Biotechnology, 31(11):1023-1031.
Fu et al., (2011). "Novel functions of endocytic player clathrin in mitosis," Cell research, 21:1655-1661.
Fuchs et al., (1991). "Targeting Recombinant Antibodies to the Surface of *Escherichia coli*: Fusion to a Peptidoglycan Associated Lipoprotein," Nature Biotechnology, 9:1370-1372.
Fuehrer et al., (2012). "ALK-1 protein expression and ALK gene rearrangements aid in the diagnosis of inflammatory myofibroblastic tumors of the female genital tract," Arch Pathol Lab Med, 136(6):623-6.
Fuse et al., (2017). "Mechanisms of Resistance to NTRK Inhibitors and Therapeutic Strategies in NTRK1-Rearranged Cancers," Molecular Cancer Therapeutics, 16(10):2130-2143.
Gainor et al., (2013). "Novel targets in non-small cell lung cancer: ROS1 and RET fusions," Oncologist, 18:865-75.
Gallop et al., (1994). "Applications of combinatorial technologies to drug discovery. 1. Background and peptide combinatorial libraries," J. Med. Chem., 37(9):1233-1251.
Garcia-Mayoral et al., (2007). "The Structure of the C-Terminal KH Domains of KSRP Reveals a Noncanonical Motif Important for mRNA Degradation," Structure, 15:485-498.
Gartside et al., (2009). "Loss-of-Function Fibroblast Growth Factor Receptor-2 Mutations in Melanoma," Molecular Cancer Research, 7(1):41-54.
Gaultier et al., (1987). "Alpha-DNA. IV: Alpha-anomeric and beta-anomeric tetrathymidylates covalently linked to intercalating oxazolopyridocarbazole. Synthesis, physicochemical properties and poly (rA) binding," Nucleic Acids. Res., 15(16):6625-6641.
Gazzano-Santoro et al., (1996). "A non-radioactive complement-dependent cytotoxicity assay for anti-CD20 monoclonal antibody," J. Immunol. Methods, 202(2):163-171.
GenBank Accession No. NM_000141 accessed Nov. 19, 2015 from <http://www.ncbi.nlm.nih.gov/nuccore/189083823>, 8 pages.
GenBank Accession No. NM_001012331 accessed Nov. 19, 2015 from <http://www.ncbi.nlm.nih.gov/nuccore/NM_001012331.1>, 6 pages.
GenBank Accession No. NM_001080512 accessed Nov. 19, 2015 from <http://www.ncbi.nlm.nih.gov/nuccore/NM_001080512.2>, 6 pages.
GenBank Accession No. NM_001127211 accessed Nov. 19, 2015 from <http://www.ncbi.nlm.nih.gov/nuccore/385198090>, 6 pages.
GenBank Accession No. NM_001144915 accessed on Nov. 17, 2015 from <http://www.ncbi.nlm.nih.gov/nuccore/NM_001144915.1>, 6 pages.
GenBank Accession No. NM_003787 accessed Nov. 19, 2015 from <http://www.ncbi.nlm.nih.gov/nuccore/NM_003787>, 4 pages.
GenBank Accession No. NM_004562 accessed Nov. 19, 2015 from <http://www.ncbi.nlm.nih.gov/nuccore/NM_004562.2>, 5 pages.
GenBank Accession No. NM_006342 accessed Nov. 19, 2015 from <http://www.ncbi.nlm.nih.gov/nuccore/NM_006342>, 6 pages.
GenBank Accession No. NM_022494 accessed Nov. 19, 2015 from <http://www.ncbi.nlm.nih.gov/nuccore/NM_022494.2>, 3 pages.
GenBank Accession No. NP_001012331 accessed Nov. 19, 2015 from <http://www.ncbi.nlm.nih.gov/protein/59889558>, 5 pages.
George et al., (1999). "Sustained in Vivo Regression of Dunning H Rat Prostate Cancers Treated with Combinations of Androgen Ablation and Trk Tyrosine Kinase Inhibitors, CEP-751 (KT-6587) or CEP-701 (KT-5555)," Cancer Res, 59(10):2395-2401, 21 pages.
Gergely et al., (2000). "The TACC domain identifies a family of centrosomal proteins that can interact with microtubules," Proc Natl Acad Sci., 97:14352-14357.
Gervais et al., (2011). "Phase II study of sunitinib as maintenance therapy in patients with locally advanced or metastatic non-small cell lung cancer," Lung Cancer 20 74(3):474-80.
Giamas et al., (2007). "Protein kinases as targets for cancer treatment," Pharmacogenomics, 8(8); 1005-1016.
Ginzonger et al., (2000). "Measurement of DNA copy number at microsatellite loci using quantitative PCR analysis," Cancer Research, 60(19):5405-5409.
Gluzman (1981). "SV40-transformed simian cells support the replication of early SV40 mutants," Cell, 23(1):175-182.
Gnirke et al., (2009). "Solution hybrid selection with ultra-long oligonucleotides for massively parallel targeted sequencing," Nat Biotechnol., 27(2):182-189.
Gollob et al., (2006). "Role of Raf kinase in cancer: therapeutic 15 potential of targeting the Raf/MEK/ERK signal transduction pathway," Semin Oncol, 33(4):392-406.
Gosenca et al., (2014). "Identification and functional characterization of imatinib-sensitive DTD1-PDGFRB and CCDC88C-PDGFRB fusion genes in eosinophilia-associated myeloid/lymphoid neoplasms," Genes Chromosomes Cancer, 53:411-21.
Gossen et al., (1992). "Tight control of gene expression in mammalian cells by tetracycline-responsive promoters," Proc. Natl. Acad Sci. USA, 89(12):5547-5551.
Gottesman, (1990). "Minimizing Proteolysis in *Escherichia coli*: Genetic Solutions," Methods in Enzymology, 185, pp. 119-128.
Gozgit et al., (2012). "Ponatinib (AP24534), a Multitargeted Pan-FGFR Inhibitor with Activity in Multiple FGFR-Amplified or Mutated Cancer Models," Molecular Cancer Therapeutics, 11(3):690-699.
Grande et al., (2011). "Targeting oncogenic ALK: a promising strategy for cancer treatment," Mol Cancer Ther, 10(4):569-79.
Greco et al., (1993). "Characterization of the NTRK1 genomic region involved in chromosomal rearrangements generating TRK oncogenes," Genomics, 18(2):397-400.
Greco et al., (1992). "TRK-T1 is a novel oncogene formed by the fusion of TPR and TRK genes in human papillary thyroid carcinomas," Oncogene, 7(2):237-42.
Greco et al., (2010). "Rearrangements of NTRK1 gene in papillary thyroid carcinoma," Mol Cell Endrocrinol, 321(1):44-49.
Greco et al., (1998). "Role of the TFG N-terminus and coiled-coil domain in the transforming activity of the thyroid TRK-T3 oncogene," Oncogene, 16:809-16.
Greco et al., (1995). "The DNA rearrangement that generates the TRK-T3 oncogene involves a novel gene on chromosome 3 whose product has a potential coiled-coil domain," Mol Cell Biol, 15(11):6118-27.
Griffin et al., (1993). "DNA sequencing. Recent innovations and future trends," Appl Biochem Biotechnol., 38(1-2):147-159.
Griffiths et al., (1993). "Human anti-self antibodies with high specificity from phage display libraries," EMBO J., 12(2):725-734.
Griono et al., (2019). "A Simple RNA Target Capture NGS Strategy for Fusion Genes Assessment in the Diagnostics of Pediatric B-cell Acute Lymphoblastic Leukemia," Hemasphere, 3:e250, 9 pages.
Gruber et al., (1994). "Efficient tumor cell lysis mediated by a bispecific single chain antibody expressed in *Escherichia coli*," J. Immunol., 152(11):5368-5374.
Grunweller et al., (2003). "Comparison of different antisense strategies in mammalian cells using locked nucleic acids, 2'-O-methyl

(56) References Cited

OTHER PUBLICATIONS

RNA, phosphorothioates and small interfering RNA," Nucleic Acids Research, 31(12):3185-3193.
Gu et al., (2011). "Survey of Tyrosine Kinase Signaling Reveals ROS Kinase Fusions in Human Cholangiocarcinoma," PLoS One, 6:e15640, 9 pages.
Guagnano et al., (2012). "FGFR Genetic Alterations Predict for Sensitivity to NVP-BGJ398, a Selective Pan-FGFR Inhibitor," Cancer Discovery, 2:1118-1133.
Guatelli et al. (1990). "Isothermal, in vitro amplification of nucleic acids by a multienzyme reaction modeled after retroviral replication," Proc. Nat. Acad. Sci. USA, 87(5):1874-1878.
Gudernova et al., (2017). "Inhibitor repurposing reveals ALK, LTK, FGFR, RET and TRK kinases as the targets of AZD1480," Oncotarget, 8(65):109319-109331.
Guyer et al., (1976). "Immunoglobulin binding by mouse intestinal epithelial cell receptors," J. Immunol., 117(2):587-593.
Han et al., (2012). "Evaluation of a multi-kinase inhibitor KRC-108 as an anti-tumor agent in vitro and in vivo," Invest New Drugs, 30(2):518-23.
Hanna et al., (2000). "Comparison of sequencing by hybridization and cycle sequencing for genotyping of human immunodeficiency virus type 1 reverse transcriptase," J. Clin. Microbiol., 38(7):2715-2721.
Hara et al., (1998). "Amplification of c-myc, K-sam, and c-met in gastric cancers: detection by fluorescence in situ hybridization," Lab Invest, 78(9):1143-53.
Harper et al., (2008). "Chromosomal rearrangements leading to MLL gene fusions: clinical and biological aspects," Cancer research, 68(24):10024-7, 7 pages.
Harvey et al., (2007). "The Salvador-Warts-Hippo 20 pathway—an emerging tumour-suppressor network," Nature reviews Cancer, 7(3):182-91.
Haselhoff et al., (1988). "Simple RNA enzymes with new and highly specific endoribonuclease activities," Nature, 334(6183):585-591.
Hatzivassiliou et al., (2010). "RAF inhibitors prime wild-type RAF to activate the MAPK pathway and enhance growth," Nature, 464(7287):431-5.
Hay et al., (1992). "Bacteriophage cloning and *Escherichia coli* expression of a human IgM Fab," Hum. Antibod. Hybridomas, 3(2):81-85.
Heiskanen et al., (2001). "CGH, cDNA and tissue microarray analyses implicate FGFR2 amplification in a small subset of breast tumors," Anal Cell Pathol, 22(4):229-34.
Helene (1991). "The anti-gene strategy: control of gene expression by triplex-forming-oligonucleotides," Anticancer Drug Des., 6(6):569-584.
Helene et al., (1992). "Control of gene expression by triple helix-forming oligonucleotides. The antigene strategy," Ann. N.Y. Acad. Sci., 660:27-36.
Helias-Rodzewicz et al., (2010). "YAP1 and VGLL3, encoding two cofactors of TEAD transcription factors, are amplified and overexpressed in a subset of soft tissue sarcomas," Genes, chromosomes cancer, 49(12):1161-71.
Hellstrom et al., (1985). "Strong antitumor activities of IgG3 antibodies to a human melanoma-associated ganglioside," Proc. Nat'l Acad. Sci. USA, 82(5):1499-1502.
Hellstrom et al., (1986). "Antitumor effects of L6, an IgG2a antibody that reacts with most human carcinomas," Proc. Nat'l Acad. Sci. USA, 83(18):7059-7063.
Hermans et al., (2009). "Overexpression of prostate-specific TMPRSS2(exon 0)-ERG fusion transcripts corresponds with favorable prognosis of 5 prostate cancer," Clin Cancer Res, 15(20):6398-403.
Herquel et al., (2011). "Transcription cofactors TRIM24, TRIM28, and TRIM33 associate to form regulatory complexes that suppress murine hepatocellular carcinoma," Proc Natl Acad Sci USA, 108(20):8212-7.

Hess, (2004). "MLL: a histone methyltransferase disrupted in leukemia," Trends in molecular medicine, 10(10):500-7.
Hirai et al., (2020). "Large-scale metabarcoding analysis of epipelagic and mesopelagic copepods in the Pacific," PLOS One, 15:e0233189, 24 pages.
Hollinger et al., (1993). "'Diabodies': small bivalent and bispecific antibody fragments," Proc. Natl. Acad. Sci. USA, 90(14):6444-6448.
Hoogenboom et al., (1992). "By-passing immunisation. Human antibodies from synthetic repertoires of germline VH gene segments rearranged in vitro," J Mol Biol., 227(2):381-388.
Hoogenboom et al., (2002). "Overview of antibody phage-display technology and its applications," Methods in Molecular Biology, 178:1-37.
Houghten et al., (1992). "The use of synthetic peptide combinatorial libraries for the identification of bioactive peptides," Biotechniques, 13(3):412-421.
Hu et al., (1998). "The immunostimulating complex (ISCOM) is an efficient mucosal delivery system for respiratory syncytial virus (RSV) envelope antigens inducing high local and systemic antibody responses," Clin. Exp. Immunol., 113:235-243.
Hudson et al., (2003). "Engineered antibodies," Nat. Med., 9(1):129-134.
Huehne et al., (2008). "Novel missense, insertion and deletion mutations in the neurotrophic tyrosine kinase receptor type 1 gene (NTRK1) associated with congenital insensitivity to pain with anhidrosis," Neuromuscul Disord, 18(2):159-66.
Huether et al., (2007). "Sorafenib alone or as combination therapy for growth control of cholangiocarcinoma," Biochemical Pharmacology, 73(9):1308-1317.
Huse et al., (1989). "Generation of a large combinatorial library of the immunoglobulin repertoire in phage lambda," Science, 246(4935):1275-1281.
Hyman et al., (2017). "The efficacy of larotrectinib (LOXO-101), a selective tropomyosin receptor kinase (TRK) inhibitor, in adult and pediatric TRK fusion cancers," Presentation from the ASCO Annual Meeting 2017, 24 pages.
Hyman et al., (2019). "445PD—Durability of response with larotrectinib in adult and pediatric patients with TRK fusion cancer," Annals of Oncology, 30(S5):v162-v163.
Hyrup et al., (1996). "Peptide nucleic acids (PNA): synthesis, properties and potential applications," Bioorganic & Medicinal Chemistry, 4(1):5-23.
Idusogie et al., (2000). "Mapping of the C1q binding site on rituxan, a chimeric antibody with a human IgG1 Fc," J. Immunol., 164(8):4178-4184.
Imanishi et al., (2002). "BNAs: novel nucleic acid analogs with a bridged sugar moiety," Chem. Commun., 16:1653-1659.
Indo et al., (1997). "Structure and organization of the human TRKA gene encoding a high affinity receptor for nerve growth factor," Jpn J Hum Genet, 42(2):343-51.
Inoue et al., (1987). "Sequence-dependent hydrolysis of RNA using modified oligonucleotide splints and RNase H," FEBS Lett., 215(2):327-330.
Inoue et al., (1987). "Synthesis and hybridization studies on two complementary nona(2'-O-methyl)ribonucleotides," Nucleic Acids Res., 15(15):6131-6148.
International Preliminary Report on Patentability and Written Opinion for International Application No. PCT/US2012/061211 issued Apr. 22, 2014, 8 pages.
International Preliminary Report on Patentability for International Application No. PCT/US2013/068604 dated May 5, 2015, 9 pages.
International Preliminary Report on Patentability from PCT/US14/12136 mailed Mar. 18, 2015, 18 pages.
International Search Report and Written Opinion for International Application No. PCT/US2013/068457 dated Jul. 11, 2014, 15 pages.
International Search Report and Written Opinion for International Application No. PCT/US2013/068604 mailed Nov. 7, 2014, 16 pages.
International Search Report and Written Opinion for PCT/US2014/012136 mailed Jul. 16, 2014, 20 pages.

(56) References Cited

OTHER PUBLICATIONS

International Search Report for International Application No. PCT/US2012/061211 mailed Feb. 5, 2013, 4 pages.
International Search Report for International Application No. PCT/US2020/034421 mailed Dec. 11, 2020, 12 pages.
International Search Report for International Application No. PCT/US2021/65561 mailed Jun. 7, 2022, 13 pages.
Isaksson-Mettavainio et al., (2011). "High SMAD4 levels appear in microsatellite instability and hypermethylated colon cancers, and indicate a better prognosis. International journal of cancer," Int J Cancer, 131:779-88.
Iyer et al., (2010) "Lestaurtinib enhances the antitumor efficacy of chemotherapy in murine xenograft models of neuroblastoma," Clin Cancer Res, 16(5):1478-85.
Jain et al., (2011). "Association of overexpression of TIF1? with colorectal carcinogenesis and advanced colorectal 5 adenocarcinoma," World journal of gastroenterology, 17(35):3994-4000.
Jani et al., (2010). "PF-03814735, an orally bioavailable small molecule aurora kinase inhibitor for cancer therapy," Mol Cancer Ther., 9(4):883-894.
Javle et al., (2016). "Biliary Cancer: Utility of Next-Generation Sequencing for Clinical Management," Cancer, 122:3838-3847.
Jepson et al., (2004). "Locked nucleic acid: a potent nucleic acid analog in therapeutics and biotechnology," Oligonucleotides, 14(2):130-146. Abstract Only.
Jiao et al., (2013). "Exome sequencing identifies frequent inactivating mutations in BAP1, ARID1A and PBRM in intrahepatic cholangiocarcinomas," Nature Genetics, 45(12):1470-1473 and Supplementary Information.
Jin et al., (2011). "The driver of malignancy in KG-la leukemic cells, FGFR10P2-FGFR1, encodes an HSP90 addicted oncoprotein," Cell Signal, 23(11):1758-66.
Jones et al., (1986). "Replacing the complementarity-determining regions in a human antibody with those from a mouse," Nature, 321(6069):552-525.
Jones et al., (1995). "Protection of mice from Bordetella pertussis respiratory infection using microencapsulated pertussis fimbriae," Vaccine, 13:675-681.
Jones et al., (2009). "Oncogenic RAF1 rearrangement and a novel BRAF mutation as alternatives to KIAA1549:BRAF fusion in activating the MAPK pathway in pilocytic astrocytoma," Oncogene, 28(20):2119-23, 8 pages.
Ju et al., (2012). "A transforming KIF5B and RET gene fusion in lung adenocarcinoma revealed from whole-genome and transcriptome sequencing," Genome Res, 22(3):436-45.
Kalampokas et al., (2017). "Primary Vaginal Melanoma, a Rare and Aggressive Entity. A Case Report and Review of the Literature," In Vivo, 31(1):133-140.
Kallioniemi et al., (1992). "ERBB2 amplification in breast cancer analyzed by fluorescence in situ hybridization," Proc. Natl Acad Sci USA, 89(12):5321-5325.
Kam et al., (2005). "Carbon nanotubes as multifunctional biological transporters and near-infrared agents for selective cancer cell destruction," Proc. Natl. Acad. Sci. USA, 102(33):11600-11605.
Kanda et al., (2006). "Comparison of cell lines for stable production of fucose-negative antibodies with enhanced ADCC," Biotechnol. Bioeng., 94(4):680-688.
Kang et al., (2012). "microRNA-99b acts as a tumor suppressor in non-small cell lung cancer by directly targeting fibroblast growth factor receptor 3," Experimental and Therapeutic Medicine, 3:149-153.
Karlin et al., (1990). "Methods for assessing the statistical significance of molecular sequence features by using general scoring schemes," Proc. Natl. Acad. Sci. USA, 87(6):2264-2268.
Karlin et al., (1993). "Applications and statistics for multiple high-scoring segments in molecular sequences," Proc. Natl. Acad. Sci. USA, 90(12):5873-5877.
Kashmiri et al., (2005). "SDR grafting—a new approach to antibody humanization," Methods, 36(1):25-34.
Keats et al., (2003). "In multiple myeloma, t(4;14)(p16;q32) is an adverse prognostic factor irrespective of FGFR3 expression," Blood, 101(4):1520-1529.
Keegan et al., (1991). "Isolation of an additional member of the fibroblast growth factor receptor family, FGFR-3," Proc Natl Acad Sci., 88(4):1095-1099.
Kelleher et al. (2010). "The emerging pathogenic and therapeutic importance of the anaplastic lymphoma kinase gene," Eur J Cancer, 46(13):2357-2368.
Kessel et al., (1990). "Murine developmental control genes," Science, 249(4967):374-379.
Kheder et al., (2018). "Emerging Targeted Therapy for Tumors with NTRK Fusion Proteins," Clin. Cancer Res, 24(23):5807-5814.
Khotskaya et al., (2017). "Targeting TRK family proteins in cancer," Pharmacol Ther., 173:58-66. Abstract Only.
Khromova et al., (2012). "Downregulation of VEGF-C expression in lung and colon cancer cells decelerates tumor growth and inhibits metastasis via multiple mechanisms," Oncogene, 31(11):1389-97.
Kim et al., (1994). "Localization of the site of the murine IgG1 molecule that is involved in binding to the murine intestinal Fc receptor," Eur J Immunol., 24(10):2429-2434.
Kim et al., (2003). "SAM domains: uniform structure, diversity of function," Trends Biochem. Sci., 28(12):625-628.
Kim et al., (2005). "Synthetic dsRNA Dicer substrates enhance RNAi potency and efficacy," Nat Biotech., 23(2):222-226.
Kim et al., (2012). "The ubiquitin-specific protease USP2a enhances tumor progression by targeting cyclin AI in bladder cancer," Cell Cycle, 11(6):1123-30.
King et al., (2009). "Cooperativity of TMPRSS2-ERG with PI3-kinase pathway activation in prostate oncogenesis," Nat Genet, 41(5):524-6, 8 pages.
Klein et al., (1991). "The trk proto-oncogene encodes a receptor for nerve growth factor," Cell, 65(1):189-97.
Klezovitch et al., (2008). "A causal role for ERG in neoplastic transformation of prostate epithelium," Proc Natl Acad Sci USA, 105(6):2105-10.
Klimka et al., (2000). "Human anti-CD30 recombinant antibodies by guided phage antibody selection using cell panning," Br. J. Cancer, 83(2):252-260.
Ko et al. (2010). "Phase II study of telatinib (T) in combination with capecitabine (X) and cisplatin (P) as first-line treatment in patients (pts) with advanced cancer of the stomach (G) or gastro-esophageal junction (GEJ)," Journal of Clinical Oncology ASCO Annual Meeting Abstracts, 28(15), 1 page.
Kohler et al., (1975). "Continuous cultures of fused cells secreting antibody of predefined specificity," Nature, 256(5517):495-497.
Kohno et al., (2012). "KIF5B-RET fusions in lung adenocarcinoma," Nat Med, 18(3):375-7, 7 pages.
Kolinsky et al., (2011). "Preclinical evaluation of the novel multi-targeted agent R1530," Cancer Chemother Pharmacol., 68(6):1585-94.
Kostelny et al., (1992). "Formation of a bispecific antibody by the use of leucine zippers," J. Immunol., 148(5):1547-1553.
Kozbor et al., (1983). "The production of monoclonal antibodies from human lymphocytes," Immunol. Today, 4(3):72-79.
Kozbor et al., (1984). "A human hybrid myeloma for production of human monoclonal antibodies," J Immunol., 133(6):3001-3005.
Krishnakumar et al., (2008). "A comprehensive assay for targeted multiplex amplification of human DNA sequences," Proc. Natl. Acad. Sci. USA, 105(27):9296-9310.
Krivtsov et al., (2008). "H3K79 methylation profiles define murine and human MLL-AF4 leukemias," Cancer Cell, 14(5):355-68.
Kwak et al., (2010). "Anaplastic lymphoma kinase inhibition in non-small-cell lung cancer," N Engl J Med., 363(18):1693-1703.
Kwoh et al., (1989). "Transcription-based amplification system and detection of amplified human immunodeficiency virus type 1 with a bead-based sandwich hybridization format," Proc. Nail. Acad. Sci. USA, 86(4):1173-1177.
Lam (1997). "Application of combinatorial library methods in cancer research and drug discovery," Anticancer Drug Des., 12(3):145-167.
Lam et al., (2005). "Abstract 883: Expression profiling in lung adenocarcinomas with or without epidermal growth factor receptor

(56) References Cited

OTHER PUBLICATIONS (EGFR) gene mutation at exons 18-21 reveals expression signatures related to the EGFR pathway," Proc Amer Assoc Cancer Res, 46, 1 page.
Lam et al., (1991). "A new type of synthetic peptide library for identifying ligand-binding activity," Nature, 354(6348):82-84.
Landegren et al., (1988). "A ligase-mediated gene detection technique," Science, 241(4869):1077-1080.
Landis et al., (1998). "Cancer Statistics, 1998" Ca Cancer J Clin, 48(1):6-29.
Lapointe et al., (2007). "A variant TMPRSS2 isoform and ERG fusion product in prostate cancer with implications for molecular diagnosis," Mod Pathol, 20(4):467-73.
Lasken (2007). "Single-cell genomic sequencing using Multiple Displacement Amplification," Curr Opin Microbiol., 10(5):510-516.
Lassen et al., (2018). "Abstract 409O: Larotrectinib efficacy and safety in TRK fusion cancer: an expanded clinical dataset showing consistency in an age and tumor agnostic approach," Annals of Oncology 29 (Supplement 8): viii133-viii148, 1 page.
Le Douarin et al., (1995). "The N-terminal part of TIF1, a putative mediator of the ligand-dependent activation function (AF-2) of nuclear receptors, is fused to B-raf in the oncogenic protein T18," EMBO J, 14(9):2020-33.
Lee et al., (2017). "The potential role of comprehensive genomic profiling to guide targeted therapy for patients with biliary cancer," Ther Adv Gastroenterol, 10(6):507-520.
Lee et al., (2004). "Bivalent antibody phage display mimics natural immunoglobulin," J. Immunol. Methods, 284(1-2):119-132.
Lee et al., (2004). "High-affinity human antibodies from phage-displayed synthetic Fab libraries with a single framework scaffold," J. Mol. Biol., 340(5):1073-1093.
Lemaitre et al., (1987). "Specific antiviral activity of a poly(L-lysine)-conjugated oligodeoxyribonucleotide sequence complementary to vesicular stomatitis virus N protein mRNA initiation site," Proc. Natl. Acad. Sci. USA, 84(3):648-652.
Leng et al., (2009). "Smad4/Smad7 balance: a role of tumorigenesis in gastric cancer," Experimental and molecular pathology, 87(1):48-53.
Letsinger et al., (1989). "Cholesteryl-conjugated oligonucleotides: synthesis, properties, and activity as inhibitors of replication of human immunodeficiency virus in cell culture," Proc. Natl. Acad Sci. USA, 86(17):6553-6556.
Li et al., (2006). "Human antibodies for immunotherapy development generated via a human B cell hybridoma technology," Proc. Natl. Acad. Sci. USA, 103(10):3557-3562.
Li et al., (2011). "Roles of VEGF-C and Smad4 in the lymphangiogenesis, lymphatic metastasis, and prognosis in colon cancer," Journal of gastrointestinal surgery, 15(11):2001-10.
Lih et al., (2016). "N of 2 Responders With LMNA-NTRK1," J Natl Cancer Inst, 108(1):djv376, 2 pages.
Lin et al., (2009). "Exon Array Profiling Detects EML4-ALK Fusion in Breast, Colorectal, and Non-Small Cell Lung Cancers," Mol Cancer Research, 7(9):1466-1476.
Lipson et al., (2012). "Identification of new ALK and RET gene fusions from colorectal and lung cancer biopsies," Nat Med, 18(3):382-4, 7 pages.
Liu et al., (1987). "Chimeric mouse-human IgG1 antibody that can mediate lysis of cancer cells," Proc. Natl. Acad. Sci. USA, 84(10):3439-3443.
Liu et al., (1987). "Production of a mouse-human chimeric monoclonal antibody to CD20 with potent Fc-dependent biologic activity," J Immunol. 139(10):3521-3526.
Liu et al., (2011). "FOXO1-FGFR1 fusion and amplification in a solid variant of alveolar rhabdomyosarcoma," Mod Pathol, 24(10):1327-35.
Lonberg (2005). "Human antibodies from transgenic animals," Nat. Biotech., 23(9):1117-1125.
Lonberg (2008). "Fully human antibodies from transgenic mouse and phage display platforms," Curr. Opin. Immunol., 20(4):450-459.
Lonberg et al., (1995). "Human antibodies from transgenic mice," Int. Rev. Immunol., 13(1):65-93.
Lorenzi et al., (1996). "FRAG1, a gene that potently activates fibroblast growth factor receptor by C-terminal fusion through chromosomal rearrangement," Proc. Natl. Acad. Sci. USA, 93:8956-8961.
Lorenzi et al., (1997). "Ligand-independent activation of fibroblast growth factor receptor-2 by carboxl terminal alterations," Oncogene, 15:817-826.
Loughran et al., (2008). "The transcription factor Erg is essential for definitive hematopoiesis and the function of adult hematopoietic stem cells," Nat Immunol, 9(7):810-9.
Lucas et al., (2008). "The androgen-regulated type II serine protease TMPRSS2 is differentially expressed and mislocalized in prostate adenocarcinoma," J Pathol, 215(2):118-25. Abstract Only.
Maher (1992). "DNA triple-helix formation: an approach to artificial gene repressors?" Bioassays, 14(12):807-815.
Malkoski et al., (2012). "Two sides of the story? Smad4 loss in 20 pancreatic cancer versus head-and-neck cancer," FEBS letters, 586:1984-92.
Marchetti et al., (2008). "Frequent Mutations in the Neurotrophic Tyrosine Receptor Kinase Gene Family in Large Cell Neuroendocrine Carcinoma of the Lung, " Human Mutation, 29(5):609-616.
Mardy et al., Congenital insensitivity to pain with anhidrosis: Novel mutations in the TRKA (NTRK1) gene encoding a high-affinity receptor for nerve growth factor, 1999, Am. J. Hum. Genet., 64, pp. 1570-1579.
Marks et al., (1992). "By-passing immunization. Human antibodies from V-gene libraries displayed on phage," J Mol Biol., 222(3):581-597.
Marks et al., (2004). "Selection of human antibodies from phage display libraries," Methods in Molecular Biology, 248:161-176.
Marschalek, (2011). "Mechanisms of leukemogenesis by MLL fusion proteins," British journal of haematology, 152:141-54.
Marshall et al., (2005). "Phase I trial of orally administered CEP-701, a novel neurotrophin receptor-linked tyrosine kinase inhibitor," Invest New Drugs, 23(1):31-7.
Martin (1995). "Ein neuer Zugang zu 2'-O-Alkylribonucleosiden und Eigenschaften deren Oligonucleotide," Helvetica, 78(2):486-504.
Martin-Zanca et al., (1986). "A human oncogene formed by the fusion of truncated tropomyosin and protein tyrosine kinase sequences." Nature, 319(6056):743-8.
Massague, (2008). "TGFbeta in Cancer," Cell, 34(2):215-30.
Masuda et al., (1999). "Analysis of chemical modification of RNA from formalin-fixed samples and optimization of molecular biology applications for such samples, " Nucleic Acids Res., 27(22):4436-4443.
Matsumoto et al., (2012). "FGFR2 gene amplification and clinicopathological features in gastric cancer," British Journal of Cancer, 106(4):727-732.
Maurer et al., (2011). "Raf kinases in cancer-roles and therapeutic opportunities," Oncogene, 30(32):3477-88.
Maxam et al., (1977). "A new method for sequencing DNA," Proc. Nat! Acad Sci USA, 74(2):560-564.
Mayer et al., (1993). "The prognostic significance of proliferating cell nuclear antigen, epidermal growth factor receptor, and mdr gene expression in colorectal cancer," Cancer, 71(8):2454-60.
Mayr et al., (2006). "KRAS and BRAF mutations in ovarian tumors: a comprehensive study of invasive carcinomas, borderline tumors and extraovarian implants," Gynecol Oncol, 103(3):883-7.
McCafferty et al., (1990). "Phage antibodies: filamentous phage displaying antibody variable domains," Nature, 348(6301):552-554.
Mckay et al., (2009). "PP58 Novel potential therapeutic targets for cholangiocarcinoma identified by array comparitive hybridization," European Journal of Cancer, 7(4), 1 page.
Meric-Bernstam et al., (2018). "Activity of larotrectinib, a highly selective inhibitor of tropomyosin receptor kinase, in TRK fusion breast cancers", SABCS Abstract p. 6-20-02.

(56) References Cited

OTHER PUBLICATIONS

Mesker et al., (2009). "Presence of a high amount of stroma and downregulation of SMAD4 predict for worse survival for stage I-II colon cancer patients," Cellular oncology, 31(3):169-78.

Metzker (2010). "Sequencing technologies—the next generation," Nature Biotechnology Reviews, 11(1):31-46.

Meulenbeld et al., (2012). "Danusertib, an aurora kinase inhibitor," Expert Opinion Investigative Drugs, 21(3):383-393.

Miki et al., (1992). "Determination of ligand-binding specificity by alternative splicing: two distinct growth factor receptors encoded by a single gene," PNAS USA, 89(1):246-250.

Milstein et al., (1983). "Hybrid hybridomas and their use in immunohistochemistry," Nature, 305(5934):537-540.

Minturn et al., (2011). "Phase I trial of lestaurtinib for children with refractory neuroblastoma: a new approaches to neuroblastoma therapy consortium study," Cancer Chemother Pharmacol, 68(4):1057-65, 18 pages.

Miura et al., (2000). "Mutation and polymorphism analysis of the TRKA (NTRK1) gene encoding a high-affinity receptor for nerve growth factor in congenital insensitivity to pain with anhidrosis (CIPA) families," Hum Genet, 106(1):116-24.

Miyaki et al., (1999). "Higher frequency of Smad4 gene mutation in human colorectal cancer with distant metastasis," Oncogene, 18(20):3098-103.

Mizukawa et al., (2011). "Inhibition of Rac GTPase signaling and downstream prosurvival Bcl-2 proteins as combination targeted therapy in MLL-AF9 leukemia," Blood, 118(19):5235-45.

Mody et al., (2015). "Integrative Clinical Sequencing in the Management of Refractory or Relapsed Cancer in Youth," JAMA, 314(9):913-925.

Mok et al., (2009). "Gefitinib or Carboplatin—Paclitaxel in Pulmonary Adenocarcinoma," N Engl J Med, 361:947-957.

Monk et al., (2010). "Phase II, Open-Label Study of Pazopanib or Lapatinib Monotherapy Compared With Pazopanib Plus Lapatinib Combination Therapy in Patients With Advanced and Recurrent Cervical Cancer," Journal of Clinical Oncology, 28(22):3562-3569.

Mook et al., (2007). "Evaluation of locked nucleic acid-modified small interfering RNA in vitro and in vivo," Mol Cancer Ther., 6(3):833-843.

Morris et al., (1994). "Fusion of a kinase gene, ALK, to a nucleolar protein gene, NPM, in non-Hodgkin's lymphoma," Science, 263(5151):1281-4. Abstract Only.

Morrison (1985). "Transfectomas provide novel chimeric antibodies," Science, 229(4719):1202-1207.

Morrison et al., (1984). "Chimeric human antibody molecules: mouse antigen-binding domains with human constant region domains," Proc. Natl. Acad. Sci. USA, 81(21):6851-6855.

Muller-Tidow et al., Identification of Metastasis-Associated Receptor Tyrosine Kinases in Non-Small Cell Lung Cancer, 2005, Cancer Res., vol. 65, No. 5 pp. 1778-1782.

Mulligan et al., (1994). "Specific mutations of the RET proto-oncogene are related to disease phenotype in MEN 2A and FMTC," Nat Genet, 6(1):70-4.

Murati et al., (2009). "Genome profiling of acute myelomonocytic leukemia: alteration of the MYB locus in MYST3-linked cases," Leukemia, 23(1):85-94.

Myers et al., (1988). "Optimal alignments in linear space," Comput Appl Biosci, 4(1):11-17.

Nacu et al., (2011). "Deep RNA sequencing analysis of readthrough gene fusions in human prostate adenocarcinoma and reference samples," BMC Med Genomics, 4:11.

Naeve et al., (1995). "Accuracy of automated DNA sequencing: a multi-laboratory comparison of sequencing results," Biotechniques, 19(3):448-453.

Nakagawara, (2001). "Trk receptor tyrosine kinases: a bridge between cancer and neural development," Cancer Lett 169(2):107-14.

Nakashima et al., (2007). "RET oncogene 10 amplification in thyroid cancer: correlations with radiation-associated and high-grade malignancy," Hum Pathol, 38(4):621-8, 8 pages.

Narong et al., (2011). "Basic fibroblast growth factor induces cholangiocarcinoma cell migration via activation of the MEK1/2 pathway," Oncology Letters, pp. 821-825.

Natale et al., (2011). "Phase III trial of vandetanib compared with erlotinib in patients with previously treated advanced non-small-cell lung cancer," J Clin Oncol, 29(8):1059-66.

Nath et al., (1998). "Fluorescence in situ hybridization (FISH): DNA probe production and hybridization criteria," Biotechnic Histochem., 73(1):6-22.

Naumann et al., (2015). "Fusion of PDGFRB to MPRIP, CPSF6, and GOLGB1 in three patients with eosinophilia-associated myeloproliferative neoplasms," Genes Chromosomes Cancer, 54:762-70.

Necchi et al., (2012). "Pazopanib in advanced and platinum-resistant urothelial cancer: an open-label, single group, phase 2 trial," Lancet Oncol, 13(8):810-6.

Ni (2006). "Research progress and future perspectives in antibodomics and antibodomic Drugs," J. General Review, 26(4):265-268. Abstract Only.

Nielsen et al., (1991). "Sequence-selective recognition of DNA by strand displacement with a thymine-substituted polyamide," Science, 254(5037):1497-1500.

Nikiforov, (2008). "Thyroid carcinoma: molecular pathways and therapeutic targets," Mod Pathol, 21(Suppl 2):S37-43.

Nishimura et al., (1987). "Recombinant human-mouse chimeric monoclonal antibody specific for common acute lymphocytic leukemia antigen," Cancer Res., 47(4):999-1005.

Nishiyama et al., (2018). "Foretinib Overcomes Entrectinib Resistance Associated with the NTRK1 G667C Mutation in NTRK1 Fusion-Positive Tumor Cells in a Brain Metastasis Model," Clin Cancer Res., 24(10):2357-2369.

Notification of Transmittal of the International Search Report and Written Opinion of the International Searching Authority from corresponding PCT/US2013/068457 dated Jul. 11, 2014, 1 page.

Notification of Transmittal of the International Search Report and Written Opinion of the International Searching Authority from corresponding PCT/US2013/068604 dated Jul. 11, 2014, 1 page.

Oi et al., (1986). "Chimeric antibodies," BioTechniques, 4(3), 214-221.

Okada et al., (2005). "hDOT1L links histone methylation to leukemogenesis," Cell, 121(2):167-78.

Okamura et al., (2018). "Analysis of NTRK Alterations in Pan-Cancer Adult and Pediatric Malignancies: Implications for NTRK-Targeted Therapeutics," JCO Precis Oncol., PO.18.00183, 20 pages.

Okazaki et al., (2004). "Fucose depletion from human IgG1 oligosaccharide enhances binding enthalpy and association rate between IgG1 and FcgammaRIIIa," J. Mol. Biol., 336(5):1239-1249.

Ono et al., (2009). "Mixed-lineage- leukemia (MLL) fusion protein collaborates with Ras to induce acute leukemia through aberrant Hox expression and Raf activation," Leukemia, 23(12):2197-209.

Osbourn et al., (2005). "From rodent reagents to human therapeutics using antibody guided selection," Methods, 36(1):61-68.

Ou et al., (2017). "Emergence of FGFR3-TACC3 fusions as a potential by-pass resistance mechanism to EGFR tyrosine kinase inhibitors in EGFR mutated NSCLC patients," Lung Cancer, 111:61-67.

Overholtzer et al., (2006). "Transforming properties of YAP, a candidate oncogene on the chromosome 11q22 amplicon," PNAS USA, 103(33):12405-10.

Padlan (1991). "A possible procedure for reducing the immunogenicity of antibody variable domains while preserving their ligand-binding properties," Mol. Immunol., 28(4-5):489-498.

Paillard (1989). "'Tet-on': a gene switch for the exogenous regulation of transgene expression," Human Gene Therapy, 9(7):983-985.

Palanisamy et al., (2010). "Rearrangements of the RAF kinase pathway in prostate cancer, gastric cancer and melanoma," Nature medicine, 16(7):793-8, 6 pages.

Papageorgis et al., (2011). "Smad4 inactivation promotes malignancy and drug resistance of colon cancer," Cancer research, 71(3):998-1008.

Pardoll, (2012). "The blockade of immune checkpoints in cancer immunotherapy," Nat Rev Cancer, 12(4):252-64.

(56) References Cited

OTHER PUBLICATIONS

Park et al., (2016). "NTRK1 fusions for the therapeutic intervention of Korean patients with colon cancer," Oncotarget, 7(7):8399-8412.
Patel et al., (2011). "Cholangiocarcinoma—controversies and challenges," Nat Rev Gastroenterol Hepatol, 8(4):1-25.
Patel et al., (2002). "Worldwide trends in mortality from biliary tract malignancies," BMC Cancer, 2(10):1-5.
Patel et al., (2010). "Abstract: ACTB-1003: An oral kinase inhibitor targeting cancer mutations (FGFR), angiogenesis (VEGFR2, TEK), and induction of apoptosis (RSK and p70S6K)," Journal of Clinical Oncology, ASCO Annual Meeting Abstracts, 28(15 suppl):e13665, 3 pages.
Pearson et al., (1988). "Improved tools for biological sequence comparison," Proc. Natl. Acad. Sci. USA, 85(8):2444-2448.
Peifer et al., (2012). "Integrative genome analyses identify key somatic driver mutations of small-cell lung cancer," Nat Genet 44, 1104-1110, 22 pages.
Penault-Llorca et al., (2019). "Testing algorithm for identification of patients with TRK fusion cancer," J Clin Pathol., 72(7):460-467.
Perez-Pinera et al., (2007). "The Trk tyrosine kinase inhibitor K252a regulates growth of lung adenocarcinomas," Mol Cell Biochem, 295(1-2):19-26.
Perner et al., (2006). "TMPRSS2:ERG fusion-associated deletions provide insight into the heterogeneity of prostate cancer," Cancer Res, 66(17):8337-41.
Perry-O'Keefe et al., (1996). "Peptide nucleic acid pre-gel hybridization: an alternative to southern hybridization," Proc. Natl. Acad. Sci., 93(25):14670-14675.
Peset et al., (2008). "The TACC proteins: TACC-ling microtubule dynamics and centrosome function," Trends in cell biology, 18.8: 379-388.
Petkova et al., (2006). "Enhanced half-life of genetically engineered human IgG1 antibodies in a humanized FcRn mouse model: potential application in humorally mediated autoimmune disease," Intl. Immunol., 18(12):1759-1769.
Phay et al., (2010). "Targeting RET receptor tyrosine kinase activation in cancer," Clin Cancer Res, 16(24):5936-41.
Pietrantonio et al., (2017). "ALK, ROS1, and NTRK Rearrangements in Metastatic Colorectal Cancer," J Natl Cancer Inst, 109(12), 10 pages.
Pinkel et al., (1988). "Fluorescence in situ hybridization with human chromosome-specific libraries: detection of trisomy 21 and translocations of chromosome 4," Proc. Natl. Acad. Sci. USA, 85(23):9138-9142.
Pinkel et al., (1998). "High resolution analysis of DNA copy number variation using comparative genomic hybridization to microarrays," Nature Genetics, 20(2):207-211.
Pinkert et al., (1987). "An albumin enhancer located 10 kb upstream functions along with its promoter to direct efficient, liver-specific expression in transgenic mice," Genes Dev., 1(3):268-277.
Pontes et al., (2010). "Immunoexpression of Ki67, proliferative cell nuclear antigen, and Bcl-2 proteins in a case of ameloblastic fibrosarcoma," Annals of diagnostic pathology, 14(6):447-52.
Porreca et al., (2007). "Multiplex amplification of large sets of human exons," Nature Methods, 4(11):931-936.
Powers et al., (2000). "Fibroblast growth factors, their receptors and signaling" Endocrine-Related Cancer, 7:165-197.
Presta et al., (1993). "Humanization of an antibody directed against IgE," J. Immunol, 151(5):2623-2632.
Presta et al., (1997). "Humanization of an anti-vascular endothelial growth factor monoclonal antibody for the therapy of solid tumors and other disorders," Cancer Res., 57(20):4593-4599.
PubChem, (2012). "Ceritinib, CID=57379345," Available online at <https://pubchem.ncbi.nlm.nih.gov/compound/Ceritinib>, 50 pages.
Qiu et al., (2008). "Mechanism of activation and inhibition of the HER4/ErbB4 kinase," Structure, 16(3):460-7.
Queen et al., (1983). "Immunoglobulin gene transcription is activated by downstream sequence elements," Cell, 33(3):741-748.
Queen et al., (1989). "A humanized antibody that binds to the interleukin 2 receptor," Proc. Nat'l Acad. Sci. USA, 86(24):10029-10033.
Rao et al., (2010). "Heat shock protein 90 inhibition depletes TrkA levels and signaling in human acute leukemia cells," Mol Cancer Ther, 9(8):2232-42.
Ravetch et al., (1991). "Fc receptors," Annu. Rev. Immunol., 9:457-492.
Reck et al., (2011). "A phase II double-blind study to investigate efficacy and safety of two doses of the triple angiokinase inhibitor BIBF 1120 in patients with relapsed advanced non-small-cell lung cancer," Annals of Oncology, 22:1374-1381.
Reindl et al., (2009). "CBL exon 8/9 mutants activate the FLT3 pathway and cluster in core binding factor/11q deletion acute myeloid leukemia/myelodysplastic syndrome subtypes," Clin Cancer Res, 15(7):2238-47.
Ren et al., (2011). "Src activation plays an important key role in lymphomagenesis induced by FGFR1 fusion kinases," Cancer Res, 71(23):7312-22.
Richelda et al., (1997). "A Novel Chromosomal Translocation t(4;14)(p16.3; q32) in Multiple Myeloma Involves the Fibroblast Growth Factor Receptor 3 Gene," Blood, 90(10):4062-4070.
Riechmann et al., (1988). "Reshaping human antibodies for therapy," Nature, 332(6162):323-329.
Ripka et al., (1986). "Two Chinese hamster ovary glycosylation mutants affected in the conversion of GDP-mannose to GDP-fucose," Arch. Biochem. Biophys., 249(2):533-545.
Robinson et al., (2019). "Phase 1/1B trial to assess the activity of entrectinib in children and adolescents with recurrent or refractory solid tumors including central nervous system (CNS) tumors," 2019 ASCO Annual Meeting I, ASCO Abstract 10009.
Roland et al., (2011). "Rab GTPase-Myo5B complexes control membrane recycling and epithelial polarization," PNAS, 108(7):2789-94.
Roongjang et al., (2007). "Inhibition of bcl-xLexpression by antisense oligonucleotides containing various bridged nucleic acids (BNAs)," Nucleic Acids Symp Ser, 51:113-114.
Rosok et al., (1996). "A combinatorial library strategy for the rapid humanization of anticarcinoma BR96 Fab," J. Biol. Chem., 271(37):22611-22618.
Ross et al., (2017). "ALK Fusions in a Wide Variety of Tumor Types Respond to Anti-ALK Targeted Therapy," Oncologist, 22(12):1444-1450.
Royle, (2011). "Mitotic moonlighting functions for membrane trafficking proteins," Traffic, 12:791-798.
Safran et al., (2008). "Lapatinib/gemcitabine and lapatinib/gemcitabine/oxaliplatin: a phase I study for advanced pancreaticobiliary cancer," Am J Clin Oncol, 31(2):140-4.
Sameer et al., (2010). "SMAD4—molecular gladiator of the TGF-beta signaling is trampled upon by mutational insufficiency in colorectal carcinoma of Kashmiri population: an analysis with relation to KRAS proto-oncogene," BMC cancer, 10:300, 11 pages.
Sanger et al., (1977). "DNA sequencing with chain-terminating inhibitors," Proc. Nat. Acad. Sci, 74(12):5463-5467.
Santra et al., (2003). "A sibset of multiple myeloma harboring the t(4;14)(p16;q32) translocation lacks FGFR3 expression but maintains an IGH/MMSET fusion transcript," Blood, 101(6):2374-2376.
Sartore-Bianchi et al., (2016). "Sensitivity to Entrectinib Associated With a Novel LMNA-NTRK1 Gene Fusion in Metastatic Colorectal Cancer," J Natl Cancer Inst, 108(1):djv306, 4 pages.
Sasaki et al., (2011). "A novel ALK secondary mutation and EGFR signaling cause resistance to ALK kinase inhibitors," Cancer Res, 71:6051-6060.
Scheble et al., (2010). "ERG rearrangement is specific to prostate cancer and does not occur in any of her common tumor," Mod Pathol, 23(8):1061-7.
Schneider et al., (2007). "The transforming acidic coiled coil 3 protein is essential for spindle-dependent chromosome alignment and mitotic survival," The Journal of Biological Chemistry, 282(40):29273-29283.

(56) References Cited

OTHER PUBLICATIONS

Schram et al., (2017). "Potential role of larotrectinib (LOXO-101), a selective pan-TRK inhibitor, in NTRK fusion-positive recurrent glioblastoma," AACR Annual Meeting 2017, AACR abstract LB-302, 1 page.

Scott et al., (1990). "Searching for peptide ligands with an epitope library," Science, 249(4967):386-390.

Shaw et al., (1988). "Mouse/human chimeric antibodies to a tumor-associated antigen: biologic activity of the four human IgG subclasses," J. Natl. Cancer Inst. 80(19):1553-1559.

Shaw et al., (2012). "LBA1_PR—Phase III Study of Crizotinib Versus Pemetrexed or Docetaxel Chemotherapy in Patients with Advanced Alk-Positive Non-Small Cell Lung Cancer (NSCLC) (Profile 1007)," Annals of Oncology, 23(9):ixe21, 1 page.

Shi et al., (2011). "Ubiquitin-specific cysteine protease 2a (USP2a) regulates the stability of Aurora-A," J Biol Chem, 286(45):38960-8.

Shields et al., (2001). "High resolution mapping of the binding site on human IgG1 for Fc gamma RI, Fc gamma RII, Fc gamma RIII, and FcRn and design of IgG1 variants with improved binding to the Fc gamma R," J. Biol. Chem., 9(2):6591-6604.

Shimomura et al., (2010). "MK-5108, a highly selective Aurora-A kinase inhibitor, shows antitumor activity alone and in combination with docetaxel," Mol Cancer Ther., 9(1):157-166.

Shu et al., (2020). "Identification of a Novel MPRIP-ROS1 Fusion and Clinical Efficacy of Crizotinib in an Advanced Lung Adenocarcinoma Patient: A Case Report," Onco Targets Ther., 13:10387-10391.

Si et al., (2012). "Prevalence of Braf V600E mutation in Chinese melanoma patients: large scale analysis of BRAF and NRAS mutations in a 432-case cohort," Eur J Cancer, 48(1):94-100. Abstract Only.

Sidhu et al., (2004). "Phage-displayed antibody libraries of synthetic heavy chain complementarity determining regions," J Mot Biol., 338(2):299-310.

Siena et al., (2019). "Efficacy of entrectinib in patients (pts) with solid tumors and central nervous system (CNS) metastases: Integrated analysis from three clinical trials," 2019 ASCO Annual Meeting I, ASCO Abstract 3017, 1 page.

Sims et al., (1993). "A humanized CD18 antibody can block function without cell destruction," J. Immunol., 151(4):2296-2308.

Singh et al., (2012). "Transforming Fusions of FGFR and TACC Genes in Human Glioblastoma," Science, 337(6099):1231-1235.

Siolas et al., (2005). "Synthetic shRNAs as potent RNAi triggers," Nat. Biotechnol., 23(2):227-231.

Sjolander et al., (1991). "Integrated fluid handling system for biomolecular interaction analysis," Anal. Chem., 63(20):2338-2345.

Smith et al., (1988). "Single-step purification of polypeptides expressed in *Escherichia coli* as fusions with glutathione S-transferase," Gene, 67(1):31-40.

Smith et al., (2018). "Antitumor Activity of Entrectinib, a Pan-TRK, ROS1, and ALK Inhibitor, in ETV6-NTRK3-Positive Acute Myeloid Leukemia," Mol Cancer Ther., 17(2):455-463.

Socinski, (2011). "Multitargeted receptor tyrosine kinase inhibition: an antiangiogenic strategy in non-small cell lung cancer," Cancer Treat Rev, 37(8):611-7. Abstract Only.

Soda et al., (2007). "Identification of the transforming EML4-ALK fusion gene in non-small-cell lung cancer," Nature, 448:561-566.

Specht et al., (2001). "Quantitative gene expression analysis in microdissected archival formalin-fixed and paraffin-embedded tumor tissue," Am J Pathol., 158(2):419-429.

Spigel et al., (2011). "Randomized, double-blind, placebo-controlled, phase II trial of sorafenib and erlotinib or erlotinib alone in previously treated advanced non-small-cell lung cancer," J Clin Oncol, 29(18):2582-9.

Stanton et al., (1989). "Definition of the human raf amino-30 terminal regulatory region by deletion mutagenesis," Molecular and cellular biology, 9(2):639-47.

Stephens et al., (1994). "Trk receptors use redundant signal transduction pathways involving SHC and PLC-gamma 1 to mediate NGF responses," Neuron, 12(3):691-705.

Stewart et al., (2004). "Correlation of TACC3, FGFR3, Mmset and p21 expression with the t(4;14) (p16.3;q32) in multiple myeloma," British Journal of Haematology, 126:72-76.

Sukov et al., (2007). "Utility of ALK-1 protein expression and ALK rearrangements in distinguishing inflammatory myofibroblastic tumor from malignant spindle cell lesions of the urinary bladder," Mod Pathol, 20(5):592-603.

Sukov et al., (2012). "ALK alterations in adult renal cell carcinoma: frequency, clinicopathologic features and outcome in a large series of consecutively treated patients," Mod Pathol, 25(11):1516-25.

Sun et al., (1987). "Chimeric antibody with human constant regions and mouse variable regions directed against carcinoma-associated antigen 17-1A," Proc. Natl. Acad. Sci. USA, 84(1):214-218.

Surks et al., (2003). "Myosin phosphatase-Rho interacting protein. A new member of the myosin phosphatase complex that directly binds RhoA," J Biol Chem, 278:51484-51493.

Szabo et al., (1995). "Surface plasmon resonance and its use in biomolecular interaction analysis (BIA)," Curr. Opin. Struct. Biol., 5(5):699-705.

Szperl et al., (2011). "Functional characterization of mutations in the myosin Vb gene associate d with microvillus inclusion disease," Journal of pediatric gastroenterology and nutrition, 52(3):307-13.

Tacconelli et al., (2004). "TrkA alternative splicing: a regulated tumor-promoting switch in human neuroblastoma," Cancer Cell, 6(4):347-60.

Takahashi et al., (1985). "Activation of a novel human transforming gene, ret, by DNA rearrangement," Cell, 42(2):581-8.

Takahashi et al., (1990). "Induction of CD8+ cytotoxic T cells by immunization with purified HIV-1 envelope protein in ISCOMs," Nature, 344:873-875.

Takeda et al., (2012). "Clinical outcome for EML4-ALK-positive patients 20 with advanced non-small-cell lung cancer treated with first-line platinum-based chemotherapy," Ann Oncol, 23(11):2931-6.

Takeuchi et al., (2008). "Multiplex reverse transcription-PCR screening for EML4-ALK fusion transcripts," Clin Cancer Res, 14(20):6618-6624.

Takeuchi et al., (2012). "RET, ROS1 and ALK fusions in lung cancer," Nat Med, 18:378-381.

Tam, (1988). "Synthetic peptide vaccine design: synthesis and properties of a high-density multiple antigenic peptide system," Proc. Natl Acad. Sci. U.S.A., 85:5409-5413.

Tam, (1996). "Recent advances in multiple antigen peptides," J. Immunol. Methods, 196:17-32.

Teixeira et al., (2006). "Recurrent Fusion Oncogenes in Carcinomas," Critical Reviews in Oncogenesis, 12(3-4):257-271.

Tewhey et al., (2009). "Microdroplet-based PCR enrichment for large-scale targeted sequencing," Nature Biotech., 27(11):1025-1031.

Thien et al., (1997). "EGF receptor binding and transformation by v-cbl is ablated by the introduction of a loss-of-function mutation from the Caenorhabditis elegans sli-1 gene," Oncogene, 14(18):2239-49.

Thien et al., (1997). "Tyrosine kinase activity of the EGF receptor is enhanced by the expression of oncogenic 70Z-Cbl," Oncogene, 15(24):2909-19.

Thress et al., (2009). "Identification and preclinical characterization of AZ-23, a novel, selective, and orally bioavailable inhibitor of the Trk kinase pathway," Mol Cancer Ther 8(7):1818-27.

Tomlins et al., (2005). "Recurrent fusion of TMPRSS2 and 15 ETS transcription factor genes in prostate cancer," Science, 310(5748):644-8.

Tomlins et al., (2008). "Role of the TMPRSS2-ERG gene fusion in prostate cancer," Neoplasia, 10(2):177-88.

Tomlinson et al., (2009). "Fibroblast growth factor receptor 1 promotes proliferation and survival via activation of the mitogen-activated protein kinase pathway in bladder cancer," Cancer Res, 69(11):4613-20.

(56) References Cited

OTHER PUBLICATIONS

Tomlinson et al., (2012). "FGFR1-induced epithelial to mesenchymal transition through MAPK/PLC/COX-2-mediated mechanisms," PLoS One, 7(6):e38972, 10 pages.
Toulme, (2001). "New candidates for true antisense," Nature Biotech., 19:17-18.
Toyokawa et al., (2009). "Co-expression of keratinocyte growth factor and K-sam is an independent prognostic factor in gastric carcinoma," Oncology Reports, 21:875-880.
Trapnell et al., (2009). "How to map billions of short reads onto genomes, " Nature Biotech., 27(5):455-457.
Traunecker et al., (1991). "Bispecific single chain molecules (Janusins) target cytotoxic lymphocytes on HIV infected cells," EMBO J., 10(12):3655-3659.
Turner et al., (2010). "Integrative molecular profiling of triple negative breast cancers identifies amplicon drivers and potential therapeutic targets," Oncogene, 8(29):2013-2023.
Turner et al., (2009). "Massively parallel exon capture and library-free resequencing across 16 genomes," Nature Methods, 6(5):315-316.
Tutt et al., (1991). "Trispecific F(ab')3 derivatives that use cooperative signaling via the TCR/CD3 complex and CD2 to activate and redirect resting cytotoxic T cells," J. Immunol., 147(1):60-69.
Tuysuz et al., (2008). "Novel NTRK1 mutations cause hereditary sensory and autonomic neuropathy type IV: demonstration of a founder mutation in the Turkish population," Neurogenetics, 9:119-125.
Undevia et al., (2004). "Phase I clinical trial of CEP-2563 dihydrochloride, a receptor tyrosine kinase inhibitor, in patients with refractory solid tumors," Invest New Drugs 22(4):449-58.
University of Colorado Denver; "NTRK1: A new oncogene and target in lung cancer". Press Release, Public release date: Jun. 3, 2013, 2 pages.
Vaishnavi et al., (2013). "Oncogenic and drug-sensitive NTRK1 rearrangements in lung cancer," Nature Medicine, 19(11):1469-1472.
Van der Krol et al., (1988). "Modulation of eukaryotic gene expression by complementary RNA or DNA sequences," Biotechniques, 6(10):958-976.
Van Dijk et al., (2001). "Human antibodies as next generation therapeutics," Curr. Opin. Pharmacol., 5(4):368-374.
Van Hattem et al., (2011). "Histologic variations in juvenile polyp phenotype correlate with genetic defect underlying juvenile polyposis," Am J Surg Path, 35(4):530-6, 16 pages.
Van Oers et al., (2009). "FGFR3 mutations indicate better survival in invasive upper urinary tract and bladder tumours," Eur Urol, 55(3):650-7.
Vendrell et al., (2017). "Detection of known and novel ALK fusion transcripts in lung cancer patients using next-generation sequencing approaches," Sci. Rep., 7(12510):1-11.
Verhoeyan et al., (1988). "Reshaping human antibodies: grafting an antilysozyme activity," Science, 239(4847):1534-1536.
Vitiello et al., (1995). "Development of a lipopeptide-based therapeutic vaccine to treat chronic HBV infection. I. Induction of a primary cytotoxic T lymphocyte response in humans," J. Clin. Invest., 95:341-9.
Vollmers et al., (2005). "Death by stress: natural IgM-induced apoptosis," Methods and Findings in Experimental and Clinical Pharmacology, 27(3):185-191.
Vollmers et al., (2005). "The 'early birds': natural IgM antibodies and immune surveillance," Histology and Histopathology, 20(3):927-937.
Wada et al., (1992). "Codon usage tabulated from the GenBank genetic sequence data," Nucleic Acids Res., 20:2111-2118.
Wan et al., (2004). "Mechanism of activation of the RAF-ERK signaling pathway by oncogenic mutations of B-RAF," Cell, 116(6):855-67.

Wang et al., (2013). "Mutations in Isocitrate Dehydrogenase 1 and 2 Occur Frequently in Intrahepatic Cholangiocarcinomas and Share Hypermethylation Targets with Glioblastomas," Oncogene, 23(25):1-22.
Wang et al., (2012). "Fusion of dynactin 1 to anaplastic lymphoma kinase in inflammatory myofibroblastic tumor," Hum Pathol, 43(11):2047-2052.
Wang et al., (2019). "Durable Clinical Response to Crizotinib in IRF2BP2-NTRK1 Non-small-cell Lung Cancer," Clin Lung Cancer, 20(3):e233-e237.
Wang et al., (2020). "Emerging Roles of ALK in Immunity and Insights for Immunotherapy," Cancers, 12(2):426, 5 pages.
Ware et al., (2010). "Rapidly Acquired Resistance to EGFR Tyrosine Kinase Inhibitors in NSCLC Cell Lines through De-Repression of FGFR2 and FGFR3 Expression," PLOS One, 5(11):e14117, 3 pages.
Warren et al., (2007). "Assembling millions of short DNA sequences using SSAKE," Bioinformatics, 23(4):500-501.
Wasag et al., (2011). "The kinase inhibitor TKI258 is active against the novel CUX1-FGFR1 fusion detected in a patient with T-lymphoblastic leukemia/lymphoma and t(7;8)(q22;p. 11)," Haematologica, 96(6):922-6.
Weiss et al., (2011). "Phase I study of the safety, tolerability and pharmacokinetics of PHA-848125AC, a dual tropomyosin receptor kinase A and cyclin-dependent kinase inhibitor, in patients with advanced solid malignancies", Invest New Drugs, 30(6):2334-2343.
Wells et al., (2010). "Abstract 5503: Vandetanib (VAN) in locally advanced or metastatic medullary thyroid cancer (Mtc): A randomized, double-blind phase III trial (ZETA)," J Clinical Oncology, 28(15 Suppl), 3 pages.
Werner et al., (2020). "Genomics based personalized oncology of cancer of unknown primary," Cancer Research, 80(16), 1 page.
Werynska et al., (2009). "Role of lymphangiogenesis in lung cancer," Folia Histochem Cytobiol, 47(3):333-42.
Wessley et al., (2001). "Gene Expression Pattern: Identification and expression of the mammalian homologue of Bicaudal-C," Mech. Dev. 101, 267-270.
Wheeless et al., (1994). "Bladder irrigation specimens assayed by fluorescence in situ hybridization to interphase nuclei," Cytometry, 17(4):319-326.
Wiesner et al., (2014). "Kinase fusions are frequent in Spitz tumours and spitzoid melanomas," Nature Communications, 5:3116, 9 pages.
Williams et al., (2013). "Oncogenic FGFR3 gene fusions in bladder cancer" Human Molecular Genetics, 22(4):795-803.
Winoto et al., (1989). "A novel, inducible and T cell-specific enhancer located at the 3' end of the T cell receptor alpha locus," EMBO J., 8(3):729-733.
Winter et al., (1994). "Making antibodies by phage display technology," Ann. Rev. Immunol., 12:433-455.
Woenckhaus et al., (2008). "Prognostic value of Fhit, CTNNB1, and MUC1 expression in non-small cell lung cancer," Human Pathology, 39:126-136.
Wong et al., (2016). "Evaluation of a Congenital Infantile Fibrosarcoma by Comprehensive Genomic Profiling Reveals an Lmna NTRK1 Gene Fusion Responsive to Crizotinib," J Natl Cancer Inst, 108(1):djv307, 3 pages.
Wood et al., (1985). "The synthesis and in vivo assembly of functional antibodies in yeast," Nature, 314(6010):446-449.
Woolf et al., (1995). "Towards the therapeutic editing of mutated RNA sequences," PNAS USA, 92:8298-8302.
Wooten et al., (2001). "The atypical protein kinase C-interacting protein p62 is a scaffold for NF-kappaB activation by nerve growth factor," J Biol Chem, 276(11):7709-12.
Wright et al., (1997). "Effect of glycosylation on antibody function: implications for genetic engineering," Trends Biotechnol., 15(1):26-32.
Wu et al., (2013). "Identification of Targetable FGFR Gene Fusions in Diverse Cancers," Cancer Discovery, pp. 636-647.
Wu et al., (1989). "The ligation amplification reaction (LAR)—amplification of specific DNA sequences using sequential rounds of template-dependent ligation," Genomics, 4(4):560-569.
Wu, (2005). "Urothelial tumorigenesis: a tale of divergent pathways," Nat Rev Cancer, 5(9):713-25.

(56) References Cited

OTHER PUBLICATIONS

Yamada et al., (2013). "Next-generation peptide vaccines for advanced cancer," Cancer Sci, 104:14-21.

Yamane-Ohnuki et al., (2004). "Establishment of FUT8 knockout Chinese hamster ovary cells: an ideal host cell line for producing completely defucosylated antibodies with enhanced antibody-dependent cellular cytotoxicity," Biotechnol Bioeng., 87(5):614-622.

Yamayoshi et al., (2004). "Expression of keratinocyte growth factor/ fibroblast growth factor-7 and its receptor in human lung cancer: correlation with tumour proliferative activity and patient prognosis," J Pathol, 204(1):110-8.

Yang et al., (2002). "Short RNA duplexes produced by hydrolysis with *Escherichia coli* RNase III mediate effective RNA interference in mammalian cells," Proc. Natl. Acad. Sci. USA, 99(15): 9942-9947.

Yankauckas et al., (1993). "Long-Term Anti-Nucleoprotein Cellular and Humoral Immunity Is Induced by Intramuscular Injection of Plasmid DNA Containing NP Gene," DNA Cell Biol., 12:771-776.

Yoon et al., (2004). "Enhanced epidermal growth factor receptor activation in human cholangiocarcinoma cells," Journal of Hepatology, pp. 808-814.

Yuan et al., (2008). "Yes-associated protein (YAP) functions as a tumor suppressor in breast," Cell death and differentiation, 15(11):1752-9.

Zerbino et al., (2008). "Velvet: algorithms for de novo short read assembly using de Bruijn graphs," Genome Res., 18(5):821-829.

Zhan et al., (2009). "Prognostic value of vascular endothelial growth factor expression in patients with lung cancer: a systematic review with meta-analysis," J Thorac Oncol., 4(9):1094-103.

Zhang et al., (2009). "Oncogenic Adenomatous polyposis coli mutants impair the mitotic checkpoint through direct interaction with Mad2," Molecular biology of the cell, 20(9):2381-8.

Zhang et al., (2010). "Fusion of EML4 and ALK is associated with development of lung adenocarcinomas lacking EGFR and KRAS mutations and is correlated with ALK expression," Mol Cancer, 9:188, 12 pages.

Zhao et al., (2011). "A novel, selective inhibitor of fibroblast growth factor receptors that shows a potent broad spectrum of antitumor activity in several tumor xenograft models," Mol Cancer Ther., 10(11):2200-10.

Zhong et al., (1999). "A RA-dependent, tumour-growth suppressive transcription complex is the target of the PML-RARalpha and T18 oncoproteins," Nat Genet, 23(3):287-95.

Zhou et al., (2009). "Novel mutant-selective EGFR kinase inhibitors against EGFR T790M," Nature, 462:1070-1074, 12 pages.

Zhou et al., (2018). "A primary undifferentiated pleomorphic sarcoma of the lumbosacral region harboring a LMNA-NTRK1 gene fusion with durable clinical response to crizotinib: a case report," BMC Cancer, 18(1):842.

Ziegler et al., (2018). "Brief Report: Potent clinical and radiological response to larotrectinib in TRK fusion-driven high-grade glioma," Br J Cancer, 119(6):693-696.

Zon (1988). "Oligonucleotide analogues as potential chemotherapeutic agents," Pharm. Res., 5(9):539-549.

Zuckermann et al., (1994). "Discovery of nanomolar ligands for 7-transmembrane G-protein-coupled receptors from a diverse N-(substituted)glycine peptoid library," J Med Chem., 37(17):2678-2685.

FIG. 1A

| Fusion | Disease | Breakpoint 1 | Breakpoint 2 | Rearrangement |
|---|---|---|---|---|
| FGFR2-TACC3 | Cholangiosarcoma | chr10:123,243,122; intron 16 | chr4:1,740,657; intron 10 | chr10:chr4 translocation |
| FGFR2-KIAA1598 | Cholangiosarcoma | chr10:123,239,241; intron 16 | chr10:118708643; intron 6 | chr10 deletion |
| BICC1-FGFR2 | Cholangiosarcoma | chr10:60,446,461; intron 2 | chr10:123,241,845; intron 16 | chr10 inversion |
| FGFR2-BICC1 | Cholangiosarcoma | chr10:123,241,713; intron 16 | chr10:60,567,607; intron 17 | chr10 inversion |
| PARK2-FGFR2 | Cholangiosarcoma | chr6:161,807,909-161,969,886; intron 9 | chr10:123,239,535-123,243,212; intron 17 | chr6:chr10 translocation |
| FGFR2-NOL4 | Cholangiosarcoma | chr10:123,239,535-123,243,212; intron 17 | chr18:31,538,203-31,599,282; intron 6 | chr10:chr18 translocation |
| ZDHHC6-FGFR2 | Cholangiosarcoma | chr10:114,198,147-114,200,292; intron 5 | chr10:123,239,535-123,243,212; intron 17 | |

FIG. 1B

| Fusion | 5' Transcript ID | Exon(s) of 5' transcript | 3' Transcript ID | Exon(s) of 3' transcript |
|---|---|---|---|---|
| FGFR2-TACC3 | NM_001144915 | exons 1-16 | NM_006342 | exons 11-16 |
| FGFR2-KIAA1598 | NM_001144915 | exons 1-16 | NM_001127211 | exons 7-17 |
| BICC1-FGFR2 | NM_001080512 | exons 1-2 | NM_001144915 | exon 17 |
| FGFR2-BICC1 | NM_001144915 | exons 1-16 | NM_001080512 | exons 18-21 |
| PARK2-FGFR2 | NM_004562 | exons 1-9 | NM_000141 | exon 18 |
| FGFR2-NOL4 | NM_000141 | exons 1-17 | NM_003787 | exons 7-11 |
| ZDHHC6-FGFR2 | NM_022494 | exons 1-5 | NM_000141 | exon 18 |

FIG. 1C

| FUSION/COMPONENT | Type of Sequence | SEQ ID NO | FIGURE |
|---|---|---|---|
| FGFR2-TACC3 | | | |
| 5' partner | Nt | 1 | 2A-2B |
| 5' partner | Aa | 2 | 3 |
| 3' partner | Nt | 3 | 4A-4B |
| 3' partner | Aa | 4 | 5 |
| FGFR2-KIAA1598 | | | |
| 5' partner | Nt | 1 | 2A-2B |
| 5' partner | Aa | 2 | 3 |
| 3' partner | Nt | 5 | 6A-6C |
| 3' partner | Aa | 6 | 7 |
| BICC1-FGFR2 | | | |
| 5' partner | Nt | 7 | 8 |
| 5' partner | Aa | 8 | 9 |
| 3' partner | Nt | 1 | 2A-2B |
| 3' partner | Aa | 2 | 3 |
| FGFR2-BICC1 | | | |
| 5' partner | Nt | 1 | 2A-2B |
| 5' partner | Aa | 2 | 3 |
| 3' partner | Nt | 7 | 8A-8B |
| 3' partner | Aa | 8 | 9 |
| PARK2-FGFR2 | | | |
| 5' partner | Nt | 9 | 10A-10B |
| 5' partner | Aa | 10 | 11 |
| 3' partner | Nt | 11 | 12A-12B |
| 3' partner | Aa | 12 | 13 |
| FGFR2-NOL4 | | | |
| 5' partner | Nt | 11 | 12A-12B |
| 5' partner | Aa | 12 | 13 |
| 3' partner | Nt | 13 | 14A-14B |
| 3' partner | Aa | 14 | 15 |
| ZDHHC6-FGFR2 | | | |
| 5' partner | Nt | 15 | 16 |
| 5' partner | Aa | 16 | 17 |
| 3' partner | Nt | 11 | 12A-12B |
| 3' partner | Aa | 12 | 13 |

FIG. 2A

```
AATTTGTTGA GGAATTTCCC CCTAGCCTTG ACCCCTTGAC AGCTCCCGCT   50
CCTACTCAGT GCTGGGGAGA AGTAGGGAGG CCTTAAGCGA AGAGATGGGT  100
CTGCACTTTG GAGGAGCCGG ACACTGTTGA CTTTCCTGAT GTGAAATCTA  150
CCCAGGAACA AAACACCAGT GACTGCAGCA GCAGCGGCAG CGCCTCGGTT  200
CCTGAGCCCA CCGCAGGCTG AAGGCATTGC GCGTAGTCCA TGCCCGTAGA  250
GGAAGTGTGC AGATGGGATT AACGTCCACA TGGAGATATG GAAGAGGACC  300
GGGGATTGGT ACCGTAACCA TGGTCAGCTG GGTCGTTTC ATCTGCCTGG   350
TCGTGGTCAC CATGGCAACC TTGTCCCTGG CCCGGCCCTC CTTCAGTTTA  400
GTTGAGGATA CCACATTAGA GCCAGAAGAT GCCATCTCAT CCGGAGATGA  450
TGAGGATGAC ACCGATGGTG CGGAAGATTT TGTCAGTGAG AACAGTAACA  500
ACAAGAGAGC ACCATACTGG ACCAACACAG AAAAGATGGA AAAGCGGCTC  550
CATGCTGTGC CTGCGGCCAA CACTGTCAAG TTTCGCTGCC CAGCCGGGGG  600
GAACCCAATG CCAACCATGC GGTGGCTGAA AAACGGGAAG GAGTTTAAGC  650
AGGAGCATCG CATTGGAGGC TACAAGGTAC GAAACCAGCA CTGGAGCCTC  700
ATTATGGAAA GTGTGGTCCC ATCTGACAAG GGAAATTATA CCTGTGTAGT  750
GGAGAATGAA TACGGGTCCA TCAATCACAC GTACCACCTG GATGTTGTGG  800
AGCGATCGCC TCACCGGCCC ATCCTCCAAG CCGGACTGCC GGCAAATGCC  850
TCCACAGTGG TCGGAGGAGA CGTAGAGTTT GTCTGCAAGG TTTACAGTGA  900
TGCCCAGCCC CACATCCAGT GGATCAAGCA CGTGGAAAAG AACGGCAGTA  950
AATACGGGCC CGACGGGCTG CCCTACCTCA AGGTTCTCAA GGCCGCCGGT 1000
GTTAACACCA CGGACAAAGA GATTGAGGTT CTCTATATTC GGAATGTAAC 1050
TTTTGAGGAC GCTGGGGAAT ATACGTGCTT GGCGGGTAAT TCTATTGGGA 1100
TATCCTTTCA CTCTGCATGG TTGACAGTTC TGCCAGCGCC TGGAAGAGAA 1150
AAGGAGATTA CAGCTTCCCC AGACTACCTG GAGATAGCCA TTTACTGCAT 1200
AGGGGTCTTC TTAATCGCCT GTATGGTGGT AACAGTCATC CTGTGCCGAA 1250
TGAAGAACAC GACCAAGAAG CCAGACTTCA GCAGCCAGCC GGCTGTGCAC 1300
AAGCTGACCA AACGTATCCC CCTGCGGAGA CAGGTAACAG TTTCGGCTGA 1350
GTCCAGCTCC TCCATGAACT CCAACACCCC GCTGGTGAGG ATAACAACAC 1400
GCCTCTCTTC AACGGCAGAC ACCCCCATGC TGGCAGGGGT CTCCGAGTAT 1450
GAACTTCCAG AGGACCCAAA ATGGGAGTTT CCAAGAGATA AGCTGACACT 1500
GGGCAAGCCC CTGGGAGAAG GTTGCTTTGG GCAAGTGGTC ATGGCGGAAG 1550
CAGTGGGAAT TGACAAAGAC AAGCCCAAGG AGGCGGTCAC CGTGGCCGTG 1600
AAGATGTTGA AAGATGATGC CACAGAGAAA GACCTTTCTG ATCTGGTGTC 1650
AGAGATGGAG ATGATGAAGA TGATTGGGAA ACACAAGAAT ATCATAAATC 1700
TTCTTGGAGC CTGCACACAG GATGGGCCTC TCTATGTCAT AGTTGAGTAT 1750
GCCTCTAAAG GCAACCTCCG AGAATACCTC CGAGCCCGGA GGCCACCCGG 1800
GATGGAGTAC TCCTATGACA TTAACCGTGT TCCTGAGGAG CAGATGACCT 1850
TCAAGGACTT GGTGTCATGC ACCTACCAGC TGGCCAGAGG CATGGAGTAC 1900
TTGGCTTCCC AAAAATGTAT TCATCGAGAT TTAGCAGCCA GAAATGTTTT 1950
GGTAACAGAA AACAATGTGA TGAAAATAGC AGACTTTGGA CTCGCCAGAG 2000
ATATCAACAA TATAGACTAT TACAAAAAGA CCACCAATGG GCGGCTTCCA 2050
GTCAAGTGGA TGGCTCCAGA AGCCCTGTTT GATAGAGTAT ACACTCATCA 2100
GAGTGATGTC TGGTCCTTCG GGGTGTTAAT GTGGGAGATC TTCACTTTAG 2150
GGGGCTCGCC CTACCCAGGG ATTCCCGTGG AGGAACTTTT TAAGCTGCTG 2200
AAGGAAGGAC ACAGAATGGA TAAGCCAGCC AACTGCACCA ACGAACTGTA 2250
CATGATGATG AGGGACTGTT GGCATGCAGT GCCCTCCCAG AGACCAACGT 2300
TCAAGCAGTT GGTAGAAGAC TTGGATCGAA TTCTCACTCT CACAACCAAT 2350
GAGGAGGAGA AGAAGGTTTC TGGAGCAGTG GACTGCCACA AGCCACCATG 2400
TAACCCCTCT CACCTGCCGT GCGTACTGGC TGTGGACCAG TAGGACTCAA 2450
GGTGGACGTG CGTTCTGCCT TCCTTGTTAA TTTTGTAATA ATTGGAGAAG 2500
ATTTATGTCA GCACACACTT ACAGAGCACA AATGCAGTAT ATAGGTGCTG 2550
GATGTATGTA AATATATTCA AATTATGTAT AAATATATAT TATATATTTA 2600
```

FIG. 2B

```
CAAGGAGTTA TTTTTTGTAT TGATTTTAAA TGGATGTCCC AATGCACCTA 2650
GAAAATTGGT CTCTCTTTTT TTAATAGCTA TTTGCTAAAT GCTGTTCTTA 2700
CACATAATTT CTTAATTTTC ACCGAGCAGA GGTGGAAAAA TACTTTTGCT 2750
TTCAGGGAAA ATGGTATAAC GTTAATTTAT TAATAAATTG GTAATATACA 2800
AAACAATTAA TCATTTATAG TTTTTTTTGT AATTTAAGTG GCATTTCTAT 2850
GCAGGCAGCA CAGCAGACTA GTTAATCTAT TGCTTGGACT TAACTAGTTA 2900
TCAGATCCTT TGAAAAGAGA ATATTTACAA TATATGACTA ATTTGGGGAA 2950
AATGAAGTTT TGATTTATTT GTGTTTAAAT GCTGCTGTCA GACGATTGTT 3000
CTTAGACCTC CTAAATGCCC CATATTAAAA GAACTCATTC ATAGGAAGGT 3050
GTTTCATTTT GGTGTGCAAC CCTGTCATTA CGTCAACGCA ACGTCTAACT 3100
GGACTTCCCA AGATAAATGG TACCAGCGTC CTCTTAAAAG ATGCCTTAAT 3150
CCATTCCTTG AGGACAGACC TTAGTTGAAA TGATAGCAGA ATGTGCTTCT 3200
CTCTGGCAGC TGGCCTTCTG CTTCTGAGTT GCACATTAAT CAGATTAGCC 3250
TGTATTCTCT TCAGTGAATT TTGATAATGG CTTCCAGACT CTTTGGCGTT 3300
GGAGACGCCT GTTAGGATCT TCAAGTCCCA TCATAGAAAA TTGAAACACA 3350
GAGTTGTTCT GCTGATAGTT TTGGGGATAC GTCCATCTTT TAAGGGATT 3400
GCTTTCATCT AATTCTGGCA GGACCTCACC AAAAGATCCA GCCTCATACC 3450
TACATCAGAC AAAATATCGC CGTTGTTCCT TCTGTACTAA AGTATTGTGT 3500
TTTGCTTTGG AAACACCCAC TCACTTTGCA ATAGCCGTGC AAGATGAATG 3550
CAGATTACAC TGATCTTATG TGTTACAAAA TTGGAGAAAG TATTTAATAA 3600
AACCTGTTAA TTTTTATACT GACAATAAAA ATGTTTCTAC AGATATTAAT 3650
GTTAACAAGA CAAATAAAT GTCACGCAAC TTATTTTTTT AATAaaaaaa 3700
aaaaaaaa (SEQ ID NO:1)
```

FIG. 3

```
MVSWGRFICLVVVTMATLSLARPSFSLVEDTTLEPEDAISSGDDEDDTDGAEDFVSENSN
NKRAPYWTNTEKMEKRLHAVPAANTVKFRCPAGGNPMPTMRWLKNGKEFKQEHRIGGYKV
RNQHWSLIMESVVPSDKGNYTCVVENEYGSINHTYHLDVVERSPHRPILQAGLPANASTV
VGGDVEFVCKVYSDAQPHIQWIKHVEKNGSKYGPDGLPYLKVLKAAGVNTTDKEIEVLYI
RNVTFEDAGEYTCLAGNSIGISFHSAWLTVLPAPGREKEITASPDYLEIAIYCIGVFLIA
CMVVTVILCRMKNTTKKPDFSSQPAVHKLTKRIPLRRQVTVSAESSSSMNSNTPLVRITT
RLSSTADTPMLAGVSEYELPEDPKWEFPRDKLTLGKPLGEGCFGQVVMAEAVGIDKDKPK
EAVTVAVKMLKDDATEKDLSDLVSEMEMMKMIGKHKNIINLLGACTQDGPLYVIVEYASK
GNLREYLRARRPPGMEYSYDINRVPEEQMTFKDLVSCTYQLARGMEYLASQKCIHRDLAA
RNVLVTENNVMKIADFGLARDINNIDYYKKTTNGRLPVKWMAPEALFDRVYTHQSDVWSF
GVLMWEIFTLGGSPYPGIPVEELFKLLKEGHRMDKPANCTNELYMMMRDCWHAVPSQRPT
FKQLVEDLDRILTLTTNEEEKKVSGAVDCHKPPCNPSHLPCVLAVDQ- (SEQ ID NO:2)
```

FIG. 4A

```
GCGTTTGAAA CTCCGGCGCG CCGGCGGCCA TCAAGGGCTA GAAGCGCGAC  50
GGCGGTAGCA GCTAGGCTTG GCCCCGGCG  TGGAGCAGAC GCGGACCCCT  100
CCTTCCTGGC GGCGGCGGCG CGGGCTCAGA GCCCGGCAAC GGGCGGGCGG  150
GCAGAATGAG TCTGCAGGTC TTAAACGACA AAAATGTCAG CAATGAAAAA  200
AATACAGAAA ATTGCGACTT CCTGTTTTCG CCACCAGAAG TTACCGGAAG  250
ATCGTCTGTT CTTCGTGTGT CACAGAAAGA AAATGTGCCA CCCAAGAACC  300
TGGCCAAAGC TATGAAGGTG ACTTTTCAGA CACCTCTGCG GGATCCACAG  350
ACGCACAGGA TTCTAAGTCC TAGCATGGCC AGCAAACTTG AGGCTCCTTT  400
CACTCAGGAT GACACCCTTG GACTGGAAAA CTCACACCCG GTCTGGACAC  450
AGAAAGAGAA CCAACAGCTC ATCAAGGAAG TGGATGCCAA AACTACTCAT  500
GGAATTCTAC AGAAACCAGT GGAGGCTGAC ACCGACCTCC TGGGGGATGC  550
AAGCCCAGCC TTTGGGAGTG GCAGCTCCAG CGAGTCTGGC CCAGGTGCCC  600
TGGCTGACCT GGACTGCTCA AGCTCTTCCC AGAGCCCAGG AAGTTCTGAG  650
AACCAAATGG TGTCTCCAGG AAAAGTGTCT GGCAGCCCTG AGCAAGCCGT  700
GGAGGAAAAC CTTAGTTCCT ATTCCTTAGA CAGAAGAGTG ACACCCGCCT  750
CTGAGACCCT AGAAGACCCT TGCAGGACAG AGTCCCAGCA CAAAGCGGAG  800
ACTCCGCACG GAGCCGAGGA AGAATGCAAA GCGGAGACTC CGCACGGAGC  850
CGAGGAGGAA TGCCGGCACG GTGGGGTCTG TGCTCCCGCA GCAGTGGCCA  900
CTTCGCCTCC TGGTGCAATC CCTAAGGAAG CCTGCGGAGG AGCACCCCTG  950
CAGGGTCTGC CTGGCGAAGC CCTGGGCTGC CCTGCGGGTG TGGGCACCCC 1000
CGTGCCAGCA GATGGCACTC AGACCCTTAC CTGTGCACAC ACCTCTGCTC 1050
CTGAGAGCAC AGCCCCAACC AACCACCTGG TGGCTGGCAG GGCCATGACC 1100
CTGAGTCCTC AGGAAGAAGT GGCTGCAGGC CAAATGGCCA GCTCCTCGAG 1150
GAGCGGACCT GTAAAACTAG AATTTGATGT ATCTGATGGC GCCACCAGCA 1200
AAAGGGCACC CCCACCAAGG AGACTGGGAG AGAGGTCCGG CCTCAAGCCT 1250
CCCTTGAGGA AAGCAGCAGT GAGGCAGCAA AAGGCCCCGC AGGAGGTGGA 1300
GGAGGACGAC GGTAGGAGCG GAGCAGGAGA GGACCCCCCC ATGCCAGCTT 1350
CTCGGGGCTC TTACCACCTC GACTGGGACA AAATGGATGA CCCAAACTTC 1400
ATCCGTTCG  GAGGTGACAC CAAGTCTGGT TGCAGTGAGG CCCAGCCCCC 1450
AGAAAGCCCT GAGACCAGGC TGGGCCAGCC AGCGGCTGAA CAGTTGCATG 1500
CTGGGCCTGC CACGGAGGAG CCAGGTCCCT GTCTGAGCCA GCAGCTGCAT 1550
TCAGCCTCAG CGGAGGACAC GCCTGTGGTG CAGTTGGCAG CCGAGACCCC 1600
AACAGCAGAG AGCAAGGAGA GAGCCTTGAA CTCTGCCAGC ACCTCGCTTC 1650
CCACAAGCTG TCCAGGCAGT GAGCCAGTGC CCACCCATCA GCAGGGGCAG 1700
CCTGCCTTGG AGCTGAAAGA GGAGAGCTTC AGAGACCCCG CTGAGGTTCT 1750
AGGCACGGGC GCGGAGGTGG ATTACCTGGA GCAGTTTGGA ACTTCCTCGT 1800
TTAAGGAGTC GGCCTTGAGG AAGCAGTCCT TATACCTCAA GTTCGACCCC 1850
CTCCTGAGGG ACAGTCCTGG TAGACCAGTG CCCGTGGCCA CCGAGACCAG 1900
CAGCATGCAC GGTGCAAATG AGACTCCCTC AGGACGTCCG CGGGAAGCCA 1950
AGCTTGTGGA GTTCGATTTC TTGGGAGCAC TGGACATTCC TGTGCCAGGC 2000
CCACCCCCAG GTGTTCCCGC GCCTGGGGGC CCACCCCTGT CCACCGGACC 2050
TATAGTGGAC CTGCTCCAGT ACAGCCAGAA GGACCTGGAT GCAGTGGTAA 2100
AGGCGACACA GGAGGAGAAC CGGGAGCTGA GGAGCAGGTG TGAGGAGCTC 2150
CACGGGAAGA ACCTGGAACT GGGAAGATC  ATGGACAGGT TCGAAGAGGT 2200
TGTGTACCAG GCCATGGAGG AAGTTCAGAA GCAGAAGGAA CTTTCCAAAG 2250
CTGAAATCCA GAAAGTTCTA AAGAAAAAG  ACCAACTTAC CACAGATCTG 2300
AACTCCATGG AGAAGTCCTT CTCCGACCTC TTCAAGCGTT TTGAGAAACA 2350
GAAAGAGGTG ATCGAGGGCT ACCGCAAGAA CGAAGAGTCA CTGAAGAAGT 2400
GCGTGGAGGA TTACCTGGCA AGGATCACCC AGGAGGGCCA GAGGTACCAA 2450
GCCCTGAAGG CCCACGCGGA GGAGAAGCTG CAGCTGGCAA ACGAGGAGAT 2500
CGCCCAGGTC CGGAGCAAGG CCCAGGCGGA AGCGTTGGCC CTCCAGGCCA 2550
GCCTGAGGAA GGAGCAGATG CGCATCCAGT CGCTGGAGAA GACAGTGGAG 2600
```

FIG. 4B

```
CAGAAGACTA AAGAGAACGA GGAGCTGACC AGGATCTGCG ACGACCTCAT    2650
CTCCAAGATG GAGAAGATCT GACCTCCACG GAGCCGCTGT CCCCGCCCCC    2700
CTGCTCCCGT CTGTCTGTCC TGTCTGATTC TCTTAGGTGT CATGTTCTTT    2750
TTTCTGTCTT GTCTTCAACT TTTTAAAAA  CTAGATTGCT TGAAAACAT     2800
GACTCAATAA AAGTTTCCTT TCAATTTAAA CACTGAAaaa aaaaaaa
(SEQ ID NO:3)
```

FIG. 5

```
MSLQVLNDKNVSNEKNTENCDFLFSPPEVTGRSSVLRVSQKENVPPKNLAKAMKVTFQTP
LRDPQTHRILSPSMASKLEAPFTQDDTLGLENSHPVWTQKENQQLIKEVDAKTTHGILQK
PVEADTDLLGDASPAFGSGSSSESGPGALADLDCSSSSQSPGSSENQMVSPGKVSGSPEQ
AVEENLSSYSLDRRVTPASETLEDPCRTESQHKAETPHGAEEECKAETPHGAEEECRHGG
VCAPAAVATSPPGAIPKEACGGAPLQGLPGEALGCPAGVGTPVPADGTQTLTCAHTSAPE
STAPTNHLVAGRAMTLSPQEEVAAGQMASSSRSGPVKLEFDVSDGATSKRAPPPRRLGER
SGLKPPLRKAAVRQQKAPQEVEEDDGRSGAGEDPPMPASRGSYHLDWDKMDDPNFIPFGG
DTKSGCSEAQPPESPETRLGQPAAEQLHAGPATEEPGPCLSQQLHSASAEDTPVVQLAAE
TPTAESKERALNSASTSLPTSCPGSEPVPTHQQGQPALELKEESFRDPAEVLGTGAEVDY
LEQFGTSSFKESALRKQSLYLKFDPLLRDSPGRPVPVATETSSMHGANETPSGRPREAKL
VEFDFLGALDIPVPGPPPGVPAPGGPPLSTGPIVDLLQYSQKDLDAVVKATQEENRELRS
RCEELHGKNLELGKIMDRFEEVVYQAMEEVQKQKELSKAEIQKVLKEKDQLTTDLNSMEK
SFSDLFKRFEKQKEVIEGYRKNEESLKKCVEDYLARITQEGQRYQALKAHAEEKLQLANE
EIAQVRSKAQAEALALQASLRKEQMRIQSLEKTVEQKTKENEELTRICDDLISKMEKI-
(SEQ ID NO:4)
```

FIG. 6A

```
ATTGCGTCCC GCTCTACCTC TGTGGTTCTT TGGGAGCGAC CCCCGGGAAG    50
CGTCCAAAGT GGAGTTCCCA CACACGCTGC GAACCCACAG CCGGTTTTCT   100
CTGAACTCGC GTCCCTGAGT CCGGGAGGTG GAGGCGGAGA AAAGGGTGCG   150
GAGCGACCCC ACGCAGGGCC GCCCCCCCTC CCACCAGCGC GTCCTGCCGC   200
GCCGGCAGCC ACAGGCTGGC ATAGCGGCTG CCGACCCGCC CTCGTTCCTC   250
CACCCCCTGA ACGGGACTGC TGGGCCCGCC CCGCCCCGCC TGCAGGTGAA   300
GCGGCCGCAG CCGCCGAGTA GGTGCGTGGG GATGATCTCA CTCGCGCGCT   350
CCGCGCCAGG AGGAGGAGGA GCGGGAGCGG ATCCAACTTC CGGGTAGTGG   400
AGCCGCAAGC CACCGGCATC TTGCTTTTTC TTCCCCCTCC TCCTGTGTGC   450
CCCGCGCCGC TCCCTCTTTC CCTTTTATTC CCGGCCCCAC CCGCCAAA*AT*   500
*G*AACAGCTCG ACGAAGAGA AGCAGCTGCA GCTCATTACC AGTCTGAAGG   550
AGCAAGCAAT AGGCGAATAT GAAGACCTTA GAGCAGAGAA CCAGAAAACA   600
AAGGAGAAGT GTGACAAAAT TAGGCAAGAA CGAGATGAAG CCGTTAAAAA   650
ACTGGAAGAA TTTCAGAAAA TTCTCACAT GGTCATAGAG GAAGTTAATT   700
TCATGCAGAA CCATCTTGAA ATAGAAGA CTTGTCGAGA AAGTGCTGAA   750
GCTTTGGCAA CAAAGCTAAA TAAAGAAAAT AAAACGTTGA AAAGAATCAG   800
CATGTTGTAC ATGGCCAAGC TGGGACCAGA TGTAATAACT GAAGAGATAA   850
ACATTGATGA TGAAGATTCG ACTACAGACA CAGACGGTGC CGCCGAGACT   900
TGTGTCTCAG TACAGTGTCA GAAGCAAATT AAAGAACTTC GAGATCAAAT   950
TGTATCTGTT CAGGAGGAAA AGAAGATTTT AGCCATTGAG CTGGAAAATC  1000
TCAAGAGCAA ACTCGTAGAA GTAATTGAAG AAGTAAATAA AGTTAAACAA  1050
GAAAAGACTG TTTTAAATTC AGAAGTTCTT GAACAGAGAA AAGTCTTAGA  1100
AAAATGCAAT AGAGTGTCCA TGTTAGCTGT AGAAGAGTAT GAGGAGATGC  1150
AAGTAAACCT GGAGCTGGAG AAGGACCTTC GAAAGAAAGC AGAGTCATTT  1200
GCACAAGAGA TGTTCATTGA GCAAAACAAG CTAAAGAGAC AAAGCCACCT  1250
TCTGCTGCAG AGCTCCATCC CTGATCAGCA GCTTTTGAAA GCTTTAGACG  1300
AAAATGCAAA ACTCACCCAG CAACTTGAAG AAGAGAGAAT TCAGCATCAA  1350
CAAAAGGTCA AAGAATTAGA AGAGCAACTA GAAAATGAAA CACTCCACAA  1400
AGAAATACAC AACCTCAAAC AGCAACTGGA GCTTCTAGAG GAAGATAAAA  1450
AGGAATTGGA ATTGAAATAT CAGAATTCTG AAGAGAAAGC CAGAAATTTA  1500
AAGCACTCTG TTGATGAACT CCAGAAACGA GTGAACCAGT CTGAGAATTC  1550
AGTACCTCCA CCACCTCCTC CTCCACCACC ACTTCCCCCT CCACCTCCCA  1600
ATCCTATCCG ATCCCTCATG TCCATGATCC GGAAACGATC CCACCCCAGT  1650
GGCAGTGGTG CTAAGAAAGA AAAGGCAACT CAACCAGAAA CAACTGAAGA  1700
AGTCACAGAT CTAAAGAGGC AAGCAGTTGA AGAGATGATG GATAGAATTA  1750
AAAAGGGAGT TCATCTTAGA CCCGTTAATC AGACAGCCAG ACCGAAGACA  1800
AAGCCAGAAT CTTCGAAAGG CTGCGAAAGT GCAGTGGATG AACTAAAAGG  1850
AATACTGGGG ACACTTAACA AATCCACTAG TTCAAGAAGC TTAAAATCCC  1900
TTGACCCTGA AAACAGTGAA ACTGAGTTAG AAAGGATTTT GCGTCGCAGA  1950
AAGGTGACAG CAGAAGCAGA TAGCAGTAGT CCAACTGGGA TATTAGCCAC  2000
CTCAGAGTCC AAATCCATGC CAGTGTTGGG TTCTGTATCC AGTGTAACAA  2050
AAACAGCCTT GAACAAGAAA ACTCTGGAGG CAGAATTCAA CAGCCCGTCC  2100
CCCCCAACAC CTGAGCCAGG TGAAGGGCCC CGTAAATTGG AAGGATGCAC  2150
AAGTTCCAAG GTTACGTTTC AGCCTCCCAG TAGCATTGGA TGCAGGAAAA  2200
AATACATTGA CGGTGAAAAA CAAGCCGAAC CAGTTGTAGT TTTAGATCCT  2250
GTTTCTACAC ATGAACCCCA AACCAAAGAC CAGGTTGCTG AAAAAGATCC  2300
AACTCAACAC AAGGAGGATG AAGGCGAAAT TCAACCAGAA AACAAAGAAG  2350
ACAGCATTGA AAACGTGAGA GAGACAGACA GCTCCAACTG C*TGA*TCCATA  2400
AACCAGAAGC CTGACATGTT TGGAAGTCCT TTTCAATAAG CACATGATTA  2450
GTGTTGTTAT ATTGGCAAGG GCTGTAGCA TTCTGCTCTG GTCACTGTAT  2500
TCAGAATACA GGTTCTTTTC TGGTGTCACT TTTGTAAGTA GCAACTATAA  2550
ACATAAGTAA GCTGTTTAGC AAAACACACA TTCCTAGTAG GTTTTGGTTT  2600
```

FIG. 6B

```
TTTGATCTTT ATAAAGATGA GGTTTTTTTC CTAGTTACTG TATTAAGTAT    2650
GACTTCTTTT AGAAGGTTAC AAAAAAATTC AGATGTTGAT ACCTTTTTAG    2700
GAAATGTGCA TACCACTCAT CAAATGGAAT GCTGAAAGTT TGAGGTGCTT    2750
GTATATAATC GGATAAACAA AACTGATCAA CCCAATGTGA TTTTAAAAGC    2800
CCCCAAAGAA GCTTCTGTTT TGGGTCTGAT CCTCTTGATG GAGAAACTGC    2850
AGCAGCATGG AAATTGTTGG GTACTGTGGC ATACAAGTTA TTTTCTACAG    2900
TAGACTGAGA TAAACTGAAA ACTCAGGAGC TGGCATCAAA CTCGTAGTCC    2950
CATAGTCAGT GTTAATTACA CACATTGTTA ACTATTGGAT GAAAAATACA    3000
TGCTATTGAT TGTGTCCAAA GCCTCCCGAG GACCTCCGTG GGGATGCTCT    3050
GGTAGCCTGA ATACAGAACT GAGGTGAAAG TCCAAACCTT GAATTTTACA    3100
GTAGTAAGTT GGTAAACCAT GTGCTCTGTG CTATGAGTTA ATTATGTTTT    3150
CCCAAATACT AATGTGGCAC AAGTACCATA TTTTATCAGA GTTCTTATGT    3200
ACAGTATGGT GAAGATAAGT GACAAGCACA CATTTTCTT GCTTCACTGC     3250
TGTTCTATAT TACACAGGTT TGTTGTTGTT TTTTTAAAA AAGAAATTAA     3300
GCAGTAGTTA GTCTCTAAAA ATACAATGTT TCAGGCTACC ACAGTGAATA    3350
AATAGAAATG TAATCAGGGA TTAAAAAAAA AACTTATGCA GCTTTTCAAA    3400
GTTGATTGTT TCAAAATTGG TGTTTATTTA AAATAAGTGG TAATGTACTT    3450
GAATGCACTT TTTATGACAA TGATTCAGTA ATGGTAATTT TACTATTAAA    3500
GAAAGTGAAA GGTTTAGTTT TGTTAGCATG GCTCAGCATG TAGCTGTCAG    3550
GTGTTTTTCA CCTAAGGGCA AAAGAAAATG ATAGTAATAA TTGCAGTAGT    3600
TGTATTGTAT TGTATTTTTG CACGTGTGGT AAGCATAGGC TTGAAGAGGT    3650
GGGTAGGCAG GTACATGTAC TTCCTAAATT TGGAGATAAT TATCTTTCTG    3700
TAAGTTCGTT ATGCTTGACT GTTCCATGT TCTCCCAATA ATGATTTAT      3750
AGTTACTTAT CACTTTACTC ATGGAGAATT AAAACGTAAT GTTTTTCAAC    3800
TGTATCTTTC TTTAACTGGA TAATACTGCT ATATGATATG CTTACTACAG    3850
ACTGCATTAA TTCACGAAAC GAATTCTGTT ATGCTGTAAT TTGAACTCTC    3900
CTCACCACAA CTTATTAAAA AGGCACCAAT AGTTTCCCAT TAAGGGTCAG    3950
TTGTGGTTAT TATTAACGTT TCTGGTTTAG TTCCCCAAGC TTGACATTCT    4000
TTAATAGAAA ATTGTATATG ATTTGACAAC TTTAGTAATT TTTAATAGTC    4050
CCTAAGATGG TTTATTGAGT TTTCTTTCAT GTTTCTTTGT GCTGTCTTCC    4100
TTCTTGCATC TGTGATCTGT CTGCCAGCAT GCAACTCACA CACATTTAGG    4150
AATATAAAAA TATGTACACT GTCTTTCCAT ATTTCATCAC ACCATCACAG    4200
AATAATATGG TTATCAAAAT ACCCTCCTTT CTAGAGTAAG AAGTTGCCCT    4250
TTGGGTGAAA TGTGTTAGCT GGACTAGGGA ACAATTAGTA ACAGGTATTT    4300
TGAAAGTATT CCTGCCTTTT TTAAGCTGCT TACTTTCTCT CACTGTGATT    4350
ACAAAGCATT TTAAATTAAT TTGACATGAA GGTATTTGAT GGAAGATATT    4400
CACTCACCTT TTTCTGCCTA CAGTTTTTCC CTTTTCACTT TGGTTTTGAG    4450
GGGGTTTTGC CCCTGGCTGG GGTGACACTG TCAACCAAAG CAAGGGATCC    4500
CAAATAGGAA GACATAGGAG AACCGTGCTT ATATCTGCAA GGTATGTTCA    4550
TAGCTATTGC ACACACAAAA CTTACATACG TCCTGCTTAC ACAATTTTAA    4600
GTTGGAAAAG ACTGCATCTT TATGTTTTTG ATTTCTCTAA AAGGTTATTT    4650
ATGCTTCCTT CTGTTTGGGA AAGATAAATT AAGTCTTGTG CGCTATAGAG    4700
GATTTTTTT CTTTAAGAAA AACGAATGTT GATGCATTTT ATAGCCCGAG     4750
TGAGGAACAG AGATAGAGGT ACTTTGTGCC ATTGCTATTA AAGAAAAAGA    4800
AAATGTCTCT TTTTTTTCT GGAAGAATAA GATTTTAATT AAAGCACTTG     4850
CACCCTTTTG TATGTGAGCT GGTCTCAAAC AAAGTCCTCA CCCACAGCAG    4900
TTTCAGCAGC TGAACAGTCC CATGGAAGTT CTGACTGGCA GGCATCAACA    4950
GGGCTATTAG CACCCAGCAT AGTTTGCCCT GAGTACGGAG GATGGATGCT    5000
TTGGCTCTAA CTACTCACCA ATAATTGCTC CTTCCTTACC TTCTTTGTTA    5050
ATGGTAAACT GCTGGAAATG GAGTAGTACA GGTAACAATT ATTTTTAATT    5100
GTCTTTCCAG ACCAGTTTTT GGTTGTGTGT TCAGTAAATG ATAGTCTGTA    5150
TCACAGCCTT CAAGTCTGGA TTATTTTTCT AAATGCATAC TCTACCTGTT    5200
```

FIG. 6C

```
CAGTTACACT CGTTGTGGAA CAACATTAGC TTATATACCA GTAAGTTGTC  5250
GAGAATGGAT AACCATCTGT CATTATCACT GACCTTCAAA GACTCATCAA  5300
GCAGTCCCTG CATAAGGATT GGAGTGGTTT GAAGTTTCTC TTCCAAGCAC  5350
TAACATGTCC C (SEQ ID NO:5)
```

FIG. 7

```
MNSSDEEKQLQLITSLKEQAIGEYEDLRAENQKTKEKCDKIRQERDEAVKKLEEFQKISH
MVIEEVNFMQNHLEIEKTCRESAEALATKLNKENKTLKRISMLYMAKLGPDVITEEINID
DEDSTTDTDGAAETCVSVQCQKQIKELRDQIVSVQEEKKILAIELENLKSKLVEVIEEVN
KVKQEKTVLNSEVLEQRKVLEKCNRVSMLAVEEYEEMQVNLELEKDLRKKAESFAQEMFI
EQNKLKRQSHLLLQSSIPDQQLLKALDENAKLTQQLEEERIQHQQKVKELEEQLENETLH
KEIHNLKQQLELLEEDKKELELKYQNSEEKARNLKHSVDELQKRVNQSENSVPPPPPPPP
PLPPPPPNPIRSLMSMIRKRSHPSGSGAKKEKATQPETTEEVTDLKRQAVEEMMDRIKKG
VHLRPVNQTARPKTKPESSKGCESAVDELKGILGTLNKSTSSRSLKSLDPENSETELERI
LRRRKVTAEADSSSPTGILATSESKSMPVLGSVSSVTKTALNKKTLEAEFNSPSPPTPEP
GEGPRKLEGCTSSKVTFQPPSSIGCRKKYIDGEKQAEPVVVLDPVSTHEPQTKDQVAEKD
PTQHKEDEGEIQPENKEDSIENVRETDSSNC- (SEQ ID NO:6)
```

FIG. 8A

```
ATGGCCGCCC AGGGAGAGCC CGGCTACCTG GCGGCGCAGT CGGACCCCGG   50
CTCCAACAGC GAGCGCAGCA CCGACTCCCC AGTGCCCGGC TCCGAGGACG  100
ACTTGGTCGC CGGGGCGACC CTGCACAGCC GGAGTGGAG CGAGGAGCGC  150
TTCCGCGTGG ACAGGAAGAA ACTTGAGGCC ATGTTACAAG CTGCTGCTGA  200
AGGGAAAGGC AGAAGTGGGG AAGACTTTTT TCAAAAGATC ATGGAGGAAA  250
CAAATACGCA GATTGCTTGG CCATCAAAAC TGAAGATCGG AGCCAAATCC  300
AAGAAAGATC CCCATATTAA GGTTTCTGGA AGAAAGAAG ATGTTAAAGA  350
AGCCAAGGAA ATGATCATGT CTGTCTTAGA CACAAAAAGC AATCGAGTCA  400
CACTGAAGAT GGATGTTTCA CATACAGAAC ATTCACATGT AATCGGCAAA  450
GGTGGCAACA ATATTAAAAA AGTGATGGAA GAAACCGGAT GCCATATCCA  500
CTTTCCAGAT TCCAACAGGA ATAACCAAGC AGAAAAAGC AACCAGGTAT  550
CTATAGCGGG ACAACCAGCA GGAGTAGAAT CTGCCCGAGT TAGAATTCGG  600
GAGCTGCTTC CTTTGGTGCT GATGTTTGAG CTACCAATTG CTGGAATTCT  650
TCAACCGGTT CCTGATCCTA ATTCCCCTC TATTCAGCAT ATATCACAAA  700
CGTACAATAT TTCAGTATCA TTTAAACAGC GTTCCCGAAT GTATGGTGCT  750
ACTGTCATAG TACGAGGGTC TCAGAATAAC ACTAGTGCTG TGAAGGAAGG  800
AACTGCCATG CTGTTAGAAC ATCTTGCTGG GAGCTTAGCA TCAGCTATTC  850
CTGTGAGCAC ACAACTAGAT ATTGCAGCTC AACATCATCT CTTTATGATG  900
GGTCGAAATG GGAGCAACAT CAAACATATC ATGCAGAGAA CAGGTGCTCA  950
GATCCACTTT CCTGATCCCA GTAATCCACA AAAGAAATCT ACCGTCTACC 1000
TCCAGGGCAC CATTGAGTCT GTCTGTCTTG CAAGGCAATA TCTCATGGGT 1050
TGTCTTCCTC TTGTGTTGAT GTTGATATG AAGGAAGAAA TTGAAGTAGA 1100
TCCACAATTC ATTGCGCAGT TGATGGAACA GCTTGATGTC TTCATCAGTA 1150
TTAAACCAAA GCCCAAACAG CCAAGCAAGT CTGTGATTGT GAAAAGTGTT 1200
GAGCGAAATG CCTTAAATAT GTATGAAGCA AGGAAATGTC TCCTCGGACT 1250
TGAAAGCAGT GGGGTTACCA TAGCAACCAG TCCATCCCA GCATCCTGCC 1300
CTGCCGGCCT GGCATGTCCC AGCCTGGATA TCTTAGCTTC AGCAGGCCTT 1350
GGACTCACTG GACTAGGTCT TTTGGGACCC ACCACCTTAT CTCTGAACAC 1400
TTCAACAACC CCAAACTCAC TCTTGAATGC TCTTAATAGC TCAGTCAGTC 1450
CTTTGCAAAG TCCAAGTTCT GGTACACCCA GCCCACATT ATGGGCACCC 1500
CCACTTGCTA ATACTTCAAG TGCCACAGGT TTTTCTGCTA TACCACACCT 1550
TATGATTCCA TCTACTGCCC AAGCCACATT AACTAATATT TTGTTGTCTG 1600
GAGTGCCCAC CTATGGGCAC ACAGCTCCAT CTCCCCCTCC TGGCTTGACT 1650
CCTGTTGATG TCCATATCAA CAGTATGCAG ACCGAAGGCA AAAAAATCTC 1700
TGCTGCTTTA AATGGACATG CACAGTCTCC AGATATAAAA TATGGTGCAA 1750
TATCCACTTC ATCACTTGGA GAAAAGTGC TGAGTGCAAA TCACGGGGAT 1800
CCGTCCATCC AGACAAGTGG GTCTGAGCAG ACATCTCCCA AATCAAGCCC 1850
CACTGAAGGT TGTAATGATG CTTTTGTTGA AGTAGGCATG CCTCGAAGTC 1900
CTTCCCATTC TGGGAATGCT GGTGACTTGA ACAGATGAT GTGTCCCTCC 1950
AAGGTTTCCT GTGCCAAAAG GCAGACAGTG GAACTATTGC AAGGCACGAA 2000
AAACTCACAC TTACACAGCA CTGACAGGTT GCTCTCAGAC CCTGAACTGA 2050
GTGCTACCGA AAGCCCTTTG GCTGACAAGA AGGCTCCAGG GAGTGAGCGC 2100
GCTGCAGAGA GGGCAGCAGC TGCCCAGCAA ACTCCGAAA GGGCCCACCT 2150
TGCTCCACGG TCATCATATG TCAACATGCA GGCATTTGAC TATGAACAGA 2200
AGAAGCTATT AGCCACCAAA GCTATGTTAA AGAAACCAGT GGTGACGGAG 2250
GTCAGAACGC CCACAAATAC CTGGAGTGGC CTGGGTTTTT CTAAATCCAT 2300
GCCAGCTGAA ACTATCAAGG AGTTGAGAAG GCCAATCAT GTGTCCTATA 2350
AGCCCACAAT GACAACCACT TATGAGGGCT CATCCATGTC CCTTTCACGG 2400
TCCAACAGTC GTGAGCACTT GGGAGGTGGA AGCGAATCTG ATAACTGGAG 2450
AGACCGAAAT GGAATTGGAC CTGGAAGTCA TAGTGAATTT GCAGCTTCTA 2500
TTGGCAGCCC TAAGCGTAAA CAAAACAAAT CAACGGAACA CTATCTCAGC 2550
AGTAGCAATT ACATGGACTG CATTTCCTCG CTGACAGGAA GCAATGGCTG 2600
```

FIG. 8B

```
TAACTTAAAT AGCTCTTTCA AAGGTTCTGA CCTCCCTGAG CTCTTCAGCA  2650
AACTGGGCCT GGGCAAATAC ACAGATGTTT TCCAGCAACA AGAGATCGAT  2700
CTTCAGACAT TCCTCACTCT CACAGATCAG GATCTGAAGG AGCTGGGAAT  2750
AACTACTTTT GGTGCCAGGA GGAAAATGCT GCTTGCAATT TCAGAACTAA  2800
ATAAAAACCG AAGAAAGCTT TTTGAATCGC CAAATGCACG CACCTCTTTC  2850
CTGGAAGGTG GAGCGAGTGG AAGGCTACCC CGTCAGTATC ACTCAGACAT  2900
TGCTAGTGTC AGTGGCCGCT GGTAGCAGCA CCCTCTTGGC ACATGCCCGC  2950
TGACTAACTG TAAAGTGGAC ACAGGAGATG TATGAACAGC CTTCACAGCA  3000
CACCATCCTT AGCACTCTGG GTGTCTGGTA TCAGGACCAA AGCATTTTAT  3050
TCGCACCTGT ACTTTATGGC AAAAAGGAAG AAGAGAGAGA AGATGTTCTT  3100
ATGATGTCAT ACAGAACAC (SEQ ID NO:7)
```

FIG. 9

```
MAAQGEPGYLAAQSDPGSNSERSTDSPVPGSEDDLVAGATLHSPEWSEERFRVDRKKLEA
MLQAAAEGKGRSGEDFFQKIMEETNTQIAWPSKLKIGAKSKKDPHIKVSGKKEDVKEAKE
MIMSVLDTKSNRVTLKMDVSHTEHSHVIGKGGNNIKKVMEETGCHIHFPDSNRNNQAEKS
NQVSIAGQPAGVESARVRIRELLPLVLMFELPIAGILQPVPDPNSPSIQHISQTYNISVS
FKQRSRMYGATVIVRGSQNNTSAVKEGTAMLLEHLAGSLASAIPVSTQLDIAAQHHLFMM
GRNGSNIKHIMQRTGAQIHFPDPSNPQKKSTVYLQGTIESVCLARQYLMGCLPLVLMFDM
KEEIEVDPQFIAQLMEQLDVFISIKPKPKQPSKSVIVKSVERNALNMYEARKCLLGLESS
GVTIATSPSPASCPAGLACPSLDILASAGLGLTGLGLLGPTTLSLNTSTTPNSLLNALNS
SVSPLQSPSSGTPSPTLWAPPLANTSSATGFSAIPHLMIPSTAQATLTNILLSGVPTYGH
TAPSPPPGLTPVDVHINSMQTEGKKISAALNGHAQSPDIKYGAISTSSLGEKVLSANHGD
PSIQTSGSEQTSPKSSPTEGCNDAFVEVGMPRSPSHSGNAGDLKQMMCPSKVSCAKRQTV
ELLQGTKNSHLHSTDRLLSDPELSATESPLADKKAPGSERAAERAAAAQQNSERAHLAPR
SSYVNMQAFDYEQKKLLATKAMLKKPVVTEVRTPTNTWSGLGFSKSMPAETIKELRRANH
VSYKPTMTTTYEGSSMSLSRSNSREHLGGGSESDNWRDRNGIGPGSHSEFAASIGSPKRK
QNKSTEHYLSSSNYMDCISSLTGSNGCNLNSSFKGSDLPELFSKLGLGKYTDVFQQQEID
LQTFLTLTDQDLKELGITTFGARRKMLLAISELNKNRRKLFESPNARTSFLEGGASGRLP
RQYHSDIASVSGRW- (SEQ ID NO:8)
```

FIG. 10A

```
ATTCCTAGGG CCGGGCGCGG GGGCGGGGAG GCCTGGAGGA TTTAACCCAG   50
GAGAGCCGCT GGTGGGAGGC GCGGCTGGCG CCGCTGCGCG CATGGGCCTG  100
TTCCTGGCCC GCAGCCGCCA CCTACCCAGT GACCATGATA GTGTTTGTCA  150
GGTTCAACTC CAGCCATGGT TTCCCAGTGG AGGTCGATTC TGACACCAGC  200
ATCTTCCAGC TCAAGGAGGT GGTTGCTAAG CGACAGGGGG TTCCGGCTGA  250
CCAGTTGCGT GTGATTTCG CAGGGAAGGA GCTGAGGAAT GACTGGACTG  300
TGCAGAATTG TGACCTGGAT CAGCAGAGCA TTGTTCACAT TGTGCAGAGA  350
CCGTGGAGAA AAGGTCAAGA AATGAATGCA ACTGGAGGCG ACGACCCCAG  400
AAACGCGGCG GGAGGCTGTG AGCGGGAGCC CCAGAGCTTG ACTCGGGTGG  450
ACCTCAGCAG CTCAGTCCTC CCAGGAGACT CTGTGGGGCT GGCTGTCATT  500
CTGCACACTG ACAGCAGGAA GGACTCACCA CCAGCTGGAA GTCCAGCAGG  550
TAGATCAATC TACAACAGCT TTATGTGTA TTGCAAAGGC CCCTGTCAAA  600
GAGTGCAGCC GGGAAAACTC AGGGTACAGT GCAGCACCTG CAGGCAGGCA  650
ACGCTCACCT TGACCCAGGG TCCATCTTGC TGGGATGATG TTTTAATTCC  700
AAACCGGATG AGTGGTGAAT GCCAATCCCC ACACTGCCCT GGGACTAGTG  750
CAGAATTTTT CTTTAAATGT GGAGCACACC CCACCTCTGA CAAGGAAACA  800
TCAGTAGCTT TGCACCTGAT CGCAACAAAT AGTCGGAACA TCACTTGCAT  850
TACGTGCACA GACGTCAGGA GCCCCGTCCT GGTTTTCCAG TGCAACTCCC  900
GCCACGTGAT TGCTTAGAC TGTTTCCACT TATACTGTGT GACAAGACTC  950
AATGATCGGC AGTTTGTTCA CGACCCTCAA CTTGGCTACT CCCTGCCTTG 1000
TGTGGCTGGC TGTCCCAACT CCTTGATTAA AGAGCTCCAT CACTTCAGGA 1050
TTCTGGGAGA AGAGCAGTAC AACCGGTACC AGCAGTATGG TGCAGAGGAG 1100
TGTGTCCTGC AGATGGGGGG CGTGTTATGC CCCCGCCCTG GCTGTGGAGC 1150
GGGGCTGCTG CCGGAGCCTG ACCAGAGGAA AGTCACCTGC GAAGGGGCA 1200
ATGGCCTGGG CTGTGGGTTT GCCTTCTGCC GGGAATGTAA AGAAGCGTAC 1250
CATGAAGGGG AGTGCAGTGC CGTATTTGAA GCCTCAGGAA CAACTACTCA 1300
GGCCTACAGA GTCGATGAAA GAGCCGCCGA GCAGGCTCGT TGGGAAGCAG 1350
CCTCCAAAGA AACCATCAAG AAAACCACCA AGCCCTGTCC CCGCTGCCAT 1400
GTACCAGTGG AAAAAAATGG AGGCTGCATG CACATGAAGT GTCCGCAGCC 1450
CCAGTGCAGG CTCGAGTGGT GCTGGAACTG TGGCTGCGAG TGGAACCGCG 1500
TCTGCATGGG GGACCACTGG TTCGACGTGT AGCCAGGGCG GCCGGGCGCC 1550
CCATCGCCAC ATCCTGGGGG AGCATACCCA GTGTCTACCT TCATTTTCTA 1600
ATTCTCTTTT CAAACACACA CACACACGCG CGCGCGCGCA CACACACTCT 1650
TCAAGTTTTT TTCAAAGTCC AACTACAGCC AAATTGCAGA AGAAACTCCT 1700
GGATCCCTTT CACTATGTCC ATGAAAAACA GCAGAGTAAA ATTACAGAAG 1750
AAGCTCCTGA ATCCCTTTCA GTTGTCCAC ACAAGACAGC AGAGCCATCT 1800
GCGACACCAC CAACAGGCGT TCTCAGCCTC CGGATGACAC AAATACCAGA 1850
GCACAGATTC AAGTGCAATC CATGTATCTG TATGGGTCAT TCTCACCTGA 1900
ATTCGAGACA GGCAGAATCA GTAGCTGGAG AGAGAGTTCT CACATTTAAT 1950
ATCCTGCCTT TTACCTTCAG TAAACACCAT GAAGATGCCA TTGACAAGGT 2000
GTTTCTCTGT AAAATGAACT GCAGTGGGTT CTCCAAACTA GATTCATGGC 2050
TTTAACAGTA ATGTTCTTAT TTAAATTTTC AGAAAGCATC TATTCCCAAA 2100
GAACCCCAGG CAATAGTCAA AAACATTTGT TTATCCTTAA GAATTCCATC 2150
TATATAAATC GCATTAATGA ATACCAACT ATGCGTAAAT CAACTTGTCA 2200
CAAAGTGAGA AATTATGAAA GTTAATTTGA ATGTTGAATG TTTGAATTAC 2250
AGGGAAGAAA TCAAGTTAAT GTACTTTCAT TCCCTTTCAT GATTTGCAAC 2300
TTTAGAAAGA AATTGTTTTT CTGAAAGTAT CACCAAAAAA TCTATAGTTT 2350
GATTCTGAGT ATTCATTTTG CAACTTGGAG ATTTTGCTAA TACATTTGGC 2400
TCCACTGTAA ATTTAATAGA TAAAGTGCCT ATAAAGGAAA CACGTTTAGA 2450
AATGATTTCA AAATGATATT CAATCTTAAC AAAAGTGAAC ATTATTAAAT 2500
CAGAATCTTT AAAGAGGAGC CTTTCAGAA CTACCAAAAT GAAGACACGC 2550
CCGACTCTCT CCATCAGAAG GGTTTATACC CCTTTGGCAC ACCCTCTCTG 2600
```

FIG. 10B

```
TCCAATCTGC AAGTCCCAGG GAGCTCTGCA TACCAGGGGT TCCCCAGGAG 2650
AGACCTTCTC TTAGGACAGT AAACTCACTA GAATATTCCT TATGTTGACA 2700
TGGATTGGAT TTCAGTTCAA TCAAACTTTC AGCTTTTTTT TCAGCCATTC 2750
ACAACACAAT CAAAAGATTA ACAACACTGC ATGCGGCAAA CCGCATGCTC 2800
TTACCCACAC TACGCAGAAG AGAAAGTACA ACCACTATCT TTTGTTCTAC 2850
CTGTATTGTC TGACTTCTCA GGAAGATCGT GAACATAACT GAGGGCATGA 2900
GTCTCACTAG CACATGGAGG CCCTTTTGGA TTTAGAGACT GTAAATTATT 2950
AAATCGGCAA CAGGGCTTCT CTTTTTAGAT GTAGCACTGA AATCCTTGCT 3000
GGAGGGAAGA GAGGGGATGA ACTCAAGTTT TCCACATCCT GGGACACCTG 3050
TCCCTCTTTT CCTAACTGCC TAAGATAACC CATTTCTTCC AACCATCTGA 3100
GGACAGTCCC GTCGTCTCAG AGGCCCTGCA CCGGGGAGAG ACTGGGCTCT 3150
GCAGCAGCCA CATCAGCATT CACAGCTTCA TGTGGCTTCA CTGTCTGAAA 3200
ATCTACCGAC TCCAACATGG CCCCACGGTG ACAACAGACC TGTGACAGGA 3250
AGCCCAAAGC TCACATAGAA ATGGTGGACA GATCAAAGTC TCTATAGTAA 3300
GGGAAAAAAA GAGAGGTGGC AGGCATGAGC CCCCTGCACC CAGTGGCTCG 3350
TGTCCATACT GAGTCCAGAC CCTGATCAAG GCCTGACTTA GTGTCACTGG 3400
CAGTCCCACT AAATTACACT TCCTTACACT GGCCCGATGC GACAAATCAG 3450
GTGGCTCCCT TCTGTCACGT GGAGCACACA GTGTTTTCCA TCATCCATAG 3500
CTTTCTTCCT GATGGTGTTT GCATTATTGC GCCTTCCCAA TCTGCATGCT 3550
GCGTTGGGCT TGCGGTGCCT GAACAAGGTT TGCTCCCATG AGCTCAGGCA 3600
CCCTAGGATC CCCTGTTAGA CTATTAGGCT GTCCAGCATG GTCTCCTTTC 3650
CCTTCTTGGT GGTGGTCTTT TCCCTTTCCA GAATAGAACA GTGATTCTTA 3700
AAATAAGTTA GAGCAGGCCG GGCGCGGTGG CTCATGCCTG TAATCCCAGC 3750
ACTTTGGGAG GCCGAGGTGG GTGGATCACG AGGTCAGGAG TTCAAGACCA 3800
GCCTGGCCAA GATGATGAAA CCCCGTCTCT ATTAAAAATA CAAAAATTAG 3850
CTGGGCGTGG TGGCAGGCAC CTGTAATCCC AGCTTCCTGG GAGGCTGAGG 3900
CAGGAGAATC ACTTGAACCC GGGGGGCAGA GGTTGCAGTG AGCCGAGATC 3950
ACGCCACTGA ACTCCAGCCT GGGCAACAGA GTGAGACTCT GTCTCAAAAA 4000
AAAAAAAAAA ACAAAAACAA AAAGCAAGA TCATCCACTA CACATGAACA 4050
TGAATCACAG TATTATTTGC ACA (SEQ ID NO:9)
```

FIG. 11

```
MIVFVRFNSSHGFPVEVDSDTSIFQLKEVVAKRQGVPADQLRVIFAGKELRNDWTVQNCD
LDQQSIVHIVQRPWRKGQEMNATGGDDPRNAAGGCEREPQSLTRVDLSSSVLPGDSVGLA
VILHTDSRKDSPPAGSPAGRSIYNSFYVYCKGPCQRVQPGKLRVQCSTCRQATLTLTQGP
SCWDDVLIPNRMSGECQSPHCPGTSAEFFFKCGAHPTSDKETSVALHLIATNSRNITCIT
CTDVRSPVLVFQCNSRHVICLDCFHLYCVTRLNDRQFVHDPQLGYSLPCVAGCPNSLIKE
LHHFRILGEEQYNRYQQYGAEECVLQMGGVLCPRPGCGAGLLPEPDQRKVTCEGGNLGC
GFAFCRECKEAYHEGECSAVFEASGTTTQAYRVDERAAEQARWEAASKETIKKTTKPCPR
CHVPVEKNGGCMHMKCPQPQCRLEWCWNCGCEWNRVCMGDHWFDV- (SEQ ID NO:10)
```

FIG. 12A

```
GCGGCGGCT GGAGGAGAGC GCGGTGGAGA GCCGAGCGGG CGGGCGGCGG    50
GTGCGGAGCG GGCGAGGGAG CGCGCGCGGC CGCCACAAAG CTCGGGCGCC   100
GCGGGGCTGC ATGCGGCGTA CCTGGCCCGG CGCGGCGACT GCTCTCCGGG   150
CTGGCGGGGG CCGGCCGCGA GCCCCGGGGG CCCCGAGGCC GCAGCTTGCC   200
TGCGCGCTCT GAGCCTTCGC AACTCGCGAG CAAAGTTTGG TGGAGGCAAC   250
GCCAAGCCTG AGTCCTTTCT TCCTCTCGTT CCCCAAATCC GAGGGCAGCC   300
CGCGGGCGTC ATGCCCGCGC TCCTCCGCAG CCTGGGGTAC GCGTGAAGCC   350
CGGGAGGCTT GGCGCCGGCG AAGACCCAAG GACCACTCTT CTGCGTTTGG   400
AGTTGCTCCC CGCAACCCCG GGCTCGTCGC TTTCTCCATC CCGACCCACG   450
CGGGGCGCGG GGACAACACA GGTCGCGGAG GAGCGTTGCC ATTCAAGTGA   500
CTGCAGCAGC AGCGGCAGCG CCTCGGTTCC TGAGCCCACC GCAGGCTGAA   550
GGCATTGCGC GTAGTCCATG CCCGTAGAGG AAGTGTGCAG ATGGGATTAA   600
CGTCCACATG GAGATATGGA AGAGGACGGG GATTGGTAC CGTAACCATG    650
GTCAGCTGGG GTCGTTTCAT CTGCCTGGTC GTGGTCACCA TGGCAACCTT   700
GTCCCTGGCC CGGCCCTCCT TCAGTTTAGT TGAGGATACC ACATTAGAGC   750
CAGAAGAGCC ACCAACCAAA TACCAAATCT CTCAACCAGA AGTGTACGTG   800
GCTGCGCCAG GGGAGTCGCT AGAGGTGCGC TGCCTGTTGA AAGATGCCGC   850
CGTGATCAGT TGGACTAAGG ATGGGGTGCA CTTGGGGCCC AACAATAGGA   900
CAGTGCTTAT TGGGGAGTAC TTGCAGATAA AGGGCGCCAC GCCTAGAGAC   950
TCCGGCCTCT ATGCTTGTAC TGCCAGTAGG ACTGTAGACA GTGAAACTTG  1000
GTACTTCATG GTGAATGTCA CAGATGCCAT CTCATCCGGA GATGATGAGG  1050
ATGACACCGA TGGTGCGGAA GATTTTGTCA GTGAGAACAG TAACAACAAG  1100
AGAGCACCAT ACTGGACCAA CACAGAAAAG ATGGAAAAGC GGCTCCATGC  1150
TGTGCCTGCG GCCAACACTG TCAAGTTTCG CTGCCCAGCC GGGGGGAACC  1200
CAATGCCAAC CATGCGGTGG CTGAAAAACG GGAAGGAGTT TAAGCAGGAG  1250
CATCGCATTG GAGGCTACAA GGTACGAAAC CAGCACTGGA GCCTCATTAT  1300
GGAAAGTGTG GTCCCATCTG ACAAGGGAAA TTATACCTGT GTAGTGGAGA  1350
ATGAATACGG GTCCATCAAT CACACGTACC ACCTGGATGT TGTGGAGCGA  1400
TCGCCTCACC GGCCCATCCT CCAAGCCGGA CTGCCGGCAA ATGCCTCCAC  1450
AGTGGTCGGA GGAGACGTAG AGTTTGTCTG CAAGGTTTAC AGTGATGCCC  1500
AGCCCCACAT CCAGTGGATC AAGCACGTGG AAAAGAACGG CAGTAAATAC  1550
GGGCCCGACG GGCTGCCCTA CCTCAAGGTT CTCAAGGCCG CCGGTGTTAA  1600
CACCACGGAC AAAGAGATTG AGGTTCTCTA TATTCGGAAT GTAACTTTTG  1650
AGGACGCTGG GGAATATACG TGCTTGGCGG GTAATTCTAT TGGGATATCC  1700
TTTCACTCTG CATGGTTGAC AGTTCTGCCA GCGCCTGGAA GAGAAAAGGA  1750
GATTACAGCT TCCCCAGACT ACCTGGAGAT AGCCATTTAC TGCATAGGGG  1800
TCTTCTTAAT CGCCTGTATG GTGGTAACAG TCATCCTGTG CCGAATGAAG  1850
AACACGACCA AGAAGCCAGA CTTCAGCAGC CAGCCGGCTG TGCACAAGCT  1900
GACCAAACGT ATCCCCCTGC GGAGACAGGT AACAGTTTCG GCTGAGTCCA  1950
GCTCCTCCAT GAACTCCAAC ACCCCGCTGG TGAGGATAAC AACACGCCTC  2000
TCTTCAACGG CAGACACCCC CATGCTGGCA GGGGTCTCCG AGTATGAACT  2050
TCCAGAGGAC CCAAAATGGG AGTTTCCAAG AGATAAGCTG ACACTGGGCA  2100
AGCCCCTGGG AGAAGGTTGC TTTGGGCAAG TGGTCATGGC GGAAGCAGTG  2150
GGAATTGACA AAGACAAGCC CAAGGAGGCG GTCACCGTGG CCGTGAAGAT  2200
GTTGAAAGAT GATGCCACAG AGAAAGACCT TTCTGATCTG GTGTCAGAGA  2250
TGGAGATGAT GAAGATGATT GGGAAACACA AGAATATCAT AAATCTTCTT  2300
GGAGCCTGCA CACAGGATGG GCCTCTCTAT GTCATAGTTG AGTATGCCTC  2350
TAAAGGCAAC CTCCGAGAAT ACCTCCGAGC CCGGAGGCCA CCCGGGATGG  2400
AGTACTCCTA TGACATTAAC CGTGTTCCTG AGGAGCAGAT GACCTTCAAG  2450
GACTTGGTGT CATGCACCTA CCAGCTGGCC AGAGGCATGG AGTACTTGGC  2500
TTCCCAAAAA TGTATTCATC GAGATTTAGC AGCCAGAAAT GTTTTGGTAA  2550
CAGAAAACAA TGTGATGAAA ATAGCAGACT TTGGACTCGC CAGAGATATC  2600
```

FIG. 12B

```
AACAATATAG ACTATTACAA AAAGACCACC AATGGGCGGC TTCCAGTCAA  2650
GTGGATGGCT CCAGAAGCCC TGTTTGATAG AGTATACACT CATCAGAGTG  2700
ATGTCTGGTC CTTCGGGGTG TTAATGTGGG AGATCTTCAC TTTAGGGGGC  2750
TCGCCCTACC CAGGGATTCC CGTGGAGGAA CTTTTTAAGC TGCTGAAGGA  2800
AGGACACAGA ATGGATAAGC CAGCCAACTG CACCAACGAA CTGTACATGA  2850
TGATGAGGGA CTGTTGGCAT GCAGTGCCCT CCCAGAGACC AACGTTCAAG  2900
CAGTTGGTAG AAGACTTGGA TCGAATTCTC ACTCTCACAA CCAATGAGGA  2950
ATACTTGGAC CTCAGCCAAC CTCTCGAACA GTATTCACCT AGTTACCCTG  3000
ACACAAGAAG TTCTTGTTCT TCAGGAGATG ATTCTGTTTT TTCTCCAGAC  3050
CCCATGCCTT ACGAACCATG CCTTCCTCAG TATCCACACA TAAACGGCAG  3100
TGTTAAAACA TGAATGACTG TGTCTGCCTG TCCCCAAACA GGACAGCACT  3150
GGGAACCTAG CTACACTGAG CAGGGAGACC ATGCCTCCCA GAGCTTGTTG  3200
TCTCCACTTG TATATATGGA TCAGAGGAGT AAATAATTGG AAAAGTAATC  3250
AGCATATGTG TAAAGATTTA TACAGTTGAA AACTTGTAAT CTTCCCCAGG  3300
AGGAGAAGAA GGTTCTGGA GCAGTGGACT GCCACAAGCC ACCATGTAAC  3350
CCCTCTCACC TGCCGTGCGT ACTGGCTGTG GACCAGTAGG ACTCAAGGTG  3400
GACGTGCGTT CTGCCTTCCT TGTTAATTTT GTAATAATTG GAGAAGATTT  3450
ATGTCAGCAC ACACTTACAG AGCACAAATG CAGTATATAG GTGCTGGATG  3500
TATGTAAATA TATTCAAATT ATGTATAAAT ATATATTATA TATTTACAAG  3550
GAGTTATTTT TTGTATTGAT TTAAATGGA TGTCCCAATG CACCTAGAAA  3600
ATTGGTCTCT CTTTTTTTAA TAGCTATTTG CTAAATGCTG TTCTTACACA  3650
TAATTTCTTA ATTTTCACCG AGCAGAGGTG GAAAATACT TTTGCTTTCA  3700
GGGAAAATGG TATAACGTTA ATTTATTAAT AAATTGGTAA TATACAAAAC  3750
AATTAATCAT TTATAGTTTT TTTTGTAATT TAAGTGGCAT TCTATGCAG  3800
GCAGCACAGC AGACTAGTTA ATCTATTGCT TGGACTTAAC TAGTTATCAG  3850
ATCCTTTGAA AAGAGAATAT TTACAATATA TGACTAATTT GGGGAAAATG  3900
AAGTTTTGAT TTATTTGTGT TTAAATGCTG CTGTCAGACG ATTGTTCTTA  3950
GACCTCCTAA ATGCCCCATA TTAAAAGAAC TCATTCATAG GAAGGTGTTT  4000
CATTTTGGTG TGCAACCCTG TCATTACGTC AACGCAACGT CTAACTGGAC  4050
TTCCCAAGAT AAATGGTACC AGCGTCCTCT TAAAAGATGC CTTAATCCAT  4100
TCCTTGAGGA CAGACCTTAG TTGAAATGAT AGCAGAATGT GCTTCTCTCT  4150
GGCAGCTGGC CTTCTGCTTC TGAGTTGCAC ATTAATCAGA TTAGCCTGTA  4200
TTCTCTTCAG TGAATTTTGA TAATGGCTTC CAGACTCTTT GGCGTTGGAG  4250
ACGCCTGTTA GGATCTTCAA GTCCCATCAT AGAAAATTGA AACACAGAGT  4300
TGTTCTGCTG ATAGTTTTGG GGATACGTCC ATCTTTTAA GGGATTGCTT  4350
TCATCTAATT CTGGCAGGAC CTCACCAAAA GATCCAGCCT CATACCTACA  4400
TCAGACAAAA TATCGCCGTT GTTCCTTCTG TACTAAAGTA TTGTGTTTTG  4450
CTTTGGAAAC ACCCACTCAC TTTGCAATAG CCGTGCAAGA TGAATGCAGA  4500
TTACACTGAT CTTATGTGTT ACAAAATTGG AGAAAGTATT TAATAAAACC  4550
TGTTAATTTT TATACTGACA ATAAAAATGT TTCTACAGAT ATTAATGTTA  4600
ACAAGACAAA ATAAATGTCA CGCAACTTAT TTTTTTAATA aaaaaaaaaa  4650
aaaa (SEQ ID NO:11)
```

FIG. 13

```
MVSWGRFICLVVVTMATLSLARPSFSLVEDTTLEPEEPPTKYQISQPEVYVAAPGESLEV
RCLLKDAAVISWTKDGVHLGPNNRTVLIGEYLQIKGATPRDSGLYACTASRTVDSETWYF
MVNVTDAISSGDDEDDTDGAEDFVSENSNNKRAPYWTNTEKMEKRLHAVPAANTVKFRCP
AGGNPMPTMRWLKNGKEFKQEHRIGGYKVRNQHWSLIMESVVPSDKGNYTCVVENEYGSI
NHTYHLDVVERSPHRPILQAGLPANASTVVGGDVEFVCKVYSDAQPHIQWIKHVEKNGSK
YGPDGLPYLKVLKAAGVNTTDKEIEVLYIRNVTFEDAGEYTCLAGNSIGISFHSAWLTVL
PAPGREKEITASPDYLEIAIYCIGVFLIACMVVTVILCRMKNTTKKPDFSSQPAVHKLTK
RIPLRRQVTVSAESSSSMNSNTPLVRITTRLSSTADTPMLAGVSEYELPEDPKWEFPRDK
LTLGKPLGEGCFGQVVMAEAVGIDKDKPKEAVTVAVKMLKDDATEKDLSDLVSEMEMMKM
IGKHKNIINLLGACTQDGPLYVIVEYASKGNLREYLRARRPPGMEYSYDINRVPEEQMTF
KDLVSCTYQLARGMEYLASQKCIHRDLAARNVLVTENNVMKIADFGLARDINNIDYYKKT
TNGRLPVKWMAPEALFDRVYTHQSDVWSFGVLMWEIFTLGGSPYPGIPVEELFKLLKEGH
RMDKPANCTNELYMMMRDCWHAVPSQRPTFKQLVEDLDRILTLTTNEEYLDLSQPLEQYS
PSYPDTRSSCSSGDDSVFSPDPMPYEPCLPQYPHINGSVKT-  (SEQ ID NO:12)
```

FIG. 14A

```
GGATGGTCCT GGTCACAAAA TATTAAAGAG ACCGACCGCT AAGGGAACAG    50
GAAAACGTC  CGAGACAGCC GTTGCAATTA CGAATGGACC AGACTTGGTA   100
GCACGGGGCA TTGATTGCTG GTGCCCAACC GGACCCTCCT CCCTCTTCC    150
CATCCCTTCC CCCACCCAAA GCAGGCTCCC GCTGCGGCCG GGACCTCGCA   200
TCCCTGCAAC GTGGCCGGGG CTGCATTTTT CATGAGCCTA GGGTGAACAG   250
GTGCGAAGTG CGCTGGGAGC ATCCGGCCAG CGGCCGAGCG CGGGGAAC*AT* 300
*G*GAGAGCGAG CGCGACATGT ACCGCCAGTT CCAGGACTGG TGCCTCAGGA 350
CTTACGGGGA CTCAGGCAAG ACCAAGACGG TGACCCGTAA AAAATACGAA   400
CGGATCGTCC AGCTCCTCAA TGGCTCCGAG TCGAGCTCCA CGGACAACGC   450
CAAATTTAAA TTCTGGGTCA AATCGAAGGG CTTCCAGCTG GCCAGCCGG    500
ACGAGGTCCG CGGGGGAGGC GGCGGCGCCA AGCAAGTGCT CTACGTGCCT   550
GTCAAGACCA CGGATGGCGT AGGGGTAGAT GAGAAGCTAT CTTTACGACG   600
GGTAGCTGTG GTTGAAGATT TCTTTGACAT TATTTATTCG ATGCATGTGG   650
AAACGGGGCC AAATGGAGAA CAAATTCGGA AACACGCTGG ACAAAAGAGA   700
ACTTACAAAG CAATTTCAGA GAGCTATGCC TTCCTACCAA GAGAAGCGGT   750
GACACGATTT CTAATGAGCT GCTCAGAGTG CCAGAAAAGA ATGCATTTAA   800
ACCCAGATGG AACAGATCAT AAAGATAATG GAAACCTCC  CACTTTGGTG   850
ACCAGCATGA TTGACTACAA CATGCCAATT ACCATGGCCT ACATGAAACA   900
CATGAAGCTG CAGCTGCTAA ACTCACAGCA AGATGAGGAT GAAAGTTCAA   950
TAGAAAGTGA TGAATTTGAC ATGAGTGATT CAACACGGAT GTCAGCTGTG  1000
AACTCTGATC TTAGCTCCAA TCTTGAAGAA AGAATGCAAA GTCCCAGAA   1050
TCTTCATGGC CAGCAAGATG ATGATTCTGC TGCAGAGAGC TTTAATGGCA  1100
ATGAGACTCT GGGGCACAGT TCAATTGCTT CAGGGGGAAC ACACAGCAGG  1150
GAGATGGGAG ACTCCAACAG TGATGGCAAA ACTGGGCTGG AGCAAGATGA  1200
ACAGCCACTG AACCTGAGTG ACAGTCCCCT CTCTGCGCAG CTAACTTCGG  1250
AATACAGAAT AGATGATCAC AACAGTAATG GAAAAACAA  GTATAAGAAT  1300
CTTCTAATTT CTGACCTCAA GATGGAACGA GAGGCGAGAG AAAATGGAAG  1350
CAAGTCTCCT GCACATAGTT ACTCCAGCTA TGACTCTGGC AAAAATGAGA  1400
GTGTAGACCG AGGAGCTGAG GACCTCTCAC TAAACAGGGG AGATGAGGAC  1450
GAAGATGACC ACGAGGACCA TGACGATTCG GAGAAAGTTA ATGAGACAGA  1500
CGGCGTTGAA GCCGAGCGGC TGAAAGCTTT TAATATGTTT GTCAGGCTGT  1550
TTGTAGATGA AAACTTGGAC CGAATGGTCC CAATCTCTAA GCAGCCCAAA  1600
GAAAAGATCC AGGCTATCAT TGACTCATGC AGGCGACAAT TCCCTGAGTA  1650
TCAAGAGCGT GCCAGAAAAC GTATACGTAC TTACCTCAAG TCCTGCAGGC  1700
GGATGAAAAG AAGTGGTTTT GAGATGTCTC GACCTATTCC TTCCCACCTT  1750
ACTTCAGCAG TTGCAGAGAG TATCTTGGCT TCAGCTTGTG AGAGTGAGAG  1800
TAGAAATGCC GCCAAGAGGA TGCGTCTGGA GAGACAGCAG GATGAGTCTG  1850
CTCCAGCTGA CAAACAGTGT AAACCAGAGG CGACCCAGGC CACTTACTCA  1900
ACATCAGCTG TTCCAGGCTC ACAGGACGTG CTGTACATCA ATGGAAATGG  1950
GACCTATAGT TACCATAGTT ACAGAGGGCT AGGAGGGGGT CTGCTAAATC  2000
TGAATGATGC TTCCAGCAGT GGACCCACTG ATCTCAGCAT GAAGAGACAA  2050
TTGGCGACTA GCTCAGGATC CTCCAGCAGC TCAAACTCCA GACCCCAGCT  2100
GAGTCCAACT GAAATCAATG CCGTGAGACA GCTTGTTGCA GGATATCGAG  2150
AATCAGCTGC ATTTTATTG  CGATCTGCAG ATGAACTGGA AAATCTCATT  2200
TTACAACAGA AC*TGA*GACAG ACGACCACCA TATTCACTGA GGTCTAAATT  2250
TGCAGTTTCC ACTAATGACA TTTTGATTTC CAACAGAGA  TACTTCTGGT  2300
CTTACTGCAC AGTCTTTTAA GAGAAATACT TCCATTATGC CACATTGTCC  2350
TTGATCCGTA AGTGATGTGT TAAGGTGCTT CAAAGGAACT CTGACCTCTG  2400
AAGTACTTGA GCTACTTTAG TATGTCCAGC CTATTGCTTT TTGTTTTAGT  2450
GTGTCACCAT AAATATCAGG GGCATAAAAG CTATCTATT  CTTAATTCAA  2500
GGATAAAACA GAAGAAGCTT GTGGTATAAA ACAATAGTTC AAGATCCAGC  2550
TGAAATATTA GTGGAATTTG CTACTGACTC ATTGGACTGA AAGCTGAAGT  2600
```

FIG. 14B

```
ACCTGGCAAA AAAAAAAAAA AGAAAAAAAA AAGCCAAATT TCTTGTTGCT    2650
ACAGGATATA ACAACAATGA AAAGGATCTC GTATTTAAA  AAAATATGTA    2700
ATTTTTATAA AAAGAAAACT TGTTTTTCAT TCAAACTTGT CATTTTTACT    2750
TTGGTAACTT TTTCATAGGT CCTAAAAGAA AACTGTTTTG AGAAACTACT    2800
GTAAGTACCT TTTCCACATC CCTTTGCCTT CTCCTCTTTC CAAATTCTTT    2850
CTACAAAAAT AACACTTGAT GCTGGAAAAA CCCTTGCCTA CGTTCTTTCA    2900
ATCGTCACAT CAGGAACTAC TTCCAAGAGA AGCCTGCATT TCTGCTCTCA    2950
TGCTGATCTC AAAAACCCCA CTCAACACTG CAACTTATC  ATAGCAGTTT    3000
TCATCCCAGA ATTTTTTTTT TAATAATGAC AAGACATGTT GTTGAAAAAA    3050
AATCACACCT TGGTTTCTTA GAGCTGCTCG TTCCTGATTG CCGCTGCTGT    3100
CTCCAGGCAT CCCTCTAGCA GCACCTGGAT GTAGATGACT GAATGTTAAG    3150
AGGTTGCAAG TGACAATCTG AAAATTTGCA CTCTTGTGTG TAGTTTTCTT    3200
TTCATTTCTT TCAGAAATAG TTTCCAAAAA GACCATTACA TCTCCTGATA    3250
TGATTTGTAT AATTTTCAGT TCTAGCTAAA AATAATGTAA GGAACTCTCA    3300
GCGGATGCAG CTGCAACTTA CAATGAACTG TGCCCTCCTA TCCCCCATAC    3350
TTTACCCTTC TTTCTTATTT TATAGTGTGG GATACACATG AGTGATGTTT    3400
TCTTTGTGCA CTGAGACAAG CCTATTTTTT AAATATTTAG GGAGAAGTAC    3450
TTTAGTTCAT GCTTCTTATA CAACTTTTTT CTGTTGTTTA GCTTGGTTG     3500
GATTACAAAT TCTTTGTGCA TTCCTGAATT TGCCTTATTT CATGTAAAAT    3550
TTATGTCATT CAGTTTTGA  CAATGAGTTT GAGGCATCAG TGATATTTCT    3600
TATCTACTTG TTACATATAG TTTTTCAAGT AATGACTGTG ATTGTGACCG    3650
AGTAATGTGC ACTTTTTCTT GTAACTGTGG ACATTGCTAT GCTTTTTCT     3700
TCTAGTGTTT CTAGAATTAC TGTTCCTTAC AATTATGTAA ACAAAAAACA    3750
AAAAAAAAAC TTTTGTGATA CTGTTGGTGA ATATAATGTG AAAAATCTTA    3800
TTGAAATATG AGTATTTTGG AAATACATAG CTGCACAAAC ATCTTTTAAG    3850
ATGTGGATTT AGAGTTTGCT TATTTAAATG AAAATTCAAA AATTGAGGGC    3900
TGGTATAATT TTCTCTGTTT TGTTTGGTTT AATAAACAGA TTTCTGTGTT    3950
AAAAGAAaaa aaaaaaaa (SEQ ID NO:13)
```

FIG. 15

```
MESERDMYRQFQDWCLRTYGDSGKTKTVTRKKYERIVQLLNGSESSSTDNAKFKFWVKSK
GFQLGQPDEVRGGGGGAKQVLYVPVKTTDGVGVDEKLSLRRVAVVEDFFDIIYSMHVETG
PNGEQIRKHAGQKRTYKAISESYAFLPREAVTRFLMSCSECQKRMHLNPDGTDHKDNGKP
PTLVTSMIDYNMPITMAYMKHMKLQLLNSQQDEDESSIESDEFDMSDSTRMSAVNSDLSS
NLEERMQSPQNLHGQQDDDSAAESFNGNETLGHSSIASGGTHSREMGDSNSDGKTGLEQD
EQPLNLSDSPLSAQLTSEYRIDDHNSNGKNKYKNLLISDLKMEREARENGSKSPAHSYSS
YDSGKNESVDRGAEDLSLNRGDEDEDDHEDHDDSEKVNETDGVEAERLKAFNMFVRLFVD
ENLDRMVPISKQPKEKIQAIIDSCRRQFPEYQERARKRIRTYLKSCRRMKRSGFEMSRPI
PSHLTSAVAESILASACESESRNAAKRMRLERQQDESAPADKQCKPEATQATYSTSAVPG
SQDVLYINGNGTYSYHSYRGLGGGLLNLDASSSGPTDLSMKRQLATSSGSSSSSNSRPQ
LSPTEINAVRQLVAGYRESAAFLLRSADELENLILQQN-     (SEQ ID NO:14)
```

FIG. 16

```
AGAGTCCTGG CGAGGGCGCT GGCCGAGAGG TGCTCGGCTT GTAGCAGGTC    50
CCGCACTCCA GCCTCTCGCT GCCAGGGTTT GCTCTCTGCT TGTCCTGGGC   100
TGAGGTGTCC ATGACGGAGT CATCCAAGGA GGAAAAAATC TGTTCCGGGT   150
GAGCCCAGGC CGCCCCGGAT ATGCGATGGC TGAGGAGCAG ACACCAGGGA   200
CCACACTGAG GTTGGGTTTC AGACCAAGAC ACTGGATTCT CCTAGTTAAG   250
ATAAAGAGCT TTGGGTGCCT GACAGTGAAA ATGGTGTAAT CTGCGTTAAC   300
AGTTCACAGC TTGAAGGCAT GACAATTAAA GAACACACAT GGACTTGTGG   350
CACATGGAAA TGTGCGCACA GAAAAGGAA ATCTATAATT CTTTTAAAGT    400
AGGAAGGCAT TCTTCCTTGC CAAAATGGGT ACgTTCTGTT CGGTTATCAA   450
GTTTGAAAAT CTACAAGAAT TAAAGAGACT GTGTCACTGG GGTCCCATCA   500
TAGCCCTTGG TGTTATAGCA ATATGTTCTA CCATGGCCAT GATTGACTCT   550
GTGTTGTGGT ATTGGCCCTT ACATACAACT GGAGGAAGTG TGAATTTCAT   600
CATGTTGATA AATTGGACTG TCATGATTCT TTATAATTAC TTCAATGCCA   650
TGTTTGTCGG TCCGGGCTTT GTCCCTCTGG GGTGGAAACC GGAAATTTCT   700
CAGGATACCA TGTATCTCCA GTATTGTAAA GTCTGCCAAG CATACAAGGC   750
ACCACGTTCA CATCACTGCA GAAAGTGTAA CAGATGTGTG ATGAAGATGG   800
ACCATCACTG TCCTTGGATC AACAACTGTT GTGGTTACCA AAATCATGCT   850
TCGTTCACAC TGTTTCTCCT TTTAGCACCA CTGGGTTGTA TCCATGCTGC   900
TTTCATTTTT GTGATGACTA TGTACACACA GCTTTATCAT CGGCTCTCCT   950
TGGGTGGAA CACAGTGAAG ATCGACATGA GTGCAGCCCG GAGAGATCCT   1000
CTTCCAATTG TTCCATTTGG ATTAGCTGCA TTTGCTACCA CCTTGTTTGC   1050
CTTGGGATTA GCTTTAGGAA CAACCATAGC TGTTGGGATG TTGTTTTTTA   1100
TCCAGATGAA AATAATTCTC AGAAACAAAA CTTCTATTGA GTCATGGATT   1150
GAAGAGAAGG CTAAAGATCG AATTCAGTAT TATCAACTAG ATGAAGTCTT   1200
TGTTTTTCCA TATGATATGG GAAGTAGATG GAGGAACTTT AAACAGGTAT   1250
TTACGTGGTC AGGGGTCCCT GAAGGAGATG GACTTGAGTG GCCAGTAAGA   1300
GAAGGCTGTC ACCAATACAG CTTAACAATA GAACAGTTGA AACAAAAAGC   1350
AGATAAGAGA GTCAGAAGTG TTCGCTATAA AGTAATAGAA GATTATAGTG   1400
GTGCCTGCTG CCCTCTGAAT AAAGGAATCA AACCTTCTT CACAAGTCCC    1450
TGCACCGAAG AGCCTCGAAT ACAGCTGCAA AAGGGGAAT TCATTTTAGC    1500
CACAAGAGGT TTACGATACT GGTTATATGG AGACAAAATT CTTGATGATT   1550
CCTTTATAGA AGGTGTTCA AGAATAAGGG GTTGGTTCCC TAGAAAATGT    1600
GTGGAAAAGT GTCCTGTGA TGCTGAAACA GATCAAGCCC CAGAGGGGGA    1650
GAAGAAAAT AGATAGCTGC TGTTAAAACA AAATTATCCT TTAAGTCTGC    1700
TTAATTACTT GAAAATTGTA CATATTACTA AAGAATTATG CAATGAGCCT   1750
ACTCTGGTTA AGATGTTCTT TTCCTCAAAG GTGCCCTAGT GCCATGATTT   1800
AAATATTTTT ATTACCATTT TGAAATGGAG AAGCCATTCT GCATATGCCT   1850
TTGAATTCCT GCCCtTCTTT ACCACCTCTT CCTCCCCCTC AAAGGAAAAA   1900
CATTTCATCC AAGTAAGTTA ACGGCATTTT CTGTAGGATT TTCTTATGCA   1950
CTGCACACTC TGGACCTCAC CTGCAGATAC AGTTCCCCCC TTGCCAGGAG   2000
CATCTGCATG TGGTACTTCT CTTTTCCCTC AGTTGATATT TCTTATATGA   2050
TATTCTAGAT ACTATAGAAC TCAATTTGTC AGATTCAGTA TAACCTCAGA   2100
TTTTGTTACC TGTCTTTTAA AAATGCAGAT TTTGTCAAAT CAAATAAAGA   2150
TCAATGGATG TTGGGTATAA aaaaaaaaaa aaaaaaa (SEQ ID NO:15)
```

FIG. 17

```
MGTFCSVIKFENLQELKRLCHWGPIIALGVIAICSTMAMIDSVLWYWPLHTTGGSVNFIM
LINWTVMILYNYFNAMFVGPGFVPLGWKPEISQDTMYLQYCKVCQAYKAPRSHHCRKCNR
CVMKMDHHCPWINNCCGYQNHASFTLFLLLAPLGCIHAAFIFVMTMYTQLYHRLSFGWNT
VKIDMSAARRDPLPIVPFGLAAFATTLFALGLALGTTIAVGMLFFIQMKIILRNKTSIES
WIEEKAKDRIQYYQLDEVFVFPYDMGSRWRNFKQVFTWSGVPEGDGLEWPVREGCHQYSL
TIEQLKQKADKRVRSVRYKVIEDYSGACCPLNKGIKTFFTSPCTEEPRIQLQKGEFILAT
RGLRYWLYGDKILDDSFIEGVSRIRGWFPRKCVEKCPCDAETDQAPEGEKKNR- (SEQ ID
NO:16)
```

METHODS OF TREATING CHOLANGIOCARCINOMA

CROSS REFERENCE TO RELATED APPLICATIONS

This application is a Continuation Application of U.S. patent application Ser. No. 17/204,830, filed on Mar. 17, 2021, now U.S. Pat. No. 11,771,698, issued on Oct. 3, 2023, which is a Divisional Application of U.S. patent application Ser. No. 14/761,518, filed on Jan. 17, 2014, now U.S. Pat. No. 10,980,804, issued on Apr. 20, 2021, which is a U.S. National Phase Application under 35 U.S.C. § 371 of International Application No. PCT/US2014/012136, filed on Jan. 17, 2014, which claims the benefit of U.S. Provisional Application No. 61/754,509, filed Jan. 18, 2013 and U.S. Provisional Application No. 61/756,372, filed Jan. 24, 2013, the contents of each of which are hereby incorporated by reference in their entirety.

REFERENCE TO AN ELECTRONIC SEQUENCE LISTING

The contents of the electronic sequence listing (197102001601SEQLIST.xml; Size: 55,296 bytes; and Date of Creation: Jun. 27, 2023) are herein incorporated by reference in their entirety.

BACKGROUND

Cancer represents the phenotypic end-point of multiple genetic lesions that endow cells with a full range of biological properties required for tumorigenesis. Indeed, a hallmark genomic feature of many cancers is the presence of numerous complex chromosome structural aberrations, including translocations, intra-chromosomal inversions, point mutations, deletions, gene copy number changes, gene expression level changes, and germline mutations, among others.

Cholangiocarcinoma is a cancer that includes mutated epithelial cells that originate in the bile ducts. Cholangiocarcinoma is a relatively rare neoplasm that is classified as an adenocarcinoma (a cancer that forms glands or secretes significant amounts of mucins). It has an annual incidence rate of about 1-2 cases per 100,000 in the Western world, but rates of cholangiocarcinoma have been rising worldwide over the past several decades (Landis S. et al. (1998) *CA Cancer J Clin* 48 (1): 6-29; Patel T (2002) *BMC Cancer* 2: 10. doi:10.1186/1471-2407-2-10).

Cancer of the bile ducts can arise within the liver as an intrahepatic cholangiocarcinoma (ICC) or originate from extrahepatic bile ducts as a bile duct carcinoma, also referred to as an extra-hepatic cholangiocarcinoma. ICC is the second most common primary hepatic malignancy after hepatocellular carcinoma (HCC), and accounts for 3% of the malignant tumors of the gastrointestinal system and 15% of primary hepatic malignancies. Because ICC has a routine histologic appearance of an adenocarcinoma, the diagnosis of ICC on a liver biopsy requires an immunohistochemical (IHC) study of the tumor and a thorough clinical workup including imaging studies to rule out a metastatic adenocarcinoma to the liver.

Numerous studies have indicated that the incidence and mortality from ICC are increasing worldwide. ICC is associated with primary sclerosing cholangitis, parasitic biliary infection, polycystic disease of the liver, congenital intrahepatic bile duct dilatation (Caroli's Disease), congenital hepatic fibrosis, and choledochal cysts. Chronic Hepatitis C infection is an established cause of ICC with some studies describing a more than 300 fold increase in ICC incidence in patients with long-standing Hepatitis C infections. ICC has also been associated with cigarette smoking, alcohol consumption and exposure to a variety of toxins and chemical carcinogens. The onset of symptoms of ICC are often vague, typically arise late in the course of the disease and include abdominal pain, anorexia and palpable abdominal mass lesions. Thus, the median survival for ICC is less than 6 months for inoperable tumors and only 20 to 40% for patients who undergo surgery and achieve clear margins.

Cholangiocarcinoma is considered to be an incurable and rapidly lethal malignancy, unless both the primary tumor and any metastases can be fully resected (removed surgically). No potentially curative treatment exists at this time except surgery; however, most patients have advanced stage disease at presentation and are inoperable at the time of diagnosis. Cholangiocarcinoma has near-100% fatality due to attendant liver complications from the damage to the organ. Patients with cholangiocarcinoma are generally managed with chemotherapy, radiation therapy, and other palliative care measures.

Thus, the need still exists for identifying novel genetic lesions associated with cancers such as cholangiocarcinomas. Such genetic lesions can be an effective approach to develop compositions, methods and assays for evaluating and treating cancer patients.

SUMMARY

The invention is based, at least in part, on the discovery, in cholagiocarcinomas, of novel rearrangement events that give rise to alterations in a fibroblast growth factor receptor 2 (FGFR2) gene or a neurotrophic tyrosine receptor kinase (NTRK1)) gene. In certain embodiments, the alteration is chosen from a translocation, a deletion, an inversion, a rearrangement, or an amplification of, an FGFR2 gene or the NTRK gene. For example, the alteration can be chosen from an alteration described in Table 1 and FIGS. 1A-1C. In one embodiment, the alteration includes a fragment of an FGFR2 gene or the NTRK1 gene, e.g., as exemplified in Table 1, FIGS. 1A-1C and FIGS. 2-17. Thus, the invention provides new insights into the treatment of these cancers, such as cholangiocarcinomas. Therefore, described herein are methods for treating a cholangiocarcinoma carcinoma, including intrahepatic cholangiocarcinoma (ICC) and extrahepatic cholangiocarcinoma, as well as novel FGFR2 and NTRK1 molecules (e.g., fusion molecules); methods and reagents for identifying, assessing or detecting an alteration in an FGFR2 and/or NTRK1.

Accordingly, in one aspect, the invention features a method of treating a subject having a cholangiocarcinoma. The method includes administering to the subject an effective amount of an agent (e.g., a therapeutic agent) that targets, antagonizes or inhibits an FGFR2 or NTRK1 (e.g., an FGFR2 or NTRK1 gene product, e.g., an FGFR2 or NTRK1 protein), thereby treating the subject.

In another aspect, the invention features, a method of treating a subject having a cholangiocarcinoma. The method includes administering to the subject an effective amount of a kinase inhibitor (e.g., a tyrosine kinase inhibitor), thereby treating the subject.

In one embodiment, the method further includes acquiring knowledge of one or both of:
(i) the presence (or absence) of an alteration in FGFR2 gene product, e.g., an FGFR2 protein; or (ii) the presence (or absence) of an alteration in NTRK1 gene product, e.g., an NTRK1 protein, in the subject, or a cancer or tumor sample from the subject.

In another embodiment, the method further includes identifying the subject, or a cancer or tumor sample from the subject, as having one or both of:
(i) the presence (or absence) of an alteration in FGFR2 gene product, e.g., an FGFR2 protein; or
(ii) the presence (or absence) of an alteration in NTRK1 gene product, e.g., an NTRK1 protein.

In certain embodiments, the presence of the FGFR2 or NTRK1 alteration, or both, in the subject is indicative that the subject is likely to respond to the agent.

In yet other embodiments, the agent is administered responsive to a determination of the presence of the FGFR2 or NTRK1 alteration, or both, in the subject, or the cancer or tumor sample from the subject.

Cholangiocarcinoma

In certain embodiments, the cholangiocarcinoma comprises one or more mutated cells that originate in the bile duct. In certain embodiments, the cholangiocarcinoma is chosen from an intrahepatic cholangiocarcinoma or an extrahepatic cholangiocarcinoma. In other embodiments, the cholangiocarcinoma comprises, or is identified as having, an alteration that is chosen from a translocation, a deletion, an inversion, a rearrangement, or an amplification of, an FGFR2 gene or the NTRK gene. In one embodiment, the cholangiocarcinoma comprises, or is identified as having, an alteration chosen from an alteration described in Table 1 or FIGS. 1A-1C. In one embodiment, the cholangiocarcinoma comprises, or is identified as having, an alteration includes a fragment of an FGFR2 gene or the NTRK1 gene, e.g., as exemplified in Table 1, FIGS. 1A-1C and FIGS. 2-17. In yet other embodiments, the cholangiocarcinoma comprises, or is identified as having, a fusion molecule of FGFR2; e.g., a fusion molecule chosen from FGFR2-TACC3, FGFR2-KIAA1598, BICC1-FGFR2, FGFR2-BICC1, PARK2-FGFR2, FGFR2-NOL4, or ZDHHC6-FGFR2 as described, e.g., in Table 1, FIGS. 1A-1C and FIGS. 2-17. In other embodiments, the cholangiocarcinoma comprises, or is identified as having, a rearrangement or an amplification of FGFR2 as described, e.g., in Table 1, FIGS. 1A-1C and FIGS. 2-17.

In certain embodiments, the alteration in FGFR2 results in upregulation, increased activity (e.g., increased transformative or oncogenic activity, kinase activity and/or dimerization), and/or increased level of an FGFR2 gene product (e.g., an FGFR2 protein), compared to a wildtype activity of FGFR2.

Subjects

In certain embodiments, the subject has an alteration in FGFR2 or NTRK1, or both, e.g., the subject has a cholangiocarcinoma comprising an alteration in FGFR2 or NTRK1, or both, e.g., as described herein. In other embodiments, the subject is identified, or has been previously identified, as having a cholangiocarcinoma (e.g., an intrahepatic cholangiocarcinoma (ICC) or an extrahepatic cholangiocarcinoma) comprising an alteration in FGFR2 or NTRK1, or both, e.g., as described herein. In other embodiments, the subject has, or is identified as having, an alteration that is chosen from a translocation, a deletion, an inversion, a rearrangement, or an amplification of, an FGFR2 gene or the NTRK gene. In one embodiment, the subject has, or is identified as having, an alteration chosen from an alteration described in Table 1 or FIGS. 1A-1C. In one embodiment, the subject has, or is identified as having, an alteration includes a fragment of an FGFR2 gene or the NTRK1 gene, e.g., as exemplified in Table 1, FIGS. 1A-1C and FIGS. 2-17. In yet other embodiments, the subject has, or is identified as having, a fusion molecule of FGFR2; e.g., a fusion molecule chosen from FGFR2-TACC3, FGFR2-KIAA1598, BICC1-FGFR2, FGFR2-BICC1, PARK2-FGFR2, FGFR2-NOL4, or ZDHHC6-FGFR2 as described, e.g., in Table 1, FIGS. 1A-1C and FIGS. 2-17. In other embodiments, the subject has, or is identified as having, a rearrangement or an amplification of FGFR2 as described, e.g., in Table 1, FIGS. 1A-1C and FIGS. 2-17.

In one embodiment, the subject is a human. In one embodiment, the subject has, or is at risk of having a cholangiocarcinoma (e.g., a cholangiocarcinoma as described herein) at any stage of disease, e.g., Stage I, II, IIIA-IIIC or IV of intrahepatic cholangiocarcinoma; Stage 0, IA-IB, IIA-IIB, III or IV of extrahepatic cholangiocarcinoma; or a metastatic cancer. In other embodiments, the subject is a cancer patient, e.g., a patient having a cholangiocarcinoma as described herein.

In one embodiment, the subject is undergoing or has undergone treatment with a different (e.g., non-FGFR2 or non-NTRK1) therapeutic agent or therapeutic modality. In one embodiment, the non-FGFR2 or non-NTRK1 therapeutic agent or therapeutic modality is a chemotherapy, immunotherapy, or a surgical procedure. In one embodiment, the non-FGFR2 or non-NTRK1 therapeutic agent or therapeutic modality comprises one or more (or all) of: a surgical procedure, flurouracil (e.g., 5-FU, Adrucil, Efudex), doxorubicin (Adriamycin, Rubex), gemcitabine (e.g., Gemzar) and/or cisplatin (Platinol).

In one embodiment, responsive to the determination of the presence of the FGFR2 or NTRK1 alteration, the different therapeutic agent or therapeutic modality is discontinued. In yet other embodiments, the subject has been identified as being likely or unlikely to respond to the different therapeutic agent or therapeutic modality.

In certain embodiments, the subject has participated previously in a clinical trial, e.g., a clinical trial for a different (e.g., non-FGFR2 or non-NTRK1) therapeutic agent or therapeutic modality. In other embodiments, the subject is a cancer patient who has participated in a clinical trial, e.g., a clinical trial for a different (e.g., non-FGFR2 or non-NTRK1) therapeutic agent or therapeutic modality.

Agents

In certain embodiments, the agent (e.g., the therapeutic agent) used in the methods targets and/or inhibits FGFR2 or NTRK1 (e.g., a FGFR2 or NTRK1 gene or gene product as described herein). In one embodiment, the agent binds and inhibits FGFR2 or NTRK1. In one embodiment, the agent is a reversible or an irreversible FGFR2 inhibitor. In certain embodiments, the agent is a pan-FGFR2 inhibitor.

In one embodiment, the agent is an antibody molecule, e.g., an anti-FGFR2 or NTRK1 antibody molecule (e.g., a monoclonal or a bispecific antibody), or a conjugate thereof (e.g., an antibody to FGFR2 or NTRK1 conjugated to a cytotoxic agent (e.g., mertansine DM1)).

In one embodiment, the agent is a kinase inhibitor. In one embodiment, the kinase inhibitor is chosen from: a multi-specific kinase inhibitor, an FGFR2 inhibitor (e.g., a pan-FGFR2 inhibitor), an NTRK1 inhibitor, and/or a small molecule inhibitor that is selective for FGFR2 or NTRK1; and/or a FGFR2 or NTRK1 cellular immunotherapy.

In an embodiment, the therapeutic agent is chosen from a kinase inhibitor; a multi-specific kinase inhibitor; an FGF receptor inhibitor (e.g., a pan FGFR2 inhibitor); an antibody molecule (e.g., a monoclonal antibody) against FGFR2;

and/or a small molecule (e.g., kinase) inhibitor that is selective for FGFR2 or NTRK1.

In an embodiment the therapeutic agent is selected from antisense molecules, ribozymes, RNAi, triple helix molecules that hybridize to a nucleic acid encoding the fusion, or a transcription regulatory region that blocks or reduces mRNA expression of FGFR2 or NTRK1.

In an embodiment the kinase inhibitor is chosen from: a kinase inhibitor; a multi-specific kinase inhibitor; an FGF receptor inhibitor (e.g., a pan FGFR2 inhibitor); and/or a kinase inhibitor that is selective for FGFR2 or NTRK1.

In an embodiment, the therapeutic agent is chosen from: Regorafenib; Ponatinib; AZD-2171 (Cediranib); AZD-4547; BGJ398; BIBF1120; Brivanib; Dovitinib; ENMD-2076; JNJ42756493; Masitinib; Lenvatinib; LY2874455; Pazopanib; PD-173955; R406; PD173074; Danusertib; Dovitinib Dilactic Acid; TSU-68; Tyrphostin AG 1296; MK-2461; Brivanib Alaninate; Lestaurtinib; PHA-848125; K252a; AZ-23; and/or Oxindole-3.

In an embodiment, the therapeutic agent is chosen from Regorafenib or Ponatinib.

Other features and embodiments of the invention include one or more of the following.

In an embodiment, the method includes acquiring knowledge of the presence of an alteration, e.g., fusion, from Table 1, FIGS. 1A-1C and FIGS. 2-17 in said subject.

In an embodiment the therapeutic agent is administered responsive to the determination of presence of the alteration, e.g., fusion, in a tumor sample from said subject.

In an embodiment the determination of the presence of the alteration, e.g., fusion, comprises sequencing.

In an embodiment the subject is undergoing or has undergone treatment with a different therapeutic agent or therapeutic modality, e.g., a non-FGFR2 or non-NTRK1 therapeutic agent or therapeutic modality.

In an embodiment responsive to a determination of the presence of the alteration, e.g., fusion, the different therapeutic agent or therapeutic modality is discontinued.

In an embodiment the different therapeutic agent or therapeutic modality is a chemotherapy or a surgical procedure. In one embodiment, the non-FGFR2 or non-NTRK1 therapeutic agent or therapeutic modality comprises one or more (or all) of: a surgical procedure, flurouracil (e.g., 5-FU, Adrucil, Efudex), doxorubicin (Adriamycin, Rubex), gemcitabine (e.g., Gemzar) and/or cisplatin (Platinol).

In another aspect, the invention features, a method of determining the presence of an alteration, e.g., a fusion, disclosed herein in cholangiocarcinoma sample, comprising:
  directly acquiring knowledge that an alteration, e.g., a fusion nucleic acid molecule, of Table 1, FIGS. 1A-1C and FIGS. 2-17 is present in a sample from a subject.

In an embodiment the acquiring step comprises sequencing.

In an embodiment the method further comprises administering a kinase inhibitor to the subject responsive to the determination of the presence of the alteration, e.g., the fusion, in the sample from the subject.

The invention also provides, methods of: identifying, assessing or detecting an alteration, e.g., fusion, of an FGFR2 or an NTRK1, e.g., that arises in a cholangiocarcinoma. Exemplary alteration, e.g., fusions, include those summarized in Table 1, FIGS. 1A-1C and FIGS. 2-17, including a fusion of FGFR2 (e.g., an FGFR2 fusion molecule (e.g., a gene product or fragment thereof)) to a partner from Table 1, FIGS. 1A-1C and FIGS. 2-17, or a fusion of NTRK1 (e.g., an NTRK1 fusion molecule (e.g., a gene product or fragment thereof)) to a partner of Table 1. In one embodiment, the FGFR2 or NTRK1 is fused to a second gene, or a fragment thereof, e.g., as described in Table 1, FIGS. 1A-1C and FIGS. 2-17. In other embodiments, the fusion molecule is chosen from FGFR2-TACC3, FGFR2-KIAA1598, BICC1-FGFR2, FGFR2-BICC1, PARK2-FGFR2, FGFR2-NOL4, ZDHHC6-FGFR2, or RABGAP1L-NTRK1, e.g., as described, e.g., in Table 1, FIGS. 1A-1C and FIGS. 2-17. Included are fusion molecules; isolated fusions nucleic acid molecules, nucleic acid constructs, host cells containing the nucleic acid molecules; purified fusion polypeptides and binding agents; detection reagents (e.g., probes, primers, antibodies, kits, capable, e.g., of specific detection of a fusion nucleic acid or protein); screening assays for identifying molecules that interact with, e.g., inhibit, fusions, e.g., novel kinase inhibitors or binders of FGFR2 or NTRK1.

Nucleic Acid Molecules

In one aspect, the invention features an isolated nucleic acid molecule, or an isolated preparation of nucleic acid molecules, that includes a genetic alteration disclosed herein. Such nucleic acid molecules or preparations thereof can include a genetic alteration described herein or can be used to detect, e.g., sequence, a genetic alteration disclosed herein. In other embodiments, the alteration of FGFR2 or NRTK1 is chosen from an alteration set forth in Table 1, FIGS. 1A-1C and FIGS. 2-17. In other embodiments, the fusion nucleic acid molecule is chosen from FGFR2-TACC3, FGFR2-KIAA1598, BICC1-FGFR2, FGFR2-BICC1, PARK2-FGFR2, FGFR2-NOL4, ZDHHC6-FGFR2, or RABGAP1L-NTRK1, e.g., as described, e.g., in Table 1, FIGS. 1A-1C and FIGS. 2-17.

Nucleic Acid Detection and Capturing Reagents

The invention also features a nucleic acid molecule, e.g., nucleic acid fragment, suitable as probe, primer, bait or library member that includes, flanks, hybridizes to, which are useful for identifying, or are otherwise based on, a fusion described herein. In certain embodiments, the probe, primer or bait molecule is an oligonucleotide that allows capture, detection or isolation of a fusion nucleic acid molecule described herein, e.g., a fusion of FGFR2 to a second gene, or fragment thereof, e.g., BICC1, KIAA1598, TACC3, PARK2, NOL4, or ZDHHC6-FGFR2; or a fusion of NTRK1 to a second gene, or a fragment thereof, e.g., RABGAP1L (e.g., as described in Table 1, FIGS. 1A-1C and FIGS. 2-17).

The oligonucleotide can comprise a nucleotide sequence substantially complementary to a fragment of a fusion between partners described herein nucleic acid molecules described herein. The sequence identity between the nucleic acid fragment, e.g., the oligonucleotide, and the target sequence need not be exact, so long as the sequences are sufficiently complementary to allow the capture, detection or isolation of the target sequence. In one embodiment, the nucleic acid fragment is a probe or primer that includes an oligonucleotide between about 5 and 25, e.g., between 10 and 20, or 10 and 15 nucleotides in length. In other embodiments, the nucleic acid fragment is a bait that includes an oligonucleotide between about 100 to 300 nucleotides, 130 and 230 nucleotides, or 150 and 200 nucleotides, in length.

In one embodiment, the nucleic acid fragment can be used to identify or capture, e.g., by hybridization, a fusion nucleic acid molecule described herein, e.g., a fusion of FGFR2 to a second gene, or fragment thereof, e.g., BICC1, KIAA1598, TACC3, PARK2, NOL4, or ZDHHC6; or a fusion of NTRK1 to a second gene, or a fragment thereof, e.g., RABGAP1L (e.g., as described in Table 1, FIGS. 1A-1C and FIGS. 2-17). For example, the nucleic acid fragment can be a probe, a primer, or a bait, for use in identifying or capturing, e.g., by hybridization, a fusion described herein. In one embodiment, the nucleic acid fragment can be useful for identifying or capturing a fusion breakpoint. In one embodiment, the nucleic acid fragment hybridizes to a nucleotide sequence that includes a breakpoint, e.g., a breakpoint of the fusion.

The probes or primers described herein can be used, for example, for FISH detection or PCR amplification. In one exemplary embodiment where detection is based on PCR, amplification of the fusion junction can be performed using a primer or a primer pair, e.g., for amplifying a sequence flanking the fusion junctions described herein, e.g., the mutations or the junction of a chromosomal rearrangement described herein.

In one embodiment, a pair of isolated oligonucleotide primers can amplify a region containing or adjacent to a position in the fusion. For example, reverse primers can be designed to hybridize to a nucleotide sequence within genomic or mRNA sequence of one partner, and the forward primers can be designed to hybridize to a nucleotide sequence within the other fusion partner.

In other embodiments, the nucleic acid fragment includes a bait that comprises a nucleotide sequence that hybridizes to a fusion nucleic acid molecule described herein, and thereby allows the capture or isolation said nucleic acid molecule. In one embodiment, a bait is suitable for solution phase hybridization. In other embodiments, a bait includes a binding entity, e.g., an affinity tag, that allows capture and separation, e.g., by binding to a binding entity, of a hybrid formed by a bait and a nucleic acid hybridized to the bait.

In other embodiments, the nucleic acid fragment includes a library member comprising a nucleic acid molecule described herein. In one embodiment, the library member includes a rearrangement that results in a fusion described herein.

The nucleic acid fragment can be detectably labeled with, e.g., a radiolabel, a fluorescent label, a bioluminescent label, a chemiluminescent label, an enzyme label, a binding pair label, or can include an affinity tag; a tag, or identifier (e.g., an adaptor, barcode or other sequence identifier).

Fusion Polypeptides

In another aspect, the invention features a fusion polypeptide (e.g., a purified fusion polypeptide), a biologically active or antigenic fragment thereof, as well as reagents (e.g., antibody molecules that bind to a fusion polypeptide), methods for modulating a fusion polypeptide activity and detection of a fusion polypeptide.

In certain embodiments, the fusion polypeptide is chosen from FGFR2-TACC3, FGFR2-KIAA1598, BICC1-FGFR2, FGFR2-BICC1, PARK2-FGFR2, FGFR2-NOL4, ZDHHC6-FGFR2, or RABGAP1L-NTRK1, e.g., as described, e.g., in Table 1, FIGS. 1A-1C and FIGS. 2-17.

In one embodiment, the fusion polypeptide has at least one biological activity of one or both of its partners.

In other embodiments, the nucleic acid molecule includes a nucleotide sequence encoding a fusion polypeptide that includes a fragment of a each partner of a fusion described herein.

In a related aspect, the invention features fusion polypeptide or fragments operatively linked to heterologous polypeptides to form fusion proteins.

In another embodiment, the fusion polypeptide or fragment is a peptide, e.g., an immunogenic peptide or protein, that contains a fusion junction described herein. Such immunogenic peptides or proteins can be used to raise antibodies specific to the fusion protein. In other embodiments, such immunogenic peptides or proteins can be used for vaccine preparation. The vaccine preparation can include other components, e.g., an adjuvant.

In another aspect, the invention features antibody molecules that binds to a fusion polypeptide or fragment described herein. In embodiments the antibody can distinguish wild type from fusion.

Detection Reagents and Detection of Mutations

In another aspect, the invention features a detection reagent, e.g., a purified or an isolated preparation thereof. Detection reagents can distinguish a nucleic acid, or protein sequence, having an alteration, e.g., a breakpoint, of a rearrangement, e.g., of a fusion nucleic acid molecule described herein. Exemplary fusions include a fusion of FGFR2 to a second gene, or fragment thereof, e.g., BICC1, KIAA1598, TACC3, PARK2, NOL4, or ZDHHC6; or a fusion of NTRK1 to a second gene, or a fragment thereof, e.g., RABGAP1L, e.g., as described, e.g., in Table 1, FIGS. 1A-1C and FIGS. 2-17.

Detection reagents, e.g., nucleic acid-based detection reagents, can be used to identify mutations in a target nucleic acid, e.g., DNA, e.g., genomic DNA or cDNA, or RNA, e.g., in a sample, e.g., a sample of nucleic acid derived from a cholangiocarcinoma. Detection reagents, e.g., antibody-based detection reagents, can be used to identify mutations in a target protein, e.g., in a sample, e.g., a sample of protein derived from, or produced by, a cholangiocarcinoma cell.

Nucleic Acid-Based Detection Reagents

In an embodiment, the detection reagent comprises a nucleic acid molecule, e.g., a DNA, RNA or mixed DNA/RNA molecule, comprising sequence which is complementary with a nucleic acid sequence on a target nucleic acid (the sequence on the target nucleic acid that is bound by the detection reagent is referred to herein as the "detection reagent binding site" and the portion of the detection reagent that corresponds to the detection reagent binding site is referred to as the "target binding site"). In an embodiment, the detection reagent binding site is disposed in relationship to the interrogation position such that binding (or in embodiments, lack of binding) of the detection reagent to the detection reagent binding site allows differentiation of mutant and reference sequences for an alteration described herein (e.g., an alteration or a fusion nucleic acid molecule described in Table 1, FIGS. 1A-1C and FIGS. 2-17), e.g., a fusion of FGFR2 to a second gene, or fragment thereof, e.g., BICC1, KIAA1598, TACC3, PARK2, NOL4, or ZDHHC6; or a fusion of NTRK1 to a second gene, or a fragment thereof, e.g., RABGAP1L), from a reference sequence. The detection reagent can be modified, e.g., with a label or other moiety, e.g., a moiety that allows capture.

In an embodiment, the detection reagent comprises a nucleic acid molecule, e.g., a DNA, RNA or mixed DNA/RNA molecule, which, e.g., in its target binding site, includes the interrogation position and which can distinguish (e.g., by affinity of binding of the detection reagent to a target nucleic acid or the ability for a reaction, e.g., a ligation or extension reaction with the detection reagent) between a mutation, e.g., a translocation described herein, and a reference sequence. In embodiments, the interrogation position can correspond to a terminal, e.g., to a 3' or 5' terminal nucleotide, a nucleotide immediately adjacent to a 3' or 5' terminal nucleotide, or to another internal nucleotide, of the detection reagent or target binding site.

In embodiments, the difference in the affinity of the detection reagent for a target nucleic acid comprising the mutant and that for a target nucleic acid comprising the reference sequence allows determination of the presence or absence of the mutation (or reference) sequence. Typically, such detection reagents, under assay conditions, will exhibit substantially higher levels of binding only to the mutant or only to the reference sequence, e.g., will exhibit substantial levels of binding only to the mutant or only to the reference sequence.

In embodiments, binding allows (or inhibits) a subsequent reaction, e.g., a subsequent reaction involving the detection reagent or the target nucleic acid. E.g., binding can allow ligation, or the addition of one or more nucleotides to a nucleic acid, e.g., the detection reagent, e.g., by DNA polymerase, which can be detected and used to distinguish mutant from reference. In embodiments, the interrogation position is located at the terminus, or sufficiently close to the terminus, of the detection reagent or its target binding site, such that hybridization, or a chemical reaction, e.g., the addition of one or more nucleotides to the detection reagent, e.g., by DNA polymerase, only occurs, or occurs at a substantially higher rate, when there is a perfect match between the detection reagent and the target nucleic acid at the interrogation position or at a nucleotide position within 1, 2, or 3 nucleotides of the interrogation position.

In an embodiment, the detection reagent comprises a nucleic acid, e.g., a DNA, RNA or mixed DNA/RNA molecule wherein the molecule, or its target binding site, is adjacent (or flanks), e.g., directly adjacent, to the interrogation position, and which can distinguish between a mutation, e.g., a translocation described herein, and a reference sequence, in a target nucleic acid.

In embodiments, the detection reagent binding site is adjacent to the interrogation position, e.g., the 5' or 3'terminal nucleotide of the detection reagent, or its target binding site, is adjacent, e.g., between 0 (directly adjacent) and 1,000, 500, 400, 200, 100, 50, 10, 5, 4, 3, 2, or 1 nucleotides from the interrogation position. In embodiments, the outcome of a reaction will vary with the identity of the nucleotide at the interrogation position allowing one to distinguish between mutant and reference sequences. E.g., in the presence of a first nucleotide at the interrogation position a first reaction will be favored over a second reaction. E.g., in a ligation or primer extension reaction, the product will differ, e.g., in charge, sequence, size, or susceptibility to a further reaction (e.g., restriction cleavage) depending on the identity of the nucleotide at the interrogation position. In embodiments the detection reagent comprises paired molecules (e.g., forward and reverse primers), allowing for amplification, e.g., by PCR amplification, of a duplex containing the interrogation position. In such embodiments, the presence of the mutation can be determined by a difference in the property of the amplification product, e.g., size, sequence, charge, or susceptibility to a reaction, resulting from a sequence comprising the interrogation position and a corresponding sequence having a reference nucleotide at the interrogation positions. In embodiments, the presence or absence of a characteristic amplification product is indicative of the identity of the nucleotide at the interrogation site and thus allows detection of the mutation.

In embodiments, the detection reagent, or its target binding site, is directly adjacent to the interrogation position, e.g., the 5' or 3'terminal nucleotide of the detection reagent is directly adjacent to the interrogation position. In embodiments, the identity of the nucleotide at the interrogation position will determine the nature of a reaction, e.g., a reaction involving the detection reagent, e.g., the modification of one end of the detection reagent. E.g., in the presence of a first nucleotide at the interrogation position a first reaction will be favored over a second reaction. By way of example, the presence of a first nucleotide at the interrogation position, e.g., a nucleotide associated with a mutation, can promote a first reaction, e.g., the addition of a complementary nucleotide to the detection reagent. By way of example, the presence of an A at the interrogation position will cause the incorporation of a T, having, e.g., a first colorimetric label, while the presence of a G and the interrogation position will cause the incorporation for a C, having, e.g., a second colorimetric label. In an embodiment, the presence of a first nucleotide at the nucleotide will result in ligation of the detection reagent to a second nucleic acid. E.g., a third nucleic acid can be hybridized to the target nucleic acid sufficiently close to the interrogation site that if the third nucleic acid has an exact match at the interrogation site it will be ligated to the detection reagent. Detection of the ligation product, or its absence, is indicative of the identity of the nucleotide at the interrogation site and thus allows detection of the mutation.

A variety of readouts can be employed. E.g., binding of the detection reagent to the mutant or reference sequence can be followed by a moiety, e.g., a label, associated with the detection reagent, e.g., a radioactive or enzymatic label. In embodiments the label comprises a quenching agent and a signaling agent and hybridization results in altering the distance between those two elements, e.g., increasing the distance and un-quenching the signaling agent. In embodiments, the detection reagent can include a moiety that allows separation from other components of a reaction mixture. In embodiments, binding allows cleavage of the bound detection reagent, e.g., by an enzyme, e.g., by the nuclease activity of the DNA polymerase or by a restriction enzyme. The cleavage can be detected by the appearance or disappearance of a nucleic acid or by the separation of a quenching agent and a signaling agent associated with the detection reagent. In embodiments, binding protects, or renders the target susceptible, to further chemical reaction, e.g., labeling or degradation, e.g., by restriction enzymes. In embodiments binding with the detection reagent allows capture separation or physical manipulation of the target nucleic acid to thereby allow for identification. In embodiments binding can result in a detectable localization of the detection reagent or target, e.g., binding could capture the target nucleic acid or displace a third nucleic acid. Binding can allow for determination of the presence of mutant or reference sequences with FISH, particularly in the case of rearrangements. Binding can allow for the extension or other size change in a component, e.g., the detection reagent, allowing distinction between mutant and reference sequences. Binding can allow for the production, e.g., by PCR, of an amplicon that distinguishes mutant from reference sequence.

In an embodiment the detection reagent, or the target binding site, is between 5 and 500, 5 and 300, 5 and 250, 5 and 200, 5 and 150, 5 and 100, 5 and 50, 5 and 25, 5 and 20, 5 and 15, or 5 and 10 nucleotides in length. In an embodiment the detection reagent, or the target binding site, is between 10 and 500, 10 and 300, 10 and 250, 10 and 200, 10 and 150, 10 and 100, 10 and 50, 10 and 25, 10 and 20, or 10 and 15, nucleotides in length. In an embodiment the detection reagent, or the target binding site, is between 20 and 500, 20 and 300, 20 and 250, 20 and 200, 20 and 150, 20 and 100, 20 and 50, or 20 and 25 nucleotides in length. In an embodiment the detection reagent, or the target binding site, is sufficiently long to distinguish between mutant and reference sequences and is less than 100, 200, 300, 400, or 500 nucleotides in length.

Preparations of Mutant Nucleic Acid and Uses Thereof

In another aspect, the invention features purified or isolated preparations of a neoplastic or tumor cell nucleic acid, e.g., DNA, e.g., genomic DNA or cDNA, or RNA, containing an interrogation position described herein, useful for determining if a mutation disclosed herein is present. The nucleic acid includes the interrogation position, and typically additional fusion sequence on one or both sides of the interrogation position. In addition the nucleic acid can contain heterologous sequences, e.g., adaptor or priming sequences, typically attached to one or both terminus of the nucleic acid. The nucleic acid also includes a label or other moiety, e.g., a moiety that allows separation or localization.

In embodiments, the nucleic acid is between 20 and 1,000, 30 and 900, 40 and 800, 50 and 700, 60 and 600, 70 and 500, 80 and 400, 90 and 300, or 100 and 200 nucleotides in length (with or without heterologous sequences). In one embodiment, the nucleic acid is between 40 and 1,000, 50 and 900, 60 and 800, 70 and 700, 80 and 600, 90 and 500, 100 and 400, 110 and 300, or 120 and 200 nucleotides in length (with or without heterologous sequences). In another embodiment, the nucleic acid is between 50 and 1,000, 50 and 900, 50 and 800, 50 and 700, 50 and 600, 50 and 500, 50 and 400, 50 and 300, or 50 and 200 nucleotides in length (with or without heterologous sequences). In embodiments, the nucleic acid is of sufficient length to allow sequencing (e.g., by chemical sequencing or by determining a difference in $T_m$ between mutant and reference preparations) but is optionally less than 100, 200, 300, 400, or 500 nucleotides in length (with or without heterologous sequences). Such preparations can be used to sequence nucleic acid from a sample, e.g., a neoplastic or tumor sample. In an embodiment the purified preparation is provided by in situ amplification of a nucleic acid provided on a substrate. In embodiments the purified preparation is spatially distinct from other nucleic acids, e.g., other amplified nucleic acids, on a substrate.

In an embodiment, the purified or isolated preparation of nucleic acid is derived from a cholangiocarcinoma.

Such preparations can be used to determine if a sample comprises mutant sequence, e.g., a translocation as described herein. In one embodiment, the translocation includes a breakpoint, e.g., a breakpoint in fusion nucleic acid molecule described herein, e.g., a fusion of FGFR2 to a second gene, or fragment thereof, e.g., BICC1, KIAA1598, TACC3, PARK2, NOL4, or ZDHHC6; or a fusion of NTRK1 to a second gene, or a fragment thereof, e.g., RABGAP1L (e.g., an alteration or a fusion nucleic acid molecule described in Table 1, FIGS. 1A-1C and FIGS. 2-17).

In another aspect, the invention features, a method of determining the sequence of an interrogation position for a mutation described herein, comprising:
providing a purified or isolated preparations of nucleic acid or fusion nucleic acid, e.g., DNA, e.g., genomic DNA or cDNA, or RNA, containing an interrogation position described herein, sequencing, by a method that breaks or forms a chemical bond, e.g., a covalent or non-covalent chemical bond, e.g., in a detection reagent or a target sequence, the nucleic acid so as to determine the identity of the nucleotide at an interrogation position. The method allows determining if a mutation described herein is present.

In an embodiment, sequencing comprises contacting the fusion nucleic acid with a detection reagent described herein.

In an embodiment, sequencing comprises determining a physical property, e.g., stability of a duplex form of the fusion nucleic acid, e.g., $T_m$, that can distinguish mutant from reference sequence.

In an embodiment, the fusion nucleic acid is derived from a cholangiocarcinoma.

Reaction Mixtures and Devices

In another aspect, the invention features, purified or isolated preparations of a fusion nucleic acid, e.g., DNA, e.g., genomic DNA or cDNA, or RNA, containing an interrogation position described herein, useful for determining if a mutation disclosed herein is present, disposed in sequencing device, or a sample holder for use in such a device. In an embodiment, the fusion nucleic acid is derived from a cholangiocarcinoma.

In another aspect, the invention features, purified or isolated preparations of a fusion nucleic acid, e.g., DNA, e.g., genomic DNA or cDNA, or RNA, containing an interrogation position described herein, useful for determining if a mutation disclosed herein is present, disposed in a device for determining a physical or chemical property, e.g., stability of a duplex, e.g., $T_m$ or a sample holder for use in such a device. In an embodiment, the device is a calorimeter. In an embodiment the fusion nucleic acid is derived from a cholangiocarcinoma.

The detection reagents described herein can be used to determine if a mutation described herein is present in a sample. In embodiments, the sample comprises a nucleic acid that is derived from a cholangiocarcinoma. The cell can be from a neoplastic or a tumor sample, e.g., a biopsy taken from the neoplasm or the tumor; from circulating tumor cells, e.g., from peripheral blood; or from a blood or plasma sample. In an embodiment, the fusion nucleic acid is derived from a cholangiocarcinoma.

Accordingly, in one aspect, the invention features a method of making a reaction mixture, comprising:
combining a detection reagent, or purified or isolated preparation thereof, described herein with a target nucleic acid derived from a cholangiocarcinoma which comprises a sequence having an interrogation position for a mutation described herein.

In another aspect, the invention features a reaction mixture, comprising:
a detection reagent, or purified or isolated preparation thereof, described herein; and
a target nucleic acid derived from a cholangiocarcinoma cell which comprises a sequence having an interrogation position for a mutation described herein.

In an embodiment of the reaction mixture, or the method of making the reaction mixture: the detection reagent comprises a nucleic acid, e.g., a DNA, RNA or mixed DNA/RNA, molecule which is complementary with a nucleic acid sequence on a target nucleic acid (the detection reagent binding site) wherein the detection reagent binding site is disposed in relationship to the interrogation position such that binding of the detection reagent to the detection reagent binding site allows differentiation of mutant and reference sequences for a mutant described herein.

In an embodiment of the reaction mixture, or the method of making the reaction mixture, the cholangiocarcinoma is as described herein.

In an embodiment of the reaction mixture, or the method of making the reaction mixture: the alteration, e.g., the mutation is an alteration, e.g., a mutation, described herein, including: a translocation, a deletion, an invention, a rearrangement, an amplification as described herein (e.g., an alteration as described in Table 1, FIGS. 1A-1C and FIGS.

2-17). In one embodiment, the alteration, e.g., mutation, is a fusion described herein, e.g., a fusion of FGFR2 to a second gene, or fragment thereof, e.g., BICC1, KIAA1598, TACC3, PARK2, NOL4 or ZDHHC6; or a fusion of NTRK1 to a second gene, or a fragment thereof, e.g., RABGAP1L).

An alteration, e.g., a mutation described herein, can be distinguished from a reference, e.g., a non-mutant or wild-type sequence, by reaction with an enzyme that reacts differentially with the mutation and the reference. E.g., they can be distinguished by cleavage with a restriction enzyme that has differing activity for the mutant and reference sequences. E.g., the invention includes a method of contacting a nucleic acid comprising an alteration, e.g., a mutation, described herein with such an enzyme and determining if a product of that cleavage which can distinguish mutant form reference sequence is present.

In one aspect the inventions provides, a purified preparation of a restriction enzyme cleavage product which can distinguish between mutant and reference sequence, wherein one end of the cleavage product is defined by an enzyme that cleaves differentially between mutant and reference sequence. In an embodiment, the cleavage product includes the interrogation position.

Protein-Based Detection Reagents, Methods, Reaction Mixtures and Devices

A mutant protein described herein can be distinguished from a reference, e.g., a non-mutant or wild-type protein, by reaction with a reagent, e.g., a substrate, e.g, a substrate for catalytic activity or functional activity, or an antibody, that reacts differentially with the mutant and reference protein. In one aspect, the invention includes a method of contacting a sample comprising a mutant protein described herein with such reagent and determining if the mutant protein is present in the sample.

In another embodiment, the invention features, an antibody that can distinguish a mutant protein described herein, e.g., a mutant protein corresponding to fusion described herein, e.g., a fusion of FGFR2 to a second gene, or fragment thereof, e.g., BICC1, KIAA1598, TACC3, PARK2, NOL4 or ZDHHC6, or a fusion of NTRK1 to a second gene, or a fragment thereof, e.g., RABGAP1L, or an associated mutation from a reference, e.g., a non-mutant or wildtype protein (e.g., a fusion polypeptide described in Table 1, FIGS. 1A-1C and FIGS. 2-17).

Accordingly, in one aspect, the invention features a method of making a reaction mixture comprising combining a detection reagent, or purified or isolated preparation thereof, e.g., a substrate, e.g., a substrate for phosphorylation or other activity, or an antibody, described herein with a target fusion protein derived from a cholangiocarcinoma cell which comprises a sequence having an interrogation position for a mutation described herein.

In another aspect, the invention features a reaction mixture, comprising:
a detection reagent, or purified or isolated preparation thereof, e.g., a substrate, e.g., a substrate for phosphorylation or other activity, or an antibody, described herein; and a target fusion protein derived from a cholangiocarcinoma cell which comprises a sequence having an interrogation position for a mutation described herein.

In an embodiment of the reaction mixture, or the method of making the reaction mixture the detection reagent comprises an antibody specific for a mutant fusion protein described herein.

In an embodiment of the reaction mixture, or the method of making the reaction mixture the cholangiocarcinoma cell.

In an embodiment of the reaction mixture, or the method of making the reaction mixture the mutation is a mutation described herein, including: a translocation event, e.g., a translocation as described herein. In one embodiment, the mutation is a breakpoint, found in a fusion described herein, e.g., a fusion of FGFR2 to a second gene, or fragment thereof, e.g., BICC1, KIAA1598, TACC3, PARK2, NOL4, or ZDHHC6; or a fusion of NTRK1 to a second gene, or a fragment thereof, e.g., RABGAP1L) (e.g., a fusion described in Table 1, FIGS. 1A-1C and FIGS. 2-17).

Kits

In another aspect, the invention features a kit comprising a detection reagent as described herein.

Screening Methods

In another aspect, the invention features a method, or assay, for screening for agents that modulate, e.g., inhibit, the expression or activity of fusion as described herein. The method includes contacting a fusion, or a cell expressing a fusion, with a candidate agent; and detecting a change in a parameter associated with a fusion, e.g., a change in the expression or an activity of the fusion. The method can, optionally, include comparing the treated parameter to a reference value, e.g., a control sample (e.g., comparing a parameter obtained from a sample with the candidate agent to a parameter obtained from a sample without the candidate agent). In one embodiment, if a decrease in expression or activity of the fusion is detected, the candidate agent is identified as an inhibitor. In another embodiment, if an increase in expression or activity of the fusion is detected, the candidate agent is identified as an activator. In certain embodiments, the fusion is a nucleic acid molecule or a polypeptide as described herein.

In one embodiment, the contacting step is effected in a cell-free system, e.g., a cell lysate or in a reconstituted system. In other embodiments, the contacting step is effected in a cell in culture, e.g., a cell expressing fusion (e.g., a mammalian cell, a tumor cell or cell line, a recombinant cell). In yet other embodiments, the contacting step is effected in a cell in vivo (a-expressing cell present in a subject, e.g., an animal subject (e.g., an in vivo animal model).

In certain embodiments, a method for screening for an agent that modulates, e.g., inhibits, the expression or activity of an FGFR2 or NTRK1 alteration, e.g., a fusion, from Table 1, FIGS. 1A-1C and FIGS. 2-17 is disclosed. The method includes:
optionally, determining if the alteration, e.g., fusion, is present;
contacting the alteration, e.g., fusion, (or a host cell expressing the alteration, e.g., fusion) with a candidate agent; and
detecting a change in a parameter associated with the alteration, e.g., fusion.

In an embodiment, the parameter is the expression or an activity of the FGFR2 or NTRK1 alteration, e.g., a fusion.

In other embodiments, the parameter is selected from one or more of:
(i) direct binding of the candidate agent to the FGFR2 or NTRK1 alteration, e.g., a fusion molecule (e.g., fusion polypeptide);
(ii) a change in kinase activity;
(iii) a change in an activity of a cell containing the alteration (e.g., the fusion), e.g., a change in proliferation, morphology or tumorigenicity of the cell;
(iv) a change in tumor present in an animal subject, e.g., size, appearance, proliferation, of the tumor; or (v) a change in the level, e.g., expression level, of the alteration, e.g., fusion polypeptide or nucleic acid molecule.

Exemplary parameters evaluated include one or more of:

(i) a change in binding activity, e.g., direct binding of the candidate agent to a fusion polypeptide; a binding competition between a known ligand and the candidate agent to a fusion polypeptide;

(ii) a change in kinase activity, e.g., phosphorylation levels of a fusion polypeptide (e.g., an increased or decreased autophosphorylation); or a change in a target of an fusion, In certain embodiments, a change in kinase activity, e.g., phosphorylation, is detected by any of Western blot (e.g., using an anti-fusion antibody, mass spectrometry, immunoprecipitation, immunohistochemistry, immunomagnetic beads, among others;

(iii) a change in an activity of a cell containing a fusion (e.g., a tumor cell or a recombinant cell), e.g., a change in proliferation, morphology or tumorigenicity of the cell;

(iv) a change in tumor present in an animal subject, e.g., size, appearance, proliferation, of the tumor; or (v) a change in the level, e.g., expression level, of a fusion polypeptide or nucleic acid molecule.

In one embodiment, a change in a cell free assay in the presence of a candidate agent is evaluated. For example, an activity of a fusion, or interaction of a fusion with a downstream ligand can be detected. In one embodiment, a fusion polypeptide is contacted with a ligand, e.g., in solution, and a candidate agent is monitored for an ability to modulate, e.g., inhibit, an interaction, e.g., binding, between the fusion polypeptide and the ligand.

In other embodiments, a change in an activity of a cell is detected in a cell in culture, e.g., a cell expressing a fusion (e.g., a mammalian cell, a tumor cell or cell line, a recombinant cell). In one embodiment, the cell is a recombinant cell that is modified to express a fusion nucleic acid, e.g., is a recombinant cell transfected with a fusion nucleic acid. The transfected cell can show a change in response to the expressed fusion, e.g., increased proliferation, changes in morphology, increased tumorigenicity, and/or acquired a transformed phenotype. A change in any of the activities of the cell, e.g., the recombinant cell, in the presence of the candidate agent can be detected. For example, a decrease in one or more of: proliferation, tumorigenicity, transformed morphology, in the presence of the candidate agent can be indicative of an inhibitor of a fusion. In other embodiments, a change in binding activity or phosphorylation as described herein is detected.

In yet other embodiment, a change in a tumor present in an animal subject (e.g., an in vivo animal model) is detected. In one embodiment, the animal model is a tumor containing animal or a xenograft comprising cells expressing a fusion (e.g., tumorigenic cells expressing a fusion). The candidate agent can be administered to the animal subject and a change in the tumor is detected. In one embodiment, the change in the tumor includes one or more of a tumor growth, tumor size, tumor burden, survival, is evaluated. A decrease in one or more of tumor growth, tumor size, tumor burden, or an increased survival is indicative that the candidate agent is an inhibitor.

In other embodiments, a change in expression of a fusion can be monitored by detecting the nucleic acid or protein levels, e.g., using the methods described herein.

In certain embodiments, the screening methods described herein can be repeated and/or combined. In one embodiment, a candidate agent that is evaluated in a cell-free or cell-based described herein can be further tested in an animal subject.

In one embodiment, the candidate agent is a small molecule compound, e.g., a kinase inhibitor, a nucleic acid (e.g., antisense, siRNA, aptamer, ribozymes, microRNA), an antibody molecule (e.g., a full antibody or antigen binding fragment thereof that binds to the fusion). The candidate agent can be obtained from a library (e.g., a commercial library of kinase inhibitors) or rationally designed.

Methods for Detecting Fusions

In another aspect, the invention features a method of determining the presence of a fusion as described herein. In one embodiment, the fusion is detected in a nucleic acid molecule or a polypeptide. The method includes detecting whether a fusion nucleic acid molecule or polypeptide is present in a cell (e.g., a circulating cell), a tissue (e.g., a tumor), or a sample, e.g., a tumor sample, from a subject. In one embodiment, the sample is a nucleic acid sample. In one embodiment, the nucleic acid sample comprises DNA, e.g., genomic DNA or cDNA, or RNA, e.g., mRNA. In other embodiments, the sample is a protein sample.

In one embodiment, the sample is, or has been, classified as non-malignant using other diagnostic techniques, e.g., immunohistochemistry.

In one embodiment, the sample is acquired from a subject (e.g., a subject having or at risk of having a cancer, e.g., a patient), or alternatively, the method further includes acquiring a sample from the subject. The sample can be chosen from one or more of: tissue, e.g., cancerous tissue (e.g., a tissue biopsy), whole blood, serum, plasma, buccal scrape, sputum, saliva, cerebrospinal fluid, urine, stool, circulating tumor cells, circulating nucleic acids, or bone marrow. In certain embodiments, the sample is a tissue (e.g., a tumor biopsy), a circulating tumor cell or nucleic acid.

In embodiments, the tumor is from a cancer described herein, e.g., is chosen from a cholangiocarcinoma, e.g., an intrahepatic or an extrahepatic cholangiocarcinoma.

In one embodiment, the subject is at risk of having, or has a cholangiocarcinoma.

In other embodiments, the fusion is detected in a nucleic acid molecule by a method chosen from one or more of: nucleic acid hybridization assay, amplification-based assays (e.g., polymerase chain reaction (PCR)), PCR-RFLP assay, real-time PCR, sequencing, screening analysis (including metaphase cytogenetic analysis by standard karyotype methods, FISH (e.g., break away FISH), spectral karyotyping or MFISH, comparative genomic hybridization), in situ hybridization, SSP, HPLC or mass-spectrometric genotyping.

In one embodiment, the method includes: contacting a nucleic acid sample, e.g., a genomic DNA sample (e.g., a chromosomal sample or a fractionated, enriched or otherwise pre-treated sample) or a gene product (mRNA, cDNA), obtained from the subject, with a nucleic acid fragment (e.g., a probe or primer as described herein (e.g., an exon-specific probe or primer) under conditions suitable for hybridization, and determining the presence or absence of the fusion nucleic acid molecule. The method can, optionally, include enriching a sample for the gene or gene product.

In a related aspect, a method for determining the presence of a fusion nucleic acid molecule is provided. The method includes: acquiring a sequence for a position in a nucleic acid molecule, e.g., by sequencing at least one nucleotide of the nucleic acid molecule (e.g., sequencing at least one nucleotide in the nucleic acid molecule that comprises the fusion), thereby determining that the fusion is present in the nucleic acid molecule. Optionally, the sequence acquired is compared to a reference sequence, or a wild type reference sequence. In one embodiment, the nucleic acid molecule is from a cell (e.g., a circulating cell), a tissue (e.g., a cholangiocarcinoma), or any sample from a subject (e.g., blood or plasma sample). In other embodiments, the nucleic acid molecule from a tumor sample (e.g., a tumor or cancer sample) is sequenced. In one embodiment, the sequence is determined by a next generation sequencing method. The method further can further include acquiring, e.g., directly or indirectly acquiring, a sample, e.g., a cholangiocarcinoma.

In another aspect, the invention features a method of analyzing a tumor or a circulating tumor cell. The method includes acquiring a nucleic acid sample from the tumor or the circulating cell; and sequencing, e.g., by a next generation sequencing method, a nucleic acid molecule, e.g., a nucleic acid molecule that includes a fusion as described herein.

In yet other embodiment, a fusion polypeptide is detected. The method includes: contacting a protein sample with a reagent which specifically binds to a fusion polypeptide; and detecting the formation of a complex of the fusion polypeptide and the reagent. In one embodiment, the reagent is labeled with a detectable group to facilitate detection of the bound and unbound reagent. In one embodiment, the reagent is an antibody molecule, e.g., is selected from the group consisting of an antibody, and antibody derivative, and an antibody fragment.

In yet another embodiment, the level (e.g., expression level) or activity the fusion is evaluated. For example, the level (e.g., expression level) or activity of the fusion (e.g., mRNA or polypeptide) is detected and (optionally) compared to a pre-determined value, e.g., a reference value (e.g., a control sample).

In yet another embodiment, the fusion is detected prior to initiating, during, or after, a treatment in a subject having a fusion.

In one embodiment, the fusion is detected at the time of diagnosis with a cancer. In other embodiment, the fusion is detected at a pre-determined interval, e.g., a first point in time and at least at a subsequent point in time.

In certain embodiments, responsive to a determination of the presence of the fusion, the method further includes one or more of:
(1) stratifying a patient population (e.g., assigning a subject, e.g., a patient, to a group or class);
(2) identifying or selecting the subject as likely or unlikely to respond to a treatment, e.g., a kinase inhibitor treatment as described herein;
(3) selecting a treatment option, e.g., administering or not administering a preselected therapeutic agent, e.g., a kinase inhibitor as described herein; or
(4) prognosticating the time course of the disease in the subject (e.g., evaluating the likelihood of increased or decreased patient survival).

In certain embodiments, responsive to the determination of the presence of a fusion, the subject is classified as a candidate to receive treatment with a therapy disclosed herein, e.g., from Table 2. In one embodiment, responsive to the determination of the presence of a fusion, the subject, e.g., a patient, can further be assigned to a particular class if a fusion is identified in a sample of the patient. For example, a patient identified as having a fusion can be classified as a candidate to receive treatment with a therapy disclosed herein, e.g., from Table 2. In one embodiment, the subject, e.g., a patient, is assigned to a second class if the mutation is not present. For example, a patient who has a tumor that does not contain a fusion, may be determined as not being a candidate to receive a therapy disclosed herein, e.g., from Table 2.

In another embodiment, responsive to the determination of the presence of the fusion, the subject is identified as likely to respond to a treatment that comprises a therapy disclosed herein, e.g., from Table 2.

In yet another embodiment, responsive to the determination of the presence of the fusion, the method includes administering a kinase inhibitor, e.g., a kinase inhibitor as described herein, to the subject.

Method of Evaluating a Tumor or a Subject

In another aspect, the invention features a method of evaluating a subject (e.g., a patient), e.g., for risk of having or developing a cancer, e.g., cholangiocarcinoma, e.g., a intrahepatic cholangiocarcinoma (ICC). The method includes: acquiring information or knowledge of the presence of a fusion as described herein in a subject (e.g., acquiring genotype information of the subject that identifies a fusion as being present in the subject); acquiring a sequence for a nucleic acid molecule identified herein (e.g., a nucleic acid molecule that includes a fusion sequence); or detecting the presence of a fusion nucleic acid or polypeptide in the subject), wherein the presence of the fusion is positively correlated with increased risk for, or having, a cancer associated with such a fusion.

The method can further include acquiring, e.g., directly or indirectly, a sample from a patient and evaluating the sample for the present of a fusion as described herein.

The method can further include the step(s) of identifying (e.g., evaluating, diagnosing, screening, and/or selecting) the subject as being positively correlated with increased risk for, or having, a cancer associated with the fusion.

In another embodiment, a subject identified has having a fusion is identified or selected as likely or unlikely to respond to a treatment, e.g., a therapy disclosed herein, e.g., from Table 2. The method can further include treating the subject with a therapy disclosed herein, e.g., from Table 2.

In a related aspect, a method of evaluating a patient or a patient population is provided. The method includes: identifying, selecting, or obtaining information or knowledge that the patient or patient population has participated in a clinical trial; acquiring information or knowledge of the presence of a fusion in the patient or patient population (e.g., acquiring genotype information of the subject that identifies a fusion as being present in the subject); acquiring a sequence for a nucleic acid molecule identified herein (e.g., a nucleic acid molecule that includes a fusion sequence); or detecting the presence of a fusion nucleic acid or polypeptide in the subject), wherein the presence of the fusion identifies the patient or patient population as having an increased risk for, or having, a cholangiocarcinoma associated with the fusion.

In some embodiments, the method further includes treating the subject with an inhibitor, e.g., a kinase inhibitor as described herein.

Reporting

Methods described herein can include providing a report, such as, in electronic, web-based, or paper form, to the patient or to another person or entity, e.g., a caregiver, e.g., a physician, e.g., an oncologist, a hospital, clinic, third-party payor, insurance company or government office. The report can include output from the method, e.g., the identification of nucleotide values, the indication of presence or absence of a fusion as described herein, or wildtype sequence. In one embodiment, a report is generated, such as in paper or electronic form, which identifies the presence or absence of an alteration described herein, and optionally includes an identifier for the patient from which the sequence was obtained.

The report can also include information on the role of a fusion as described herein, or wild-type sequence, in disease. Such information can include information on prognosis, resistance, or potential or suggested therapeutic options. The report can include information on the likely effectiveness of a therapeutic option, the acceptability of a therapeutic option, or the advisability of applying the therapeutic option to a patient, e.g., a patient having a sequence, alteration or mutation identified in the test, and in embodiments, identified in the report. For example, the report can include information, or a recommendation on, the administration of a drug, e.g., the administration at a preselected dosage or in a preselected treatment regimen, e.g., in combination with other drugs, to the patient. In an embodiment, not all mutations identified in the method are identified in the report. For example, the report can be limited to mutations in genes having a preselected level of correlation with the occurrence, prognosis, stage, or susceptibility of the cancer to treatment, e.g., with a preselected therapeutic option. The report can be delivered, e.g., to an entity described herein, within 7, 14, or 21 days from receipt of the sample by the entity practicing the method.

In another aspect, the invention features a method for generating a report, e.g., a personalized cancer treatment report, by obtaining a sample, e.g., a tumor sample, from a subject, detecting a fusion as described herein in the sample, and selecting a treatment based on the mutation identified. In one embodiment, a report is generated that annotates the selected treatment, or that lists, e.g., in order of preference, two or more treatment options based on the mutation identified. In another embodiment, the subject, e.g., a patient, is further administered the selected method of treatment.

Unless otherwise defined, all technical and scientific terms used herein have the same meaning as commonly understood by one of ordinary skill in the art to which this invention belongs. Although methods and materials similar or equivalent to those described herein can be used in the practice or testing the invention, suitable methods and materials are described below. All publications, patent applications, patents, and other references mentioned herein are incorporated by reference in their entirety. In case of conflict, the present specification, including definitions, will control. In addition, the materials, methods, and the example are illustrative only and not intended to be limiting.

The details of one or more embodiments featured in the invention are set forth in the accompanying drawings and the description below. Other features, objects, and advantages featured in the invention will be apparent from the description and drawings, and from the claims.

BRIEF DESCRIPTION OF DRAWINGS

FIGS. 1A-1C are tables summarizing the fusion molecules and the rearrangement events described herein.

FIG. 1A summarizes the following: the name of the fusion (referred to as "fusion"); the tissue source (referred to as "disease"); the approximate locations of the first and second breakpoints that give rise to the rearrangement events (±50 nucleotides) (referred to as "Breakpoint 1" and "Breakpoint 2," respectively); and the type of rearrangement (referred to as "rearrangement").

FIG. 1B summarizes the following: the name of the fusion (referred to as "fusion"); the accession number of the full length sequences that contain the 5'- and the 3'-exon sequences (referred to as "5' Transcript ID" and "3' Transcript ID," respectively); and the identity of the exon(s) of the 5' transcript and the exon(s) of the 3' transcript. The sequences corresponding to the accession numbers provided in FIG. 1B are set forth in the figures appended herein. Alternatively, the sequences can be found by searching the RefSeq Gene as databased at UCSC Genome Browser (genome.ucsc.edu). For example, the following link can be used: http://genome.ucsc.edu/cgi-bin/hgc?hgsid=359255927&c=chr10&o=123237843&t=123356159&g=refGene&i=NM_001144915 to search for Accession Number=NM_001144915.

FIG. 1C summarizes the following: the name of the fusion; the SEQ ID NOs. of the 5' partner and the 3' partner; and the figure in which the sequence is shown. For example, the Nt and Aa sequences of FGFR2 have SEQ ID NOs: 1 and 2, respectively, which are shown in FIGS. 2 and 3, respectively. The Nt and Aa sequences of TACC3 have SEQ ID NOs: 3 and 4, which are shown in FIGS. 4 and 5, respectively.

FIGS. 2A-2B depict the nucleotide sequence of FGFR2 cDNA (NM_001144915, SEQ ID NO: 1). The exon boundaries are shown in bold and underlined. The start of the first exon and the end of the last exon are shown by a single underline (e.g., shown as A). Further exons (second, third, fourth and so on) are indicated consecutively from 5' to 3' orientation by the underline of two consecutive nucleotides. For example, nucleotides GT at positions 169-170 correspond to the 3'-end of the first exon at position G, and the 5'-start of the second exon is at position T. The start codon is shown in bold and italics. The stop codon is shown in italics and underlined.

FIG. 3 depicts the amino acid sequence of FGFR2 (SEQ ID NO: 2).

FIGS. 4A-4B depict the nucleotide sequence of TACC3 cDNA (NM_006342, SEQ ID NO: 3). The exon boundaries are shown in bold and underlined. The start of the first exon is shown by a single underline. Further exons (second, third, fourth) are indicated consecutively from 5' to 3' orientation by the underline of two consecutive nucleotides (as exemplified in FIGS. 2A-2B above). The start codon is shown in bold and italics. The stop codon is shown in italics and underlined.

FIG. 5 depicts the amino acid sequence of TACC3 (SEQ ID NO: 4).

FIGS. 6A-6C depict the nucleotide sequence of KIAA1598 cDNA (NM_001127211, SEQ ID NO: 5). The exon boundaries are shown in bold and underlined. The start of the first exon is shown by a single underline. Further exons (second, third, fourth) are indicated consecutively from 5' to 3' orientation by the underline of two consecutive nucleotides (as exemplified in FIGS. 2A-2B above). The start codon is shown in bold and italics. The stop codon is shown in italics and underlined.

FIG. 7 depicts the amino acid sequence of KIAA1598 (SEQ ID NO: 6).

FIGS. 8A-8B depict the nucleotide sequence of BICC1 cDNA (NM_001080512, SEQ ID NO: 7). The exon boundaries are shown in bold and underlined. The start of the first exon is shown by a single underline. Further exons (second, third, fourth) are indicated consecutively from 5' to 3' orientation by the underline of two consecutive nucleotides (as exemplified in FIGS. 2A-2B above). The start codon is shown in bold and italics. The stop codon is shown in italics and underlined.

FIG. 9 depicts the amino acid sequence of BICC1 (SEQ ID NO: 8).

FIGS. 10A-10B depict the nucleotide sequence of PARK2 cDNA (NM_004562, SEQ ID NO: 9). The exon boundaries are shown in bold and underlined. The start of the first exon is shown by a single underline. Further exons (second, third, fourth) are indicated consecutively from 5' to 3' orientation by the underline of two consecutive nucleotides (as exemplified in FIGS. 2A-2B above). The start codon is shown in bold and italics. The stop codon is shown in italics and underlined.

FIG. 11 depicts the amino acid sequence of PARK2 (SEQ ID NO: 10).

FIGS. 12A-12B depict the nucleotide sequence of FGFR2 cDNA (NM_000141, SEQ ID NO: 11). The exon boundaries are shown in bold and underlined. The start of the first exon is shown by a single underline. Further exons (second, third, fourth) are indicated consecutively from 5' to 3' orientation by the underline of two consecutive nucleotides (as exemplified in FIGS. 2A-2B above). The start codon is shown in bold and italics. The stop codon is shown in italics and underlined.

FIG. 13 depicts the amino acid sequence of FGFR2 (SEQ ID NO: 12).

FIGS. 14A-14B depict the nucleotide sequence of NOL4 cDNA (NM_003787, SEQ ID NO: 13). The exon boundaries are shown in bold and underlined. The start of the first exon is shown by a single underline. Further exons (second, third, fourth) are indicated consecutively from 5' to 3' orientation by the underline of two consecutive nucleotides (as exemplified in FIGS. 2A-2B above). The start codon is shown in bold and italics. The stop codon is shown in italics and underlined.

FIG. 15 depicts the amino acid sequence of NOL4 (SEQ ID NO: 14).

FIG. 16 depicts the nucleotide sequence of ZDHHC6 cDNA (NM_022494, SEQ ID NO: 15). The exon boundaries are shown in bold and underlined. The start of the first exon is shown by a single underline. Further exons (second, third, fourth) are indicated consecutively from 5' to 3' orientation by the underline of two consecutive nucleotides (as exemplified in FIGS. 2A-2B above). The start codon is shown in bold and italics. The stop codon is shown in italics and underlined.

FIG. 17 depicts the amino acid sequence of ZDHHC6 (SEQ ID NO: 16).

DETAILED DESCRIPTION

Described herein are novel alterations, e.g., rearrangement events, found in cholangiocarcinomas. In certain embodiments, the rearrangement events are found in an FGFR2 gene or an NTRK gene, e.g., as exemplified in Table 1, FIGS. 1A-1C and FIGS. 2-17. In certain embodiments, the novel rearrangement events give rise to fusion molecules that includes a fragment of a first gene and a fragment of a second gene, e.g., a fusion that includes a 5'-exon and a 3'-exon summarized in FIGS. 1A-1C and FIGS. 2-17. The term "fusion" or "fusion molecule" is used generically herein, and includes any fusion molecule (e.g., gene, gene product (e.g., cDNA, mRNA, or polypeptide), and variant thereof) that includes a fragment of first gene and a fragment of second gene described herein, including, e.g., an FGFR2-TACC3, FGFR2-KIAA1598, BICC1-FGFR2, FGFR2-BICC1, PARK2-FGFR2, FGFR2-NOL4, ZDHHC6-FGFR2, or RABGAP1L-NTRK1, e.g., as described in Table 1, FIGS. 1A-1C and FIGS. 2-17. Expression of the fusion molecules was detected in cholangiocarcinomas, thus suggesting an association with neoplastic growth or cancer (including pre-malignant, or malignant and/or metastatic growth).

Cholangiocarcinoma (also known as bile duct cancer) can arise from the tissues in the bile duct. Cholangiocarcinoma can occur in any part of the bile duct. The part of the tube that is outside of the liver is called extrahepatic. It is in this portion of the bile duct where cancer usually arises. A perihilar cancer, also called a Klatskin tumor, begins where many small channels join into the bile duct at the point where it leaves the liver. About two-thirds of all cholangiocarcinomas occur here. Distal cholangiocarcinoma occurs at the opposite end of the duct from perihilar cancer, near where the bile duct empties into the small intestine. About one-fourth of all cholangiocarcinomas are distal cholangiocarcinomas. About 5% to 10% of cholangiocarcinomas are intrahepatic, or inside the liver. Adenocarcinoma is the most common type of extrahepatic cholangiocarcinoma, and accounting for up to 95% of all cholangiocarcinomas. Adenocarcinoma is cancer arising from the mucus glands lining the inside of the bile duct. Cholangiocarcinoma is another term that may be used to describe this type of cancer.

Accordingly, the invention provides, at least in part, the following: methods for treating a cholangiocarcinoma using an inhibitor of one of the alterations described herein, e.g., an FGFR2 or an NTRK1 inhibitor; methods for identifying, assessing or detecting an alteration, e.g., fusion molecule as described herein; methods for identifying, assessing, evaluating, and/or treating a subject having a cancer, e.g., a cholangiocarcinoma having a fusion molecule as described herein; isolated fusion nucleic acid molecules, nucleic acid constructs, host cells containing the nucleic acid molecules; purified fusion polypeptides and binding agents; detection reagents (e.g., probes, primers, antibodies, kits, capable, e.g., of specific detection of a fusion nucleic acid or protein); screening assays for identifying molecules that interact with, e.g., inhibit, the fusions, e.g., novel kinase inhibitors; as well as assays and kits for evaluating, identifying, assessing and/or treating a subject having a cancer, e.g., a cholangiocarcinoma having a fusion. The compositions and methods identified herein can be used, for example, to identify new inhibitors; to evaluate, identify or select a subject, e.g., a patient, having a cancer; and to treat or prevent a cancer, such as a cholangiocarcinoma.

Certain terms are defined. Additional terms are defined throughout the specification.

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

"Acquire" or "acquiring" as the terms are used herein, refer to obtaining possession of a physical entity, or a value, e.g., a numerical value, by "directly acquiring" or "indirectly acquiring" the physical entity or value. "Directly acquiring" means performing a process (e.g., performing a synthetic or analytical method) to obtain the physical entity or value. "Indirectly acquiring" refers to receiving the physical entity or value from another party or source (e.g., a third party laboratory that directly acquired the physical entity or value). Directly acquiring a physical entity includes performing a process that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent.

"Acquiring a sequence" as the term is used herein, refers to obtaining possession of a nucleotide sequence or amino acid sequence, by "directly acquiring" or "indirectly acquiring" the sequence. "Directly acquiring a sequence" means performing a process (e.g., performing a synthetic or analytical method) to obtain the sequence, such as performing a sequencing method (e.g., a Next Generation Sequencing (NGS) method). "Indirectly acquiring a sequence" refers to receiving information or knowledge of, or receiving, the sequence from another party or source (e.g., a third party laboratory that directly acquired the sequence). The sequence acquired need not be a full sequence, e.g., sequencing of at least one nucleotide, or obtaining information or knowledge, that identifies a fusion disclosed herein as being present in a subject constitutes acquiring a sequence.

Directly acquiring a sequence includes performing a process that includes a physical change in a physical substance, e.g., a starting material, such as a tissue sample, e.g., a biopsy, or an isolated nucleic acid (e.g., DNA or RNA) sample. Exemplary changes include making a physical entity from two or more starting materials, shearing or fragmenting a substance, such as a genomic DNA fragment; separating or purifying a substance (e.g., isolating a nucleic acid sample from a tissue); combining two or more separate entities into a mixture, performing a chemical reaction that includes breaking or forming a covalent or non-covalent bond. Directly acquiring a value includes performing a process that includes a physical change in a sample or another substance as described above.

"Acquiring a sample" as the term is used herein, refers to obtaining possession of a sample, e.g., a tissue sample or nucleic acid sample, by "directly acquiring" or "indirectly acquiring" the sample. "Directly acquiring a sample" means performing a process (e.g., performing a physical method such as a surgery or extraction) to obtain the sample. "Indirectly acquiring a sample" refers to receiving the sample from another party or source (e.g., a third party laboratory that directly acquired the sample). Directly acquiring a sample includes performing a process that includes a physical change in a physical substance, e.g., a starting material, such as a tissue, e.g., a tissue in a human patient or a tissue that has was previously isolated from a patient. Exemplary changes include making a physical entity from a starting material, dissecting or scraping a tissue; separating or purifying a substance (e.g., a sample tissue or a nucleic acid sample); combining two or more separate entities into a mixture; performing a chemical reaction that includes breaking or forming a covalent or non-covalent bond. Directly acquiring a sample includes performing a process that includes a physical change in a sample or another substance, e.g., as described above.

"Binding entity" means any molecule to which molecular tags can be directly or indirectly attached that is capable of specifically binding to an analyte. The binding entity can be an affinity tag on a nucleic acid sequence. In certain embodiments, the binding entity allows for separation of the nucleic acid from a mixture, such as an avidin molecule, or an antibody that binds to the hapten or an antigen-binding fragment thereof. Exemplary binding entities include, but are not limited to, a biotin molecule, a hapten, an antibody, an antibody binding fragment, a peptide, and a protein.

"Complementary" refers to sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In certain embodiments, the first region comprises a first portion and the second region comprises a second portion, whereby, when the first and second portions are arranged in an antiparallel fashion, at least about 50%, at least about 75%, at least about 90%, or at least about 95% of the nucleotide residues of the first portion are capable of base pairing with nucleotide residues in the second portion. In other embodiments, all nucleotide residues of the first portion are capable of base pairing with nucleotide residues in the second portion.

The term "cancer" or "tumor" is used interchangeably herein. These terms refer to the presence of cells possessing characteristics typical of cancer-causing cells, such as uncontrolled proliferation, immortality, metastatic potential, rapid growth and proliferation rate, and certain characteristic morphological features. In one embodiment, the cancer is a cholangiocarcinoma.

The term "neoplasm" or "neoplastic" cell refers to an abnormal proliferative stage, e.g., a hyperproliferative stage, in a cell or tissue that can include a benign, pre-malignant, malignant (cancer) or metastatic stage.

Cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

"Chemotherapeutic agent" means a chemical substance, such as a cytotoxic or cytostatic agent, that is used to treat a condition, particularly cancer.

As used herein, "cancer therapy" and "cancer treatment" are synonymous terms.

As used herein, "chemotherapy" and "chemotherapeutic" and "chemotherapeutic agent" are synonymous terms.

The terms "homology" or "identity," as used interchangeably herein, refer to sequence similarity between two polynucleotide sequences or between two polypeptide sequences, with identity being a more strict comparison. The phrases "percent identity or homology" and "% identity or homology" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value there between. Identity or similarity can be determined by comparing a position in each sequence that can be aligned for purposes of comparison. When a position in the compared sequence is occupied by the same nucleotide base or amino acid, then the molecules are identical at that position. A degree of similarity or identity between polynucleotide sequences is a function of the number of identical or matching nucleotides at positions shared by the polynucleotide sequences. A degree of identity of polypeptide sequences is a function of the number of identical amino acids at positions shared by the polypeptide sequences. A degree of homology or similarity of polypeptide sequences is a function of the number of amino acids at positions shared by the polypeptide sequences. The term "substantially identical," as used herein, refers to an identity or homology of at least 75%, at least 80%, at least 85%, at least 90%, 91%, 92%, 93%, 94%, 95%, 96%, 97%, 98%, 99%, or more.

"Likely to" or "increased likelihood," as used herein, refers to an increased probability that an item, object, thing or person will occur. Thus, in one example, a subject that is likely to respond to treatment with a kinase inhibitor, alone or in combination, has an increased probability of responding to treatment with the inhibitor alone or in combination, relative to a reference subject or group of subjects.

"Unlikely to" refers to a decreased probability that an event, item, object, thing or person will occur with respect to a reference. Thus, a subject that is unlikely to respond to treatment with a kinase inhibitor, alone or in combination, has a decreased probability of responding to treatment with a kinase inhibitor, alone or in combination, relative to a reference subject or group of subjects.

"Sequencing" a nucleic acid molecule requires determining the identity of at least 1 nucleotide in the molecule. In embodiments, the identity of less than all of the nucleotides in a molecule are determined. In other embodiments, the identity of a majority or all of the nucleotides in the molecule is determined.

"Next-generation sequencing or NGS or NG sequencing" as used herein, refers to any sequencing method that determines the nucleotide sequence of either individual nucleic acid molecules (e.g., in single molecule sequencing) or clonally expanded proxies for individual nucleic acid molecules in a highly parallel fashion (e.g., greater than $10^5$ molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. (2010) *Nature Biotechnology Reviews* 11:31-46, incorporated herein by reference. Next generation sequencing can detect a variant present in less than 5% of the nucleic acids in a sample.

"Sample," "tissue sample," "patient sample," "patient cell or tissue sample" or "specimen" each refers to a collection of similar cells obtained from a tissue of a subject or patient. The source of the tissue sample can be solid tissue as from a fresh, frozen and/or preserved organ, tissue sample, biopsy, or aspirate; blood or any blood constituents; bodily fluids such as cerebral spinal fluid, amniotic fluid, peritoneal fluid or interstitial fluid; or cells from any time in gestation or development of the subject. The tissue sample can contain compounds that are not naturally intermixed with the tissue in nature such as preservatives, anticoagulants, buffers, fixatives, nutrients, antibiotics or the like. In one embodiment, the sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample.

A "tumor nucleic acid sample" as used herein, refers to nucleic acid molecules from a tumor or cancer sample. Typically, it is DNA, e.g., genomic DNA, or cDNA derived from RNA, from a tumor or cancer sample. In certain embodiments, the tumor nucleic acid sample is purified or isolated (e.g., it is removed from its natural state).

A "control" or "reference" "nucleic acid sample" as used herein, refers to nucleic acid molecules from a control or reference sample. Typically, it is DNA, e.g., genomic DNA, or cDNA derived from RNA, not containing the alteration or variation in the gene or gene product, e.g., not containing a fusion. In certain embodiments, the reference or control nucleic acid sample is a wild type or a non-mutated sequence. In certain embodiments, the reference nucleic acid sample is purified or isolated (e.g., it is removed from its natural state). In other embodiments, the reference nucleic acid sample is from a non-tumor sample, e.g., a blood control, a normal adjacent tumor (NAT), or any other non-cancerous sample from the same or a different subject.

"Adjacent to the interrogation position," as used herein, means that a site sufficiently close such that a detection reagent complementary with the site can be used to distinguish between a mutation, e.g., a mutation described herein, and a reference sequence, e.g., a non-mutant or wild-type sequence, in a target nucleic acid. Directly adjacent, as used herein, is where 2 nucleotides have no intervening nucleotides between them.

"Associated mutation," as used herein, refers to a mutation within a preselected distance, in terms of nucleotide or primary amino acid sequence, from a definitional mutation, e.g., a mutant as described herein, e.g., a translocation, breakpoint or fusion molecule described herein. In embodiments, the associated mutation is within n, wherein n is 2, 5, 10, 20, 30, 50, 100, or 200 nucleotides from the definitional mutation (n does not include the nucleotides defining the associated and definitional mutations). In embodiments, the associated mutation is a translocation mutation.

"Interrogation position," as used herein, comprises at least one nucleotide (or, in the case of polypeptides, an amino acid residue) which corresponds to a nucleotide (or amino acid residue) that is mutated in a mutation of interest, e.g., a mutation being identified, or in a nucleic acid (or protein) being analyzed, e.g., sequenced, or recovered.

A "reference sequence," as used herein, e.g., as a comparator for a mutant sequence, is a sequence which has a different nucleotide or amino acid at an interrogation position than does the mutant(s) being analyzed. In an embodiment, the reference sequence is wild-type for at least the interrogation position.

Headings, e.g., (a), (b), (i) etc, are presented merely for ease of reading the specification and claims. The use of headings in the specification or claims does not require the steps or elements be performed in alphabetical or numerical order or the order in which they are presented.

Various aspects featured in the invention are described in further detail below. Additional definitions are set out throughout the specification.

FGFR2 and NTRK1 Alterations

Described herein are novel rearrangements of the FGFR2 and NTRK1 genes in cholangiocarcinomas.

FGFR2 Alterations

The FGFR family plays an important role in cell differentiation, growth and angiogenesis (reviewed in Powers et al. (2000), *Endocr. Relat. Cancer*, 7(3):165-197, and gain of function mutations in FGFRs have been reported in several cancer types (reviewed in Eswarakumar et al. (2005), *Cytokine Growth Factor Rev.*, 16(2):139-149).

FGFR2 (Fibroblast growth factor receptor 2) is a member of the fibroblast growth factor receptor family, where amino acid sequence is highly conserved between members and throughout evolution. FGFR family members differ from one another in their ligand affinities and tissue distribution. A full-length representative protein consists of an extracellular region, composed of three immunoglobulin-like domains, a single hydrophobic membrane-spanning segment and a cytoplasmic tyrosine kinase domain. FGFR2 is composed of three immunoglobulin c-2 type domains, one transmembrane domain, and one tyrosine kinase catalytic domain. The extracellular portion of the protein interacts with fibroblast growth factors, setting in motion a cascade of downstream signals, ultimately influencing mitogenesis and differentiation. This particular family member is a high-affinity receptor for acidic, basic and/or keratinocyte growth factor, depending on the isoform. Multiple alternatively spliced transcript variants encoding different isoforms have been noted for the FGFR2 gene. The FGFR2 amino and nucleotide sequences are known in the art. Exemplary sequences for human FGFR2 are provided herein as SEQ ID NOs:1 and 11, and FIGS. 2 and 12 (nucleotide), and SEQ ID NOs:2 and 12, and FIGS. 3 and 13 (amino acid).

FGFR2 amplification has been reported in several cancer types, most frequently in gastric cancer (3-4%) (Matsumoto et al., 2012, *Br. J. Cancer*, 106(4):727-732, Hara et al., 1998, *Lab Invest.*, 78(9):1143-1153) and breast cancer (1-11%) (Heiskanen et al., 2001, *Anal Cell Pathol.* 22(4):229-234, Adnane et al., 1991; *Oncogene* 6(4):659-663, Turner et al., 2010, *Oncogene* 29(14):2013-2023). FGFR2 has been shown to be expressed in cholangiocarcinoma, leading to activation of the MEK1/2 pathway (Narong et al., 2011, *Oncol. Lett.* 2(5):821-825). The FGFR2 alterations described herein are expected to result in activation and/or upregulation of the FGFR2 protein. Accordingly, treatment with an agent that reduces (e.g., inhibits) FGFR2 is encompassed by the invention. In one embodiment, the agent is Regorafenib. Regorafenib inhibits cellular kinases including FGFR2, and has been approved for treatment of some metastatic colorectal cancer (mCRC) patients (FDA.gov, November 2012). The multi-kinase inhibitor ponatinib (AP24534), recently approved by the FDA for use in chronic myelogenous leukemia based on the results of a Phase 2 trial, has also been shown in preclinical studies to have substantial activity against all four FGFR kinases (Cortes et al., 2012, American Society of Hematology ASH, Abstract 163, Gozgit et al., 2012, *Mol. Cancer Ther.*, 11(3):690-699). Clinical trials of multiple Fgfr inhibitors are currently underway (Turner and Grose, 2010, *Nat. Rev. Cancer*, 10(2):116-129).

Each of the FGFR2 alterations is described herein in more detail

FGFR2-TACC3

The FGFR2-TACC3 fusion has not been reported. However, similar FGFR3-TACC3 fusions have been previously reported in glioblastoma and in a bladder cancer cell line; these fusions were found to be activating and to have transformative potential (Williams et al., *Hum. Mol. Genet* ePub, December 2012, Singh et al., 2012, *Science* 337 (6099):1231-1235). The FGFR2-TACC3 fusion is therefore expected to be oncogenic. FGFR2 amplification has also been reported in several cancer types, most frequently in gastric cancer and breast cancer as described herein. Inhibitors of FGFR2, such as Regorafenib and ponatinib can be used to treat cholangiosarcoma.

In one embodiment, the rearrangement, nucleotide and amino acid sequences for FGFR2 (exons 1-16)-TACC3 (exons 11-16) are depicted in FIGS. 1A-5 and SEQ ID NOs. 1-4.

FGFR2-KIAA1598

The FGFR2-KIAA1598 rearrangement results in truncation of the 3'UTR of the FGFR2 gene, which can result in upregulation of the FGFR2 protein. FGFR2 amplification has also been reported in several cancer types, most frequently in gastric cancer and breast cancer as described herein. Inhibitors of FGFR2, such as Regorafenib and ponatinib can be used to treat cholangiosarcoma.

In one embodiment, the rearrangement, nucleotide and amino acid sequences for FGFR2 (exons 1-16)-KIAA1598 (exons 7-17) are depicted in FIGS. 1A-1C, 2-3 and 6-7 and SEQ ID NOs. 1-2 and 5-6.

BICC1-FGFR2

The BICC1-FGFR2 fusion has not been reported in cholangiocarcinoma, or other cancers. FGFR2 amplification has also been reported in several cancer types, most frequently in gastric cancer and breast cancer as described herein. Treatment Inhibitors of FGFR2, such as Regorafenib and ponatinib can be used to treat cholangiosarcoma.

In one embodiment, the rearrangement, nucleotide and amino acid sequences for BICC1 (exons 1-2)-FGFR2 (exon 17) are depicted in FIGS. 1A-1C, 2-3 and 8-9 and SEQ ID NOs. 1-2 and 7-8.

FGFR2-BICC1

The FGFR2-BICC1 result in an in-frame fusion including the N-terminal portion of FGFR2 (containing the kinase domain) nearly the entire coding sequence of BICC1 (García-Mayoral et al., 2007, *Structure* 15(4):485-498, Kim and Bowie, 2003, *Trends Biochem. Sci.* 28(12):625-628). Other in-frame fusions containing the kinase domain of FGFR2 have been shown to result in kinase activation (Singh et al., 2012, *Science* 337(6099):1231-1235, Lorenzi et al., 1996, *Proc. Natl. Acad. Sci. USA*, 93(17):8956-8961). A recent report has described an FGFR2 fusion gene in cholangiocarcinoma (Wu et al. *Cancer Discov ePub*, May 2013). FGFR2 mutations have been reported in 2% of tumors analyzed in COSMIC, with the highest prevalence in endometrial cancer (10%) and lower incidence in several other cancers (COSMIC, February 2013). FGFR2 signaling has been described as tumorigenic in lung, pancreatic and gastric cancers (Yamayoshi et al., 2004, *J. Pathol.*, 204(1): 110-118; Cho et al., 2007, *Am. J. Pathol.*, 170(6):1964-1974; Toyokawa et al., 2009, *Oncol. Rep.*, 21(4):875-880). However, FGFR2 has also been described as a tumor suppressor in the context of other cancers, such as melanoma (Gartside et al., 2009, *Mol. Cancer Res.*, 7(1):41-54). Clinical trials of multiple FGFR inhibitors are currently underway (Turner and Grose, 2010, *Oncogene*, 29(14):2013-2023). Inhibitors of FGFR2, such as Regorafenib and ponatinib can be used to treat cholangiosarcoma.

In one embodiment, the rearrangement, nucleotide and amino acid sequences for FGFR2 (exons 1-16)-BICC1 (exons 18-21) are depicted in FIGS. 1A-1C, 2-3 and 8-9 and SEQ ID NOs. 1-2 and 7-8.

PARK2-FGFR2

The PARK2-FGFR2 fusion results in a fusion that includes the N-terminal portion of PARK2, which encodes the E3 ligase parkin, and the last exon (aa 768-821) of FGFR2 (Uniprot). The portion of FGFR2 not included in this fusion is predicted to encode a protein truncated after the functional kinase domain. Similar truncations of FGFR2 (764* and 776*) have been described as oncogenic, efficiently transforming cultured cells (Lorenzi et al., 1997, *Oncogene* 15(7):817-26). Therefore, this fusion is expected to activate the FGFR2 signaling.

FGFR2 amplification has also been reported in several cancer types, most frequently in gastric cancer and breast cancer as described herein. Treatment Inhibitors of FGFR2, such as Regorafenib and ponatinib can be used to treat cholangiosarcoma.

In one embodiment, the rearrangement, nucleotide and amino acid sequences for PARK2 (exons 1-9)-FGFR2 (exon 18) are depicted in FIGS. 1A-1C and 10-13 and SEQ ID NOs. 9-12.

In one embodiment, the rearrangement comprises a fusion of PARK2 (intron9) to FGFR2 (intron17). The expected genomic coordinates are:

FGFR2 breakpoint: chr10:123239535-123243212.
PARK2 breakpoint: chr6:161807909-161969886.

The fusion is comprised of 10 complete exons, all coming from the reverse strand. The fusion is in frame. The orientation of the fusion is expected to be 5' fusion partner exons: PARK2 (exons1-9) to 3' fusion partner exons: FGFR2 (exon18).

The fused domains include:
(i) PARK2, E3 ubiquitin-protein ligase parkin, has one ubiquitin homologue domain and two zink finger domains. The fusion, which includes exons 1-9 of PARK2 contains the entire ubiquitin homologue domain and part of the first zink finger domain, which are the core set of exons to give reasonable activity; and
(ii) FGFR2, the fusion includes the last exon of FGFR2.

The refSeq IDs for the nucleotide and amino acid sequences are:
PARK2: NM_004562 provided herein as SEQ ID NOs: 9-10 and FIGS. 10-11, respectively.
FGFR2: NM_000141 provided herein as SEQ ID NOs: 11-12 and FIGS. 12-13, respectively.

FGFR2-NOL4

The FGFR2-NOL4 fusion results in an in-frame fusion, containing transcribed exons 1-17 of FGFR2 (coding for amino acids 1-768) fused to NOL4 transcribed exons 7-11 (coding for amino acids 353-638). The resulting fusion protein contains the N-terminus of FGFR2, which includes the protein kinase domain, fused to the C-terminus of the NOL4 protein (UniProt.org). FGFR2-involving fusions containing the FGFR2 kinase domain have been reported to be activating and oncogenic, including FGFR-TACC and FGFR2-FRAG1 (Singh et al., 2012, *Science* 337(6099): 1231-1235, Lorenzi et al., 1996, *Proc. Natl. Acad. Sci. USA*, 93(17):8956-8961). FGFR2 mRNA has been shown to be expressed in cholangiocarcinoma cell lines, leading to activation of the MEK1/2 pathway (Narong and Leelawat, 2011, supra). Tumors with FGFR2 amplification or activating mutations can be sensitive to FGFR inhibitors as described herein. FGFR2 has been associated with resistance to chemotherapeutics; shRNA inhibition of FGFR2 increased the sensitivity of ovarian epithelial cancer cells to cisplatin (Cole et al., 2010, *Cancer Biol Ther* 10(5):495-504). Inhibitors of FGFR2, such as Regorafenib and ponatinib can be used to treat cholangiosarcoma.

In one embodiment, the rearrangement, nucleotide and amino acid sequences for FGFR2 (exons 1-17) and NOL4 (exons 7-11) are depicted in FIGS. 1A-1C and 12-15 and SEQ ID NOs. 11-14.

In one embodiment, the rearrangement comprises a fusion of FGFR2 (intron17) to NOL4 (intron 6). The expected genomic coordinates are:

FGFR2 breakpoint: chr10:123239535-123243212.
NOL4 breakpoint: chr18:31538203-31599282.

The fusion is comprised of 22 complete exons, all coming from the reverse strand. The fusion is in frame.

The orientation of the fusion is expected to be 5' fusion partner exons: FGFR2 (exons1-17) to 3' fusion partner exons: NOL4 (exons7-11).

The fused domains include:
FGFR2, the fusion includes the core set of exons for all active domains of this transmembrane protein.

The refSeq IDs for the nucleotide and amino acid sequences are:
FGFR2: NM_000141 provided herein as SEQ ID NOs: 11-12 and FIGS. 12-13, respectively.
NOL4: NM_003787 provided herein as SEQ ID NOs: 13-14 and FIGS. 14-15, respectively.

ZDHHC6-FGFR2

The ZDHHC6-FGFR2 fusion results in a fusion including the N-terminal portion of ZDHHC6 (exons 1-5), which encodes the integral transmembrane domain of a palmitoyltransferase ZDHHC6, and the last exon (aa 768-821) of FGFR2 (Uniprot). The portion of FGFR2 not included in this fusion is predicted to encode a protein truncated after the functional kinase domain. Similar truncations of FGFR2 (764* and 776*) have been described as oncogenic, efficiently transforming cultured cells (Lorenzi et al., 1997, *Oncogene* 15(7):817-26). Therefore, the ZDHHC6-FGFR2 fusion is predicted to activate FGFR2 signaling by truncating the remaining FGFR2 allele. A recent report has described an FGFR2 fusion gene in cholangiocarcinoma, as well as a truncated FGFR2 similar to the one observed here in a patient with prostate cancer (Wu et al. *Cancer Discov ePub*, May 2013). Inhibitors of FGFR2, such as Regorafenib and ponatinib can be used to treat cholangiosarcoma.

In one embodiment, the rearrangement, nucleotide and amino acid sequences for ZDHHC6 (exons 1-5) and FGFR2 (exon 18) are depicted in FIGS. 1A-1C and 12-13 and 16-17 and SEQ ID NOs. 11-12 and 15-16.

In one embodiment, the rearrangement comprises a fusion of ZDHHC6 (intron5) to FGFR2 (intron17). The expected genomic coordinates are:

FGFR2 breakpoint: chr10:123239535-123243212
ZDHHC6 breakpoint: chr10:114198147-114200292

The fusion is comprised of 6 complete exons, all coming from the reverse strand. The fusion is in frame.

The orientation of the fusion is expected to be 5' fusion partner exons: ZDHHC6 (exons1-5) to 3' fusion partner exons: FGFR2 (exon18).

The fused domains include:
(i) ZDHHC6 is a zinc-finger involved in transferase activity, transferring acyl groups and zinc ion binding. It contains 4 potential transmembrane domains and one zinc finger domain. All of these domains are contained within the first 5 exons, and therefore retained in the fusion product; and
(ii) FGFR2, the fusion includes the last exon of FGFR2.

The annotations above are based on the following refSeq IDs
 ZDHHC6: NM_022494 provided herein as SEQ ID NOs: 15-16 and FIGS. 16-17, respectively.
 FGFR2: NM_000141 provided herein as SEQ ID NOs: 11-12 and FIGS. 12-13, respectively.

RABGAP1L-NTRK1

NTRK1 (Neurotrophic Tyrosine Kinase, Receptor, Type 1) is a member of the neurotrophic tyrosine kinase receptor (NTKR) family. This kinase is a membrane-bound receptor that, upon neurotrophin binding, phosphorylates itself and members of the MAPK pathway. The presence of this kinase leads to cell differentiation and may play a role in specifying sensory neuron subtypes. Mutations in this gene have been associated with congenital insensitivity to pain, anhidrosis, self-mutilating behavior, mental retardation and cancer. Alternate transcriptional splice variants of this gene have been found. The NTRK1 amino and nucleotide sequences are known in the art. An exemplary amino acid and nucleotide sequence for human NTRK1 are provided herein as SEQ ID NO:9 and SEQ ID NO:10, respectively.

```
NCBI Reference Sequence: NP_001012331
                                                              (SEQ ID NO: 9)
    1   mlrggrrgql   gwhswaagpg   sllawlilas   agaapcpdac   cphgssglrc   trdgaldslh
   61   hlpgaenlte   lyienqqhlq   hlelrdlrgl   gelrnltivk   sglrfvapda   fhftprlsrl
  121   nlsfnalesl   swktvqglsl   qelvlsgnpl   hcscalrwlq   rweeeglggv   peqklqchgq
  181   gplahmpnas   cgvptlkvqv   pnasvdvgdd   vllrcqvegr   gleqagwilt   eleqsatvmk
  241   sgglpslglt   lanvtsdlnr   knvtcwaend   vgraevsvqv   nvsfpasvql   htavemhhwc
  301   ipfsvdgqpa   pslrwlings   vlnetsfift   eflepaanet   vrhgclrlnq   pthvnngnyt
  361   llaanpfgqa   sasimaafmd   npfefnpedp   ipdtnstsgd   pvekkdetpf   gvsvavglav
  421   faclflstll   lvlnkcgrrn   kfginrpavl   apedglamsl   hfmtlggssl   sptegkgsgl
  481   qghiienpqy   fsdacvhhik   rrdivlkwel   gegafgkvfl   aechnllpeq   dkmlvavkal
  541   keasesarqd   fqreaelltm   lqhqhivrff   gvctegrpll   mvfeymrhgd   lnrflrshgp
  601   dakllagged   vapgplglgq   llavasqvaa   gmvylaglhf   vhrdlatrnc   lvgqglvvki
  661   gdfgmsrdiy   stdyyrvggr   tmlpirwmpp   esilyrkftt   esdvwsfgvv   lweiftygkq
  721   pwyqlsntea   idcitqgrel   erpracppev   yaimrgcwqr   epqqrhsikd   vharlqalaq
  781   appvyldvlg Reference Sequence: NM_001012331
                                                              (SEQ ID NO: 10)
    1   tgcagctggg   agcgcacaga   cggctgcccc   gcctgagcga   ggcgggcgcc   gccgcgatgc
   61   tgcgaggcgg   acggcgcggg   cagcttggct   ggcacagctg   ggctgcgggg   ccgggcagcc
  121   tgctggcttg   gctgatactg   gcatctgcgg   gcgccgcacc   ctgccccgat   gcctgctgcc
  181   cccacggctc   ctcgggactg   cgatgcaccc   gggatggggc   cctggatagc   ctccaccacc
  241   tgcccggcgc   agagaacctg   actgagctct   acatcgagaa   ccagcagcat   ctgcagcatc
  301   tggagctccg   tgatctgagg   ggcctggggg   agctgagaaa   cctcaccatc   gtgaagagtg
  361   gtctccgttt   cgtggcgcca   gatgccttcc   atttcactcc   tcggctcagt   cgcctgaatc
  421   tctccttcaa   cgctctggag   tctctctcct   ggaaaactgt   gcagggcctc   tccttacagg
  481   aactggtcct   gtcggggaac   cctctgcact   gttcttgtgc   cctgcgctgg   ctacagcgct
  541   gggaggagga   gggactgggc   ggagtgcctg   aacagaagct   gcagtgtcat   gggcaagggc
  601   ccctggccca   catgcccaat   gccagctgtg   gtgtgcccac   gctgaaggtc   caggtgccca
  661   atgcctcggt   ggatgtgggg   gacgacgtgc   tgctgcggtg   ccaggtggag   ggcgggggcc
  721   tggagcaggc   cggctggatc   ctcacagagc   tggagcagtc   agccacggtg   atgaaatctg
  781   ggggtctgcc   atccctgggg   ctgaccctgg   ccaatgtcac   cagtgacctc   aacaggaaga
  841   acgtgacgtg   ctgggcagag   aacgatggtg   gccgggcaga   ggtctctgtt   caggtcaacg
```

```
-continued
 901   tctccttccc ggccagtgtg cagctgcaca cggcggtgga gatgcaccac tggtgcatcc 961   ccttctctgt ggatgggcag ccggcaccgt ctctgcgctg gctcttcaat ggctccgtgc 1021   tcaatgagac cagcttcatc ttcactgagt tcctggagcc ggcagccaat gagaccgtgc 1081   ggcacgggtg tctgcgcctc aaccagccca cccacgtcaa caacggcaac tacacgctgc 1141   tggctgccaa ccccttcggc caggcctccg cctccatcat ggctgccttc atggacaacc 1201   ctttcgagtt caaccccgag gacccatcc ctgacactaa cagcacatct ggagacccgg 1261   tggagaagaa ggacgaaaca cctttggggg tctcggtggc tgtgggcctg gccgtctttg 1321   cctgcctctt cctttctacg ctgctccttg tgctcaacaa atgtggacgg agaaacaagt 1381   ttgggatcaa ccgcccggct gtgctggctc cagaggatgg gctggccatg tccctgcatt 1441   tcatgacatt gggtggcagc tccctgtccc ccaccgaggg caaaggctct gggctccaag 1501   gccacatcat cgagaaccca caatacttca gtgatgcctg tgttcaccac atcaagcgcc 1561   gggacatcgt gctcaagtgg gagctggggg agggcgcctt tgggaaggtc ttccttgctg 1621   agtgccacaa cctcctgcct gagcaggaca agatgctggt ggctgtcaag gcactgaagg 1681   aggcgtccga gagtgctcgg caggacttcc agcgtgaggc tgagctgctc accatgctgc 1741   agcaccagca catcgtgcgc ttcttcggcg tctgcaccga gggccgcccc ctgctcatgg 1801   tctttgagta tatgcggcac ggggacctca accgcttcct ccgatcccat ggacctgatg 1861   ccaagctgct ggctggtggg gaggatgtgg ctccaggccc cctgggtctg gggcagctgc 1921   tggccgtggc tagccaggtc gctgcgggga tggtgtacct ggcgggtctg cattttgtgc 1981   accgggacct ggccacacgc aactgtctag tgggccaggg actggtggtc aagattggtg 2041   attttggcat gagcagggat atctacagca ccgactatta ccgtgtggga ggccgcacca 2101   tgctgcccat tcgctggatg ccgcccgaga gcatcctgta ccgtaagttc accaccgaga 2161   gcgacgtgtg gagcttcggc gtggtgctct gggagatctt cacctacggc aagcagccct 2221   ggtaccagct ctccaacacg gaggcaatcg actgcatcac gcagggacgt gagttggagc 2281   ggccacgtgc ctgcccacca gaggtctacg ccatcatgcg gggctgctgg cagcgggagc 2341   cccagcaacg ccacagcatc aaggatgtgc acgcccggct gcaagccctg gcccaggcac 2401   ctcctgtcta cctggatgtc ctgggctagg gggccggccc aggggctggg agtggttagc 2461   cggaatactg gggcctgccc tcagcatccc ccatagctcc cagcagcccc agggtgatct 2521   caaagtatct aattcaccct cagcatgtgg gaagggacag gtgggggctg ggagtagagg 2581   atgttcctgc ttctctaggc aaggtcccgt catagcaatt atatttatta tcccttgaaa 2641   aaaaaa
```

Therapeutic Methods and Agents

The invention features methods of treating a cholangiocarcinoma, e.g., a cholangiocarcinoma harboring a fusion described herein. The methods include administering a therapeutic agent, e.g., which antagonizes the function of FGFR2 or NTRK1. The therapeutic agent can be a small molecule, protein, polypeptide, peptide, nucleic acid, e.g., a siRNA, antisense or micro RNA. Exemplary agents and classes of agents are provided in Table 2.

TABLE 2

Kinase inhibitors
Multi-kinase inhibitors
Pan-kinase inhibitors
Kinase inhibitors having activity for or selectivity for FGFR2
Kinase inhibitors having activity for or selectivity for NTRK

TABLE 2-continued siRNA, antisense RNA, or other nucleic acid based inhibitors of FGFR2 or NTRK
Antagonists of FGFR2, e.g., antibodies or small molecules that bind FGFR2
Antagonists of NTRK1, e.g., antibodies or small molecules that bind NTRK
AZD-2171
BGJ398
AZD-4547
BIBF1120
Brivanib
Cediranib
Dovitinib
ENMD-2076
Masitinib
JNJ42756493
Lenvatinib
LY2874455

TABLE 2-continued

Ponatinib
Pazopanib
R406
Regorafenib
Other therapeutic agents disclosed herein.
PD173074
PD173955
Danusertib
Dovitinib Dilactic Acid
TSU-68
Tyrphostin AG 1296
MK-2461
Brivanib Alaninate
Lestaurtinib
K252a
PHA-848125
AZ-23
Oxindole-3
AV369b
ACTB 1003
Volasertib
R1530
Loxo-101
ARRY-470
ARRY-786
RXDX-101
RXDX-102

These treatments can be provided to a patient having had unsatisfactory response to a cytotoxic chemotherapy or opportunistic resection.

An agent from Table 2 can be administered, alone or in combination, e.g., in combination with other chemotherapeutic agents or procedures, in an amount sufficient to reduce or inhibit the tumor cell growth, and/or treat or prevent the cancer(s), in the subject.

Exemplary agents are discussed in more detail below.

Regorafenib

Regorafenib is a multi-kinase inhibitor that inhibits multiple membrane-bound and intracellular kinases, including those in the RET, VEGFR1/2/3, KIT, PDGFR, FGFR1/2, and RAF pathways. Regorafenib has been approved to treat patients with metastatic colorectal cancer who have been previously treated with fluoropyrimidine-, oxaliplatin-, and irinotecan-based chemotherapy, an anti-VEGF therapy, and, if KRAS wild type, an anti-EGFR therapy. Tumors with Fgfr2 activation may be sensitive to regorafenib. Regorafenib is being studied in clinical trials for multiple solid tumor types.

In some embodiments, the kinase inhibitor is regorafenib. Regorafenib (STIVARGA, Bayer) is a small molecule inhibitor of multiple membrane-bound and intracellular kinases. In in vitro biochemical or cellular assays, regorafenib or its major human active metabolites M-2 and M-5 inhibited the activity of FGFR1 and FGFR-2 as well as multiple other kinases. STIVARGA Product Label dated Sep. 27, 2012. Regorafenib has the chemical name: 1-(4-chloro-3-(trifluoromethyl)phenyl)-3-(2-fluoro-4-(2-(methylcarbamoyl)pyridin-4-yloxy)phenyl)urea; and has the following structure:

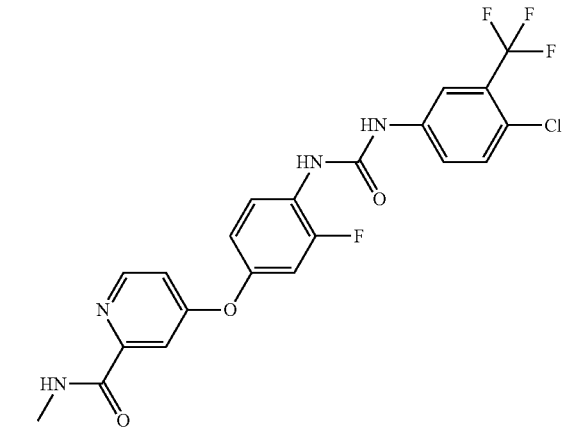

Regorafenib Chemical Structure
Molecular Weight: 482.82.

Ponatinib

Ponatinib is a multi-kinase inhibitor targeting BCR-ABL, as well as VEGFRs and FGFRs. Ponatinib has been approved by the FDA for use in chronic myeloid leukemia (CML) and Philadelphia chromosome-positive acute lymphoblastic leukemia (ALL). Activating mutations or amplification of FGFR2 can result in sensitivity to ponatinib (Gozgit et al., 2012, Mol. Cancer Ther., 11(3):690-699).

In some embodiments, the kinase inhibitor is ponatinib (AP24534, ICLUSIG, Ariad). Ponatinib is a small molecule kinase inhibitor. Ponatinib inhibited the in vitro tyrosine kinase activity of ABL and T315I mutant ABL with IC50 concentrations of 0.4 and 2.0 nM, respectively. Ponatinib inhibited the in vitro activity of additional kinases with IC50 concentrations between 0.1 and 20 nM, including members of the PDGFR, FGFR, EPH receptors and SRC families of kinases, and KIT, RET, TIE2, and FLT3. ICLUSIG Product Label dated Dec. 14, 2012. Ponatinib has the chemical name: 3-(2-(imidazo[1,2-b]pyridazin-3-yl)ethynyl)-4-methyl-N-(4-((4-methylpiperazin-1-yl)methyl)-3-(trifluoromethyl)phenyl)benzamide; and has the following structure:

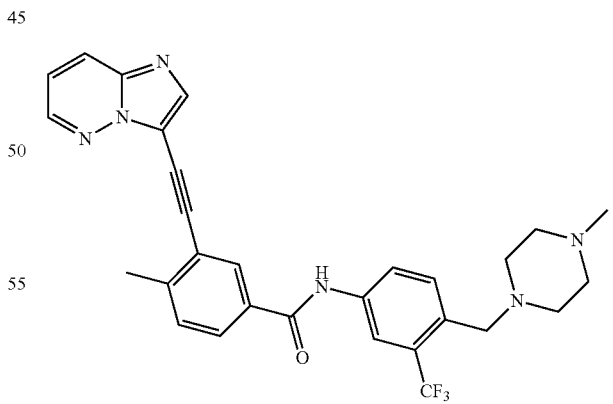

Ponatinib Chemical Structure
Molecular Weight: 532.56.

AZD-4547

In certain embodiments the kinase inhibitor is AZD-4547. AZD-4547 is an orally bioavailable small molecule inhibitor of the fibroblast growth factor receptor (FGFR). AZD-4547 binds to and inhibits FGFR1, 2 and 3 tyrosine kinases. FGFR, up-regulated in many tumor cell types, is a receptor tyrosine kinase essential to tumor cellular proliferation, differentiation and survival. AZD4547 is under clinical investigation for the treatment of FGFR-dependent tumors. AZD-4547 has the chemical name N-(5-(3,5-dimethoxyphenethyl)-1H-pyrazol-3-yl)-4-((3S,5R)-3,5-dimethylpiperazin-1-yl)benzamide; and has the following structure:

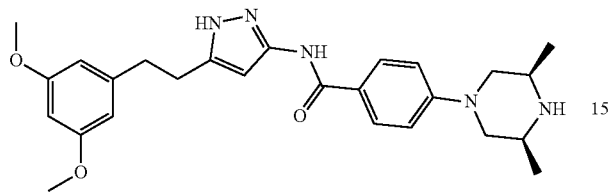

AZD-4547 Chemical Structure
Molecular Weight: 463.57.

BGJ398

In some embodiments, the kinase inhibitor is BGJ398. BGJ398 (NVP-BGJ398) is a potent, selective, and orally bioavailable small molecule inhibitor of the FGFR2 tyrosine kinases. BGJ398 inhibits the proliferation of various FGFR-dependent cell lines including breast and lung cancers harboring FGFR1 amplification, FGFR2-amplified gastric cancer cell lines and FGFR3-mutated bladder cancers. BGJ398 has the chemical name 3-(2,6-dichloro-3,5-dimethoxyphenyl)-1-(6-(4-(4-ethylpiperazin-1-yl)phenylamino)pyrimidin-4-yl)-1-methylurea; and has the following structure:

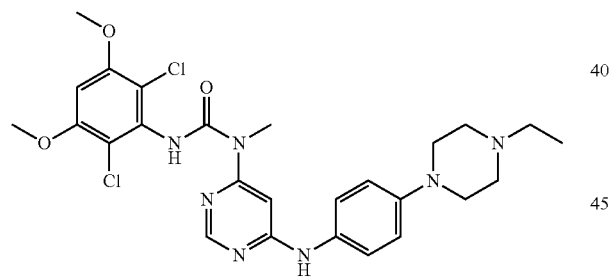

BGJ398 Chemical Structure
Molecular Weight: 560.48

Masitinib

In some embodiments, the kinase inhibitor is masitinib. Masitinib (AB1010) (commercial names Masivet, Kinavet) is a small molecule tyrosine-kinase inhibitor that is used in the treatment of mast cell tumors in animals, particularly dogs. Masitinib inhibits the receptor tyrosine kinase c-Kit, as well as the platelet derived growth factor receptor (PDGFR) and fibroblast growth factor receptor (FGFR). Masitinib has the chemical name N-(4-methyl-3-(4-(pyridin-3-yl)thiazol-2-ylamino)phenyl)-4-((4-methylpiperazin-1-yl)methyl)benzamide; and has the following structure:

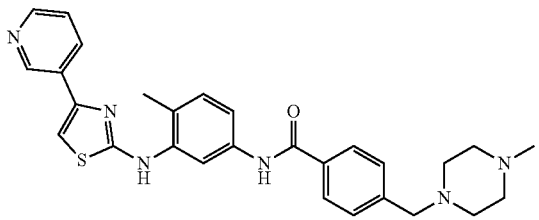

Masitinib Chemical Structure
Molecular Weight: 498.64.

Lenvatinib

In some embodiments, the kinase inhibitor is Lenvatinib (E7080). Lenvatinib is a small molecule multi-kinase inhibitor that is being investigated for the treatment of various types of cancer by Eisai Co. It inhibits multiple receptor tyrosine kinases including VEGF, FGF and SCF receptors. Lenvatinib (E7080) has the chemical name: 1-(4-(6-carbamoyl-7-methoxyquinolin-4-yloxy)-2-chlorophenyl)-3-cyclopropylurea; and has the following structure:

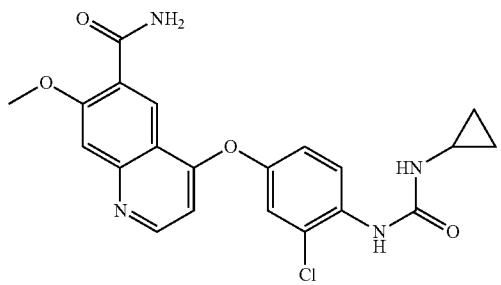

Lenvatinib (E7080) Chemical Structure
Molecular Weight: 426.85.

Dovitinib

In some embodiments, the kinase inhibitor is dovitinib. Dovitinib (dovitinib lactate, also known as receptor tyrosine kinase inhibitor TKI258; code names: TKI258 or CHIR-258) is an orally bioavailable lactate salt of a benzimidazole-quinolinone compound. Dovitinib strongly binds to fibroblast growth factor receptor 3 (FGFR3) and inhibits its phosphorylation. In addition, dovitinib may inhibit other members of the RTK superfamily, including the vascular endothelial growth factor receptor; fibroblast growth factor receptor 1; platelet-derived growth factor receptor type 3; FMS-like tyrosine kinase 3; stem cell factor receptor (c-KIT); and colony-stimulating factor receptor 1. See National Cancer Institute Drug Dictionary at cancer.gov/drugdictionary?cdrid=488976. Dovitinib has the chemical name: 1-amino-5-fluoro-3-(6-(4-methylpiperazin-1-yl)-1H-benzo[d]imidazol-2-yl)quinolin-2(1H)-one; and has the following structure:

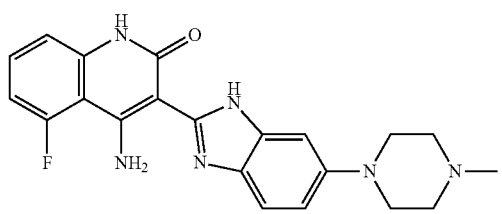

Dovitinib Chemical Structure
Molecular Weight: 392.43.

Dovitinib Dilactic Acid

In some embodiments, the kinase inhibitor is dovitinib dilactic acid (TKI258 dilactic acid). Dovitinib dilactic acid is a multitargeted RTK inhibitor, mostly for class III (FLT3/c-Kit) with IC50 of 1 nM/2 nM, also potent to class IV (FGFR1/3) and class V (VEGFR1-4) RTKs with IC50 from 8-13 nM, less potent to InsR, EGFR, c-Met, EphA2, Tie2, IGFR1 and HER2. Dovitinib dilactic acid has the chemical name: Propanoic acid, 2-hydroxy-, compd. with 4-amino-5-fluoro-3-[6-(4-methyl-1-piperazinyl)-1H-benzimidazol-2-yl]-2(1H)-quinolinone; and has the following structure:

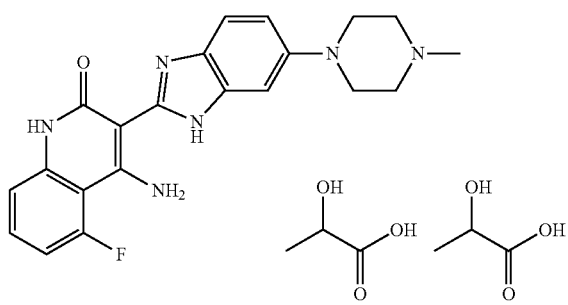

Dovitinib Dilactic Acid Chemical Structure
Molecular Weight: 572.59

Brivanib

In some embodiments, the kinase inhibitor is brivanib (BMS-540215). Brivanib is the alaninate salt of the VEGFR-2 inhibitor BMS-540215 and is hydrolyzed to the active moiety BMS-540215 in vivo. BMS-540215, a dual tyrosine kinase inhibitor, shows potent and selective inhibition of VEGFR and fibroblast growth factor receptor (FGFR) tyrosine kinases. Brivanib has the chemical name: (R)-1-(4-(4-fluoro-2-methyl-1H-indol-5-yloxy)-5-methylpyrrolo[1,2-][1,2,4]triazin-6-yloxy)propan-2-ol; and has the following structure:

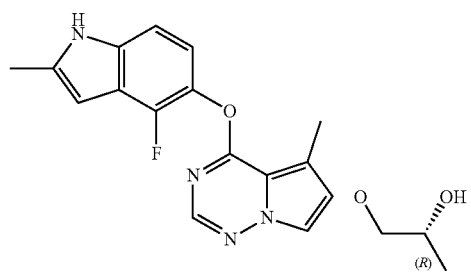

Brivanib Chemical Structure
Molecular Weight: 370.38.

ENMD-2076

In certain embodiments the kinase inhibitor is ENMD-2076. ENMD-2076 is orally bioavailable small molecule inhibitor of the Aurora kinase A, as well as kinases involved in angiogenesis (VEGFRs, FGFRs). The mechanism of action of ENMD-2076 involves several pathways key to tumor growth and survival: angiogenesis, proliferation, and the cell cycle. ENMD-2076 has received orphan drug designation from the United States Food and Drug Administration (the "FDA") for the treatment of ovarian cancer, multiple myeloma and acute myeloid leukemia ("AML"). ENMD-2076 has the chemical name (E)-N-(5-methyl-1H-pyrazol-3-yl)-6-(4-methylpiperazin-1-yl)-2-styrylpyrimidin-4-amine; and has the following structure:

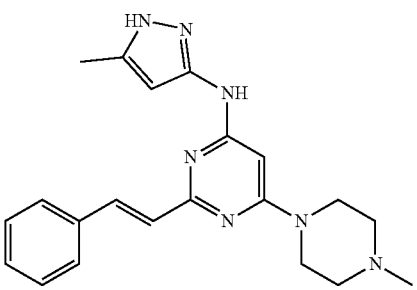

ENMD-2076 Chemical Structure
Molecular Weight: 375.47.

Cediranib

In some embodiments, the kinase inhibitor is Cediranib. Cediranib (also Recentin or AZD2171) is a small molecule inhibitor of vascular endothelial growth factor (VEGF) receptor tyrosine kinases. See, e.g., WO 2007/060402. Cediranib also inhibits platelet derived growth factor (PDGFR)-associated kinases c-Kit, PDGFR-α, and PDGFR-β. Cediranib also inhibits FGFR-1 and FGFR-4. Brave, S. R. Molecular Cancer Ther, 10(5): 861-873, published online Mar. 25, 2011, doi: 10.1158/1535-71634. Cediranib has the chemical name 4-(4-fluoro-2-methyl-1H-indol-5-yloxy)-6-methoxy-7-(3-(pyrrolidin-1-yl)propoxy)quinazoline; and has the following structure:

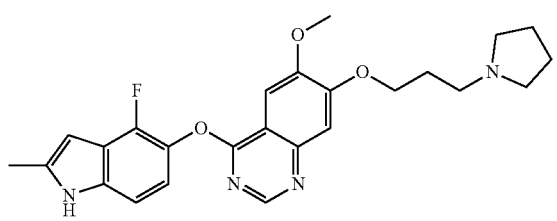

Cediranib Chemical Structure
Molecular Weight: 450.51.

BIBF 1120

In some embodiments, the kinase inhibitor is BIBF1120 (Nintedanib). BIBF 1120 (Nintedanib) is an indolinone derivative that inhibits the process of blood vessel formation (angiogenesis) in tumors. See, e.g., WO2001/27081; WO2004/13099; WO2010/081817. It potently blocks the VEGF receptor (VEGFR), PDGFR and fibroblast growth factor receptor (FGFR) kinase activity in enzymatic assays (IC(50), 20-100 nmol/L). BIBF 1120 inhibits mitogen-activated protein kinase and Akt signaling pathways in three cell types contributing to angiogenesis, endothelial cells, pericytes, and smooth muscle cells, resulting in inhibition of cell proliferation (EC(50), 10-80 nmol/L) and apoptosis. BIBF1120 has the chemical name: (Z)-methyl 3-((4-(N-methyl-2-(4-methylpiperazin-1-yl)acetamido)phenylamino)(phenyl)methylene)-2-oxoindoline-6-carboxylate; and has the following structure:

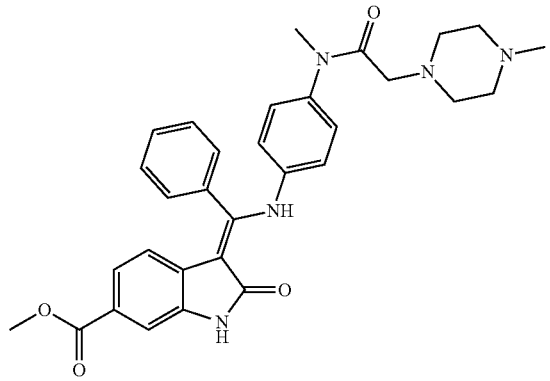

Nintedanib Chemical Structure
Molecular Weight: 539.62.

LY2874455

In some embodiments, the kinase inhibitor is LY2874455. LY2874455 is a small molecule that inhibits all four FGFRs with a similar potency in biochemical assays. It exhibits potent activity against FGF/FGFR-mediated signaling in several cancer cell lines and shows a broad spectrum of antitumor activity in several tumor xenograft models representing the major FGF/FGFR2 relevant tumor histologies including lung, gastric, and bladder cancers and multiple myeloma. LY2874455 exhibits a 6- to 9-fold in vitro and in vivo selectivity on inhibition of FGF-over VEGF-mediated target signaling in mice. Furthermore, LY2874455 did not show VEGF receptor 2-mediated toxicities such as hypertension at efficacious doses. See Zhao, G. et al. Mol Cancer Ther. 2011 November; 10(11):2200-10. doi: 10.1158/1535-7163. LY2874455 has the chemical name (R)-(E)-2-(4-(2-(5-(1-(3,5-Dichloropyridin-4-yl)ethoxy)-1H-indazol-3yl)vinyl)-1H-pyrazol-1-yl)ethanol; and has the following structure:

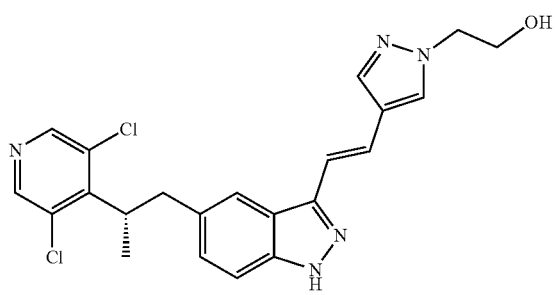

LY2874455 Chemical Structure
Molecular Weight: 444.31.

JNJ42756493

In some embodiments, the kinase inhibitor is JNJ42756493. JNJ42756493 is an orally bioavailable, pan fibroblast growth factor receptor (FGFR) inhibitor. Upon oral administration, JNJ-42756493 binds to and inhibits FGFR, which may result in the inhibition of FGFR-related signal transduction pathways and thus the inhibition of tumor cell proliferation and tumor cell death in FGFR-overexpressing tumor cells.

Pazopanib

In some embodiments, the kinase inhibitor is pazopanib. Pazopanib (Votrient) is a potent and selective multi-targeted receptor tyrosine kinase inhibitor. The FDA has approved it for renal cell carcinoma and soft tissue sarcoma. Pazopanib has the chemical name: 5-[[4-[(2,3-dimethyl-2H-indazol-6yl)methylamino]-2-pyrimidinyl]amino]-2-methylbenzenesulfonamide monohydrochloride; and has the following structure:

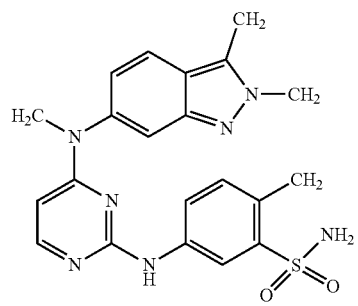

Pazopanib Chemical Structure
Molecular Weight: 473.99.

PD-173955

In some embodiments, the kinase inhibitor is PD-173955. PD-173955 is a potent tyrosine kinase inhibitor. PD-173955 is a src tyrosine kinase inhibitor. PD173955 inhibited Bcr-Abl-dependent cell growth. PD173955 showed cell cycle arrest in G(1). PD173955 has an IC(50) of 1-2 nM in kinase inhibition assays of Bcr-Abl, and in cellular growth assays it inhibits Bcr-Abl-dependent substrate tyrosine phosphorylation. PD173955 inhibited kit ligand-dependent c-kit autophosphorylation (IC(50)=approximately 25 nM) and kit ligand-dependent proliferation of M07e cells (IC(50)=40 nM) but had a lesser effect on interleukin 3-dependent (IC(50)=250 nM) or granulocyte macrophage colony-stimulating factor (IC(50)=1 microM)-dependent cell growth. PD-173955 has the chemical name: 6-(2,6-dichlorophenyl)-8-methyl-2-(3-methylsulfanylanilino)pyrido[2,3-d]pyrimidin-7-one; and has the following structure:

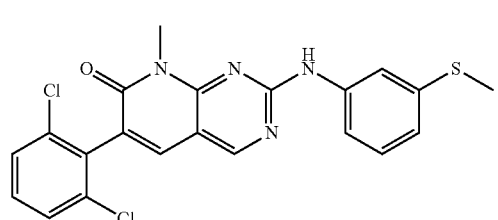

PD-173955 Chemical Structure
Molecular Weight: 443.35.

R406

In some embodiments, the kinase inhibitor is R406. R406 is a potent tyrosine kinase inhibitor. R406 is a potent Syk inhibitor with IC50 of 41 nM, strongly inhibits Syk but not Lyn, 5-fold less potent to Flt3. R406 has the chemical name:

6-(2,6-dichlorophenyl)-8-methyl-2-(3-methylsulfanylanilino)pyrido[2,3-d]pyrimidin-7-one; and has the following structure:

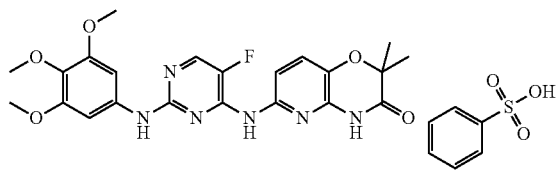

R406 Chemical Structure
Molecular Weight: 628.63

PD173074

In some embodiments, the kinase inhibitor is PD173074. PD173074 is a potent FGFR1 inhibitor with IC50 of ~25 nM and also inhibits VEGFR2 with IC50 of 100-200 nM, ~1000-fold selective for FGFR1 than PDGFR and c-Src. PD173074 has the chemical name: 1-tert-butyl-3-(2-(4-(diethylamino)butylamino)-6-(3,5-dimethoxyphenyl)pyrido[2,3-d]pyrimidin-7-yl)urea; and has the following structure:

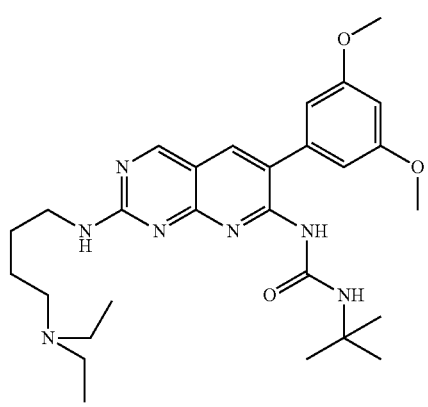

PD173074 Chemical Structure
Molecular Weight: 523.67.

Danusertib

In some embodiments, the kinase inhibitor is danusertib (PHA-739358). Danusertib is an Aurora kinase inhibitor for Aurora A/B/C with IC50 of 13 nM/79 nM/61 nM, modestly potent to Abl, TrkA, c-RET and FGFR1, and less potent to Lck, VEGFR2/3, c-Kit, and CDK2. Danusertib has the chemical name: (R)—N-(5-(2-methoxy-2-phenylacetyl)-1,4,5,6-tetrahydropyrrolo[3,4-c]pyrazol-3-yl)-4-(4-methylpiperazin-1-yl)benzamide; and has the following structure:

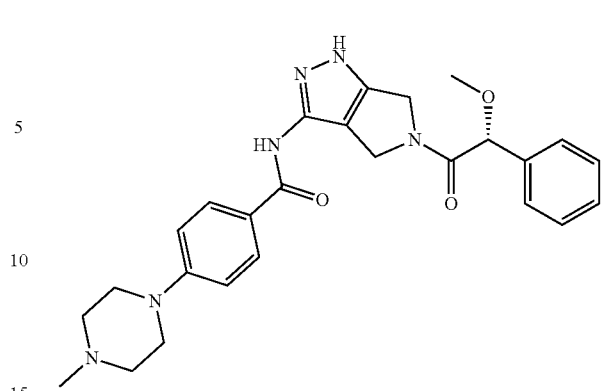

Danusertib Chemical Structure
Molecular Weight: 474.55.

TSU-680

In some embodiments, the kinase inhibitor is TSU-68 (SU6668). SU6668 has greatest potency against PDGFR autophosphorylation with K, of 8 nM, but also strongly inhibits Flk-1 and FGFR1 trans-phosphorylation, little activity against IGF-1R, Met, Src, Lck, Zap70, Abl and CDK2; and does not inhibit EGFR. SU6668 has the chemical name: (Z)-3-(2,4-dimethyl-5-((2-oxoindolin-3-ylidene)methyl)-1H-pyrrol-3-yl)propanoic acid; and has the following structure:

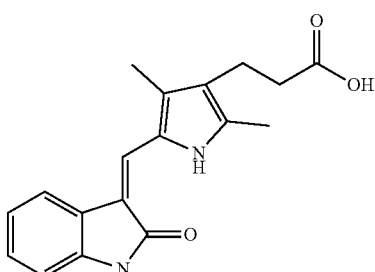

SU6668 Chemical Structure
Molecular Weight: 310.35.

Tyrphostin AG 1296 In some embodiments, the kinase inhibitor is tyrphostin AG 1296 (AG 1296). Tyrphostin AG 1296 (AG 1296) is an inhibitor of PDGFR with IC50 of 0.3-0.5 μM, no activity to EGFR. Tyrphostin AG 1296 has the chemical name Quinoxaline, 6,7-dimethoxy-2-phenyl-; and has the following structure:

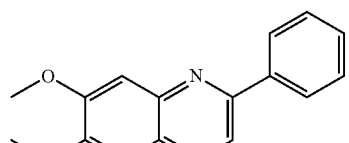

Tyrphostin AG 1296 Chemical Structure
Molecular Weight: 266.29.

MK-2461

In some embodiments, the kinase inhibitor is MK-2461. MK-2461 is a potent, multi-targeted inhibitor for c-Met (WT/mutants) with IC50 of 0.4-2.5 nM, less potent to Ron, Flt1; 8- to 30-fold greater selectivity of c-Met targets versus FGFR1, FGFR2, FGFR3, PDGFRβ, KDR, Flt3, Flt4, TrkA, and TrkB. MK-2461 has the chemical name: N-((2R)-1,4-Dioxan-2-ylmethyl)-N-methyl-N'-[3-(1-methyl-1H-pyrazol-4-yl)-5-oxo-5H-benzo[4,5]cyclohepta[1,2-b]pyridin-7-yl]sulfamide; and has the following structure:

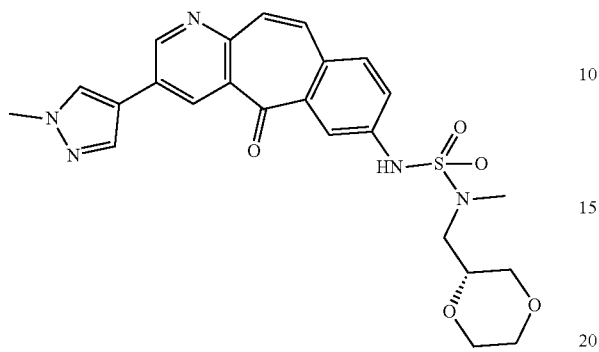

MK-2461 Chemical Structure
Molecular Weight: 495.55.

Brivanib Alaninate

In some embodiments, the kinase inhibitor is brivanib alaninate (BMS-582664). Brivanib alaninate (BMS-582664) is the prodrug of BMS-540215, an ATP-competitive inhibitor against VEGFR2 with IC50 of 25 nM. Brivanib alaninate has the chemical name: (S)—((R)-1-(4-(4-fluoro-2-methyl-1H-indol-5-yloxy)-5-methylpyrrolo[1,2-f][1,2,4]triazin-6-yloxy)propan-2-yl) 2-aminopropanoate; and has the following structure:

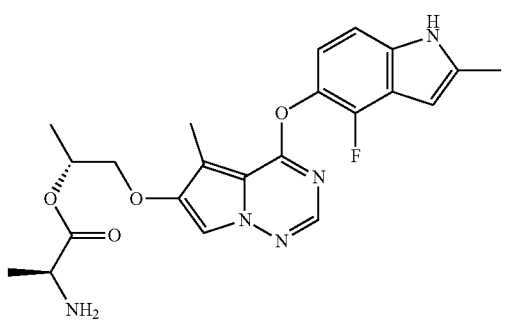

Brivanib Alaninate Chemical Structure
Molecular Weight: 441.46.

Lestaurtinib

In certain embodiments the kinase inhibitor is lestaurtinib. Lestaurtinib is a potent JAK2, FLT3 and TrkA inhibitor ($IC_{50}$ values are 0.9, 3 and <25 nM respectively) that prevents STAT5 phosphorylation ($IC_{50}$=20-30 nM). Exhibits antiproliferative activity in vitro ($IC_{50}$=30-100 nM in HEL92.1.7 cells) and is effective against myeloproliferative disorders in vivo. Lestaurtinib has the chemical name (9S,10S,12R)-2,3,9,10,11,12-Hexahydro-10-hydroxy-10-(hydroxymethyl)-9-methyl-9,12-epoxy-1H-diindolo[1,2,3-fg:3',2',1'-kl]pyrrolo[3,4-i][1,6]benzodiazocin-1-one; and has the following structure:

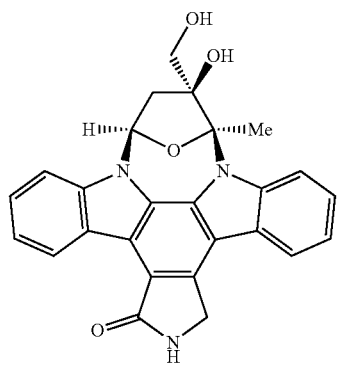

Lestaurtinib Chemical Structure
Molecular Weight: 439.46.

PHA-848125

In certain embodiments the kinase inhibitor is PHA-848125 (Milciclib). Milciclib is an orally bioavailable inhibitor of cyclin-dependent kinases (CDKs) and thropomyosin receptor kinase A (TRKA), with potential antineoplastic activity. CDK2/TRKA inhibitor PHA-848125 AC potently inhibits cyclin-dependent kinase 2 (CDK2) and exhibits activity against other CDKs including CDK1 and CDK4, in addition to TRKA. PHA-848125 (Milciclib) has the chemical name: N,1,4,4-tetramethyl-8-((4-(4-methylpiperazin-1-yl)phenyl)amino)-4,5-dihydro-1H-pyrazolo[4,3-h]quinazoline-3-carboxamide; and has the following structure:

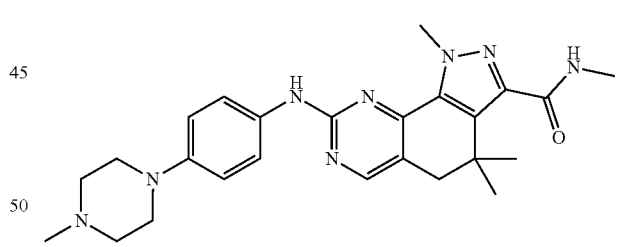

Milciclib Chemical Structure
Molecular Weight: 460.57.

K252a

In certain embodiments the kinase inhibitor is K252a. K252a is an analog of Staurosporine (Cat. No. 1048) that acts as a non-selective protein kinase inhibitor. Inhibits PKA (Ki=18 nM), PKC (Ki=25 nM), and PKG (Ki=20 nM). Potently inhibits CaMK (Ki=1.8 nM), competitively with ATP and noncompetitively with the substrate. K252a has the following structure:

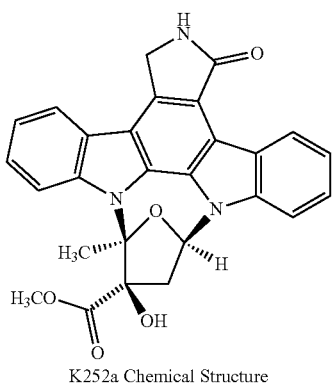

K252a Chemical Structure
Molecular Weight: 467.47.

AZ-23

In certain embodiments the kinase inhibitor is AZ-23. AZ-23 is a potent and selective tyrosine kinase Trk inhibitor with IC50 to 2 and 8 nM for TrkA and TrkB respectively; AZ-23 showed in vivo TrkA kinase inhibition and efficacy in mice following oral administration; having potential for therapeutic utility in neuroblastoma and multiple other cancer indications. AZ-23 has the chemical name 5-chloro-N-[(1S)-1-(5-fluoropyridin-2-yl)ethyl]-N'-(5-propan-2-yloxy-1H-pyrazol-3-yl)pyrimidine-2,4-diamine; and has the following structure:

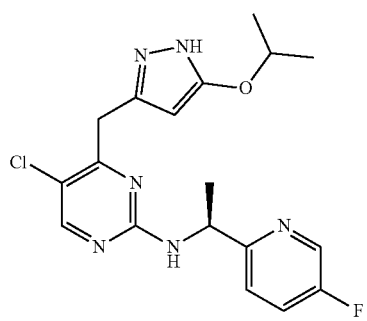

AZ-23 Chemical Structure
Molecular Weight: 391.83.

Oxindole 3

In certain embodiments the kinase inhibitor is oxindole 3. Oxindole 3 has the chemical name: 1,2 Dihydro-3H-indol-3-one; and has the following structure:

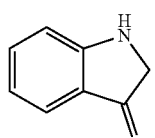

Oxindole 3 Chemical Structure
Molecular Weight: 133.147.

In other embodiments, the inhibitor is a pan FGFR inhibitor. For example, the inhibitor is ACTB-1003 as described in Burd, A. et al. (2010) *EJC Supplements* Vol. 8(7): page 51; Patel, K. et al. (2010) *Journal of Clinical Oncology*, ASCO Annual Meeting Abstracts. Vol 28, No 15_suppl (May 20 Supplement), 2010: e13665.

In other embodiments, the inhibitor is an oral inhibitor.

In other embodiments, the inhibitor is Volasertib. Volasertib has the following chemical structure:

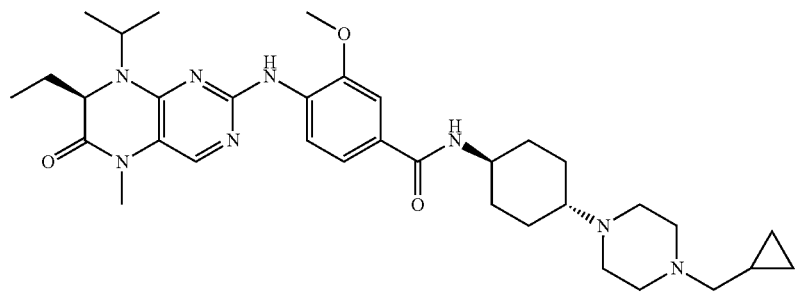

Volasertib (BI 6727) Chemical Structure
Molecular Weight: 618.81

In another embodiment, the inhibitor is R1530. R1530 is a pyrazolobenzodiazepine small molecule with potential antiangiogenesis and antineoplastic activities. R1530 is also a mitosis-angiogenesis inhibitor (MAI) that inhibits multiple receptor tyrosine kinases involved in angiogenesis, such as vascular endothelial growth factor receptor (VEGFR)-1, -2, -3, platelet-derived growth factor receptor (PDGFR) beta, FMS-like tyrosine kinase (Flt)-3, and fibroblast growth factor receptor (FGFR)-1, -2. In addition, this agents exhibits anti-proliferative activity by initiating mitotic arrest and inducing apoptosis. R1530 has a chemical name: 5-(2-chlorophenyl)-7-fluoro-8-methoxy-3-methyl-2,10-dihydrobenzo[e]pyrazolo[4,3-b][1,4]diazepine (described in, e.g., Kolinsky K, et al. *Cancer Chemother Pharmacol.* 2011 December; 68(6):1585-94. Epub 2011 May 8. PubMed PMID: 21553286).

In another embodiment, the inhibitor is ARRY-470. ARRY-470 has the following structure and chemical name

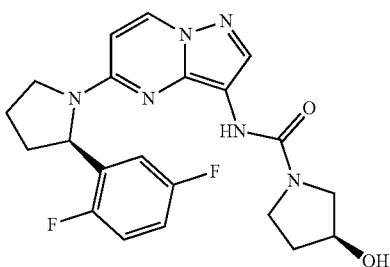

ARRY-470

(S)-N-(5-((R)-(2,5-difluorophenyl)pyrrolidin-1-yl)pyrazolo[1,5-a]pyrimidin-3-yl)-3-hydroxypyrrolidine-1-carboximide In another embodiment, the inhibitor is RXDX-101 or RXDX-102. RXDX-101 is an orally available, selective tyrosine kinase inhibitor of the TrkA, ROS1 and ALK proteins. RXDX-101 is designed as a targeted therapeutic candidate to treat patients with cancers that harbor activating alterations to TrkA, ROS1 and ALK. RXDX-102 is an orally available, selective pan-TRK tyrosine kinase inhibitor, or inhibitor of the TrkA, TrkB and TrkC proteins. RXDX-102 is designed as an oncogene-targeted therapeutic candidate to treat patients with cancers that harbor activating alterations to TrkA, TrkB or TrkC.

In one embodiment, the therapeutic agent is a kinase inhibitor. For example, the kinase inhibitor is a multi-kinase inhibitor or a specific inhibitor. Exemplary kinase inhibitors include, but are not limited to, axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib, vatalanib (PTK787, PTK/ZK), sorafenib (NEXAVAR®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and XL228.

In other embodiments, the anti-cancer agent inhibits the expression of nucleic acid encoding fusions. Examples of such antagonists include nucleic acid molecules, for example, antisense molecules, ribozymes, RNAi, triple helix molecules that hybridize to a nucleic acid encoding a fusion, and blocks or reduces mRNA expression of a fusion.

In other embodiments, the kinase inhibitor is administered in combination with a second therapeutic agent or a different therapeutic modality, e.g., anti-cancer agents, and/or in combination with surgical and/or radiation procedures.

In yet another embodiment, the inhibitor is an antibody molecule (e.g., an antibody or an antigen-binding fragment thereof). In one embodiment, the antibody molecule binds to FGFR2, e.g., binds to the extracellular ligand binding domain of FGFR2. In one embodiment, the antibody molecule binds to an isoform of FGFR2, e.g., binds to a IIIb-isoform of FGFR2. In one embodiment, the antibody molecule is AV369b described in Bai et al. (2010) 22nd EORTC-NCI-AACR Symposium, Berlin, Germany 16-19, 2010. In one embodiment, the antibody molecule: competes for binding, binds to a similar epitope as AV369b and/or has one or more of the properties as AV369b.

By "in combination with," it is not intended to imply that the therapy or the therapeutic agents must be administered at the same time and/or formulated for delivery together, although these methods of delivery are within the scope of the invention. The pharmaceutical compositions can be administered concurrently with, prior to, or subsequent to, one or more other additional therapies or therapeutic agents. In general, each agent will be administered at a dose and/or on a time schedule determined for that agent. In will further be appreciated that the additional therapeutic agent utilized in this combination can be administered together in a single composition or administered separately in different compositions. The particular combination to employ in a regimen will take into account compatibility of the inventive pharmaceutical composition with the additional therapeutically active agent and/or the desired therapeutic effect to be achieved.

"Treat," "treatment," and other forms of this word refer to the administration of a kinase inhibitor, alone or in combination with a second agent to impede growth of a cancer, to cause a cancer to shrink by weight or volume, to extend the expected survival time of the subject and or time to progression of the tumor or the like. In those subjects, treatment can include, but is not limited to, inhibiting tumor growth, reducing tumor mass, reducing size or number of metastatic lesions, inhibiting the development of new metastatic lesions, prolonged survival, prolonged progression-free survival, prolonged time to progression, and/or enhanced quality of life.

As used herein, unless otherwise specified, the terms "prevent," "preventing" and "prevention" contemplate an action that occurs before a subject begins to suffer from the re-growth of the cancer and/or which inhibits or reduces the severity of the cancer.

As used herein, and unless otherwise specified, a "therapeutically effective amount" of a compound is an amount sufficient to provide a therapeutic benefit in the treatment or management of the cancer, or to delay or minimize one or more symptoms associated with the cancer. A therapeutically effective amount of a compound means an amount of therapeutic agent, alone or in combination with other therapeutic agents, which provides a therapeutic benefit in the treatment or management of the cancer. The term "therapeutically effective amount" can encompass an amount that improves overall therapy, reduces or avoids symptoms or causes of the cancer, or enhances the therapeutic efficacy of another therapeutic agent.

As used herein, and unless otherwise specified, a "prophylactically effective amount" of a compound is an amount sufficient to prevent re-growth of the cancer, or one or more symptoms associated with the cancer, or prevent its recurrence. A prophylactically effective amount of a compound means an amount of the compound, alone or in combination with other therapeutic agents, which provides a prophylactic benefit in the prevention of the cancer. The term "prophylactically effective amount" can encompass an amount that improves overall prophylaxis or enhances the prophylactic efficacy of another prophylactic agent.

As used herein, the term "patient" or "subject" refers to an animal, typically a human (i.e., a male or female of any age group, e.g., a pediatric patient (e.g, infant, child, adolescent) or adult patient (e.g., young adult, middle-aged adult or senior adult) or other mammal, such as a primate (e.g., cynomolgus monkey, rhesus monkey). When the term is used in conjunction with administration of a compound or drug, then the patient has been the object of treatment, observation, and/or administration of the compound or drug.

Isolated Nucleic Acid Molecules

One aspect featured in the invention pertains to isolated nucleic acid molecules that include a fusion, including nucleic acids which encode a fusion polypeptide or a portion of such a polypeptide. The nucleic acid molecules include those nucleic acid molecules which reside in genomic regions identified herein. As used herein, the term "nucleic acid molecule" includes DNA molecules (e.g., cDNA or genomic DNA) and RNA molecules (e.g., mRNA) and analogs of the DNA or RNA generated using nucleotide analogs. The nucleic acid molecule can be single-stranded or double-stranded; in certain embodiments the nucleic acid molecule is double-stranded DNA.

Isolated nucleic acid molecules also include nucleic acid molecules sufficient for use as hybridization probes or primers to identify nucleic acid molecules that correspond to a fusion, e.g., those suitable for use as PCR primers for the amplification or mutation of nucleic acid molecules.

An "isolated" nucleic acid molecule is one which is separated from other nucleic acid molecules which are present in the natural source of the nucleic acid molecule. In certain embodiments, an "isolated" nucleic acid molecule is free of sequences (such as protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, less than about 4 kB, less than about 3 kB, less than about 2 kB, less than about 1 kB, less than about 0.5 kB or less than about 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

The language "substantially free of other cellular material or culture medium" includes preparations of nucleic acid molecule in which the molecule is separated from cellular components of the cells from which it is isolated or recombinantly produced. Thus, nucleic acid molecule that is substantially free of cellular material includes preparations of nucleic acid molecule having less than about 30%, less than about 20%, less than about 10%, or less than about 5% (by dry weight) of other cellular material or culture medium.

A fusion nucleic acid molecule can be isolated using standard molecular biology techniques and the sequence information in the database records described herein. Using all or a portion of such nucleic acid sequences, fusion nucleic acid molecules as described herein can be isolated using standard hybridization and cloning techniques (e.g., as described in Sambrook et al., ed., *Molecular Cloning: A Laboratory Manual*, 2nd ed., Cold Spring Harbor Laboratory Press, Cold Spring Harbor, N Y, 1989).

A fusion nucleic acid molecule can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule featured in the invention can be prepared by standard synthetic techniques, e.g., using an automated DNA synthesizer.

In another embodiment, a fusion nucleic acid molecule comprises a nucleic acid molecule which has a nucleotide sequence complementary to the nucleotide sequence of the fusion nucleic acid molecule or to the nucleotide sequence of a nucleic acid encoding a fusion protein. A nucleic acid molecule which is complementary to a given nucleotide sequence is one which is sufficiently complementary to the given nucleotide sequence that it can hybridize to the given nucleotide sequence thereby forming a stable duplex.

Moreover, a fusion nucleic acid molecule can comprise only a portion of a nucleic acid sequence, wherein the full length nucleic acid sequence or which encodes a fusion polypeptide. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, at least about 15, at least about 25, at least about 50, at least about 75, at least about 100, at least about 125, at least about 150, at least about 175, at least about 200, at least about 250, at least about 300, at least about 350, at least about 400, at least about 500, at least about 600, at least about 700, at least about 800, at least about 900, at least about 1 kb, at least about 2 kb, at least about 3 kb, at least about 4 kb, at least about 5 kb, at least about 6 kb, at least about 7 kb, at least about 8 kb, at least about 9 kb, at least about 10 kb, at least about 15 kb, at least about 20 kb, at least about 25 kb, at least about 30 kb, at least about 35 kb, at least about 40 kb, at least about 45 kb, at least about 50 kb, at least about 60 kb, at least about 70 kb, at least about 80 kb, at least about 90 kb, at least about 100 kb, at least about 200 kb, at least about 300 kb, at least about 400 kb, at least about 500 kb, at least about 600 kb, at least about 700 kb, at least about 800 kb, at least about 900 kb, at least about 1 mb, at least about 2 mb, at least about 3 mb, at least about 4 mb, at least about 5 mb, at least about 6 mb, at least about 7 mb, at least about 8 mb, at least about 9 mb, at least about 10 mb or more consecutive nucleotides of a fusion nucleic acid.

In another embodiment, an isolated fusion nucleic acid molecule is at least 7, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 250, at least 300, at least 350, at least 400, at least 450, at least 550, at least 650, at least 700, at least 800, at least 900, at least 1000, at least 1200, at least 1400, at least 1600, at least 1800, at least 2000, at least 2200, at least 2400, at least 2600, at least 2800, at least 3000, or more nucleotides in length and hybridizes under stringent conditions to a fusion nucleic acid molecule or to a nucleic acid molecule encoding a protein corresponding to a marker featured in the invention.

As used herein, the term "hybridizes under stringent conditions" is intended to describe conditions for hybridization and washing under which nucleotide sequences at least 60%, at least 65%, at least 70%, at least 75%, at least 80%, or at least 85% identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). Another, non-limiting example of stringent hybridization conditions are hybridization in 6× sodium chloride/sodium citrate (SSC) at about 45° C., followed by one or more washes in 0.2×SSC, 0.1% SDS at 50-65° C.

The invention also includes molecular beacon nucleic acid molecules having at least one region which is complementary to a fusion nucleic acid molecule, such that the molecular beacon is useful for quantitating the presence of the nucleic acid molecule featured in the invention in a sample. A "molecular beacon" nucleic acid is a nucleic acid molecule comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid molecules are not annealed with one another, fluorescence of the fluorophore is quenched to a lesser degree. Molecular beacon nucleic acid molecules are described, for example, in U.S. Pat. No. 5,876,930.

In one embodiment, a fusion includes an in-frame fusion of an exon of fibroblast growth factor receptor 2 (FGFR2), e.g., one more exons of FGFR2 (e.g., one or more of exons 1-16 of FGFR2) or a fragment thereof, and an exon of a partner as set forth in FIG. 1B (e.g., a transforming, acidic coiled-coil containing protein 3 (TACC3), e.g., one or more exons of a TACC3 (e.g., one or more of exons 11-16 of TACC3) or a fragment thereof. In other embodiments, one or more exons of KIAA1598, BICC1, PARK2, NOL4 or ZDHHC6 are fused as summarized in FIGS. 1A-1C. For example, the FGFR3-TACC3 fusion can include an in-frame fusion within an intron of FGFR2 or a fragment thereof, with an intron of TACC3, KIAA1598, BICC1 PARK2, NOL4 or ZDHHC6, or a fragment thereof, as depicted in FIG. 1A. In one embodiment, the fusion of the FGFR2-fusion comprises the nucleotide sequence of: chromosome 10 at one or more of the nucleotides shown in FIG. 1A (plus or minus 10, 20, 30, 50, 60, 70, 80, 100 or more nucleotides) and a partner in chromosome 4 or 10 at one or more of the nucleotides shown in FIG. 1A (plus or minus 10, 20, 30, 50, 60, 70, 80, 100 or more nucleotides). In one embodiment, the FGFR3-TACC3 fusion is a translocation, e.g., a translocation of a portion of chromosome 10 and 4. In another embodiment, the FGFR2-KIAA1598 fusion is a deletion, e.g., a deletion of chromosome 10. In another embodiment, the FGFR2-BICC1 fusion is an inversion, e.g., a an inversion of chromosome 10 (e.g., as summarized in FIG. 1A).

In certain embodiments, the FGFR2-TACC3, FGFR2-KIAA1598, FGFR2-BICC1, BICC1-FGFR2, PARK2-FGFR2, FGFR2-NOL4, or ZDHHC6-FGFR2 fusion is in a 5'- to 3'-configuration (also referred to herein as, for example, "5'-FGFR2-TACC-3')." The term "fusion" or "fusion molecule" can refer to a polypeptide or a nucleic acid fusion, depending on the context. It may include a full-length sequence or a fragment thereof, e.g., a fusion junction (e.g., a fragment including a portion of FGFR2 and a portion of TAC3, KIAA1598, BICC1 PARK2, NOL4 or ZDHHC6, e.g., a portion of the FGFR3-TACC3, FGFR2-KIAA1598, FGFR2-BICC1, BICC1-FGFR2 PARK2-FGFR2, FGFR2-NOL4, or ZDHHC6-FGFR2 fusion described herein). In one embodiment, the FGFR2-TACC3 fusion polypeptide includes the amino acid sequence shown in FIG. 3 (SEQ ID NO:2) and/or FIG. 5 (SEQ ID NO:4), or an amino acid sequence substantially identical thereto. In another embodiment, the FGFR2-TACC3 fusion nucleic acid includes the nucleotide sequence shown in FIGS. 2A-2B (SEQ ID NO:1) and/or FIGS. 4A-4B (SEQ ID NO:3), or a nucleotide sequence substantially identical thereto. In another embodiment, the FGFR2-KIAA1598 fusion polypeptide includes the amino acid sequence shown in FIG. 3 (SEQ ID NO:2) and/or FIG. 7 (SEQ ID NO:6), or an amino acid sequence substantially identical thereto. In another embodiment, the FGFR2-KIAA1598 fusion nucleic acid includes the nucleotide sequence shown in FIGS. 2A-2B (SEQ ID NO:1) and/or FIGS. 6A-6C (SEQ ID NO:5), or a nucleotide sequence substantially identical thereto. In another embodiment, the FGFR2-BICC1 fusion polypeptide includes the amino acid sequence shown in FIG. 3 (SEQ ID NO:2) and/or FIG. 9 (SEQ ID NO:8), or an amino acid sequence substantially identical thereto. In another embodiment, the FGFR2-BICC1 fusion nucleic acid includes the nucleotide sequence shown in FIG. 2 (SEQ ID NO:1) and/or FIG. 8 (SEQ ID NO:7), or a nucleotide sequence substantially identical thereto. In another embodiment, the BICC1-FGFR2 fusion polypeptide includes the amino acid sequence shown in FIG. 9 (SEQ ID NO:8) and/or FIG. 3 (SEQ ID NO:2), or an amino acid sequence substantially identical thereto. In another embodiment, the BICC1-FGFR2 fusion nucleic acid includes the nucleotide sequence shown in FIGS. 8A-8B (SEQ ID NO:7) and/or FIGS. 2A-2B (SEQ ID NO:1), or a nucleotide sequence substantially identical thereto. In another embodiment, the PARK2-FGFR2 fusion polypeptide includes the amino acid sequence shown in FIG. 11 (SEQ ID NO:10) and/or FIG. 13 (SEQ ID NO:12), or an amino acid sequence substantially identical thereto. In another embodiment, the FGFR2-NOL4 fusion polypeptide includes the amino acid sequence shown in FIG. 15 (SEQ ID NO:14) and/or FIG. 13 (SEQ ID NO:12), or an amino acid sequence substantially identical thereto. In another embodiment, the ZDHHC6-FGFR2 fusion polypeptide includes the amino acid sequence shown in FIG. 16 (SEQ ID NO:15) and/or FIG. 13 (SEQ ID NO:12), or an amino acid sequence substantially identical thereto.

In one embodiment, the FGFR2 fusion polypeptide comprises sufficient FGFR2 and sufficient partner sequence such that the fusion has kinase activity, e.g., has elevated activity, e.g., FGFR2 tyrosine kinase activity, as compared with wild type FGFR2, e.g., in a cell of a cancer referred to herein (a cholangiocarcinoma). In one embodiment, the partner, e.g., TACC3 sequence, has a coiled-coil domain, e.g., it may dimerize with one or more partners.

In certain embodiments, the FGFR2-TACC3 fusion comprises one or more (or all of) exons 1-16 from FGFR2 and one or more (or all of) exons 11-16 from TACC3 (e.g., one or more of the exons shown in FIGS. 2-5). In certain embodiments, the FGFR2-TACC3 fusion comprises at least 1, 2, 3, 4, 5, 6, 7, 9, 10, 11, 12, 13, 14, 15, 16 or more exons from FGFR2 and at least 1, 2, 3, 4, 5, 6, 7, 8, or more exons from TACC3 (e.g., from the FGFR3 and TACC3 sequences shown in FIGS. 2-5 (SEQ ID NOs:1-4).

In certain embodiments, the FGFR2-KIAA1598 fusion comprises one or more (or all of) exons 1-16 from FGFR2 and one or more (or all of) exons 7-17 from KIAA1598 (e.g., one or more of the exons shown in FIGS. 2-3 and 6-7). In certain embodiments, the FGFR2-KIAA1598 fusion comprises at least 1, 2, 3, 4, 5, 6, 7, 9, 10, 11, 12, 13, 14, 15, 16 or more exons from FGFR2 and at least 1, 2, 3, 4, 5, 6, 7, 8, or more exons from KIAA1598 (e.g., from the FGFR2 and KIAA1598 sequences shown in FIGS. 2-3 and 6-7 (SEQ ID NOs:1-2 and 5-6).

In certain embodiments, the FGFR2-BICC1 fusion comprises one or more (or all of) exons 1-16 from FGFR2 and one or more (or all of) exons 18-21 from BICC1 (e.g., one or more of the exons shown in FIGS. 2-3 and 8-9). In certain embodiments, the FGFR2-BICC1 fusion comprises at least 1, 2, 3, 4, 5, 6, 7, 9, 10, 11, 12, 13, 14, 15, 16 or more exons from FGFR2 and at least 1, 2, 3, 4, or more exons from BICC1 (e.g., from the FGFR2 and BICC1 sequences shown in FIGS. 2-3 and 8-9 (SEQ ID NOs:1-2 and 7-8).

In certain embodiments, the BICC1-FGFR2-fusion comprises one or more (or all of) exons 1-2 FROM BICC1 and exon 17 from FGFR2 (e.g., one or more of the exons shown in FIGS. 2-3 and 8-9) (e.g., from the FGFR2 and BICC1 sequences shown in FIGS. 2-3 and 8-9 (SEQ ID NOs:1-2 and 7-8).

In certain embodiments, the PARK2-FGFR2-fusion comprises one or more (or all of) exons 1-9 of PARK2 and exon 18 from FGFR2 (e.g., one or more of the exons shown in FIGS. 10-11 and 12-13) (e.g., from the PARK2 and FGFR2 sequences shown in FIGS. 10-11 and 12-13 (SEQ ID NOs: 9-10 and 11-12).

In certain embodiments, the FGFR2-NOL4-fusion comprises one or more (or all of) exons 1-17 of FGFR2 and exon 7-11 from NOL4 (e.g., one or more of the exons shown in FIGS. 12-13 and 14-15 and) (e.g., from the FGFR2 and NOL4 sequences shown in FIGS. 12-13 and 14-15 (SEQ ID NOs: 11-12 and 13-14).

In certain embodiments, the ZDHHC6-FGFR2-fusion comprises one or more (or all of) exons 1-5 of ZDHHC6 and exon 18 from FGFR2 (e.g., one or more of the exons shown in FIGS. 16-17 and 12-13) (e.g., from the ZDHHC6 and FGFR2 sequences shown in FIGS. 16-17 and 12-13 (SEQ ID NOs:15-16 and 11-12).

FGFR2 Fusion Nucleic Acid Molecules

In one aspect, the invention features a nucleic acid molecule (e.g., an isolated or purified) nucleic acid molecule that includes a fragment of an FGFR2 gene, and a fragment of a TACC3, KIAA1598, BICC1, PARK2, NOL4 or ZDHHC6 as summarized in FIGS. 1A-1C gene. In one embodiment, the nucleotide sequence encodes a FGFR2 fusion polypeptide that includes an FGFR2 tyrosine kinase domain or a functional fragment thereof. In another embodiment, the nucleotide sequence encodes a fragment of the FGFR2 polypeptide of SEQ ID NO:2 or 12, or a fragment thereof; or a sequence substantially identical thereto. In other embodiments, the nucleic acid molecule includes a fragment of the TACC3 gene encoding the amino acid sequence of SEQ ID NO:4, or a fragment thereof; or a sequence substantially identical thereto. In other embodiments, the nucleic acid molecule includes a fragment of the KIAA1598 gene encoding the amino acid sequence of SEQ ID NO:6, or a fragment thereof; or a sequence substantially identical thereto. In other embodiments, the nucleic acid molecule includes a fragment of the BICC1 gene encoding the amino acid sequence of SEQ ID NO: 8, or a fragment thereof; or a sequence substantially identical thereto. In other embodiments, the nucleic acid molecule includes a fragment of the PARK2 gene encoding the amino acid sequence of SEQ ID NO:10, or a fragment thereof; or a sequence substantially identical thereto. In other embodiments, the nucleic acid molecule includes a fragment of the NOL4 gene encoding the amino acid sequence of SEQ ID NO:14, or a fragment thereof; or a sequence substantially identical thereto. In other embodiments, the nucleic acid molecule includes a fragment of the ZDHHC6 gene encoding the amino acid sequence of SEQ ID NO:16, or a fragment thereof; or a sequence substantially identical thereto.

In one embodiment, the nucleic acid molecule includes a fusion, e.g., an in-frame fusion, between an intron of FGFR2, or a fragment thereof), and an intron of TACC3, KIAA1598, BICC1 PARK2, NOL4 or ZDHHC6, or a fragment thereof, as depicted in FIG. 1A. The FGFR2 fusion can comprise a fusion of the nucleotide sequence of: chromosome 10 at one or more of the nucleotides depicted in FIG. 1A (plus or minus 10, 20, 30, 50, 60, 70, 80, 100 nucleotides) and chromosome 4 or 10 at one or more of the nucleotides depicted in FIG. 1A (plus or minus 10, 20, 30, 50, 60, 70, 80, 100 nucleotides), or a fragment thereof. In another embodiment, the FGFR2 fusion comprises a nucleotide sequence shown in FIGS. 2A-2B (SEQ ID NO: 1) or FIGS. 12A-12B (SEQ ID NO:11) and a partner chosen from: FIGS. 4A-4B (SEQ ID NO:3), or a fragment thereof; FIGS. 6A-6C (SEQ ID NO:5), or a fragment thereof; FIGS. 8A-8B (SEQ ID NO:3), or a fragment thereof; FIGS. 10A-10B (SEQ ID NO:9), or a fragment thereof; FIGS. 14A-14B (SEQ ID NO:13), or a fragment thereof; or FIG. 16 (SEQ ID NO:15), or a fragment thereof.

In one embodiment, the FGFR2 fusion comprises a nucleotide sequence substantially identical to the nucleotide sequence shown in FIGS. 2A-2B (SEQ ID NO: 1), or a fragment thereof or FIGS. 12A-12B (SEQ ID NO:11) and a partner chosen from: FIGS. 4A-4B (SEQ ID NO:3), or a fragment thereof; FIGS. 6A-6C (SEQ ID NO:5), or a fragment thereof; FIGS. 8A-8B (SEQ ID NO:3), or a fragment thereof; FIGS. 10A-10B (SEQ ID NO:9), or a fragment thereof; FIGS. 14A-14B (SEQ ID NO:13), or a fragment thereof; or FIG. 16 (SEQ ID NO:15), or a fragment thereof; or a nucleotide sequence at least 70%, at least 75%, at least 80%, at least 85%, at least 90%, at least 95%, at least 99%, at least 99.5 or greater, identical thereto. In one embodiment, the FGFR2 fusion comprises a nucleotide sequence containing at least 50, 100, 150, 200, 500, 1000, 1500, 2000, 2500, 3000, or more nucleotides of the nucleotide sequence shown in FIGS. 2A-2B (SEQ ID NO: 1) or FIGS. 12A-12B (SEQ ID NO:11) and a partner chosen from: FIGS. 4A-4B (SEQ ID NO:3), or a fragment thereof; FIGS. 6A-6C (SEQ ID NO:5), or a fragment thereof; FIGS. 8A-8B (SEQ ID NO:3), or a fragment thereof; FIGS. 10A-10B (SEQ ID NO:9), or a fragment thereof; FIGS. 14A-14B (SEQ ID NO:13), or a fragment thereof; or FIG. 16 (SEQ ID NO:15), or a fragment thereof, or a sequence substantially identical thereto.

In certain embodiments, the BICC1-FGFR2-fusion comprises one or more (or all of) exons 1-2 and exon 17 from FGFR2 (e.g., one or more of the exons shown in FIGS. 2-3 and 8-9, or a sequence substantially identical thereto) (e.g., from the FGFR2 and BICC1 sequences shown in FIGS. 2-3 and 8-9 (SEQ ID NOs:1-2 and 7-8, or a sequence substantially identical thereto).

In one embodiment, the nucleic acid molecule is complementary to at least a portion of a nucleotide sequence disclosed herein, e.g., is capable of hybridizing under a stringency condition described herein to SEQ ID NO:1 or SEQ ID NO:11 and/or SEQ ID NO:3, SEQ ID NO:5, SEQ ID NO:7, SEQ ID NO:9, SEQ ID NO:13, or SEQ ID NO:15, or a fragment thereof. In yet another embodiment, the nucleic acid molecule hybridizes to a nucleotide sequence that is complementary to at least a portion of a nucleotide sequence disclosed herein, e.g., is capable of hybridizing under a stringency condition to a nucleotide sequence complementary to SEQ ID NO:1 or SEQ ID NO:11 and/or SEQ ID NO:3, SEQ ID NO:5, SEQ ID NO:7, SEQ ID NO:9, SEQ ID NO:13, or SEQ ID NO:15, or a fragment thereof.

In an embodiment, the FGFR2-TACC3 nucleic acid molecule comprises sufficient FGFR2 and sufficient TACC3 sequence such that the encoded 5' FGFR3-2' TACC3 fusion has kinase activity, e.g., has elevated activity, e.g., FGFR2 kinase activity, as compared with wild type FGFR2, e.g., in a cell of a cancer referred to herein. In certain embodiments, the 5' FGFR2-3' TACC3 fusion comprises exons 1-16 from FGFR2 and exon 11-16 from TACC3. In certain embodiments, the FGFR3-TACC3 fusion comprises at least 1, 2, 3, 4, 5, 6, 7, 9, 10, 11, 12, 13, 14, 15, 16, or more exons from FGFR2 and at least 1, 2, 3, 4, 5, 6, 7, 9, 10, or more exons from TACC3. In certain embodiments, the FGFR2-KIAA1598 fusion comprises one or more (or all of) exons 1-16 from FGFR2 and one or more (or all of) exons 7-17 from KIAA1598 (e.g., one or more of the exons shown in FIGS. 2-3 and 6-7 or a sequence substantially identical thereto). In certain embodiments, the FGFR2-KIAA1598 fusion comprises at least 1, 2, 3, 4, 5, 6, 7, 9, 10, 11, 12, 13, 14, 15, 16 or more exons from FGFR2 and at least 1, 2, 3, 4, 5, 6, 7, 8, or more exons from KIAA1598 (e.g., from the FGFR2 and KIAA1598 sequences shown in FIGS. 2-3 and 6-7 (SEQ ID NOs:1-2 and 5-6), or a sequence substantially identical thereto. In certain embodiments, the FGFR2-BICC1 fusion comprises one or more (or all of) exons 1-16 from FGFR2 and one or more (or all of) exons 18-21 from BICC1 (e.g., one or more of the exons shown in FIGS. 2-3 and 8-9, or a sequence substantially identical thereto). In certain embodiments, the FGFR2-BICC1 fusion comprises at least 1, 2, 3, 4, 5, 6, 7, 9, 10, 11, 12, 13, 14, 15, 16 or more exons from FGFR2 and at least 1, 2, 3, 4, or more exons from BICC1 (e.g., from the FGFR2 and BICC1 sequences shown in FIGS. 2-3 and 8-9 (SEQ ID NOs:1-2 and 7-8, or a sequence substantially identical thereto). In certain embodiments, the BICC1-FGFR2-fusion comprises one or more (or all of) exons 1-2 and exon 17 from FGFR2 (e.g., one or more of the exons shown in FIGS. 2-3 and 8-9, or a sequence substantially identical thereto) (e.g., from the FGFR2 and BICC1 sequences shown in FIGS. 2-3 and 8-9 (SEQ ID NOs:1-2 and 7-8, or a sequence substantially identical thereto). Additional fusions and exon combinations are disclosed in FIG. 1B.

In another embodiment, the nucleic acid molecule includes a nucleotide sequence that includes a breakpoint, e.g., a breakpoint depicted in FIG. 1A, or a sequence substantially identical thereto. In one embodiment, the nucleic acid molecule is complementary to at least a portion of a nucleotide sequence disclosed herein, e.g., is capable of hybridizing under a stringency condition described herein to SEQ ID NO:1 or SEQ ID NO:11 and/or SEQ ID NO:3, SEQ ID NO:5, SEQ ID NO:7, SEQ ID NO:9, SEQ ID NO:13, or SEQ ID NO:15 or a fragment thereof. In yet other embodiment, the nucleic acid molecule hybridizes to a nucleotide sequence that is complementary to at least a portion of a nucleotide sequence disclosed herein, e.g., is capable of hybridizing under a stringency condition described herein to a nucleotide sequence complementary to SEQ ID NO:1 or SEQ ID NO:11 and/or SEQ ID NO:3, SEQ ID NO:5, SEQ ID NO:7, SEQ ID NO:9, SEQ ID NO:13, or SEQ ID NO:15, or a fragment thereof.

In a related aspect, the invention features nucleic acid constructs that include the FGFR2 nucleic acid molecules described herein. In certain embodiments, the nucleic acid molecules are operatively linked to a native or a heterologous regulatory sequence. Also included are vectors and host cells that include the FGFR2 nucleic acid molecules described herein, e.g., vectors and host cells suitable for producing the nucleic acid molecules and polypeptides described herein.

In a related aspect, methods of producing the nucleic acid molecules and polypeptides described herein are also described.

In another aspect, the invention features nucleic acid molecules that reduce or inhibit the expression of a nucleic acid molecule that encodes a FGFR2 fusion described herein. Examples of such nucleic acid molecules include, for example, antisense molecules, ribozymes, RNAi, triple helix molecules that hybridize to a nucleic acid encoding FGFR2, or a transcription regulatory region of FGFR2, and blocks or reduces mRNA expression of FGFR2.

Nucleic Acid Detection and Capturing Reagents

The invention also features a nucleic acid molecule, e.g., nucleic acid fragment, suitable as probe, primer, bait or library member that includes, flanks, hybridizes to, which are useful for identifying, or are otherwise based on, the FGFR2 fusions described herein. In certain embodiments, the probe, primer or bait molecule is an oligonucleotide that allows capture, detection or isolation of an FGFR2 fusion nucleic acid molecule described herein. The oligonucleotide can comprise a nucleotide sequence substantially complementary to a fragment of the FGFR2 fusion nucleic acid molecules described herein. The sequence identity between the nucleic acid fragment, e.g., the oligonucleotide, and the target FGFR2 sequence need not be exact, so long as the sequences are sufficiently complementary to allow the capture, detection or isolation of the target sequence. In one embodiment, the nucleic acid fragment is a probe or primer that includes an oligonucleotide between about 5 and 25, e.g., between 10 and 20, or 10 and 15 nucleotides in length. In other embodiments, the nucleic acid fragment is a bait that includes an oligonucleotide between about 100 to 300 nucleotides, 130 and 230 nucleotides, or 150 and 200 nucleotides, in length.

In one embodiment, the nucleic acid fragment can be used to identify or capture, e.g., by hybridization, an FGFR2 fusion. For example, the nucleic acid fragment can be a probe, a primer, or a bait, for use in identifying or capturing, e.g., by hybridization, an FGFR2 fusion described herein. In one embodiment, the nucleic acid fragment can be useful for identifying or capturing an FGFR2 breakpoint, e.g., the nucleotide sequence of: chromosome 10 at the nucleotides depicted in FIG. 1A plus or minus 10, 20, 30, 40 50, 60, 80, 100, 150 nucleotides and chromosome 4 at the nucleotides depicted in FIG. 1A plus or minus 10, 20, 30, 40 50, 60, 80, 100, 150 nucleotides.

In one embodiment, the nucleic acid fragment hybridizes to a nucleotide sequence within a chromosomal rearrangement that creates an in-frame fusion of intron 16 of FGFR3 with an intron depicted in FIG. 1A. In one embodiment, the nucleic acid fragment hybridizes to a nucleotide sequence in the region In another embodiment, the nucleic acid fragment hybridizes to a nucleotide sequence that comprises at least 6, 12, 15, 20, 25, 50, 75, 100, 150 or more nucleotides from exon 16 of FGFR2 (e.g., from the nucleotide sequence of FGFR3 preceding the fusion junction with the partner, e.g., a partner depicted in FIGS. 1A-1C.

In another embodiment, the nucleic acid fragment hybridizes to a nucleotide sequence that comprises at least 6, 12, 15, 20, 25, 50, 75, 100, 150 or more nucleotides from exon 16 of FGFR2 (e.g., from the nucleotide sequence of FGFR2 preceding the fusion junction with a partner TACC3, KIAA1598, BICC1, PARK2, NOL4 or ZDHHC6.

The probes or primers described herein can be used, for example, for FISH detection or PCR amplification. In one exemplary embodiment where detection is based on PCR, amplification of the FGFR2 fusion junction fusion junction can be performed using a primer or a primer pair, e.g., for amplifying a sequence flanking the fusion junctions described herein, e.g., the mutations or the junction of a chromosomal rearrangement described herein, e.g., FGFR2.

In one embodiment, a pair of isolated oligonucleotide primers can amplify a region containing or adjacent to a position in the FGFR2 fusion. For example, forward primers can be designed to hybridize to a nucleotide sequence within FGFR2 genomic or mRNA sequence, and the reverse primers can be designed to hybridize to a nucleotide sequence of TACC3, KIAA1598, BICC1, PARK2, NOL4 or ZDHHC6.

In another embodiment, the nucleic acid fragments can be used to identify, e.g., by hybridization, an FGFR2 fusion. In one embodiment, the nucleic acid fragment hybridizes to a nucleotide sequence that includes a fusion junction between the FGFR2 transcript and the partner transcript.

In other embodiments, the nucleic acid fragment includes a bait that comprises a nucleotide sequence that hybridizes to the FGFR2 fusion nucleic acid molecule described herein, and thereby allows the capture or isolation said nucleic acid molecule. In one embodiment, a bait is suitable for solution phase hybridization. In other embodiments, a bait includes a binding entity, e.g., an affinity tag, that allows capture and separation, e.g., by binding to a binding entity, of a hybrid formed by a bait and a nucleic acid hybridized to the bait.

In other embodiments, the nucleic acid fragment includes a library member comprising the FGFR2 nucleic acid molecule described herein. In one embodiment, the library member includes a rearrangement that results in the FGFR2 fusion described herein.

The nucleic acid fragment can be detectably labeled with, e.g., a radiolabel, a fluorescent label, a bioluminescent label, a chemiluminescent label, an enzyme label, a binding pair label, or can include an affinity tag; a tag, or identifier (e.g., an adaptor, barcode or other sequence identifier).

Detection Reagents and Detection of Mutations

In another aspect, the invention features a detection reagent, e.g., a purified or an isolated preparation thereof. Detection reagents can distinguish a nucleic acid, or protein sequence, having a breakpoint, e.g., a FGFR2 breakpoint; from a reference sequence (e.g., a breakpoint disclosed herein, e.g., in FIGS. 1A-1C. In one embodiment, the detection reagent detects (e.g., specifically detects) a FGFR2 fusion nucleic acid or a polypeptide (e.g., distinguishes a wild type TACC3 or another TACC3 fusion (or FGFR2) from a FGFR2 nucleic acid (e.g., as described herein).

Detection reagents, e.g., nucleic acid-based detection reagents, can be used to identify mutations in a target nucleic acid, e.g., DNA, e.g., genomic DNA or cDNA, or RNA, e.g., in a sample, e.g., a sample of nucleic acid derived from a neoplastic or tumor cell, e.g., a melanocytic neoplasm, melanoma or metastatic cell. Detection reagents, e.g., antibody-based detection reagents, can be used to identify mutations in a target protein, e.g., in a sample, e.g., a sample of protein derived from, or produced by, a neoplastic or tumor cell, e.g., a cholangiocarcinoma or metastatic cell.

Probes

The invention also provides isolated nucleic acid molecules useful as probes. Such nucleic acid probes can be designed based on the sequence of a fusion.

Probes based on the sequence of a fusion nucleic acid molecule as described herein can be used to detect transcripts or genomic sequences corresponding to one or more markers featured in the invention. The probe comprises a label group attached thereto, e.g., a radioisotope, a fluorescent compound, an enzyme, or an enzyme co-factor. Such probes can be used as part of a test kit for identifying cells or tissues which express the fusion protein such as by measuring levels of a nucleic acid molecule encoding the protein in a sample of cells from a subject, e.g., detecting mRNA levels or determining whether a gene encoding the protein has been mutated or deleted.

Probes featured in the invention include those that will specifically hybridize to a gene sequence described in herein. Typically these probes are 12 to 20, e.g., 17 to 20 nucleotides in length (longer for large insertions) and have the nucleotide sequence corresponding to the region of the mutations at their respective nucleotide locations on the gene sequence. Such molecules can be labeled according to any technique known in the art, such as with radiolabels, fluorescent labels, enzymatic labels, sequence tags, biotin, other ligands, etc. As used herein, a probe that "specifically hybridizes" to a fusion gene sequence will hybridize under high stringency conditions.

A probe will typically contain one or more of the specific mutations described herein. Typically, a nucleic acid probe will encompass only one mutation. Such molecules may be labeled and can be used as allele-specific probes to detect the mutation of interest.

In one aspect, the invention features a probe or probe set that specifically hybridizes to a nucleic acid comprising an inversion resulting in a fusion. In another aspect, the invention features a probe or probe set that specifically hybridizes to a nucleic acid comprising a deletions resulting in a fusion.

Isolated pairs of allele specific oligonucleotide probes are also provided, where the first probe of the pair specifically hybridizes to the mutant allele, and the second probe of the pair specifically hybridizes to the wildtype allele. For example, in one exemplary probe pair, one probe will recognize the fusion junction in the fusion, and the other probe will recognize a sequence downstream or upstream of, neither of which includes the fusion junction. These allele-specific probes are useful in detecting an fusion partner somatic mutation in a tumor sample, e.g., cholangiocarcinoma sample.

Primers

The invention also provides isolated nucleic acid molecules useful as primers.

The term "primer" as used herein refers to a sequence comprising two or more deoxyribonucleotides or ribonucleotides, e.g., more than three, and more than eight, or at least 20 nucleotides of a gene described in herein, where the sequence corresponds to a sequence flanking one of the mutations or a wild type sequence of a gene identified herein gene. Primers may be used to initiate DNA synthesis via the PCR (polymerase chain reaction) or a sequencing method. Primers featured in the invention include the sequences recited and complementary sequences which would anneal to the opposite DNA strand of the sample target. Since both strands of DNA are complementary and mirror images of each other, the same segment of DNA will be amplified.

Primers can be used to sequence a nucleic acid, e.g., an isolated nucleic acid described herein, such as by an NGS method, or to amplify a gene described in the Example, such as by PCR. The primers can specifically hybridize, for example, to the ends of the exons or to the introns flanking the exons. The amplified segment can then be further analyzed for the presence of the mutation such as by a sequencing method. The primers are useful in directing amplification of a target polynucleotide prior to sequencing. In another aspect, the invention features a pair of oligonucleotide primers that amplify a region that contains or is adjacent to a fusion junction identified in the Example. Such primers are useful in directing amplification of a target region that includes a fusion junction identified herein, e.g., prior to sequencing. The primer typically contains 12 to 20, or 17 to 20, or more nucleotides, although a primer may contain fewer nucleotides.

A primer is typically single stranded, e.g., for use in sequencing or amplification methods, but may be double stranded. If double stranded, the primer may first be treated to separate its strands before being used to prepare extension products. A primer must be sufficiently long to prime the synthesis of extension products in the presence of the inducing agent for polymerization. The exact length of primer will depend on many factors, including applications (e.g., amplification method), temperature, buffer, and nucleotide composition. A primer typically contains 12-20 or more nucleotides, although a primer may contain fewer nucleotides.

Primers are typically designed to be "substantially" complementary to each strand of a genomic locus to be amplified. Thus, the primers must be sufficiently complementary to specifically hybridize with their respective strands under conditions which allow the agent for polymerization to perform. In other words, the primers should have sufficient complementarity with the 5' and 3' sequences flanking the mutation to hybridize therewith and permit amplification of the genomic locus.

The term "substantially complementary to" or "substantially the sequence" refers to sequences that hybridize to the sequences provided under stringent conditions and/or sequences having sufficient homology with a sequence comprising a fusion junction identified in the Example, or the wildtype counterpart sequence, such that the allele specific oligonucleotides hybridize to the sequence. In one embodiment, a sequence is substantially complementary to a fusion junction in an inversion event, e.g., to a fusion junction. "Substantially the same" as it refers to oligonucleotide sequences also refers to the functional ability to hybridize or anneal with sufficient specificity to distinguish between the presence or absence of the mutation. This is measurable by the temperature of melting being sufficiently different to permit easy identification of whether the oligonucleotide is binding to the normal or mutant gene sequence identified in the Example.

In one aspect, the invention features a primer or primer set for amplifying a nucleic acid comprising an inversion resulting in a fusion. In another aspect, the invention features a primer or primer set for amplifying a nucleic acid comprising a deletion resulting in an fusion.

Isolated pairs of allele specific oligonucleotide primer are also provided, where the first primer of the pair specifically hybridizes to the mutant allele, and the second primer of the pair specifically hybridizes to a sequence upstream or downstream of a mutation, or a fusion junction resulting from, e.g., an inversion, duplication, deletion, insertion or translocation. For example, in one exemplary primer pair, one probe will recognize a translocation, such as by hybridizing to a sequence at the fusion junction between the fusion partner transcripts, and the other primer will recognize a sequence upstream or downstream of the fusion junction. These allele-specific primers are useful for amplifying a fusion sequence from a tumor sample, e.g., cholangiocarcinoma. Similarly, in one exemplary primer pair, one probe will recognize a fusion, such as by hybridizing to a sequence at the fusion junction between the transcripts, and the other primer will recognize a sequence upstream or downstream of the fusion junction. These allele-specific primers are useful for amplifying a fusion sequence from a tumor sample.

In another exemplary primer pair, one primer can recognize an translocation such as by hybridizing to a sequence at the fusion junction between the transcripts, and the other primer will recognize a sequence upstream or downstream of the fusion junction. These allele-specific primers are useful for amplifying a fusion sequence from a cholangiocarcinoma sample.

In addition, an exemplary primer pair can be designed such that one primer recognizes an fusion, such as by hybridizing to a sequence at the fusion junction between the transcripts, and the other primer will recognize a sequence upstream or downstream of the fusion junction. These allele-specific primers are useful for amplifying a fusion sequence from a tumor sample, e.g., a cholangiocarcinoma sample.

Primers can be prepared using any suitable method, such as conventional phosphotriester and phosphodiester methods or automated embodiments thereof. In one such automated embodiment, diethylphosphoramidites are used as starting materials and may be synthesized as described by Beaucage, et al., Tetrahedron Letters, 22:1859-1862, (1981). One method for synthesizing oligonucleotides on a modified solid support is described in U.S. Pat. No. 4,458,066.

An oligonucleotide probe or primer that hybridizes to a mutant or wildtype allele is said to be the complement of the allele. As used herein, a probe exhibits "complete complementarity" when every nucleotide of the probe is complementary to the corresponding nucleotide of the allele. Two polynucleotides are said to be "minimally complementary" if they can hybridize to one another with sufficient stability to permit them to remain annealed to one another under at least conventional "low-stringency" conditions. Similarly, the polynucleotides are said to be "complementary" if they can hybridize to one another with sufficient stability to permit them to remain annealed to one another under conventional "high-stringency" conditions. Conventional stringency conditions are known to those skilled in the art and can be found, for example in *Molecular Cloning: A Laboratory Manual,* 3rd edition Volumes 1, 2, and 3. J. F. Sambrook, D. W. Russell, and N. Irwin, Cold Spring Harbor Laboratory Press, 2000.

Departures from complete complementarity are therefore permissible, as long as such departures do not completely preclude the capacity of a probe to hybridize to an allele. Thus, in order for a polynucleotide to serve as a primer or probe it need only be sufficiently complementary in sequence to be able to form a stable double-stranded structure under the particular solvent and salt concentrations employed. Appropriate stringency conditions which promote DNA hybridization are, for example, 6.0× sodium chloride/sodium citrate (SSC) at about 45° C., followed by a wash of 2.0×SSC at 50° C. Such conditions are known to those skilled in the art and can be found, for example in *Current Protocols in Molecular Biology*, John Wiley & Sons, N.Y. (1989). Salt concentration and temperature in the wash step can be adjusted to alter hybridization stringency. For example, conditions may vary from low stringency of about 2.0×SSC at 40° C. to moderately stringent conditions of about 2.0×SSC at 50° C. to high stringency conditions of about 0.2×SSC at 50° C.

Fusion Proteins and Antibodies

One aspect featured in the invention pertains to purified fusion polypeptides, and biologically active portions thereof. In one embodiment, the native fusion polypeptide can be isolated from cells or tissue sources by an appropriate purification scheme using standard protein purification techniques. In another embodiment, fusion polypeptide is produced by recombinant DNA techniques. Alternative to recombinant expression, a fusion polypeptide can be synthesized chemically using standard peptide synthesis techniques.

FGFR2 Fusion Polypeptides

In another embodiment, the FGFR2 fusion comprises an amino acid sequence shown in FIG. 3 (SEQ ID NO:2) or FIG. 13 (SEQ ID NO:12) or a fragment thereof, and a partner chosen from an amino acid sequence of SEQ ID NO: 4, SEQ ID NO: 6, SEQ ID NO: 8, SEQ ID NO: 10, SEQ ID NO: 14, or SEQ ID NO: 16, or a fragment thereof. In one embodiment, the FGFR2 fusion comprises an amino acid sequence substantially identical to the amino acid sequence shown in FIG. 3 (SEQ ID NO:2) or FIG. 13 (SEQ ID NO:12) and SEQ ID NO: 4, SEQ ID NO: 6, SEQ ID NO: 8, SEQ ID NO: 10, SEQ ID NO: 14, or SEQ ID NO: 16, or a fragment thereof. In one embodiment, the FGFR2 fusion comprises an amino acid sequence at least 70%, at least 75%, at least 80%, at least 85%, at least 90%, at least 95%, at least 99%, at least 99.5 or greater, identical to the amino acid sequence shown in FIG. 3 (SEQ ID NO:2) or FIG. 13 (SEQ ID NO:12) and SEQ ID NO: 4, SEQ ID NO: 6, SEQ ID NO: 8, SEQ ID NO: 10, SEQ ID NO: 14, or SEQ ID NO: 16. In one embodiment, the FGFR2 fusion comprises a sequence containing at least 10, 20, 50, 100, 500, 600, 700, 800, 900, 1000, or more amino acids of the amino acid sequence shown in FIG. 3 (SEQ ID NO:2) or FIG. 13 (SEQ ID NO:12); and at least 5, 10, 20, 50, 100, 500, 600, 700, 800, 900, 1000, or more amino acids of the amino acid sequence shown in SEQ ID NO: 4, SEQ ID NO: 6, SEQ ID NO: 8, SEQ ID NO: 10, SEQ ID NO: 14, or SEQ ID NO: 16. In one embodiment, the FGFR2 fusion comprises an amino acid sequence containing at least 10, 20, 50, 100, 500, 600, 700, 800, 900, 1000, or more contiguous amino acids of the amino acid sequence shown in FIG. 3 (SEQ ID NO:2) or FIG. 13 (SEQ ID NO:12); and at least 5, 10, 20, 50, 100, 500, 600, 700, 800, 900, 1000, or more contiguous amino acids of the amino acid sequence shown in SEQ ID NO: 4, SEQ ID NO: 6, SEQ ID NO: 8, SEQ ID NO: 10, SEQ ID NO: 14, or SEQ ID NO: 16. In one embodiment, the FGFR2 fusion polypeptide includes a FGFR2 receptor tyrosine kinase domain or a functional fragment thereof. In an embodiment, the FGFR2 fusion polypeptide comprises sufficient partner sequence, e.g., TACC3, and sufficient FGFR2 sequence such that it has kinase activity, e.g., has elevated activity, e.g., FGFR2 kinase activity, as compared with wild type FGFR2, e.g., in a cell of a cancer referred to herein.

In another aspect, the invention features a FGFR2 fusion polypeptide (e.g., a purified FGFR2 fusion polypeptide), a biologically active or antigenic fragment thereof, as well as reagents (e.g., antibody molecules that bind to a FGFR2 fusion polypeptide), methods for modulating a FGFR2 polypeptide activity and detection of a FGFR2 polypeptide.

In one embodiment, the FGFR2 fusion polypeptide has at least one biological activity, e.g., an FGFR2 kinase activity. In one embodiment, at least one biological activity of the FGFR2 fusion polypeptide is reduced or inhibited by an anti-cancer drug, e.g., a kinase inhibitor (e.g., a multikinase inhibitor or an FGFR2-specific inhibitor). In one embodiment, at least one biological activity of the FGFR2 fusion polypeptide is reduced or inhibited by an FGFR2 kinase inhibitor chosen from an inhibitor depicted in Table 2.

In yet other embodiments, the FGFR2 fusion polypeptide is encoded by a nucleic acid molecule described herein.

In certain embodiments, the FGFR2 fusion polypeptide comprises one or more of encoded exons 1-16 from FGFR2 and one or more of encoded exons of a partner depicted in FIGS. 1A-1C.

In one embodiment, the FGFR2 fusion polypeptide includes a FGFR2 tyrosine kinase domain or a functional fragment thereof. In a related aspect, the invention features FGFR2 fusion polypeptide or fragments operatively linked to heterologous polypeptides to form fusion proteins.

In another embodiment, the FGFR2 fusion polypeptide or fragment is a peptide, e.g., an immunogenic peptide or protein, that contains a fusion junction described herein. Such immunogenic peptides or proteins can be used to raise antibodies specific to the fusion protein. In other embodiments, such immunogenic peptides or proteins can be used for vaccine preparation. The vaccine preparation can include other components, e.g., an adjuvant.

In another aspect, the invention features antibody molecules that bind to a FGFR2 fusion polypeptide or fragment described herein. In embodiments the antibody can distinguish wild type TACC3, KIAA1598, BICC1 or PARK2, NOL4 or ZDHHC6 (or FGFR2) from FGFR2.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, less than about 20%, less than about 10%, or less than about 5% (by dry weight) of heterologous protein (also referred to herein as a "contaminating protein"). When the protein or biologically active portion thereof is recombinantly produced, it can be substantially free of culture medium, i.e., culture medium represents less than about 20%, less than about 10%, or less than about 5% of the volume of the protein preparation. When the protein is produced by chemical synthesis, it can substantially be free of chemical precursors or other chemicals, i.e., it is separated from chemical precursors or other chemicals which are involved in the synthesis of the protein. Accordingly such preparations of the protein have less than about 30%, less than about 20%, less than about 10%, less than about 5% (by dry weight) of chemical precursors or compounds other than the polypeptide of interest.

Biologically active portions of a fusion polypeptide include polypeptides comprising amino acid sequences sufficiently identical to or derived from the amino acid sequence of the fusion protein, which include fewer amino acids than the full length protein, and exhibit at least one activity of the corresponding full-length protein, e.g., a kinase activity. A biologically active portion of a protein featured in the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide.

In certain embodiments, the fusion polypeptide has an amino acid sequence of a protein encoded by a nucleic acid molecule disclosed herein. Other useful proteins are substantially identical (e.g., at least 60, at least 65, at least 70, at least 75, at least 80, at least 85, at least 86, at least 87, at least 88, at least 89, at least 90, at least 91, at least 92, at least 93, at least 94, at least 95, at least 96, at least 97, at least 98, at least 99, at least 99.5% or greater) to one of these sequences and retain the functional activity of the protein of the corresponding full-length protein yet differ in amino acid sequence.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. Another, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules featured in the invention. BLAST protein searches can be performed with the XBLAST program, score=50, word length=3 to obtain amino acid sequences homologous to protein molecules featured in the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See http://www.ncbi.nlm.nih.gov. Another non-limiting example of a mathematical algorithm utilized for the comparison of sequences is the algorithm of Myers and Miller, (1988) *Comput Appl Biosci,* 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

An isolated fusion polypeptide, or a fragment thereof, can be used as an immunogen to generate antibodies using standard techniques for polyclonal and monoclonal antibody preparation. The full-length fusion polypeptide can be used or, alternatively, the invention provides antigenic peptide fragments for use as immunogens. The antigenic peptide of a protein featured in the invention comprises at least 8 (or at least 10, at least 15, at least 20, or at least 30 or more) amino acid residues of the amino acid sequence of one of the polypeptides featured in the invention, and encompasses an epitope of the protein such that an antibody raised against the peptide forms a specific immune complex with a marker featured in the invention to which the protein corresponds. Exemplary epitopes encompassed by the antigenic peptide are regions that are located on the surface of the protein, e.g., hydrophilic regions. Hydrophobicity sequence analysis, hydrophilicity sequence analysis, or similar analyses can be used to identify hydrophilic regions.

An immunogen typically is used to prepare antibodies by immunizing a suitable (i.e., immunocompetent) subject such as a rabbit, goat, mouse, or other mammal or vertebrate. An appropriate immunogenic preparation can contain, for example, recombinantly-expressed or chemically-synthesized polypeptide. The preparation can further include an adjuvant, such as Freund's complete or incomplete adjuvant, or a similar immunostimulatory agent.

Accordingly, another aspect featured in the invention pertains to antibodies directed against a fusion polypeptide. In one embodiment, the antibody molecule specifically binds to fusion, e.g., specifically binds to an epitope formed by the fusion. In embodiments the antibody can distinguish wild type from fusion.

Another aspect featured in the invention provides antibodies directed against a fusion polypeptide are contemplated. In one embodiment, the antibody molecule specifically binds to La fusion, e.g., specifically binds to an epitope formed by the fusion. In embodiments the antibody can distinguish wild type from the fusion.

The terms "antibody" and "antibody molecule" as used interchangeably herein refer to immunoglobulin molecules and immunologically active portions of immunoglobulin molecules, i.e., molecules that contain an antigen binding site which specifically binds an antigen, such as a polypeptide featured in the invention. A molecule which specifically binds to a given polypeptide featured in the invention is a molecule which binds the polypeptide, but does not substantially bind other molecules in a sample, e.g., a biological sample, which naturally contains the polypeptide. Examples of immunologically active portions of immunoglobulin molecules include F(ab) and F(ab')2 fragments which can be generated by treating the antibody with an enzyme such as pepsin. The invention provides polyclonal and monoclonal antibodies. The term "monoclonal antibody" or "monoclonal antibody composition," as used herein, refers to a population of antibody molecules that contain only one species of an antigen binding site capable of immunoreacting with a particular epitope.

Polyclonal antibodies can be prepared as described above by immunizing a suitable subject with a fusion polypeptide as an immunogen. Antibody-producing cells can be obtained from the subject and used to prepare monoclonal antibodies by standard techniques, such as the hybridoma technique originally described by Kohler and Milstein (1975) *Nature* 256:495-497, the human B cell hybridoma technique (see Kozbor et al., 1983, *Immunol. Today* 4:72), the EBV-hybridoma technique (see Cole et al., pp. 77-96 In *Monoclonal Antibodies and Cancer Therapy*, Alan R. Liss, Inc., 1985) or trioma techniques. The technology for producing hybridomas is well known (see generally *Current Protocols in Immunology*, Coligan et al. ed., John Wiley & Sons, New York, 1994). Hybridoma cells producing a monoclonal antibody are detected by screening the hybridoma culture supernatants for antibodies that bind the polypeptide of interest, e.g., using a standard ELISA assay.

Alternative to preparing monoclonal antibody-secreting hybridomas, a monoclonal antibody can be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant Phage Antibody System*, Catalog No. 27-9400-01; and the *Stratagene SurfZAP Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734.

Additionally, recombinant antibodies, such as chimeric and humanized monoclonal antibodies, comprising both human and non-human portions can be made using standard recombinant DNA techniques. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559; Morrison (1985) *Science* 229:1202-1207; Oi et al. (1986) *Bio/Techniques* 4:214; U.S. Pat. No. 5,225,539; Jones et al. (1986) *Nature* 321:552-525; Verhoeyan et al. (1988) *Science* 239: 1534; and Beidler et al. (1988) *J. Immunol.* 141:4053-4060.

Completely human antibodies can be produced using transgenic mice which are incapable of expressing endogenous immunoglobulin heavy and light chains genes, but which can express human heavy and light chain genes. For an overview of this technology for producing human antibodies, see Lonberg and Huszar (1995) *Int. Rev. Immunol.* 13:65-93). For a detailed discussion of this technology for producing human antibodies and human monoclonal antibodies and protocols for producing such antibodies, see, e.g., U.S. Pat. Nos. 5,625,126; 5,633,425; 5,569,825; 5,661, 016; and 5,545,806. In addition, companies such as Abgenix, Inc. (Freemont, CA), can be engaged to provide human antibodies directed against a selected antigen using technology similar to that described above.

An antibody directed against a fusion polypeptide or a fusion polypeptide (e.g., a monoclonal antibody) can be used to isolate the polypeptide by standard techniques, such as affinity chromatography or immunoprecipitation. Moreover, such an antibody can be used to detect the marker (e.g., in a cellular lysate or cell supernatant) in order to evaluate the level and pattern of expression of the marker. Detection can be facilitated by coupling the antibody to a detectable substance. Examples of detectable substances include, but are not limited to, various enzymes, prosthetic groups, fluorescent materials, luminescent materials, bioluminescent materials, and radioactive materials. Examples of suitable enzymes include, but are not limited to, horseradish peroxidase, alkaline phosphatase, β-galactosidase, or acetylcholinesterase; examples of suitable prosthetic group complexes include, but are not limited to, streptavidin/biotin and avidin/biotin; examples of suitable fluorescent materials include, but are not limited to, umbelliferone, fluorescein, fluorescein isothiocyanate, rhodamine, dichlorotriazinylamine fluorescein, dansyl chloride or phycoerythrin; an example of a luminescent material includes, but is not limited to, luminol; examples of bioluminescent materials include, but are not limited to, luciferase, luciferin, and aequorin, and examples of suitable radioactive materials include, but are not limited to, $^{125}I$, $^{131}I$, $^{35}S$ or $^{3}H$.

An antibody directed against a fusion polypeptide can also be used diagnostically to monitor protein levels in tissues or body fluids (e.g., in a tumor cell-containing body fluid) as part of a clinical testing procedure, e.g., to, for example, determine the efficacy of a given treatment regimen.

Antigens and Vaccines

Embodiments featured in the invention include preparations, e.g., antigenic preparations, of the entire fusion or a fragment thereof, e.g., a fragment capable of raising antibodies specific to the fusion protein, e.g., a fusion junction containing fragment (collectively referred to herein as a fusion specific polypeptides or FSP). The preparation can include an adjuvant or other component.

An FSP can be used as an antigen or vaccine. For example, an FSP can be used as an antigen to immunize an animal, e.g., a rodent, e.g., a mouse or rat, rabbit, horse, goat, dog, or non-human primate, to obtain antibodies, e.g., fusion protein specific antibodies. In an embodiment a fusion specific antibody molecule is an antibody molecule described herein, e.g., a polyclonal. In other embodiments a fusion specific antibody molecule is monospecific, e.g., monoclonal, human, humanized, chimeric or other monospecific antibody molecule. A fusion protein specific antibody molecule can be used to treat a subject having a cholangiocarcinoma.

Embodiments featured in the invention include vaccine preparations that comprise an FSP capable of stimulating an immune response in a subject, e.g., by raising, in the subject, antibodies specific to the fusion protein. The vaccine preparation can include other components, e.g., an adjuvant. The vaccine preparations can be used to treat a subject having cholangiocarcinoma.

Expression Vectors, Host Cells and Recombinant Cells

In another aspect, the invention includes vectors (e.g., expression vectors), containing a nucleic acid encoding a fusion polypeptide or encoding an fusion polypeptide as described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a fusion nucleic acid in a form suitable for expression of the nucleic acid in a host cell.

Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors can be introduced into host cells to thereby produce a fusion polypeptide, including fusion proteins or polypeptides encoded by nucleic acids as described herein, mutant forms thereof, and the like).

The term "recombinant host cell" (or simply "host cell" or "recombinant cell"), as used herein, is intended to refer to a cell into which a recombinant expression vector has been introduced. It should be understood that such terms are intended to refer not only to the particular subject cell, but to the progeny of such a cell. Because certain modifications may occur in succeeding generations due to either mutation or environmental influences, such progeny may not, in fact, be identical to the parent cell, but are still included within the scope of the term "host cell" as used herein.

The recombinant expression vectors can be designed for expression of a fusion polypeptide in prokaryotic or eukaryotic cells. For example, polypeptides featured in the invention can be expressed in *E. coli*, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, CA. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, MA) and pRITS (Pharmacia, Piscataway, NJ) which fuse glutathione S-transferase (GST), maltose E binding protein, or protein A, respectively, to the target recombinant protein.

Purified fusion polypeptides can be used in activity assays (e.g., direct assays or competitive assays described in detail below), or to generate antibodies specific for fusion polypeptides.

To maximize recombinant protein expression in *E. coli* is to express the protein in a host bacteria with an impaired capacity to proteolytically cleave the recombinant protein (Gottesman, S., (1990) *Gene Expression Technology: Methods in Enzymology* 185, Academic Press, San Diego, California 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences can be carried out by standard DNA synthesis techniques.

The fusion polypeptide expression vector can be a yeast expression vector, a vector for expression in insect cells, e.g., a baculovirus expression vector or a vector suitable for expression in mammalian cells.

When used in mammalian cells, the expression vector's control functions can be provided by viral regulatory elements. For example, commonly used promoters are derived from polyoma, Adenovirus 2, cytomegalovirus and Simian Virus 40.

In another embodiment, the promoter is an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., CA, Gossen and Bujard (1992) *Proc. Natl. Acad. Sci. USA* 89:5547, and Paillard (1989) *Human Gene Therapy* 9:983).

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-1716), and mammary gland-specific promoters (e.g., milk whey promoter; U.S. Pat. No. 4,873,316 and European Application Publication No. 264, 166). Developmentally-regulated promoters are also encompassed, for example, the murine hox promoters (Kessel and Gruss (1990) *Science* 249:374-379) and the □-fetoprotein promoter (Campes and Tilghman (1989) *Genes Dev.* 3:537-546).

The invention further provides a recombinant expression vector comprising a DNA molecule featured in the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus.

Another aspect the invention provides a host cell which includes a nucleic acid molecule described herein, e.g., fusion nucleic acid molecule within a recombinant expression vector or a fusion nucleic acid molecule containing sequences which allow it to homologous recombination into a specific site of the host cell's genome.

A host cell can be any prokaryotic or eukaryotic cell. For example, a fusion polypeptide can be expressed in bacterial cells (such as *E. coli*), insect cells, yeast or mammalian cells (such as Chinese hamster ovary cells (CHO) or COS cells, e.g., COS-7 cells, CV-1 origin SV40 cells; Gluzman (1981) *Cell* 23:175-182). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell can be used to produce (e.g., express) a fusion polypeptide. Accordingly, the invention further provides methods for producing a fusion polypeptide using the host cells. In one embodiment, the method includes culturing the host cell (into which a recombinant expression vector encoding a polypeptide has been introduced) in a suitable medium such that the fusion polypeptide is produced. In another embodiment, the method further includes isolating a fusion polypeptide from the medium or the host cell.

In another aspect, the invention features, a cell or purified preparation of cells which include a fusion transgene, or which otherwise misexpress fusion. In another aspect, the invention features, a cell or purified preparation of cells which include a fusion transgene, or which otherwise misexpress a fusion.

The cell preparation can consist of human or non-human cells, e.g., rodent cells, e.g., mouse or rat cells, rabbit cells, or pig cells. In embodiments, the cell or cells include a fusion transgene, e.g., a heterologous form of a fusion, e.g., a gene derived from humans (in the case of a non-human cell) or a fusion transgene, e.g., a heterologous form of a fusion. The fusion transgene can be misexpressed, e.g., overexpressed or underexpressed. In other preferred embodiments, the cell or cells include a gene that misexpresses an endogenous fusion, e.g., a gene the expression of which is disrupted, e.g., a knockout. Such cells can serve as a model for studying disorders that are related to mutated or mis-expressed fusion alleles (e.g., cancers) or for use in drug screening, as described herein.

Screening Methods

In another aspect, the invention features a method, or assay, for screening for agents that modulate, e.g., inhibit, the expression or activity of a fusion, described herein. The method includes contacting a fusion, or a cell expressing a fusion, with a candidate agent; and detecting a change in a parameter associated with a fusion, e.g., a change in the expression or an activity of the fusion. The method can, optionally, include comparing the treated parameter to a reference value, e.g., a control sample (e.g., comparing a parameter obtained from a sample with the candidate agent to a parameter obtained from a sample without the candidate agent). In one embodiment, if a decrease in expression or activity of the fusion is detected, the candidate agent is identified as an inhibitor. In another embodiment, if an increase in expression or activity of the fusion is detected, the candidate agent is identified as an activator. In certain embodiments, the fusion is a nucleic acid molecule or a polypeptide as described herein.

In one embodiment, the contacting step is effected in a cell-free system, e.g., a cell lysate or in a reconstituted system. In other embodiments, the contacting step is effected in a cell in culture, e.g., a cell expressing a fusion (e.g., a mammalian cell, a tumor cell or cell line, a recombinant cell). In yet other embodiments, the contacting step is effected in a cell in vivo.

Exemplary parameters evaluated include one or more of:
(i) a change in binding activity, e.g., direct binding of the candidate agent to a fusion polypeptide; a binding competition between a known ligand and the candidate agent to a fusion polypeptide;
(ii) a change in kinase activity, e.g., phosphorylation levels of a fusion polypeptide (e.g., an increased or decreased autophosphorylation); or a change in phosphorylation of a target of fusion. In certain embodiments, a change in kinase activity, e.g., phosphorylation, is detected by any of Western blot, mass spectrometry, immunoprecipitation, immunohistochemistry, immunomagnetic beads, among others;
(iii) a change in an activity of a cell containing a fusion (e.g., a tumor cell or a recombinant cell), e.g., a change in proliferation, morphology or tumorigenicity of the cell;
(iv) a change in tumor present in an animal subject, e.g., size, appearance, proliferation, of the tumor; or
(v) a change in the level, e.g., expression level, of a fusion polypeptide or nucleic acid molecule.

In one embodiment, a change in a cell free assay in the presence of a candidate agent is evaluated. For example, an activity of a Fusion, or interaction of a Fusion with a downstream ligand can be detected. In one embodiment, a Fusion polypeptide is contacted with a ligand, e.g., in solution, and a candidate agent is monitored for an ability to modulate, e.g., inhibit, an interaction, e.g., binding, between the Fusion polypeptide and the ligand. In one exemplary assay, purified Fusion protein is contacted with a ligand, e.g., in solution, and a candidate agent is monitored for an ability to inhibit interaction of the fusion protein with the ligand, or to inhibit phosphorylation of the ligand by the fusion protein. An effect on an interaction between the fusion protein and a ligand can be monitored by methods known in the art, such as by absorbance, and an effect on phosphorylation of the ligand can be assayed, e.g., by Western blot, immunoprecipitation, or immunomagnetic beads.

In other embodiments, a change in an activity of a cell is detected in a cell in culture, e.g., a cell expressing a Fusion (e.g., a mammalian cell, a tumor cell or cell line, a recombinant cell). In one embodiment, the cell is a recombinant cell that is modified to express a Fusion nucleic acid, e.g., is a recombinant cell transfected with a Fusion nucleic acid. The transfected cell can show a change in response to the expressed K Fusion, e.g., increased proliferation, changes in morphology, increased tumorigenicity, and/or acquired a transformed phenotype. A change in any of the activities of the cell, e.g., the recombinant cell, in the presence of the candidate agent can be detected. For example, a decrease in one or more of: proliferation, tumorigenicity, transformed morphology, in the presence of the candidate agent can be indicative of an inhibitor of a Fusion. In other embodiments, a change in binding activity or phosphorylation as described herein is detected.

In an exemplary cell-based assay, a nucleic acid comprising a Fusion can be expressed in a cell, such as a cell (e.g., a mammalian cell) in culture. The cell containing a nucleic acid expressing the Fusion can be contacted with a candidate agent, and the cell is monitored for an effect of the candidate agent. A candidate agent that causes decreased cell proliferation or cell death can be determined to be a candidate for treating a tumor (e.g., a cancer) that carries a Fusion.

In one embodiment, a cell containing a nucleic acid expressing a Fusion can be monitored for expression of the Fusion protein. Protein expression can be monitored by methods known in the art, such as by, e.g., mass spectrometry (e.g., tandem mass spectrometry), a reporter assay (e.g., a fluorescence-based assay), Western blot, and immunohistochemistry. By one method, decreased expression is detected. A candidate agent that causes decreased expression of the Fusion protein as compared to a cell that does not contain the nucleic acid fusion can be determined to be a candidate for treating a tumor (e.g., a cancer) that carries a Fusion.

In yet other embodiment, a change in a tumor present in an animal subject (e.g., an in vivo animal model) is detected. In one embodiment, the animal model is a tumor containing animal or a xenograft comprising cells expressing a Fusion (e.g., tumorigenic cells expressing a Fusion). The candidate agent can be administered to the animal subject and a change in the tumor is detected. In one embodiment, the change in the tumor includes one or more of a tumor growth, tumor size, tumor burden, survival, is evaluated. A decrease in one or more of tumor growth, tumor size, tumor burden, or an increased survival is indicative that the candidate agent is an inhibitor.

In one exemplary animal model, a xenograft is created by injecting cells into mouse. A candidate agent is administered to the mouse, e.g., by injection (such as subcutaneous, intraperitoneal, or tail vein injection, or by injection directly into the tumor) or oral delivery, and the tumor is observed to determine an effect of the candidate anti-cancer agent. The health of the animal is also monitored, such as to determine if an animal treated with a candidate agent survives longer. A candidate agent that causes growth of the tumor to slow or stop, or causes the tumor to shrink in size, or causes decreased tumor burden, or increases survival time, can be considered to be a candidate for treating a tumor (e.g., a cancer) that carries a Fusion.

In another exemplary animal assay, cells expressing a Fusion are injected into the tail vein, e.g., of a mouse, to induce metastasis. A candidate agent is administered to the mouse, e.g., by injection (such as subcutaneous, intraperitoneal, or tail vein injection, or by injection directly into the tumor) or oral delivery, and the tumor is observed to determine an effect of the candidate anti-cancer agent. A candidate agent that inhibits or prevents or reduces metastasis, or increases survival time, can be considered to be a candidate for treating a tumor (e.g., a cancer) that carries a Fusion.

Cell proliferation can be measured by methods known in the art, such as PCNA (Proliferating cell nuclear antigen) assay, 5-bromodeoxyuridine (BrdUrd) incorporation, Ki-67 assay, mitochondrial respiration, or propidium iodide staining. Cells can also be measured for apoptosis, such as by use of a TUNEL (Terminal Deoxynucleotide Transferase dUTP Nick End Labeling) assay. Cells can also be assayed for presence of angiogenesis using methods known in the art, such as by measuring endothelial tube formation or by measuring the growth of blood vessels from subcutaneous tissue, such as into a solid gel of basement membrane.

In other embodiments, a change in expression of a Fusion can be monitored by detecting the nucleic acid or protein levels, e.g., using the methods described herein.

In certain embodiments, the screening methods described herein can be repeated and/or combined. In one embodiment, a candidate agent that is evaluated in a cell-free or cell-based described herein can be further tested in an animal subject.

In one embodiment, the candidate agent is identified and re-tested in the same or a different assay. For example, a test compound is identified in an in vitro or cell-free system, and re-tested in an animal model or a cell-based assay. Any order or combination of assays can be used. For example, a high throughput assay can be used in combination with an animal model or tissue culture.

Candidate agents suitable for use in the screening assays described herein include, e.g., small molecule compounds, nucleic acids (e.g., siRNA, aptamers, short hairpin RNAs, antisense oligonucleotides, ribozymes, antagomirs, microRNA mimics or DNA, e.g., for gene therapy) or polypeptides, e.g., antibodies (e.g., full length antibodies or antigen-binding fragments thereof, Fab fragments, or scFv fragments). The candidate anti-cancer agents can be obtained from a library (e.g., a commercial library), or can be rationally designed, such as to target an active site in a functional domain of fusion partner.

In other embodiments, the method, or assay, includes providing a step based on proximity-dependent signal generation, e.g., a two-hybrid assay that includes a first fusion protein (e.g., a Fusion protein), and a second fusion protein (e.g., a ligand), contacting the two-hybrid assay with a test compound, under conditions wherein said two hybrid assay detects a change in the formation and/or stability of the complex, e.g., the formation of the complex initiates transcription activation of a reporter gene.

In one non-limiting example, the three-dimensional structure of the active site of Fusion is determined by crystallizing the complex formed by the Fusion and a known inhibitor. Rational drug design is then used to identify new test agents by making alterations in the structure of a known inhibitor or by designing small molecule compounds that bind to the active site of the Fusion.

The candidate agents can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. 5,223,409), plasmids (Cull et al. (1992) *Proc Natl Acad Sci USA* 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

The interaction between two molecules can also be detected, e.g., using fluorescence energy transfer (FET) (see, for example, Lakowicz et al., U.S. Pat. No. 5,631,169;

Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means known in the art (e.g., using a fluorimeter).

In another embodiment, determining the ability of the Fusion protein to bind to a target molecule can be accomplished using real-time Biomolecular Interaction Analysis (BIA) (see, e.g., Sjolander, S. and Urbaniczky, C. (1991) *Anal. Chem.* 63:2338-2345 and Szabo et al. (1995) *Curr. Opin. Struct. Biol.* 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Nucleic Acid Inhibitors

In yet another embodiment, the Fusion inhibitor inhibits the expression of nucleic acid encoding the fusion. Examples of such fusion inhibitors include nucleic acid molecules, for example, antisense molecules, ribozymes, siRNA, triple helix molecules that hybridize to a nucleic acid encoding a Fusion, or a transcription regulatory region, and blocks or reduces mRNA expression of the fusion.

In one embodiment, the nucleic acid antagonist is a siRNA that targets mRNA encoding a Fusion. Other types of antagonistic nucleic acids can also be used, e.g., a dsRNA, a ribozyme, a triple-helix former, or an antisense nucleic acid. Accordingly, isolated nucleic acid molecules that are nucleic acid inhibitors, e.g., antisense, RNAi, to a Fusion-encoding nucleic acid molecule are provided.

An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire fusion coding strand, or to only a portion thereof. In another embodiment, the antisense nucleic acid molecule is antisense to a "noncoding region" of the coding strand of a nucleotide sequence encoding fusion (e.g., the 5' and 3' untranslated regions). Anti-sense agents can include, for example, from about 8 to about 80 nucleobases (i.e., from about 8 to about 80 nucleotides), e.g., about 8 to about 50 nucleobases, or about 12 to about 30 nucleobases. Anti-sense compounds include ribozymes, external guide sequence (EGS) oligonucleotides (oligozymes), and other short catalytic RNAs or catalytic oligonucleotides which hybridize to the target nucleic acid and modulate its expression. Anti-sense compounds can include a stretch of at least eight consecutive nucleobases that are complementary to a sequence in the target gene. An oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA can interfere with one or more of the normal functions of mRNA. The functions of mRNA to be interfered with include all key functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

Exemplary antisense compounds include DNA or RNA sequences that specifically hybridize to the target nucleic acid, e.g., the mRNA encoding Fusion. The complementary region can extend for between about 8 to about 80 nucleobases. The compounds can include one or more modified nucleobases. Modified nucleobases are known in the art. Descriptions of modified nucleic acid agents are also available. See, e.g., U.S. Pat. Nos. 4,987,071; 5,116,742; and 5,093,246; Woolf et al. (1992) *Proc Natl Acad Sci USA; Antisense RNA and DNA*, D. A. Melton, Ed., Cold Spring Harbor Laboratory, Cold Spring Harbor, N.Y. (1988); 89:7305-9; Haselhoff and Gerlach (1988) *Nature* 334:585-59; Helene, C. (1991) *Anticancer Drug Des.* 6:569-84; Helene (1992) *Ann. N.Y. Acad. Sci.* 660:27-36; and Maher (1992) *Bioassays* 14:807-15.

The antisense nucleic acid molecules are typically administered to a subject (e.g., by direct injection at a tissue site), or generated in situ such that they hybridize with or bind to cellular mRNA and/or genomic DNA encoding a fusion to thereby inhibit expression of the protein, e.g., by inhibiting transcription and/or translation. Alternatively, antisense nucleic acid molecules can be modified to target selected cells and then be administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

siRNAs are small double stranded RNAs (dsRNAs) that optionally include overhangs. For example, the duplex region of an siRNA is about 18 to 25 nucleotides in length, e.g., about 19, 20, 21, 22, 23, or 24 nucleotides in length. Typically, the siRNA sequences are exactly complementary to the target mRNA. dsRNAs and siRNAs in particular can be used to silence gene expression in mammalian cells (e.g., human cells). siRNAs also include short hairpin RNAs (shRNAs) with 29-base-pair stems and 2-nucleotide 3' overhangs. See, e.g., Clemens et al. (2000) *Proc. Natl. Acad. Sci. USA* 97:6499-6503; Billy et al. (2001) *Proc. Natl. Sci. USA* 98:14428-14433; Elbashir et al. (2001) *Nature.* 411:494-8; Yang et al. (2002) *Proc. Natl. Acad. Sci. USA* 99:9942-17947; Siolas et al. (2005), *Nat. Biotechnol.* 23(2):227-31; 20040086884; U.S. 20030166282; 20030143204; 20040038278; and 20030224432.

In still another embodiment, an antisense nucleic acid featured in the invention is a ribozyme. A ribozyme having specificity for a Fusion-encoding nucleic acid can include one or more sequences complementary to the nucleotide sequence of a fusion cDNA disclosed herein (i.e., SEQ ID NO:6), and a sequence having known catalytic sequence responsible for mRNA cleavage (see U.S. Pat. No. 5,093,246 or Haseloff and Gerlach (1988) *Nature* 334:585-591). For example, a derivative of a *Tetrahymena* L-19 IVS RNA can be constructed in which the nucleotide sequence of the active site is complementary to the nucleotide sequence to be cleaved in a Fusion-encoding mRNA. See, e.g., Cech et al. U.S. Pat. No. 4,987,071; and Cech et al. U.S. Pat. No. 5,116,742. Alternatively, fusion mRNA can be used to select a catalytic RNA having a specific ribonuclease activity from a pool of RNA molecules. See, e.g., Bartel, D. and Szostak, J. W. (1993) *Science* 261:1411-1418.

Inhibition of a Fusion gene can be accomplished by targeting nucleotide sequences complementary to the regulatory region of the fusion to form triple helical structures that prevent transcription of the Fusion gene in target cells. See generally, Helene, C. (1991) *Anticancer Drug Des.* 6:569-84; Helene, C. i (1992) *Ann. N.Y. Acad. Sci.* 660:27-36; and Maher, L. J. (1992) *Bioassays* 14:807-15. The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A fusion nucleic acid molecule can be modified at the base moiety, sugar moiety or phosphate backbone to improve, e.g., the stability, hybridization, or solubility of the molecule. For non-limiting examples of synthetic oligonucleotides with modifications see Toulmé (2001) *Nature Biotech.* 19:17 and Faria et al. (2001) *Nature Biotech.* 19:40-44. Such phosphoramidite oligonucleotides can be effective antisense agents.

For example, the deoxyribose phosphate backbone of the nucleic acid molecules can be modified to generate peptide nucleic acids (see Hyrup B. et al. (1996) *Bioorganic & Medicinal Chemistry* 4: 5-23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra and Perry-O'Keefe et al. *Proc. Natl. Acad. Sci.* 93: 14670-675.

PNAs of Fusion nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of fusion nucleic acid molecules can also be used in the analysis of single base pair mutations in a gene, (e.g., by PNA-directed PCR clamping); as 'artificial restriction enzymes' when used in combination with other enzymes, (e.g., 51 nucleases (Hyrup B. et al. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; WO88/09810) or the blood-brain barrier (see, e.g., WO 89/10134). In addition, oligonucleotides can be modified with hybridization-triggered cleavage agents (see, e.g., Krol et al. (1988) *Bio-Techniques* 6:958-976) or intercalating agents (See, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

In some embodiments, a nucleic acid inhibitor described herein is provided for the inhibition of expression of an fusion nucleic acid in vitro.

Evaluation of Subjects

Subjects, e.g., patients, can be evaluated for the presence of a fusion. A patient can be evaluated, for example, by determining the genomic sequence of the patient, e.g., by an NGS method. Alternatively, or in addition, evaluation of a patient can include directly assaying for the presence of a fusion in the patient, such as by an assay to detect a fusion nucleic acid (e.g., DNA or RNA), such as by, Southern blot, Northern blot, or RT-PCR, e.g., qRT-PCR. Alternatively, or in addition, a patient can be evaluated for the presence of a protein fusion, such as by immunohistochemistry, Western blot, immunoprecipitation, or immunomagnetic bead assay.

Evaluation of a patient can also include a cytogenetic assay, such as by fluorescence in situ hybridization (FISH), to identify the chromosomal rearrangement resulting in the fusion. For example, to perform FISH, at least a first probe tagged with a first detectable label can be designed to target one fusion partner, and at least a second probe tagged with a second detectable label can be designed to target the other fusion partner. The at least one first probe and the at least one second probe will be closer together in patients who carry the fusion than in patients who do not carry the Fusion. Additional methods for fusion detection are provided below.

In one aspect, the results of a clinical trial, e.g., a successful or unsuccessful clinical trial, can be repurposed to identify agents that target a fusion. By one exemplary method, a candidate agent used in a clinical trial can be reevaluated to determine if the agent in the trial targets a fusion, or is effective to treat a tumor containing a particular fusion. For example, subjects who participated in a clinical trial for an agent, such as a kinase inhibitor, can be identified. Patients who experienced an improvement in symptoms, e.g., cancer (e.g., lung cancer) symptoms, such as decreased tumor size, or decreased rate of tumor growth, can be evaluated for the presence of a Fusion. Patients who did not experience an improvement in cancer symptoms can also be evaluated for the presence of a Fusion. Where patients carrying a Fusion are found to have been more likely to respond to the test agent than patients who did not carry such a fusion, then the agent is determined to be an appropriate treatment option for a patient carrying the fusion.

"Reevaluation" of patients can include, for example, determining the genomic sequence of the patients, or a subset of the clinical trial patients, e.g., by an NGS method. Alternatively, or in addition, reevaluation of the patients can include directly assaying for the presence of a Fusion in the patient, such as by an assay to detect a fusion nucleic acid (e.g., RNA), such as by RT-PCR, e.g., qRT-PCR. Alternatively, or in addition, a patient can be evaluated for the presence of a protein fusion, such as by immunohistochemistry, Western blot, immunoprecipitation, or immunomagnetic bead assay.

Methods for Detection of Fusion Nucleic Acids and Polypeptides

Methods for evaluating a fusion gene, mutations and/or gene products are known to those of skill in the art. In one embodiment, the fusion is detected in a nucleic acid molecule by a method chosen from one or more of: nucleic acid hybridization assay, amplification-based assays (e.g., polymerase chain reaction (PCR)), PCR-RFLP assay, real-time PCR, sequencing, screening analysis (including metaphase cytogenetic analysis by standard karyotype methods, FISH (e.g., break away FISH), spectral karyotyping or MFISH, comparative genomic hybridization), in situ hybridization, SSP, HPLC or mass-spectrometric genotyping.

Additional exemplary methods include, traditional "direct probe" methods such as Southern blots or in situ hybridization (e.g., fluorescence in situ hybridization (FISH) and FISH plus SKY), and "comparative probe" methods such as comparative genomic hybridization (CGH), e.g., cDNA-based or oligonucleotide-based CGH, can be used. The methods can be used in a wide variety of formats including, but not limited to, substrate (e.g., membrane or glass) bound methods or array-based approaches.

In certain embodiments, the evaluation methods include the probes/primers described herein.

In one embodiment, probes/primers can be designed to detect a fusion or a reciprocal thereof. These probes/primers are suitable, e.g., for FISH or PCR amplification. In one embodiment, FISH analysis is used to identify the chromosomal rearrangement resulting in the fusions as described above. In one approach, a variation of a FISH assay, e.g., "break-away FISH", is used to evaluate a patient. Other variations of the FISH method known in the art are suitable for evaluating a patient.

Probes are used that contain DNA segments that are essentially complementary to DNA base sequences existing in different portions of chromosomes. Examples of probes useful according to the invention, and labeling and hybridization of probes to samples are described in two U.S. patents to Vysis, Inc. U.S. Pat. Nos. 5,491,224 and 6,277,569 to Bittner, et al.

Additional protocols for FISH detection are described below.

Chromosomal probes are typically about 50 to about $10^5$ nucleotides in length. Longer probes typically comprise smaller fragments of about 100 to about 500 nucleotides in length. Probes that hybridize with centromeric DNA and locus-specific DNA are available commercially, for example, from Vysis, Inc. (Downers Grove, Ill.), Molecular Probes, Inc. (Eugene, Oreg.) or from Cytocell (Oxfordshire, UK).

Alternatively, probes can be made non-commercially from chromosomal or genomic DNA through standard techniques. For example, sources of DNA that can be used include genomic DNA, cloned DNA sequences, somatic cell hybrids that contain one, or a part of one, chromosome (e.g., human chromosome) along with the normal chromosome complement of the host, and chromosomes purified by flow cytometry or microdissection. The region of interest can be isolated through cloning, or by site-specific amplification via the polymerase chain reaction (PCR). See, for example, Nath and Johnson, Biotechnic Histochem., 1998, 73(1):6-22, Wheeless et al., Cytometry 1994, 17:319-326, and U.S. Pat. No. 5,491,224.

The probes to be used hybridize to a specific region of a chromosome to determine whether a cytogenetic abnormality is present in this region. One type of cytogenetic abnormality is a deletion. Although deletions can be of one or more entire chromosomes, deletions normally involve loss of part of one or more chromosomes. If the entire region of a chromosome that is contained in a probe is deleted from a cell, hybridization of that probe to the DNA from the cell will normally not occur and no signal will be present on that chromosome. If the region of a chromosome that is partially contained within a probe is deleted from a cell, hybridization of that probe to the DNA from the cell can still occur, but less of a signal can be present. For example, the loss of a signal is compared to probe hybridization to DNA from control cells that do not contain the genetic abnormalities which the probes are intended to detect. In some embodiments, at least 1, 5, 10, 20, 30, 40, 50, 60, 70, 80, 90, 100, 110, 120, 130, 140, 150, 160, 170, 180, 190, 200, or more cells are enumerated for presence of the cytogenetic abnormality.

Cytogenetic abnormalities to be detected can include, but are not limited to, non-reciprocal translocations, balanced translocations, intra-chromosomal inversions, point mutations, deletions, gene copy number changes, gene expression level changes, and germ line mutations. In particular, one type of cytogenetic abnormality is a duplication. Duplications can be of entire chromosomes, or of regions smaller than an entire chromosome. If the region of a chromosome that is contained in a probe is duplicated in a cell, hybridization of that probe to the DNA from the cell will normally produce at least one additional signal as compared to the number of signals present in control cells with no abnormality of the chromosomal region contained in the probe.

Chromosomal probes are labeled so that the chromosomal region to which they hybridize can be detected. Probes typically are directly labeled with a fluorophore, an organic molecule that fluoresces after absorbing light of lower wavelength/higher energy. The fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, U.S. Pat. No. 5,491,224.

U.S. Pat. No. 5,491,224 describes probe labeling as a number of the cytosine residues having a fluorescent label covalently bonded thereto. The number of fluorescently labeled cytosine bases is sufficient to generate a detectable fluorescent signal while the individual so labeled DNA segments essentially retain their specific complementary binding (hybridizing) properties with respect to the chromosome or chromosome region to be detected. Such probes are made by taking the unlabeled DNA probe segment, transaminating with a linking group a number of deoxycytidine nucleotides in the segment, covalently bonding a fluorescent label to at least a portion of the transaminated deoxycytidine bases.

Probes can also be labeled by nick translation, random primer labeling or PCR labeling. Labeling is done using either fluorescent (direct)- or haptene (indirect)-labeled nucleotides. Representative, non-limiting examples of labels include: AMCA-6-dUTP, CascadeBlue-4-dUTP, Fluorescein-12-dUTP, Rhodamine-6-dUTP, TexasRed-6-dUTP, Cy3-6-dUTP, Cy5-dUTP, Biotin (BIO)-11-dUTP, Digoxygenin (DIG)-11-dUTP or Dinitrophenyl (DNP)-11-dUTP.

Probes also can be indirectly labeled with biotin or digoxygenin, or labeled with radioactive isotopes such as $32p$ and $0.3H$, although secondary detection molecules or further processing then is required to visualize the probes. For example, a probe labeled with biotin can be detected by avidin conjugated to a detectable marker. For example, avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

Probes can also be prepared such that a fluorescent or other label is not part of the DNA before or during the hybridization, and is added after hybridization to detect the probe hybridized to a chromosome. For example, probes can be used that have antigenic molecules incorporated into the DNA. After hybridization, these antigenic molecules are detected using specific antibodies reactive with the antigenic molecules. Such antibodies can themselves incorporate a fluorochrome, or can be detected using a second antibody with a bound fluorochrome.

However treated or modified, the probe DNA is commonly purified in order to remove unreacted, residual products (e.g., fluorochrome molecules not incorporated into the DNA) before use in hybridization.

Prior to hybridization, chromosomal probes are denatured according to methods well known in the art. Probes can be hybridized or annealed to the chromosomal DNA under hybridizing conditions. "Hybridizing conditions" are conditions that facilitate annealing between a probe and target chromosomal DNA. Since annealing of different probes will vary depending on probe length, base concentration and the like, annealing is facilitated by varying probe concentration, hybridization temperature, salt concentration and other factors well known in the art.

Hybridization conditions are facilitated by varying the concentrations, base compositions, complexities, and lengths of the probes, as well as salt concentrations, temperatures, and length of incubation. For example, in situ hybridizations are typically performed in hybridization buffer containing 1-2×SSC, 50-65% formamide and blocking DNA to suppress non-specific hybridization. In general, hybridization conditions, as described above, include temperatures of about 25° C. to about 55° C., and incubation lengths of about 0.5 hours to about 96 hours.

Non-specific binding of chromosomal probes to DNA outside of the target region can be removed by a series of washes. Temperature and concentration of salt in each wash are varied to control stringency of the washes. For example, for high stringency conditions, washes can be carried out at about 65° C. to about 80° C., using 0.2× to about 2×SSC, and about 0.1% to about 1% of a non-ionic detergent such as Nonidet P-40 (NP40). Stringency can be lowered by decreasing the temperature of the washes or by increasing the concentration of salt in the washes. In some applications it is necessary to block the hybridization capacity of repetitive sequences. Thus, in some embodiments, tRNA, human genomic DNA, or Cot-I DNA is used to block non-specific hybridization. After washing, the slide is allowed to drain and air dry, then mounting medium, a counterstain such as DAPI, and a coverslip are applied to the slide. Slides can be viewed immediately or stored at −20° C. before examination.

For fluorescent probes used in fluorescence in situ hybridization (FISH) techniques, fluorescence can be viewed with a fluorescence microscope equipped with an appropriate filter for each fluorophore, or by using dual or triple bandpass filter sets to observe multiple fluorophores. See, for example, U.S. Pat. No. 5,776,688. Alternatively, techniques such as flow cytometry can be used to examine the hybridization pattern of the chromosomal probes.

In CGH methods, a first collection of nucleic acids (e.g., from a sample, e.g., a possible tumor) is labeled with a first label, while a second collection of nucleic acids (e.g., a control, e.g., from a healthy cell/tissue) is labeled with a second label. The ratio of hybridization of the nucleic acids is determined by the ratio of the two (first and second) labels binding to each fiber in the array. Where there are chromosomal deletions or multiplications, differences in the ratio of the signals from the two labels will be detected and the ratio will provide a measure of the copy number. Array-based CGH can also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays.

Hybridization protocols suitable for use with the methods featured in the invention are described, e.g., in Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology*, Vol. 33: In situ Hybridization Protocols, Choo, ed., Humana Press, Totowa, N.J. (1994), etc. In one embodiment, the hybridization protocol of Pinkel, et al. (1998) *Nature Genetics* 20: 207-211, or of Kallioniemi (1992) *Proc. Natl Acad Sci USA* 89:5321-5325 (1992) is used. Array-based CGH is described in U.S. Pat. No. 6,455,258, the contents of each of which are incorporated herein by reference.

In still another embodiment, amplification-based assays can be used to measure presence/absence and copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g., healthy tissue, provides a measure of the copy number.

Methods of "quantitative" amplification are well known to those of skill in the art. For example, quantitative PCR involves simultaneously co-amplifying a known quantity of a control sequence using the same primers. This provides an internal standard that can be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR can also be used. In fluorogenic quantitative PCR, quantitation is based on amount of fluorescence signals, e.g., TaqMan and sybr green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Nucleic Acid Samples

A variety of tissue samples can be the source of the nucleic acid samples used in the present methods. Genomic or subgenomic DNA fragments can be isolated from a subject's sample (e.g., a tumor sample, a normal adjacent tissue (NAT), a blood sample or any normal control)). In certain embodiments, the tissue sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample. The isolating step can include flow-sorting of individual chromosomes; and/or micro-dissecting a subject's sample (e.g., a tumor sample, a NAT, a blood sample).

Protocols for DNA isolation from a tissue sample are known in the art. Additional methods to isolate nucleic acids (e.g., DNA) from formaldehyde- or paraformaldehyde-fixed, paraffin-embedded (FFPE) tissues are disclosed, e.g., in Cronin M. et al., (2004) *Am J Pathol.* 164(1):35-42; Masuda N. et al., (1999) *Nucleic Acids Res.* 27(22):4436-4443; Specht K. et al., (2001) *Am J Pathol.* 158(2):419-429, Ambion RecoverAll™ Total Nucleic Acid Isolation Protocol (Ambion, Cat. No. AM1975, September 2008), and QIAamp® DNA FFPE Tissue Handbook (Qiagen, Cat. No. 37625, October 2007). RecoverAll™ Total Nucleic Acid Isolation Kit uses xylene at elevated temperatures to solubilize paraffin-embedded samples and a glass-fiber filter to capture nucleic acids. QIAamp® DNA FFPE Tissue Kit uses QIAamp® DNA Micro technology for purification of genomic and mitochondrial DNA.

The isolated nucleic acid samples (e.g., genomic DNA samples) can be fragmented or sheared by practicing routine techniques. For example, genomic DNA can be fragmented by physical shearing methods, enzymatic cleavage methods, chemical cleavage methods, and other methods well known to those skilled in the art. The nucleic acid library can contain all or substantially all of the complexity of the genome. The term "substantially all" in this context refers to the possibility that there can in practice be some unwanted loss of genome complexity during the initial steps of the procedure. The methods described herein also are useful in cases where the nucleic acid library is a portion of the genome, i.e., where the complexity of the genome is reduced by design. In some embodiments, any selected portion of the genome can be used with the methods described herein. In certain embodiments, the entire exome or a subset thereof is isolated.

Methods can further include isolating a nucleic acid sample to provide a library (e.g., a nucleic acid library). In certain embodiments, the nucleic acid sample includes whole genomic, subgenomic fragments, or both. The isolated nucleic acid samples can be used to prepare nucleic acid libraries. Thus, in one embodiment, the methods featured in the invention further include isolating a nucleic acid sample to provide a library (e.g., a nucleic acid library as described herein). Protocols for isolating and preparing libraries from whole genomic or subgenomic fragments are known in the art (e.g., Illumina's genomic DNA sample preparation kit). In certain embodiments, the genomic or subgenomic DNA fragment is isolated from a subject's sample (e.g., a tumor sample, a normal adjacent tissue (NAT), a blood sample or any normal control)). In one embodiment, the sample (e.g., the tumor or NAT sample) is a preserved. For example, the sample is embedded in a matrix, e.g., an FFPE block or a frozen sample. In certain embodiments, the isolating step includes flow-sorting of individual chromosomes; and/or microdissecting a subject's sample (e.g., a tumor sample, a NAT, a blood sample). In certain embodiments, the nucleic acid sample used to generate the nucleic acid library is less than 5, less than 1 microgram, less than 500 ng, less than 200 ng, less than 100 ng, less than 50 ng or less than 20 ng (e.g., 10 ng or less).

In still other embodiments, the nucleic acid sample used to generate the library includes RNA or cDNA derived from RNA. In some embodiments, the RNA includes total cellular RNA. In other embodiments, certain abundant RNA sequences (e.g., ribosomal RNAs) have been depleted. In some embodiments, the poly(A)-tailed mRNA fraction in the total RNA preparation has been enriched. In some embodiments, the cDNA is produced by random-primed cDNA synthesis methods. In other embodiments, the cDNA synthesis is initiated at the poly(A) tail of mature mRNAs by priming by oligo(dT)-containing oligonucleotides. Methods for depletion, poly(A) enrichment, and cDNA synthesis are well known to those skilled in the art.

The method can further include amplifying the nucleic acid sample (e.g., DNA or RNA sample) by specific or non-specific nucleic acid amplification methods that are well known to those skilled in the art. In some embodiments, certain embodiments, the nucleic acid sample is amplified, e.g., by whole-genome amplification methods such as random-primed strand-displacement amplification.

In other embodiments, the nucleic acid sample is fragmented or sheared by physical or enzymatic methods and ligated to synthetic adapters, size-selected (e.g., by preparative gel electrophoresis) and amplified (e.g., by PCR). In other embodiments, the fragmented and adapter-ligated group of nucleic acids is used without explicit size selection or amplification prior to hybrid selection.

In other embodiments, the isolated DNA (e.g., the genomic DNA) is fragmented or sheared. In some embodiments, the library includes less than 50% of genomic DNA, such as a subfraction of genomic DNA that is a reduced representation or a defined portion of a genome, e.g., that has been subfractionated by other means. In other embodiments, the library includes all or substantially all genomic DNA.

In some embodiments, the library includes less than 50% of genomic DNA, such as a subfraction of genomic DNA that is a reduced representation or a defined portion of a genome, e.g., that has been subfractionated by other means. In other embodiments, the library includes all or substantially all genomic DNA. Protocols for isolating and preparing libraries from whole genomic or subgenomic fragments are known in the art (e.g., Illumina's genomic DNA sample preparation kit). Alternative DNA shearing methods can be more automatable and/or more efficient (e.g., with degraded FFPE samples). Alternatives to DNA shearing methods can also be used to avoid a ligation step during library preparation.

The methods described herein can be performed using a small amount of nucleic acids, e.g., when the amount of source DNA is limiting (e.g., even after whole-genome amplification). In one embodiment, the nucleic acid comprises less than about 5 µg, 4 µg, 3 µg, 2 µg, 1 µg, 0.8 µg, 0.7 µg, 0.6 µg, 0.5 µg, or 400 ng, 300 ng, 200 ng, 100 ng, 50 ng, or 20 ng or less of nucleic acid sample. For example, to prepare 500 ng of hybridization-ready nucleic acids, one typically begins with 3 µg of genomic DNA. One can start with less, however, if one amplifies the genomic DNA (e.g., using PCR) before the step of solution hybridization. Thus it is possible, but not essential, to amplify the genomic DNA before solution hybridization.

In some embodiments, a library is generated using DNA (e.g., genomic DNA) from a sample tissue, and a corresponding library is generated with RNA (or cDNA) isolated from the same sample tissue.

Design of Baits

A bait can be a nucleic acid molecule, e.g., a DNA or RNA molecule, which can hybridize to (e.g., be complementary to), and thereby allow capture of a target nucleic acid. In one embodiment, a bait is an RNA molecule. In other embodiments, a bait includes a binding entity, e.g., an affinity tag, that allows capture and separation, e.g., by binding to a binding entity, of a hybrid formed by a bait and a nucleic acid hybridized to the bait. In one embodiment, a bait is suitable for solution phase hybridization.

Baits can be produced and used by methods and hybridization conditions as described in US 2010/0029498 and Gnirke, A. et al. (2009) *Nat Biotechnol.* 27(2):182-189, and U.S. Ser. No. 61/428,568, filed Dec. 30, 2010, incorporated herein by reference. For example, biotinylated RNA baits can be produced by obtaining a pool of synthetic long oligonucleotides, originally synthesized on a microarray, and amplifying the oligonucleotides to produce the bait sequences. In some embodiments, the baits are produced by adding an RNA polymerase promoter sequence at one end of the bait sequences, and synthesizing RNA sequences using RNA polymerase. In one embodiment, libraries of synthetic oligodeoxynucleotides can be obtained from commercial suppliers, such as Agilent Technologies, Inc., and amplified using known nucleic acid amplification methods.

Each bait sequence can include a target-specific (e.g., a member-specific) bait sequence and universal tails on each end. As used herein, the term "bait sequence" can refer to the target-specific bait sequence or the entire oligonucleotide including the target-specific "bait sequence" and other nucleotides of the oligonucleotide.

In one embodiment, the bait is an oligonucleotide about 200 nucleotides in length, of which 170 nucleotides are target-specific "bait sequence". The other 30 nucleotides (e.g., 15 nucleotides on each end) are universal arbitrary tails used for PCR amplification. The tails can be any sequence selected by the user. The bait sequences described herein can be used for selection of exons and short target sequences. In one embodiment, the bait is between about 100 nucleotides and 300 nucleotides in length. In another embodiment, the bait is between about 130 nucleotides and 230 nucleotides in length. In yet another embodiment, the bait is between about 150 nucleotides and 200 nucleotides in length. The target-specific sequences in the baits, e.g., for selection of exons and short target sequences, are between about 40 nucleotides and 1000 nucleotides in length. In one embodiment, the target-specific sequence is between about 70 nucleotides and 300 nucleotides in length. In another embodiment, the target-specific sequence is between about 100 nucleotides and 200 nucleotides in length. In yet another embodiment, the target-specific sequence is between about 120 nucleotides and 170 nucleotides in length.

Sequencing

The invention also includes methods of sequencing nucleic acids. In one embodiment, any of a variety of sequencing reactions known in the art can be used to directly sequence at least a portion of a fusion. In one embodiment, the fusion sequence is compared to a corresponding reference (control) sequence.

In one embodiment, the sequence of the fusion nucleic acid molecule is determined by a method that includes one or more of: hybridizing an oligonucleotide, e.g., an allele specific oligonucleotide for one alteration described herein to said nucleic acid; hybridizing a primer, or a primer set (e.g., a primer pair), that amplifies a region comprising the mutation or a fusion junction of the allele; amplifying, e.g., specifically amplifying, a region comprising the mutation or a fusion junction of the allele; attaching an adapter oligonucleotide to one end of a nucleic acid that comprises the mutation or a fusion junction of the allele; generating an optical, e.g., a colorimetric signal, specific to the presence of the one of the mutation or fusion junction; hybridizing a nucleic acid comprising the mutation or fusion junction to a second nucleic acid, e.g., a second nucleic acid attached to a substrate; generating a signal, e.g., an electrical or fluorescent signal, specific to the presence of the mutation or fusion junction; and incorporating a nucleotide into an oligonucleotide that is hybridized to a nucleic acid that contains the mutation or fusion junction.

In another embodiment, the sequence is determined by a method that comprises one or more of: determining the nucleotide sequence from an individual nucleic acid molecule, e.g., where a signal corresponding to the sequence is derived from a single molecule as opposed, e.g., from a sum of signals from a plurality of clonally expanded molecules; determining the nucleotide sequence of clonally expanded proxies for individual nucleic acid molecules; massively parallel short-read sequencing; template-based sequencing; pyrosequencing; real-time sequencing comprising imaging the continuous incorporation of dye-labeling nucleotides during DNA synthesis; nanopore sequencing; sequencing by hybridization; nano-transistor array based sequencing; polony sequencing; scanning tunneling microscopy (STM) based sequencing; or nanowire-molecule sensor based sequencing.

Any method of sequencing known in the art can be used. Exemplary sequencing reactions include those based on techniques developed by Maxam and Gilbert (*Proc. Natl Acad Sci USA* (1977) 74:560) or Sanger (Sanger et al. (1977) *Proc. Nat. Acad. Sci* 74:5463). Any of a variety of automated sequencing procedures can be utilized when performing the assays (*Biotechniques* (1995) 19:448), including sequencing by mass spectrometry (see, for example, U.S. Pat. No. 5,547,835 and international patent application Publication Number WO 94/16101, entitled DNA Sequencing by Mass Spectrometry by H. Koster; U.S. Pat. No. 5,547,835 and international patent application Publication Number WO 94/21822 entitled DNA Sequencing by Mass Spectrometry Via Exonuclease Degradation by H. Koster), and U.S. Pat.

No. 5,605,798 and International Patent Application No. PCT/US96/03651 entitled DNA Diagnostics Based on Mass Spectrometry by H. Köster; Cohen et al. (1996) *Adv Chromatogr* 36:127-162; and Griffin et al. (1993) *Appl Biochem Biotechnol* 38:147-159).

Sequencing of nucleic acid molecules can also be carried out using next-generation sequencing (NGS). Next-generation sequencing includes any sequencing method that determines the nucleotide sequence of either individual nucleic acid molecules or clonally expanded proxies for individual nucleic acid molecules in a highly parallel fashion (e.g., greater than $10^5$ molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. (2010) *Nature Biotechnology Reviews* 11:31-46, incorporated herein by reference.

In one embodiment, the next-generation sequencing allows for the determination of the nucleotide sequence of an individual nucleic acid molecule (e.g., Helicos BioSciences' HeliScope Gene Sequencing system, and Pacific Biosciences' PacBio RS system). In other embodiments, the sequencing method determines the nucleotide sequence of clonally expanded proxies for individual nucleic acid molecules (e.g., the Solexa sequencer, Illumina Inc., San Diego, Calif; 454 Life Sciences (Branford, Conn.), and Ion Torrent). e.g., massively parallel short-read sequencing (e.g., the Solexa sequencer, Illumina Inc., San Diego, Calif.), which generates more bases of sequence per sequencing unit than other sequencing methods that generate fewer but longer reads. Other methods or machines for next-generation sequencing include, but are not limited to, the sequencers provided by 454 Life Sciences (Branford, Conn.), Applied Biosystems (Foster City, Calif.; SOLiD sequencer), and Helicos BioSciences Corporation (Cambridge, Mass.).

Platforms for next-generation sequencing include, but are not limited to, Roche/454's Genome Sequencer (GS) FLX System, Illumina/Solexa's Genome Analyzer (GA), Life/APG's Support Oligonucleotide Ligation Detection (SOLiD) system, Polonator's G.007 system, Helicos BioSciences' HeliScope Gene Sequencing system, and Pacific Biosciences' PacBio RS system.

NGS technologies can include one or more of steps, e.g., template preparation, sequencing and imaging, and data analysis.

Template Preparation

Methods for template preparation can include steps such as randomly breaking nucleic acids (e.g., genomic DNA or cDNA) into smaller sizes and generating sequencing templates (e.g., fragment templates or mate-pair templates). The spatially separated templates can be attached or immobilized to a solid surface or support, allowing massive amounts of sequencing reactions to be performed simultaneously. Types of templates that can be used for NGS reactions include, e.g., clonally amplified templates originating from single DNA molecules, and single DNA molecule templates.

Methods for preparing clonally amplified templates include, e.g., emulsion PCR (emPCR) and solid-phase amplification.

EmPCR can be used to prepare templates for NGS. Typically, a library of nucleic acid fragments is generated, and adapters containing universal priming sites are ligated to the ends of the fragment. The fragments are then denatured into single strands and captured by beads. Each bead captures a single nucleic acid molecule. After amplification and enrichment of emPCR beads, a large amount of templates can be attached or immobilized in a polyacrylamide gel on a standard microscope slide (e.g., Polonator), chemically crosslinked to an amino-coated glass surface (e.g., Life/APG; Polonator), or deposited into individual PicoTiterPlate (PTP) wells (e.g., Roche/454), in which the NGS reaction can be performed.

Solid-phase amplification can also be used to produce templates for NGS. Typically, forward and reverse primers are covalently attached to a solid support. The surface density of the amplified fragments is defined by the ratio of the primers to the templates on the support. Solid-phase amplification can produce hundreds of millions spatially separated template clusters (e.g., Illumina/Solexa). The ends of the template clusters can be hybridized to universal sequencing primers for NGS reactions.

Other methods for preparing clonally amplified templates also include, e.g., Multiple Displacement Amplification (MDA) (Lasken R. S. *Curr Opin Microbiol.* 2007; 10(5): 510-6). MDA is a non-PCR based DNA amplification technique. The reaction involves annealing random hexamer primers to the template and DNA synthesis by high fidelity enzyme, typically $\Phi 29$ at a constant temperature. MDA can generate large sized products with lower error frequency.

Template amplification methods such as PCR can be coupled with NGS platforms to target or enrich specific regions of the genome (e.g., exons). Exemplary template enrichment methods include, e.g., microdroplet PCR technology (Tewhey R. et al., *Nature Biotech.* 2009, 27:1025-1031), custom-designed oligonucleotide microarrays (e.g., Roche/NimbleGen oligonucleotide microarrays), and solution-based hybridization methods (e.g., molecular inversion probes (MIPs) (Porreca G. J. et al., *Nature Methods*, 2007, 4:931-936; Krishnakumar S. et al., *Proc. Natl. Acad. Sci. USA*, 2008, 105:9296-9310; Turner E. H. et al., *Nature Methods*, 2009, 6:315-316), and biotinylated RNA capture sequences (Gnirke A. et al., *Nat. Biotechnol.* 2009; 27(2): 182-17)

Single-molecule templates are another type of templates that can be used for NGS reaction. Spatially separated single molecule templates can be immobilized on solid supports by various methods. In one approach, individual primer molecules are covalently attached to the solid support. Adapters are added to the templates and templates are then hybridized to the immobilized primers. In another approach, single-molecule templates are covalently attached to the solid support by priming and extending single-stranded, single-molecule templates from immobilized primers. Universal primers are then hybridized to the templates. In yet another approach, single polymerase molecules are attached to the solid support, to which primed templates are bound.

Sequencing and Imaging

Exemplary sequencing and imaging methods for NGS include, but are not limited to, cyclic reversible termination (CRT), sequencing by ligation (SBL), single-molecule addition (pyrosequencing), and real-time sequencing.

CRT uses reversible terminators in a cyclic method that minimally includes the steps of nucleotide incorporation, fluorescence imaging, and cleavage. Typically, a DNA polymerase incorporates a single fluorescently modified nucleotide corresponding to the complementary nucleotide of the template base to the primer. DNA synthesis is terminated after the addition of a single nucleotide and the unincorporated nucleotides are washed away. Imaging is performed to determine the identity of the incorporated labeled nucleotide. Then in the cleavage step, the terminating/inhibiting group and the fluorescent dye are removed. Exemplary NGS platforms using the CRT method include, but are not limited to, Illumina/Solexa Genome Analyzer (GA), which uses the clonally amplified template method coupled with the four-color CRT method detected by total internal reflection fluorescence (TIRF); and Helicos BioSciences/HeliScope, which uses the single-molecule template method coupled with the one-color CRT method detected by TIRF.

SBL uses DNA ligase and either one-base-encoded probes or two-base-encoded probes for sequencing. Typically, a fluorescently labeled probe is hybridized to its complementary sequence adjacent to the primed template. DNA ligase is used to ligate the dye-labeled probe to the primer. Fluorescence imaging is performed to determine the identity of the ligated probe after non-ligated probes are washed away. The fluorescent dye can be removed by using cleavable probes to regenerate a 5'-$PO_4$ group for subsequent ligation cycles. Alternatively, a new primer can be hybridized to the template after the old primer is removed. Exemplary SBL platforms include, but are not limited to, Life/APG/SOLiD (support oligonucleotide ligation detection), which uses two-base-encoded probes.

Pyrosequencing method is based on detecting the activity of DNA polymerase with another chemiluminescent enzyme. Typically, the method allows sequencing of a single strand of DNA by synthesizing the complementary strand along it, one base pair at a time, and detecting which base was actually added at each step. The template DNA is immobile, and solutions of A, C, G, and T nucleotides are sequentially added and removed from the reaction. Light is produced only when the nucleotide solution complements the first unpaired base of the template. The sequence of solutions which produce chemiluminescent signals allows the determination of the sequence of the template. Exemplary pyrosequencing platforms include, but are not limited to, Roche/454, which uses DNA templates prepared by emPCR with 1-2 million beads deposited into PTP wells.

Real-time sequencing involves imaging the continuous incorporation of dye-labeled nucleotides during DNA synthesis. Exemplary real-time sequencing platforms include, but are not limited to, Pacific Biosciences platform, which uses DNA polymerase molecules attached to the surface of individual zero-mode waveguide (ZMW) detectors to obtain sequence information when phospholinked nucleotides are being incorporated into the growing primer strand; Life/VisiGen platform, which uses an engineered DNA polymerase with an attached fluorescent dye to generate an enhanced signal after nucleotide incorporation by fluorescence resonance energy transfer (FRET); and LI-COR Biosciences platform, which uses dye-quencher nucleotides in the sequencing reaction.

Other sequencing methods for NGS include, but are not limited to, nanopore sequencing, sequencing by hybridization, nano-transistor array based sequencing, polony sequencing, scanning tunneling microscopy (STM) based sequencing, and nanowire-molecule sensor based sequencing.

Nanopore sequencing involves electrophoresis of nucleic acid molecules in solution through a nano-scale pore which provides a highly confined space within which single-nucleic acid polymers can be analyzed. Exemplary methods of nanopore sequencing are described, e.g., in Branton D. et al., *Nat Biotechnol.* 2008; 26(10):1146-53.

Sequencing by hybridization is a non-enzymatic method that uses a DNA microarray. Typically, a single pool of DNA is fluorescently labeled and hybridized to an array containing known sequences. Hybridization signals from a given spot on the array can identify the DNA sequence. The binding of one strand of DNA to its complementary strand in the DNA double-helix is sensitive to even single-base mismatches when the hybrid region is short or is specialized mismatch detection proteins are present. Exemplary methods of sequencing by hybridization are described, e.g., in Hanna G. J. et al., *J. Clin. Microbiol.* 2000; 38 (7): 2715-21; and Edwards J. R. et al., *Mut. Res.* 2005; 573 (1-2): 3-12.

Polony sequencing is based on polony amplification and sequencing-by-synthesis via multiple single-base-extensions (FISSEQ). Polony amplification is a method to amplify DNA in situ on a polyacrylamide film. Exemplary polony sequencing methods are described, e.g., in US Patent Application Publication No. 2007/0087362.

Nano-transistor array based devices, such as Carbon NanoTube Field Effect Transistor (CNTFET), can also be used for NGS. For example, DNA molecules are stretched and driven over nanotubes by micro-fabricated electrodes. DNA molecules sequentially come into contact with the carbon nanotube surface, and the difference in current flow from each base is produced due to charge transfer between the DNA molecule and the nanotubes. DNA is sequenced by recording these differences. Exemplary Nano-transistor array based sequencing methods are described, e.g., in U.S. Patent Application Publication No. 2006/0246497.

Scanning tunneling microscopy (STM) can also be used for NGS. STM uses a piezo-electric-controlled probe that performs a raster scan of a specimen to form images of its surface. STM can be used to image the physical properties of single DNA molecules, e.g., generating coherent electron tunneling imaging and spectroscopy by integrating scanning tunneling microscope with an actuator-driven flexible gap. Exemplary sequencing methods using STM are described, e.g., in U.S. Patent Application Publication No. 2007/0194225.

A molecular-analysis device which is comprised of a nanowire-molecule sensor can also be used for NGS. Such device can detect the interactions of the nitrogenous material disposed on the nanowires and nucleic acid molecules such as DNA. A molecule guide is configured for guiding a molecule near the molecule sensor, allowing an interaction and subsequent detection. Exemplary sequencing methods using nanowire-molecule sensor are described, e.g., in U.S. Patent Application Publication No. 2006/0275779.

Double ended sequencing methods can be used for NGS. Double ended sequencing uses blocked and unblocked primers to sequence both the sense and antisense strands of DNA. Typically, these methods include the steps of annealing an unblocked primer to a first strand of nucleic acid; annealing a second blocked primer to a second strand of nucleic acid; elongating the nucleic acid along the first strand with a polymerase; terminating the first sequencing primer; deblocking the second primer; and elongating the nucleic acid along the second strand. Exemplary double ended sequencing methods are described, e.g., in U.S. Pat. No. 7,244,567.

Data Analysis

After NGS reads have been generated, they can be aligned to a known reference sequence or assembled de novo.

For example, identifying genetic variations such as single-nucleotide polymorphism and structural variants in a sample (e.g., a tumor sample) can be accomplished by aligning NGS reads to a reference sequence (e.g., a wild-type sequence). Methods of sequence alignment for NGS are described e.g., in Trapnell C. and Salzberg S. L. *Nature Biotech.,* 2009, 27:455-457.

Examples of de novo assemblies are described, e.g., in Warren R. et al., *Bioinformatics,* 2007, 23:500-501; Butler J.

et al., *Genome Res.*, 2008, 18:810-820; and Zerbino D. R. and Birney E., *Genome Res.*, 2008, 18:821-829.

Sequence alignment or assembly can be performed using read data from one or more NGS platforms, e.g., mixing Roche/454 and Illumina/Solexa read data.

Algorithms and methods for data analysis are described in U.S. Ser. No. 61/428,568, filed Dec. 30, 2010, incorporated herein by reference.

Fusion Expression Level

In certain embodiments, fusion expression level can also be assayed. Fusion expression can be assessed by any of a wide variety of methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In certain embodiments, activity of a particular gene is characterized by a measure of gene transcript (e.g., mRNA), by a measure of the quantity of translated protein, or by a measure of gene product activity. fusion expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

Methods of detecting and/or quantifying the fusion gene transcript (mRNA or cDNA made therefrom) using nucleic acid hybridization techniques are known to those of skill in the art (see Sambrook et al. supra). For example, one method for evaluating the presence, absence, or quantity of cDNA involves a Southern transfer as described above. Briefly, the mRNA is isolated (e.g., using an acid guanidinium-phenol-chloroform extraction method, Sambrook et al. supra.) and reverse transcribed to produce cDNA. The cDNA is then optionally digested and run on a gel in buffer and transferred to membranes. Hybridization is then carried out using the nucleic acid probes specific for the fusion cDNA, e.g., using the probes and primers described herein.

In other embodiments, expression is assessed by preparing genomic DNA or mRNA/cDNA (i.e., a transcribed polynucleotide) from cells in a subject sample, and by hybridizing the genomic DNA or mRNA/cDNA with a reference polynucleotide which is a complement of a polynucleotide comprising the fusion, and fragments thereof. cDNA can, optionally, be amplified using any of a variety of polymerase chain reaction methods prior to hybridization with the reference polynucleotide. Expression of a fusion as described herein can likewise be detected using quantitative PCR (QPCR) to assess the level of expression.

Detection of Fusion Polypeptide

The activity or level of a fusion polypeptide can also be detected and/or quantified by detecting or quantifying the expressed polypeptide. The fusion polypeptide can be detected and quantified by any of a number of means known to those of skill in the art. These can include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, immunohistochemistry (IHC) and the like. A skilled artisan can adapt known protein/antibody detection methods.

Another agent for detecting a fusion polypeptide is an antibody molecule capable of binding to a polypeptide corresponding to a marker, e.g., an antibody with a detectable label. Techniques for generating antibodies are described herein. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

In another embodiment, the antibody is labeled, e.g., a radio-labeled, chromophore-labeled, fluorophore-labeled, or enzyme-labeled antibody. In another embodiment, an antibody derivative (e.g., an antibody conjugated with a substrate or with the protein or ligand of a protein-ligand pair {e.g., biotin-streptavidin}), or an antibody fragment (e.g., a single-chain antibody, an isolated antibody hypervariable domain, etc.) which binds specifically with a fusion protein, is used.

Fusion polypeptides from cells can be isolated using techniques that are known to those of skill in the art. The protein isolation methods employed can, for example, be such as those described in Harlow and Lane (Harlow and Lane, 1988, *Antibodies: A Laboratory Manual*, Cold Spring Harbor Laboratory Press, Cold Spring Harbor, New York).

Means of detecting proteins using electrophoretic techniques are well known to those of skill in the art (see generally, R. Scopes (1982) *Protein Purification*, Springer-Verlag, N.Y.; Deutscher, (1990) *Methods in Enzymology* Vol. 182: *Guide to Protein Purification*, Academic Press, Inc., N.Y.).

In another embodiment, Western blot (immunoblot) analysis is used to detect and quantify the presence of a polypeptide in the sample.

In another embodiment, the polypeptide is detected using an immunoassay. As used herein, an immunoassay is an assay that utilizes an antibody to specifically bind to the analyte. The immunoassay is thus characterized by detection of specific binding of a polypeptide to an anti-antibody as opposed to the use of other physical or chemical properties to isolate, target, and quantify the analyte.

The fusion polypeptide is detected and/or quantified using any of a number of immunological binding assays (see, e.g., U.S. Pat. Nos. 4,366,241; 4,376,110; 4,517,288; and 4,837,168). For a review of the general immunoassays, see also Asai (1993) *Methods in Cell Biology* Volume 37: *Antibodies in Cell Biology*, Academic Press, Inc. New York; Stites & Ten (1991) *Basic and Clinical Immunology* 7th Edition.

Kits

In one aspect, the invention features, a kit, e.g., containing an oligonucleotide having a mutation described herein, e.g., a fusion. Optionally, the kit can also contain an oligonucleotide that is the wildtype counterpart of the mutant oligonucleotide.

A kit featured in the invention can include a carrier, e.g., a means being compartmentalized to receive in close confinement one or more container means. In one embodiment the container contains an oligonucleotide, e.g., a primer or probe as described above. The components of the kit are useful, for example, to diagnose or identify a mutation in a tumor sample in a patient. The probe or primer of the kit can be used in any sequencing or nucleotide detection assay known in the art, e.g., a sequencing assay, e.g., an NGS method, RT-PCR, or in situ hybridization.

In some embodiments, the components of the kit are useful, for example, to diagnose or identify a fusion in a tumor sample in a patient, and to accordingly identify an appropriate therapeutic agent to treat the cancer.

A kit featured in the invention can include, e.g., assay positive and negative controls, nucleotides, enzymes (e.g., RNA or DNA polymerase or ligase), solvents or buffers, a stabilizer, a preservative, a secondary antibody, e.g., an anti-HRP antibody (IgG) and a detection reagent.

An oligonucleotide can be provided in any form, e.g., liquid, dried, semi-dried, or lyophilized, or in a form for storage in a frozen condition.

Typically, an oligonucleotide, and other components in a kit are provided in a form that is sterile. An oligonucleotide, e.g., an oligonucleotide that contains an mutation, e.g., a fusion, described herein, or an oligonucleotide complementary to a fusion described herein, is provided in a liquid solution, the liquid solution generally is an aqueous solution, e.g., a sterile aqueous solution. When the oligonucleotide is provided as a dried form, reconstitution generally is accomplished by the addition of a suitable solvent. The solvent, e.g., sterile buffer, can optionally be provided in the kit.

The kit can include one or more containers for the composition containing an oligonucleotide in a concentration suitable for use in the assay or with instructions for dilution for use in the assay. In some embodiments, the kit contains separate containers, dividers or compartments for the oligonucleotide and assay components, and the informational material. For example, the oligonucleotides can be contained in a bottle or vial, and the informational material can be contained in a plastic sleeve or packet. In other embodiments, the separate elements of the kit are contained within a single, undivided container. For example, an oligonucleotide composition is contained in a bottle or vial that has attached thereto the informational material in the form of a label. In some embodiments, the kit includes a plurality (e.g., a pack) of individual containers, each containing one or more unit forms (e.g., for use with one assay) of an oligonucleotide. For example, the kit includes a plurality of ampoules, foil packets, or blister packs, each containing a single unit of oligonucleotide for use in sequencing or detecting a mutation in a tumor sample. The containers of the kits can be air tight and/or waterproof. The container can be labeled for use.

For antibody-based kits, the kit can include: (1) a first antibody (e.g., attached to a solid support) which binds to a fusion polypeptide; and, optionally, (2) a second, different antibody which binds to either the polypeptide or the first antibody and is conjugated to a detectable agent.

In one embodiment, the kit can include informational material for performing and interpreting the sequencing or diagnostic. In another embodiment, the kit can provide guidance as to where to report the results of the assay, e.g., to a treatment center or healthcare provider. The kit can include forms for reporting the results of a sequencing or diagnostic assay described herein, and address and contact information regarding where to send such forms or other related information; or a URL (Uniform Resource Locator) address for reporting the results in an online database or an online application (e.g., an app). In another embodiment, the informational material can include guidance regarding whether a patient should receive treatment with a particular chemotherapeutic drug, depending on the results of the assay.

The informational material of the kits is not limited in its form. In many cases, the informational material, e.g., instructions, is provided in printed matter, e.g., a printed text, drawings, and/or photographs, e.g., a label or printed sheet. However, the informational material can also be provided in other formats, such as computer readable material, video recording, or audio recording. In another embodiment, the informational material of the kit is contact information, e.g., a physical address, email address, website, or telephone number, where a user of the kit can obtain substantive information about the sequencing or diagnostic assay and/or its use in the methods described herein. The informational material can also be provided in any combination of formats.

In some embodiments, a biological sample is provided to an assay provider, e.g., a service provider (such as a third party facility) or a healthcare provider, who evaluates the sample in an assay and provides a read out. For example, in one embodiment, an assay provider receives a biological sample from a subject, such as a blood or tissue sample, e.g., a biopsy sample, and evaluates the sample using an assay described herein, e.g., a sequencing assay or in situ hybridization assay, and determines that the sample contains a fusion. The assay provider, e.g., a service provider or healthcare provider, can then conclude that the subject is, or is not, a candidate for a particular drug or a particular cancer treatment regimen.

Exemplary Rearrangements

TABLE 1

| | |
|---|---|
| BICC1-FGFR2 | This is an in-frame fusion (chr10 inversion). The breakpoint in FGFR2 is found approximately in the middle of the kinase domain. This was selected since the breakpoint is close to a rare exon that was baited. There are possibly additional breakpoints. |
| FGFR2-KIAA1598 | This is a chr10 deletion. The breakpoint is in the 3' utr of FGFR2 so the entire protein is intact. This is similar to the FGFR3-TACC3 structure. |
| FGFR2-TACC3 | This is an in-frame fusion (chr4; 10 translocation). The breakpoints are in FGFR2 intron 17 and TACC3 intron10. The FGFR2 brkpt is right after the kinase domain. FGFR3-TACC3 has been recently reported as a potential driver in GBM (e.g., PMID: 22837387). |
| RABGAP1L-NTRK1 | This is an in-frame fusion (chr1 tandem duplication). Again the breakpoint found within the tyrosine kinase domain. This rearrangement is complex. NTRK1 is also amplified. |

Additional description of the alterations disclosed herein in provided in FIGS. 1A-1C and FIGS. 2-17, which are summarized below.

| Fusion | Description |
|---|---|
| FGFR2-TACC3 | chr10: chr4 translocation |
| FGFR2-KIAA1598 | chr10 deletion |
| BICC1-FGFR2 | chr10 inversion |
| FGFR2-BICC1 | chr10: inversion |

Genomic Location

| Fusion | Breakpoint 1 | Breakpoint 2 |
|---|---|---|
| FGFR2-TACC3 | FGFR2(NM_001144915): chr10: 123,243,122; intron16 | TACC3(NM_006342): chr4: 1,740,657; intron10 |
| FGFR2-KIAA1598 | FGFR2(NM_001144915): chr10: 123,239,241; intron 16 | KIAA1598(NM_001127211): chr10: 118708643; intron6 |
| BICC1-FGFR2 | BICC1(NM_001080512): chr10: 60446461; intron2 | FGFR2(NM_001144915): chr10: 123,241,845; intron 16 |
| FGFR2-BICC1 | FGFR2(NM_001144915): chr10: 123,241,713; intron16 | BICC1(NM_001080512): chr10: 60,567,607; intron 17 |

Exons

| Fusion | Exons |
|---|---|
| FGFR2-TACC3 | FGFR2 (exon 1-16) – TACC3 (exon11-16) |
| FGFR2-KIAA1598 | FGFR2 (exon 1-16) – KIAA1598 (exon7-17) |
| BICC1-FGFR2 | BICC1 (exon 1-2) – FGFR2 (exon17) |
| FGFR2-BICC1 | FGFR2 (exon 1-16) – BICC1(exon18-21) |

Exons in the 5'-Partner and the 3'-Partner

| Fusion | 5' Partner | 3' Partner |
|---|---|---|
| FGFR2-TACC3 | FGFR2: kinase domain exon 10-16, included in fusion product | TACC3: coiled-coil region exon 11-16, included in fusion product |
| FGFR2-KIAA1598 | FGFR2: kinase domain exon 10-16, included in fusion product | KIAA1598 |
| BICC1-FGFR2 | BICC1: unknown function in fusion product | FGFR2: kinase domain exon 10-16, not included in fusion product |
| FGFR2-BICC1 | FGFR2: kinase domain included exon 10-16, in fusion product | BICC1: |

The RefSeq Gene are databased at UCSC Genome Browser (http://genome.ucsc.edu/cgi-bin/hgc?hgsid=309144129&c=chr4&o=1795038&t=1810599&g=refGene&i=NM_000142

| Fusion | 5' Partner | 3' Partner |
|---|---|---|
| FGFR2-TACC3 | FGFR2: NM_001144915 | TACC3: NM_006342 |
| FGFR2-KIAA1598 | FGFR2: NM_001144915 | KIAA1598: NM_001127211 |
| BICC1-FGFR2 | BICC1: NM_001080512 | FGFR2: NM_001144915 |
| FGFR2-BICC1 | FGFR2: NM_001144915 | BICC1: NM_001080512 |

The invention is further illustrated by the following example, which should not be construed as further limiting.

EXAMPLE

Sequencing of approximately 30 cholangiocarcinomas has revealed 3 FGFR2 fusions, 1 FGFR2 amplification and 1 NTRAK 1 fusion. Hepatocellular carcinomas are far more common worldwide. HCC is a tumor derived from hepatocytes and ICC is derived from the intrahepatic bile duct epithelium (also known as the cholangiole. Both HCC and ICC are related to hepatitis C infection. As these rearrangements were not selected through hybridization capture reaction it is believed that rearrangements of this type are far more common in these cancers than the observed frequency.

EQUIVALENTS

Those skilled in the art will recognize, or be able to ascertain using no more than routine experimentation, many equivalents to the specific embodiments described herein. Such equivalents are intended to be encompassed by the following claims.

We claim:

1. A method of determining presence of a fibroblast growth factor receptor (FGFR) gene fusion or a neurotrophic tyrosine receptor kinase (NTRK) gene fusion, comprising:
    detecting an FGFR or NTRK gene fusion in an FGFR or NTRK nucleic acid molecule or polypeptide in a sample obtained from a subject that has or is at risk of having a cholangiocarcinoma, thereby determining that the FGFR or NTRK gene fusion is present in the sample; and
    responsive to the determination of the presence of the FGFR or NTRK gene fusion in the sample, generating a report comprising one or more therapeutic options comprising a therapeutic agent that antagonizes or inhibits an FGFR gene or gene product or an NTRK gene or gene product.

2. The method of claim 1, further comprising administering to the subject an effective amount of the therapeutic agent.

3. The method of claim 1, wherein said therapeutic agent comprises one or more of:
    a kinase inhibitor;
    a tyrosine kinase inhibitor;
    a pan-FGFR2 inhibitor;
    a pan-TRK inhibitor;
    a multi-specific kinase inhibitor;
    an FGF receptor inhibitor;
    a reversible or an irreversible FGFR2 inhibitor;
    a small molecule that binds to the FGFR2 gene product or the NTRK1 gene product;
    an antibody molecule against the FGFR2 gene product or the NTRK1 gene product;
    a kinase inhibitor that is selective for the FGFR2 gene product or the NTRK1 gene product; and
    a siRNA, antisense RNA, or other nucleic acid based inhibitor of the FGFR2 gene or gene product or the NTRK1 gene or gene product.

4. The method of claim 1, wherein said therapeutic agent comprises one or more of AZD-2171, AZD-4547, BGJ398, BIBF1120, Brivanib, Cediranib, Dovitinib, ENMD-2076, JNJ 42756493, Masitinib, Lenvatinib, LY2874455, Ponatinib, Pazopanib, R406, Regorafenib, PD173074, PD-173955, Danusertib, Dovitinib Dilactic Acid, TSU-68, Tyrphostin AG 1296, MK-2461, Brivanib Alaninate, Lestaurtinib, PHA-848125, K252a, AZ-23, Oxindole-3, AV369b, ACTB1003, Volasertib, R1530, Loxo-101, ARRY-470, ARRY-786, RXDX-101, RXDX-102, axitinib, bosutinib, dasatinib, erlotinib, gefitinib, imatinib, lapatinib, neratinib, nilotinib, semaxanib, sunitinib, toceranib, vandetanib, vatalanib, sorafenib, PCI-32765, AC220, dovitinib lactate, BIBW 2992, SGX523, PF-04217903, PF-02341066, PF-299804, BMS-777607, ABT-869, MP470, AP24534, JNJ-26483327, MGCD265, DCC-2036, BMS-690154, CEP-11981, tivozanib, OSI-930, MM-121, XL-184, XL-647, and XL228.

5. The method of claim 1, wherein the cholangiocarcinoma is an intrahepatic cholangiocarcinoma (ICC).

6. The method of claim 1, wherein the cholangiocarcinoma is an extrahepatic cholangiocarcinoma.

7. The method of claim 1, wherein the cholangiocarcinoma is a metastatic cholangiocarcinoma.

8. The method of claim 1, further comprising acquiring the sample from the subject.

9. The method of claim 1, wherein the sample comprises genomic DNA, cDNA, or RNA.

10. The method of claim 1, wherein the sample comprises cancerous tissue, whole blood, serum, plasma, buccal scrape, sputum, saliva, cerebrospinal fluid, urine, stool, circulating tumor cells, circulating nucleic acids, or bone marrow.

11. The method of claim 10, wherein the sample is a tissue biopsy sample.

12. The method of claim 10, wherein the sample comprises circulating tumor cells or circulating nucleic acids.

13. The method of claim 1, further comprising, prior to acquiring the sequence, enriching the sample for an FGFR or NTRK nucleic acid molecule.

14. The method of claim 1, wherein the FGFR gene fusion is an FGFR1, FGFR2, or FGFR3 gene fusion.

15. The method of claim 1, wherein the NTRK gene fusion is an NTRK1 gene fusion.

16. The method of claim 1, wherein detecting the FGFR or NTRK gene fusion comprises sequencing at least nucleic acid molecule that comprises the FGFR or NTRK gene fusion.

17. The method of claim 16, wherein the sequencing is next-generation sequencing (NGS).

18. The method of claim 1, wherein the sequencing comprises:
(a) hybridizing an oligonucleotide specific for the FGFR or NTRK gene fusion to the FGFR or NTRK nucleic acid molecule;
(b) hybridizing a primer that amplifies a region comprising the fusion junction of the FGFR or NTRK gene fusion to the FGFR or NTRK nucleic acid molecule;
(c) amplifying the region comprising the fusion junction of the FGFR or NTRK gene fusion;
(d) attaching an adapter oligonucleotide to one end of a nucleic acid that comprises the fusion junction of the FGFR or NTRK gene fusion;
(e) generating a signal specific to the presence of the fusion junction of the FGFR or NTRK gene fusion; and/or
(f) incorporating a nucleotide into an oligonucleotide that is hybridized to a nucleic acid that contains the fusion junction of the FGFR or NTRK gene fusion.

19. The method of claim 1, wherein the FGFR or NTRK gene fusion is:
(a) an FGFR2-TACC3 gene fusion comprising exons 1-16 of SEQ ID NO: 1 and exons 11-16 of SEQ ID NO: 3;
(b) an FGFR2-KIAA1598 gene fusion comprising exons 1-16 of SEQ ID NO: 1 and exons 7-17 of SEQ ID NO: 5;
(c) a BICC1-FGFR2 gene fusion comprising exons 1-2 of SEQ ID NO: 7 and exon 17 of SEQ ID NO: 1;
(d) an FGFR2-BICC1 gene fusion comprising exons 1-16 of SEQ ID NO: 1 and exons 18-21 of SEQ ID NO: 7;
(e) a PARK2-FGFR2 gene fusion comprising exons 1-9 of SEQ ID NO: 9 and exon 18 of SEQ ID NO: 11;
(f) an FGFR2-NOL4 gene fusion comprising exons 1-17 of SEQ ID NO: 11 and exons 7-11 of SEQ ID NO: 13;
(g) a ZDHHC6-FGFR2 gene fusion comprising exons 1-5 of SEQ ID NO: 15 and exon 18 of SEQ ID NO: 11; or
(h) a RABGAP1L-NTRK1 gene fusion.

20. The method of claim 1, wherein the report is in electronic, web-based, or paper form.

21. The method of claim 1, further comprising providing the report to the patient or to a caregiver, physician, oncologist, hospital, clinic, third-party payor, insurance company, or government office.

22. The method of claim 1, wherein the report further comprises information on likely effectiveness of a therapeutic option, acceptability of a therapeutic option, advisability of applying the therapeutic option to a patient, information or a recommendation on administration of the therapeutic agent at a preselected dosage or in a preselected treatment regimen, information or a recommendation on administration of the therapeutic agent in combination with another drug, or information on the role of an FGFR or NTRK gene fusion or a wild-type FGFR or NTRK gene sequence in disease.

23. A method of stratifying a subject that has or is at risk of having a cholangiocarcinoma for treatment, comprising:
detecting presence or absence of a fibroblast growth factor receptor (FGFR) gene fusion or a neurotrophic tyrosine receptor kinase (NTRK) gene fusion in an FGFR or NTRK nucleic acid molecule or polypeptide in a sample obtained from the subject;
responsive to a determination of the presence of the FGFR or NTRK gene fusion in the sample, classifying the subject as a candidate to receive a treatment comprising a therapeutic agent that antagonizes or inhibits an FGFR gene or gene product or an NTRK gene or gene product; and
responsive to a determination of the absence of the FGFR or NTRK gene fusion in the sample, classifying the subject as a candidate to receive a treatment other than a therapeutic agent that antagonizes or inhibits an FGFR gene or gene product or an NTRK gene or gene product.

24. A method of identifying a subject that has or is at risk of having a cholangiocarcinoma as likely or unlikely to respond to a treatment, comprising:
detecting presence or absence of a fibroblast growth factor receptor (FGFR) gene fusion or a neurotrophic tyrosine receptor kinase (NTRK) gene fusion in an FGFR or NTRK nucleic acid molecule or polypeptide in a sample obtained from the subject;
responsive to a determination of the presence of the FGFR or NTRK gene fusion in the sample, identifying the subject as likely to respond to a treatment comprising a therapeutic agent that antagonizes or inhibits an FGFR gene or gene product or an NTRK gene or gene product; and
responsive to a determination of the absence of the FGFR or NTRK gene fusion in the sample, identifying the subject as unlikely to respond to a treatment comprising a therapeutic agent that antagonizes or inhibits an FGFR gene or gene product or an NTRK gene or gene product.

* * * * *

SEQUENCE LISTING

```
Sequence total quantity: 18
SEQ ID NO: 1              moltype = DNA  length = 3708
FEATURE                   Location/Qualifiers
source                    1..3708
                          mol_type = unassigned DNA
                          organism = Homo sapiens
SEQUENCE: 1
aatttgttga ggaatttccc cctagccttg acccttgac agctcccgct cctactcagt   60
gctgggaga agtagggagg ccttaagcga agagatgggt ctgcactttg gaggagccgg  120
acactgttga ctttcctgat gtgaaatcta cccaggaaca aaacaccagt gactgcagca  180
gcagcggcag cgcctcggtt cctgagccca ccgcaggctg aaggcattgc gcgtagtcca  240
tgcccgtaga ggaagtgtgc agatgggatt aacgtccaca tggagatatg gaagaggacc  300
ggggattggt accgtaacca tggtcagctg gggtcgtttc atctgcctgg tcgtggtcac  360
catggcaacc ttgtccctgg cccggccctc cttcagttta gttgaggata ccacattaga  420
gccagaagat gccatctcat ccggaagatga tgaggatgac accgatggtg cggaagattt  480
tgtcagtgag aacagtaaca acaagagagc accatactgg accaacacag aaaagatgga  540
aaagcggctc catgctgtgc ctgcgccaa cactgtcaag tttcgctgcc cagccggggg  600
gaacccaatg ccaaccatgc ggtggctgaa aaacgggaag gagtttaagc aggagcatcg  660
cattggaggc tacaaggtac gaaaccagca ctggagcctc attatggaaa gtgtggtcca  720
atctgacaag ggaaattata cctgtgtagt ggagaatgaa tacgggtcca tcaatcacac  780
gtaccacctg gatgttgtgg agcgatcgcc tcaccggccc atcctccaag ccggactgcc  840
ggcaaatgcc tccacagtgg tcggaggaga cgtagagttt gtctgcaagg tttacagtga  900
tgcccagccc cacatccagt ggatcaagca cgtggaaaag aacggcagta aatacgggcc  960
```

```
cgacgggctg ccctacctca aggttctcaa ggccgccggt gttaacacca cggacaaaga 1020
gattgaggtt ctctatattc ggaatgtaac ttttgaggac gctggggaat atacgtgctt 1080
ggcgggtaat tctattggga tatcctttca ctctgcatgg ttgacagttc tgccagcgcc 1140
tggaagagaa aaggagatta cagcttcccc agactacctg gagatagcca tttactgcat 1200
aggggtcttc ttaatcgcct gtatggtggt aacagtcatc ctgtgccgca tgaagaacac 1260
gaccaagaag ccagacttca gcagccagcc ggctgtgcac aagctgacca acgtatccc 1320
cctgcggaga caggtaacag tttcggctga gtccagctcc tccatgaact ccaacacccc 1380
gctggtgagg ataacaacac gcctctcttc aacggcagac cccccatgc tggcagggg 1440
ctccgagtat gaacttccag aggacccaaa atggagagat ccaagagata agctgacact 1500
gggcaagccc ctgggagaag gttgctttgg gcaagtggtc atgcggaag cagtgggaat 1560
tgacaaagac aagcccaagg aggcggtcac cgtggccgtg aagatgttga agatgatgc 1620
cacagagaaa gacctttctg atctggtgtc agagatggag atgatgaaga tgattgggaa 1680
acacaagaat atcataaatc ttcttggagc ctgcacacag gatgggcctc tctatgtcat 1740
agttgagtat gcctccaaag gcaacctccg agaatacctc cgagcccgga ggcaccccgg 1800
gatggagtac tcctatgaca ttaaccgtgt tcctgaggag cagatgacct tcaaggactt 1860
ggtgtcatgc acctaccagc tggccagagg catggagtac ttggcttccc aaaaatgtat 1920
tcatcgagat ttagcagcca gaaatgtttt ggtaacagaa aacaatgtga tgaaaatagc 1980
agactttgga ctcgccagag atatcaacaa tatagactat tacaaaaaga ccaccaatgg 2040
gcggcttcca gtcaagtgga tggctccaga agccctgttt gatagagtat acactcatca 2100
gagtgatgtc tggtccttcg gggtgttaat gtgggagatc ttcactttag ggggctcgcc 2160
ctacccaggg attcccgtgg aggaactttt taagctgctg aaggaaggac acagaatgga 2220
taagcagcc aactgcacca acgaactgta catgatgagg gggactgtt ggcatgcagt 2280
gccctcccag agaccaacgt tcaagcagtt ggtagaagac ttggatcgaa ttctcactct 2340
cacaaccaat gaggaggaga agaaggtttc tggagcagtg gactgccaca gccaccatg 2400
taaccccctct cacctgccgt gcgtactggc tgtggaccag taggactcaa ggtggacgtg 2460
cgttctgcct tccttgttaa ttttgtaata attggaaagg attttatgtca gcacacactt 2520
acagagcaca aatgcagtat ataggtgctg gatgtatgta aatatattca aattatgtat 2580
aaatatatat tatatattta caaggagtta tttttgtat tgattttaaa tggatgtccc 2640
aatgcaccta gaaaattggt ctctcttttt ttaatagcta tttgctaaat gctgttctta 2700
cacataattt cttaatttc accgagcaga ggtggaaaaa tacttttgct ttcagggaaa 2760
atggtataac gttaatttat taataaattg gtaatataca aaacaattaa tcatttatag 2820
tttttttgt aatttaagtg gcatttctat gcaggcagca cagcagacta gttaatctat 2880
tgcttggact taactagtta tcagatcctt tgaaaagaga atatttacaa tatatgacta 2940
atttgggaa aatgaagttt tgatttattt gtgtttaaat gctgctgtca gacgattgtt 3000
cttagaccct ctaaatgccc catattaaaa gaactcattc ataggaaggt gtttcatttt 3060
ggtgtgcaac cctgtcatta cgtcaacgca acgtctaact ggacttccca agataaatgg 3120
taccagcgtc ctcttaaaag atgccttaat ccattcctgt aggacagacc ttagttgaaa 3180
tgatagcaga atgtgcttct ctctggcagc tggccttctg cttctgagtt gcacattaat 3240
cagattagcc tgtattctct tcagtgaatt ttgataatgg cttccagact ctttggcgtt 3300
ggagacgcct gttaggatct tcaagtccca tcatagaaaa ttgaaacaca gagttgttct 3360
gctgatagtt ttggggatac gtccatcttt taagggatt gctttcatct aattctggca 3420
ggacctcacc aaaagatcca gcctcatacc tacatcgac aaaatatcgc cgttgttcct 3480
tctgtactaa agtattgtgt tttgctttgg aaacacccac tcactttgca atagccgtgc 3540
aagatgaatg cagattacac tgatcttatg tgttacaaaa ttggagaaag tatttaataa 3600
aacctgttaa tttttatact gacaataaaa atgtttctac agatattaat gttaacaaga 3660
caaaataaat gtcacgcaac ttattttttt aataaaaaaa aaaaaaaa   3708
```

```
SEQ ID NO: 2         moltype = AA   length = 707
FEATURE              Location/Qualifiers
source               1..707
                     mol_type = protein
                     organism = Homo sapiens
SEQUENCE: 2
MVSWGRFICL VVVTMATLSL ARPSFSLVED TTLEPEDAIS SGDDEDDTDG AEDFVSENSN   60
NKRAPYWTNT EKMEKRLHAV PAANTVKFRC PAGGNPMPTM RWLKNGKEFK QEHRIGGYKV  120
RNQHWSLIME SVVPSDKGNY TCVVENEYGS INHTYHLDVV ERSPHRPILQ AGLPANASTV  180
VGGDVEFVCK VYSDAQPHIQ WIKHVEKNGS KYGPDGLPYL KVLKAAGVNT TDKEIEVLYI  240
RNVTFEDAGE YTCLAGNSIG ISFHSAWLTV LPAPGREKEI TASPDYLEIA IYCIGVFLIA  300
CMVVTVILCR MKNTTKKPDF SSQPAVHKLT KRIPLRRQVT VSAESSSSMN SNTPLVRITT  360
RLSSTADTPM LAGVSEYELP EDPKWEFPRD KLTLGKPLGE GCFGQVVMAE AVGIDKDKPK  420
EAVTVAVKML KDDATEKDLS DLVSEMEMMK MIGKHKNIIN LLGACTQDGP LYVIVEYASK  480
GNLREYLRAR RPPGMEYSYD INRVPEEQMT FKDLVSCTYQ LARGMEYLAS QKCIHRDLAA  540
RNVLVTENNV MKIADFGLAR DINNIDYYKK TTNGRLPVKW MAPEALFDRV YTHQSDVWSF  600
GVLMWEIFTL GGSPYPGIPV EELFKLLKEG HRMDKPANCT NELYMMMRDC WHAVPSQRPT  660
FKQLVEDLDR ILTLTTNEEE KKVSGAVDCH KPPCNPSHLP CVLAVDQ              707

SEQ ID NO: 3         moltype = DNA   length = 2847
FEATURE              Location/Qualifiers
source               1..2847
                     mol_type = unassigned DNA
                     organism = Homo sapiens
SEQUENCE: 3
gcgtttgaaa ctccggcgcg ccggcggcca tcaagggcta gaagcgcgac ggcggtagca   60
gctaggcttg gccccggcgc tggagcagac gcggaccct ccttcctggc ggcggcggcg  120
cgggctcaga gcccggcaac gggcgggcgg gcagaatgag tctgcaggtc ttaaacgaca  180
aaaatgtcag caatgaaaaa aatacagaaa attgcgactt cctgtttttcg ccaccagaag  240
ttaccggaag atcgtctgtt cttcgtgtgt cacagaaaga aaatgtgcca cccaagaacc  300
tggccaaagc tatgaaggtg acttttcaga cacctctgcg ggatccacag acgcacagga  360
ttctaagtcc tagcatggcc agcaaacttg aggctccttt cactcaggat gacacccttg  420
```

```
gactggaaaa ctcacacccg gtctggacac agaaagagaa ccaacagctc atcaaggaag   480
tggatgccaa aactactcat ggaattctac agaaaccagt ggaggctgac accgacctcc   540
tggggatgc aagcccagcc tttgggagtg gcagctccag cgagtctggc ccaggtgccc    600
tggctgacct ggactgctca agctcttccc agagcccagg aagttctgag aaccaaatgg   660
tgtctccagg aaaagtgtct ggcagccctg agcaagccgt ggaggaaaac cttagttcct   720
attccttaga cagaagagtg acacccgcct ctgagaccct agaagaccct tgcaggacag   780
agtcccagca caaagcggag actccgcacg gagccgagga agaatgcaaa gcggagactc   840
cgcacggagc cgaggaggaa tgccggcacg gtggggtctg tgctcccgca gcagtggcca   900
cttcgcctcc tggtgcaatc cctaaggaag cctgcgggag agcaccoctg cagggtgcag   960
ctggcgaagc cctgggctgc cctgcgggtg tgggcacccc cgtgccagca gatggcactc   1020
agacccttac ctgtgcacac acctctgctc tgagagcac agcccaacc aaccacctgg    1080
tggctggcag ggccatgacc ctgagtcctc aggaagaagt ggctgcaggc caaatgggca   1140
gctcctcgag gagcggacct gtaaaactag aatttgatgt atctgatggc gccaccagca   1200
aaagggcacc cccaccaagg agactgggag agaggtccgg cctcaagcct cccttgagga   1260
aagcagcagt gaggcagcaa aaggcccgc aggaggtgga ggaggacgac ggtaggagcg    1320
gagcaggaga ggaccccccc atgccagctt ctcggggctc ttaccacctc gactgggaca   1380
aaatggatga cccaaaactc atcccgttcg gaggtgacac caagtctggt tgcagtgagg   1440
cccagccccc agaaagccct gagaccaggc tgggccaagc agccgctgaa cagttgcatg   1500
ctgggcctgc cacggaggag ccaggtcccc gtctgagcca gcagctgcat tcagcctcag   1560
cggaggacac gcctgtggtg cagttggcag ccgagacccc aacagcagag agcaaggaga   1620
gagccttgaa ctctgccagc acctcgcttc ccacaagctg tccaggcagt gagccagtgc   1680
ccacccatca gcaggggcag cctgccttgg agctgaaaga ggagagcttc agagacccg   1740
ctgaggttct aggcacgggc gcggaggtgg attacctgga gcagtttgga acttcctcgt   1800
ttaaggagtc ggccttgagg aagcagtcct tatacctcaa gttcgacccc ctcctgaggg   1860
acagtcctgg tagaccagtg cccgtggcca ccgagaccag cagcatgcac ggtgcaaatg   1920
agactccctc aggacgtccg cggaaagcca agcttgtgga gttcgatttc ttgggagcac   1980
tggacattcc tgtgccaggc ccaccccag gtgttcccgc gcctggggc ccacccctgt     2040
ccaccggacc tatagtggac ctgctccagt acagccagaa ggacctggat gcagtggtaa   2100
aggcgacaca ggaggagaac cgggagctga ggagcaggtg tgaggagctc cacgggaaga   2160
acctggaact gggaaagatc atggacaggt tcgaagaggt tgtgtaccag gccatggagg   2220
aagttcagaa gcagaaggaa ctttccaaag ctgaaatcca gaaagttcta aagaaaaag   2280
accaacttac cacagatctg aactccatgg agaagtcctt ctccgacctc ttcaagcgtt   2340
tgagaaaca gaaagaggtg atcgagggct accgcaagaa cgaagagtca ctgaagaagt   2400
gcgtggagga ttacctggca aggatcaccc aggagggcca gaggtaccaa gccctgaagg   2460
cccacgcgga ggagaagctg cagctggcaa acgaggagat cgcccaggtc ggagcaaggc   2520
cccaggcgga agcgttggcc ctccaggcca gcctgaggaa ggagcagatg cgcatccagt   2580
cgctggagaa gacagtggag cagaagacta aagagaacga ggagctgacc aggatctgcg   2640
acgacctcat ctccaagatg gagaagatct gacctcacg gagccgctgt ccccgcccc    2700
ctgctcccgt ctgtctgtcc tgtctgattc tcttaggtgt catgttcttt tttctgtctt   2760
gtcttcaact tttttaaaaa ctagattgct ttgaaaacat gactcaataa aagtttcctt   2820
tcaatttaaa cactgaaaaa aaaaaaa                                       2847

SEQ ID NO: 4           moltype = AA   length = 838
FEATURE                Location/Qualifiers
source                 1..838
                       mol_type = protein
                       organism = Homo sapiens
SEQUENCE: 4
MSLQVLNDKN VSNEKNTENC DFLFSPPEVT GRSSVLRVSQ KENVPPKNLA KAMKVTFQTP   60
LRDPQTHRIL SPSMASKLEA PFTQDDTLGL ENSHPVWTQK ENQQLIKEVD AKTTHGILQK   120
PVEADTDLLG DASPAFGSGS SSESGPGALA DLDCSSSSQS PGSSENQMVS PGKVSGSPEQ   180
AVEENLSSYS LDRRVTPASE TLEDPCRTES QHKAETPHGA EEECKAETPH GAEEECRHGG   240
VCAPAAVATS PPGAIPKEAC GGAPLQGLPG EALGCPAGVG TPVPADGTQT LTCAHTSAPE   300
STAPTNHLVA GRAMTLSPQE EVAAGQMASS SRSGPVKLEF DVSDGATSKR APPPRRLGER   360
SGLKPPLRKA AVRQQKAPQE VEEDDGRSGA GEDPPMPASR GSYHLDWDKM DDPNFIPFGG   420
DTKSGCSEAQ PPESPETRLG QPAAEQLHAG PATEEPGPCL SQQLHSASAE DTPVVQLAAE   480
TPTAESKERA LNSASTSLPT SCPGSEPVPT HQQGQPALEL KEESFRDPAE VLGTGAEVDY   540
LEQFGTSSFK ESALRKQSLY LKFDPLLRDS PGRPVPVATE TSSMHGANET PSGRPREAKL   600
VEFDFLGALD IPVPGPPPGV PAPGGPPLST GPIVDLLQYS QKDLDAVVKA TQEENRELRS   660
RCEELHGKNL ELGKIMDRFE EVVYQAMEEV QKQKELSKAE IQKVLKEKDQ LTTDLNSMEK   720
SFSDLFKRFE KQKEVIEGYR KNEESLKKCV EDYLARITQE GQRYQALKAH AEEKLQLANE   780
EIAQVRSKAQ AEALALQASL RKEQMRIQSL EKTVEQKTKE NEELTRICDD LISKMEKI     838

SEQ ID NO: 5           moltype = DNA   length = 5361
FEATURE                Location/Qualifiers
source                 1..5361
                       mol_type = unassigned DNA
                       organism = Homo sapiens
SEQUENCE: 5
attgcgtccc gctctacctc tgtggttctt tgggagcgac cccgggaag cgtccaaagt     60
ggagttccca cacacgctgc gaacccacag ccggttttct ctgaactcgc gtccctgagt   120
ccgggaggtg gaggcggaga aagggtgcg gagcgacccc acgcagggcc gccccctc      180
ccaccagcgc gtcctgccgc gccggcagcc acaggctggc atagcggctg ccgacccgcc   240
ctcgttcctc cacccctga acgggactgc tgggcccgcc tcgcaggtgaa              300
gcggccgcag ccgccagta ggtcgtgggc gatgatctca ctcgcgcgct cgcgccagg     360
aggaggagga gcgggagcgg atccaacttc cgggtagtgg agccgcaagc caccggcatc   420
ttgctttttc ttccccctcc tcctgtgtgc cccgcgccgc tccctctttc ccttttattc   480
ccggccccac ccgccaaaat gaacagctcg gacgaagaga agcagctgca gctcattacc   540
agtctgaagg agcaagcaat aggcgaatat gaagacctta gcagagaa ccagaaaaca    600
```

-continued

```
aaggagaagt gtgacaaaat taggcaagaa cgagatgaag ccgttaaaaa actggaagaa    660
tttcagaaaa tttctcacat ggtcatagag gaagttaatt tcatgcagaa ccatcttgaa    720
atagagaaga cttgtcgaga aagtgctgaa gctttggcaa caaagctaaa taaagaaaat    780
aaaacgttga aaagaatcag catgttgtac atggccaagc tgggaccaga tgtaataact    840
gaagagataa acattgatga tgaagattcg actacagaca cagacggtgc cgccgagact    900
tgtgtctcag tacagtgtca gaagcaaatt aaagaacttc gagatcaaat tgtatctgtt    960
caggaggaaa agaagatttt agccattgag ctggaaaatc tcaagagcaa actcgtagaa   1020
gtaattgaag aagtaaataa agttaaacaa gaaaagactg tttttaaattc agaagttctt   1080
gaacagagaa aagtcttaga aaaatgcaat agagtgtcca tgttagctgt agaagagtat   1140
gaggagatgc aagtaaacct ggagctggag aaggaccttc gaaagaaagc agagtcattt   1200
gcacaagaga tgttcattga gcaaaacaag ctaaagagac aaagccacct tctgctgcag   1260
agctccatcc ctgatcagca gcttttgaaa gctttagacg aaaatgcaaa actcacccag   1320
caacttgaag aagagagaat tcagcatcaa caaaaggtca aagaattaga agagcaacta   1380
gaaaatgaaa cactccacaa agaaatacac aacctcaaac agcaactgga gcttctagag   1440
gaagataaaa aggaattgga attgaaatat cagaattctg aagagaaagc cagaaattta   1500
aagcactctg ttgatgaact ccagaaacga gtgaaccagt ctgagaattc agtacctcca   1560
ccacctcctc ctccaccacc acttccccct ccacctccca atcctatccg atccctcatg   1620
tccatgatcc ggaaacgatc ccacccccagt ggcagtggtg ctaagaaaga aaaggcaact   1680
caaccagaaa caactgaaga agtcacagat ctaaagaggc aagcagttga agagatgatg   1740
gatagaatta aaaagggagt tcatcttaga cccgttaatc agacagccag accgaagaca   1800
aagccagaat cttcgaaagg ctgcgaaagt gcagtggatg aactaaaagg aatactgggg   1860
acacttaaca atccactag ttcaagaagc ttaaaatccc ttgaccctga aaacagtgaa   1920
actgagttag aaaggatttt gcgtcgcaga aaggtgacag cagaagcaga tagcagtagt   1980
ccaactggga tattagccac ctcagagtcc aaatccatgc cagtgttggg ttctgtatcc   2040
agtgtaacaa aaacagcctt gaacaagaaa actctgaggg cagaattcaa cagcccgtcc   2100
ccccaacac ctgagccagg tgagggccc cgtaaattgg aaggatgcac aagttccaag   2160
gttacgtttc agcctcccag tagcattgga tgcaggaaaa aatacattga cggtgaaaaa   2220
caagccgaac cagttgtagt tttagatcct gttctacac atgaaccca aaccaaagac   2280
caggttgctg aaaaagatcc aactcaacac aaggaggatg aaggcgaaat tcaaccagaa   2340
aacaaagaag acagcattga aaacgtgaga gagcagacaa gctccaactg ctgatccata   2400
aaccagaagc ctgacatgtt tggaagtcct tttcaataag cacatgatta gtgttgttat   2460
attggcaagg gctgtagaca ttctgctctg gtcactgtat tcagaataca ggttcttttc   2520
tggtgtcact tttgtaagta gcaactataa acataagtaa gctgtttagc aaaacacaca   2580
ttcctagtag gttttggttt tttgatcttt ataaagatga ggttttttttc ctagttactg   2640
tattaagtat gacttcttt agaaggttac aaaaaaaattc agatgttgat acctttttag   2700
gaaatgtgca taccactcat caaatggaat gctgaaagtt tgaggtgctt gtatataatc   2760
ggataaacaa aactgatcaa cccaatgtga ttttaaaagc ccccaaagaa gcttctgttt   2820
tgggtctgat cctcttgatg gagaaactgc agcagcatgg aaattgttgg gtactgtggc   2880
atacaagtta tttttctacag tagactgaga taactgaaa actcaggagc tggcatcaaa   2940
ctcgtagtcc catagtcagt gttaattaca cacattgtta actattggat gaaaaataca   3000
tgctattgat tgtgtccaaa gcctcccgag gacctccgtg gggatgctct ggtagcctga   3060
atacagaact gaggtgaaag tccaaacctt gaatttttaca gtagtaagtt ggtaaaccat   3120
gtgctctgtg ctatgagtta attatgtttt cccaaatact aatgtggcac agtaccata   3180
ttttatcaga gttcttatgt acagtatggt gaagataagt gacaagcaca cattttttctt   3240
gcttcactgc tgttctatat tacacaggtt tgttgttgtt tttttttaaaa aagaaattaa   3300
gcagtagtta gtctctaaaa atacaatgtt tcaggctacc acagtgaata aatagaaatg   3360
taatcaggga ttaaaaaaaa aacttatgca gcttttcaaa gttgattgtt tcaaaattgg   3420
tgtttattta aaataagtgg taatgtactt gaatgcactt tttatgacaa tgattcagta   3480
atggtaatt tactattaaaa gaaagtgaaa ggtttagttt tgttagcatg gctcagcatg   3540
tagctgtcag gtgttttttca cctaagggca aagaaaatg atagtaataa ttgcagtagt   3600
tgtattgtat tgtatttttg cacgtgttggt aagcatagagc ttgaagaggt gggtaggcag   3660
gtacatgtac ttcctaaaatt tggagataat tatctttctg taagttcgtt atgcttgact   3720
gtttccatgt tctcccaata atgatttttat agttacttat cactttactc atggagaatt   3780
aaaacgtaat gtttttcaac tgtatctttc tttaactgga taatactgct atatgatatg   3840
cttactacag actgcattaa ttcacgaaac gaattcgtt atgctgtaat ttgaactctc   3900
ctcaccacaa cttattaaaa aggcaccaat agtttcccat taagggtcag ttgtggttat   3960
tattaacgtt tctggtttag ttccccaagc ttgacattct ttaatagaaa attgtatatg   4020
atttgacaac tttagtaatt tttaatagtc cctaagatgg tttattgagt tttctttcat   4080
gtttcttttgt gctgtcttcc ttcttgcatc tgtgatctgt ctgccagcat ggcaactcaca   4140
cacatttagg aatataaaaa tatgtacact gtcttccat atttcatcac accatcacag   4200
aataatatgg ttatcaaaat accctccttt ctagagtaag aagttgccct ttgggtgaaa   4260
tgtgttagct ggactaggga acaattagta acaggtattt tgaaagtatt cctgcctttt   4320
ttaagctgct tactttctct cactgtgatt acaaagcatt taaattaat ttgacatgaa   4380
ggtatttgat ggaagatatt cactccactt tttctgccta cagttttttcc cttttcagtt   4440
tggttttgag ggggttttgc ccctggctgg ggtgacactg tcaaccaaag caagggatcc   4500
caaataggaa gacataggag aaccgtgctt atatctgcaa ggtatgttca tagctattgc   4560
acacacaaaa cttacatacg tcctgcttac acaattttaa gttggaaaag actgcatctt   4620
tatgtttttg atttctctaa aaggttattt atgcttcctt ctgtttggga aagataaatt   4680
aagtcttgtg cgctatagag gatttttttt ctttaagaaa aacgaatgtt gatgcatttt   4740
atagcccgag tgaggaacag agatagaggt actttgtgcc attgctatta aagaaaagag   4800
aaatgtctct tttttttttct ggaagaataa gatttttaatt aaagcacttg cacccttttg   4860
tatgtgagct ggtctcaaac aaagtcctca cccacagcag tttcagcagc tgaacagtcc   4920
catggaagtt ctgactggca ggcatcaaca gggctattag cacccagcat agtttgccct   4980
gagtacggag gatggatgct ttggctctca ctactcacca ataattgctc cttccttacc   5040
ttctttgtta atggtaaact gctgaaaatg gagtagtaca ggtaacaatt ttttttaatt   5100
gtctttccag accagttttt ggttgtgtgt tcagtaaatg atagtctgta tcacagcctt   5160
caagtctgga ttatttttct aaatgcatac tctacctgtt cagttacact cgttgtgaa   5220
caacattagc ttatataccca gtaagttgtc agaatggat aaccatctgt cattatcact   5280
gaccttcaaa gactcatcaa gcagtccctg cataaggatt ggagtggttt gaagtttctc   5340
```

-continued

```
ttccaagcac taacatgtcc c                                             5361

SEQ ID NO: 6           moltype = AA  length = 631
FEATURE                Location/Qualifiers
source                 1..631
                       mol_type = protein
                       organism = Homo sapiens
SEQUENCE: 6
MNSSDEEKQL QLITSLKEQA IGEYEDLRAE NQKTKEKCDK IRQERDEAVK KLEEFQKISH     60
MVIEEVNFMQ NHLEIEKTCR ESAEALATKL NKENKTLKRI SMLYMAKLGP DVITEEINID    120
DEDSTTDTDG AAETCVSVQC QKQIKELRDQ IVSVQEEKKI LAIELENLKS KLVEVIEEVN    180
KVKQEKTVLN SEVLEQRKVL EKCNRVSMLA VEEYEEMQVN LELEKDLRKK AESFAQEMFI    240
EQNKLKRQSH LLLQSSIPDQ QLLKALDENA KLTQQLEEER IQHQQKVKEL EEQLENETLH    300
KEIHNLKQQL ELLEEDKKEL ELKYQNSEEK ARNLKHSVDE LQKRVNQSEN SVPPPPPPPP    360
PLPPPPPNPI RSLMSMIRKR SHPSGSGAKK EKATQPETTE EVTDLKRQAV EEMMDRIKKG    420
VHLRPVNQTA RPKTKPESSK GCESAVDELK GILGTLNKST SSRSLKSLDP ENSETELERI    480
LRRRKVTAEA DSSSPTGILA TSESKSMPVL GSVSSVTKTA LNKKTLEAEF NSPSPPTPEP    540
GEGPRKLEGC TSSKVTFQPP SSIGCRKKYI DGEKQAEPVV VLDPVSTHEP QTKDQVAEKD    600
PTQHKEDEGE IQPENKEDSI ENVRETDSSN C                                  631

SEQ ID NO: 7           moltype = DNA  length = 3119
FEATURE                Location/Qualifiers
source                 1..3119
                       mol_type = unassigned DNA
                       organism = Homo sapiens
SEQUENCE: 7
atggccgccc agggagagcc cggctacctg gcggcgcagt cggacccggg ctccaacagc     60
gagcgcagca ccgactcccc agtgcccggc tccgaggacg acttggtcgc cggggcgacc    120
ctgcacagcc cggagtggag cgaggagcgc ttccgcgtgg acaggaagaa acttgaggcc    180
atgttacaag ctgctgctga agggaaaggc agaagtgggg aagacttttt tcaaaagatc    240
atggaggaaa caaatacgca gattgcttgg ccatcaaaac tgaagatcgg agccaaatcc    300
aagaaagatc cccatattaa ggtttctgga agaaagaag atgttaaaga agccaaggaa    360
atgatcatgt ctgtcttaga cacaaaaagc aatcgagtca cactgaagat ggatgtttca    420
catacagaac attcacatgt aatcggcaaa ggtggcaaca atattaaaaa agtgatggaa    480
gaaaccggat gccatatcca cttttccagat tccaacagga ataaccaagc agaaaaaagc    540
aaccaggtat ctatagcggg acaaccagca ggagtagaat ctgcccgagt tagaattcgg    600
gagctgcttc ctttggtgct gatgtttgag ctaccaattg ctggaattct tcaaccggtt    660
cctgatccta atttccctc tattcagcat atatcacaaa cgtacaatat ttcagtatca    720
tttaaacagc gttcccgaat gtatggtgct actgtcatag tacgagggtc tcagaataac    780
actagtgctg tgaaggaagg aactgccatg ctgttagaaa atcttgctgg agcttagca    840
tcagctattc ctgtgagcac acaactagat attgcagctc aacatcatct ctttatgatg    900
ggtcgaaatg ggagcaacat caaacatatc atgcagagaa caggtgctca gatccacttt    960
cctgatccca gtaatctcaca aaagaaatct accgtctacc tccagggcac cattgagtct   1020
gtctgtcttg caaggcaata tctcatgggt tgtcttcctc ttgtgttgat gtttgatatg   1080
aaggaagaaa ttgaagtaga tccacaattc attgcgcagt tgatggaaca gcttgatgtc   1140
ttcatcagta ttaaaccaaa gcccaaacag ccaagcaagt ctgtgattgt gaaaagtgtt   1200
gagcgaaatg ccttaaatat gtatgaagca aggaaatgtc tcctcgaact tgaaagcagt   1260
ggggttacca tagcaaccag tccatcccca gcatcctgcc ctgccggcct ggcatgtccc   1320
agcctgata tcttagcttc agcaggcctt ggactcactg gactaggtct tttgggaccc   1380
accacctat ctctgaacac ttcaacaacc caaactcac tcttgaatgc tcttaatagc   1440
tcagtcagtc ctttgcaaag tccaagttct ggtacaccca gccccacatt atgggccact   1500
ccacttgcta atacttcaag tgccacaggt ttttctgcta taccacacct tatgattcca   1560
tctactgccc aagccacatt aactaatatt tgttgtctg gagtgccac ctatgggcac   1620
acagctccat ctccccctcc tggcttgact cctgttgatg tccatatcaa cagtatgcag   1680
accgaaggca aaaaatctc tgctgcttta aatgacatg cacagtctcc agatataaaa   1740
tatggtgcaa tatccacttc atcacttgga gaaaaagtgc tgagtgcaaa tcacgggat   1800
ccgtccatcc agacaagtgg gtctgagcag acatctccca aatcaagccc cactgaaggt   1860
tgtaatgatg cttttgttga agtaggcatg cctcgaagtc cttcccattc tgggaatgct   1920
ggtgacttga aacagatgat gtgtccctcc aaggttcct gtgccaaaag gcagacagtg   1980
gaactattgc aagcagcgaaca aaactcacac ttacacagca ctgacaggtt gctctcagac   2040
cctgaactga gtgctaccga aagccctttg gctgacaaga aggctccagg gagtgagcgc   2100
gctgcagaga gggcagcagc tgcccagcaa aactccgaaa gggcccacct tgctccacgg   2160
tcatcatatg tcaacatgca ggcatttgac tatgaacaga gaagctatt agccaccaaa   2220
gctatgttaa agaaaccagt ggtgacggag gtcagaacgc ccacaaatac ctggagtggc   2280
ctgggttttt ctaaatccat gccagctgaa actatcaagg agttgagaag gccaatcat   2340
gtgtcctata gcccacaat gacaaccact tatgagggct catccatgtc cctttcacgg   2400
tccaacagtc gtgagcactt gggaggtgga agcgaatctg ataactggag agaccgaaat   2460
ggaattggac ctggaagtca tagtgaattt gcagcttcta ttggcagcct taagcgtaaa   2520
caaaacaaat caacggaaca ctatctcagc agtagcaatt acatgactg catttcctcg   2580
ctgacaggaa gcaatggctg taacttaaat agctctttca aaggttctga cctccctgag   2640
ctcttcagca aactgggcct gggcaaatac acagatgttt tccagcaaca agagatcgat   2700
cttcagacat tcctcactct cacagatcag gatctgaagg agctgggaat aactactttt   2760
ggtgccagga ggaaaatgct gcttgcaatt tcagaactaa ataaaaccg aagaaagctt   2820
tttgaatcgc acacacg caccctcttttc ctggaaggtg gagcgagtgg aaggctaccc   2880
cgtcagtatc actcagacat tgctagtgtc agtggccgct ggtagcagca ccctcttggc   2940
acatgcccgc tgactaactg taaagtggac acaggagatg tatgaacagc cttcacagca   3000
caccatcctc agcactctgg gtgtctggta tcaggaccaa agcatttat tcgcacctgt   3060
actttatggc aaaaaggaag aagagagaga agatgttctt atgatgtcat acagaacac   3119
```

```
SEQ ID NO: 8              moltype = AA   length = 974
FEATURE                   Location/Qualifiers
source                    1..974
                          mol_type = protein
                          organism = Homo sapiens
SEQUENCE: 8
MAAQGEPGYL AAQSDPGSNS ERSTDSPVPG SEDDLVAGAT LHSPEWSEER FRVDRKKLEA    60
MLQAAAEGKG RSGEDFFQKI MEETNTQIAW PSKLKIGAKS KKDPHIKVSG KKEDVKEAKE   120
MIMSVLDTKS NRVTLKMDVS HTEHSHVIGK GGNNIKKVME ETGCHIHFPD SNRNNQAEKS   180
NQVSIAGQPA GVESARVRIR ELLPLVLMFE LPIAGILQPV PDPNSPSIQH ISQTYNISVS   240
FKQRSRMYGA TVIVRGSQNN TSAVKEGTAM LLEHLAGSLA SAIPVSTQLD IAAQHHLFMM   300
GRNGSNIKHI MQRTGAQIHF PDPSNPQKKS TVYLQGTIES VCLARQYLMG CLPLVLMFDM   360
KEEIEVDPQF IAQLMEQLDV FISIKPKPKQ PSKSVIVKSV ERNALNMYEA RKCLLGLESS   420
GVTIATSPSP ASCPAGLACP SLDILASAGL GLTGLGLLGP TTLSLNTSTT PNSLLNALNS   480
SVSPLQSPSS GTPSPTLWAP PLANTSSATG FSAIPHLMIP STAQATLTNI LLSGVPTYGH   540
TAPSPPPGLT PVDVHINSMQ TEGKKISAAL NGHAQSPDIK YGAISTSSLG EKVLSANHGD   600
PSIQTSGSEQ TSPKSSPTEG CNDAFVEVGM PRSPSHSGNA GDLKQMMCPS KVSCAKRQTV   660
ELLQGTKNSH LHSTDRLLSD PELSATESPL ADKKAPGSER AAERAAAAQQ NSERAHLAPR   720
SSYVNMQAFD YEQKKLLATK AMLKKPVVTE VRTPTNTWSG LGFSKSMPAE TIKELRRANH   780
VSYKPTMTTT YEGSSMSLSR SNSREHLGGG SESDNWRDRN GIGPGSHSEF AASIGSPKRK   840
QNKSTEHYLS SSNYMDCISS LTGSNGCNLN SSFKGSDLPE LFSKLGLGKY TDVFQQQEID   900
LQTFLTLTDQ DLKELGITTF GARRKMLLAI SELNKNRRKL FESPNARTSF LEGGASGRLP   960
RQYHSDIASV SGRW                                                    974

SEQ ID NO: 9              moltype = DNA   length = 4073
FEATURE                   Location/Qualifiers
source                    1..4073
                          mol_type = unassigned DNA
                          organism = Homo sapiens
SEQUENCE: 9
attcctaggg ccgggcgcgg gggcggggag gcctggagga tttaacccag gagagccgct    60
ggtgggaggc gcggctggcg ccgctgcgcg catgggcctg ttcctggccc gcagccgcca   120
cctacccagt gaccatgata gtgtttgtca ggttcaactc cagccatggt ttcccagtgg   180
aggtcgattc tgacaccagc atcttccagc tcaaggaggt ggttgctaag cgacaggggg   240
ttccggctga ccagttgcgt gtgattttcg cagggaagga gctgaggaat gactggactg   300
tgcagaattg tgacctggat cagcagagca ttgttcacat tgtgcagaga ccgtggagaa   360
aaggtcaaga aatgaatgca actggaggcg acgacccccag aaacgcggcg ggaggctgtg   420
agcgggagcc ccagagcttg actcgggtgg acctcagcag ctcagtcctc ccaggagact   480
ctgtggggct ggctgtcatt ctgcacactg acagcaggaa ggactcacca ctgactgaa    540
gtccagcagg tagatcaatc tacaacagct tttatgtgta ttgcaaaggc ccctgtcaaa   600
gagtgcagcc gggaaaactc agggtacagt gcagcacctg caggcaggca acgctcacct   660
tgacccaggg tccatcttgc tgggatgatg tttttaattc aaaccggatg agtggtgaat   720
gccaatcccc acactgccct gggactagtg cagaatttt ctttaaatgt ggagcacact   780
ccacctctga caaggaaaca tcagtagctt tgcacctgat cgcaacaaat agtcggaaca   840
tcacttgcat tacgtgcaca gacgtcagga gcccgtcct ggttttccag tgcaactccc   900
gccacgtgat ttgcttagac tgtttccact tatactgtgt gacaagactc aatgatcggc   960
agtttgttca cgaccctcaa cttggctact ccctgccttg tggctggc tgtcccaact    1020
ccttgattaa agagctccat cacttcagga ttctgggaga gagcagtac aaccggtacc   1080
agcagtatgg tgcagaggag tgtgtcctgc agatgggggg cgtgttatgc cccgccctg    1140
gctgtggagc gggctgctg ccggagcctg accagaggaa agtcacctgc gaaggggca    1200
atggcctggg ctgtgggttt gccttctgcc gggaatgtaa agaagcgtac catgaaggg    1260
agtgcagtgc cgtatttgaa gcctcaggaa caactactca ggcctacaga gtcgatgaaa   1320
gagccgccga gcaggctcgt tgggaagcag cctccaaaga aaccatcaag aaaaccacca   1380
agccctgtcc ccgctgccat gtaccagtgg aaaaaatgg aggctgcatg cacatgaagt   1440
gtccgcagcc ccagtgcagg tcgactggt gctggaactg tggctgcgag tggaaccgcg   1500
tctgcatggg ggaccactgg ttcgacgtgt agccagggcg gccggcgcc ccatcgccac    1560
atcctggggg agcataccca gtgtctacct tcattttcta attctctttt caaacacaca   1620
cacacacgcg cgcgcgcgca cacacactct tcaagtttt ttcaaagtcc aactacagcc   1680
aaattgcaga agaactctt ggatccctt cactatgtcc atgaaaaaca gcagagtaaa   1740
attacagaag aagctcctga atccctttca gtttgtccac acaagacagc agagccatct   1800
gcgacaccac caacaggcgt tctcagcctc cggatgacac aaataccaga gcacagattc   1860
aagtgcaatc catgtatctg tatgggtcat tctcacctga attcgagaca gcagaatca    1920
gtagctggag agagagttct cacatttaat atcctgcctt ttaccttcag taaacaccat   1980
gaagatgcca ttgacaaggt gtttctctgt aaaatgaact gcagtgggtt ctccaaacta   2040
gattcatggc tttaacagta atgttcttat ttaaatttc agaaagcatc tattcccaaa   2100
gaacccccagg caatagtcaa aaacatttgt ttatccttaa gaattccatc tatataaatc   2160
gcattaatga aataccaact atgcgtaaat caacttgtca caagtgaga aattatgaaa   2220
gttaatttga atgttgaatg tttgaattac agggaagaaa tcaagttaat gtactttcat   2280
tccctttcat gatttgcaac tttagaaaga aattgttttt ctgaaagtat caccaaaaaa   2340
tctatagttt gattctgagt attcattttg caacttggag attttgctaa tacatttggc   2400
tccactgtaa atttaataga taaagtgcct ataaggaaa cacgtttaga aatgattca    2460
aaatgatatt caatcttaac aaaagtgaac attattaaat cagaatcttt aaagaggagc   2520
cttttccagaa ctaccaaat gaagacacgc ccgactctct ccatcagaag ggtttatacc   2580
ccttggcac accctctctg tccaatctgc aagtccagg gagctgca tcaccagggt    2640
tccccaggag agacctctc tctaggacagt aaactcacta gaatattcct tatgttgaca   2700
tggattggat ttcagttcaa tcaaacttc agctttttt tcagccattc acaacacaat   2760
caaaagatta acaacactgc atgcggcaaa ccgcatgctc ttacccacac tacgcagaag   2820
agaaagtaca accactatct tttgttctac ctgtattgtc tgacttctca ggaagatcgt   2880
gaacataact gagggcatga gtctcactag cacatggagg ccctttggga tttagagact   2940
```

-continued

```
gtaaattatt aaatcggcaa cagggcttct cttttagat gtagcactga aatccttgct    3000
ggagggaaga gaggggatga actcaagttt tccacatcct gggacacctg tccctctttt    3060
cctaactgcc taagataacc catttcttcc aaccatctga ggacagtccc gtcgtctcag    3120
aggccctgca ccgggagag actgggctct gcagcagcca catcagcatt cacagcttca    3180
tgtggcttca ctgtctgaaa atctaccgac tccaacatgg cccacggtg acaacagacc    3240
tgtgacagga agcccaaagc tcacatagaa atggtggaca gatcaaagtc tctatagtaa    3300
gggaaaaaaa gagaggtggc aggcatgagc ccctgcacc cagtggctcg tgtccatact    3360
gagtccagac cctgatcaag gcctgactta gtgtcactgg cagtcccact aaattacact    3420
tccttacact ggcccgatgc gacaaatcag gtggctccct tctgtcacgt ggagcacaca    3480
gtgttttcca tcatccatag cttcttcct gatggtgttt gcattattgc gccttcccaa    3540
tctgcatgct gcgttgggct tgcggtgcct gaacaaggtt tgctcccatg agctcaggca    3600
ccctaggatc ccctgttaga ctattaggct gtccagcatg gtctcctttc ccttcttggt    3660
ggtggtcttt tccctttcca gaatagaaca gtgattctta aaataagtta gagcaggccg    3720
ggcgcggtgg ctcatgcctg taatcccagc actttgggag gccgaggtgg gtggatcacg    3780
aggtcaggag ttcaagacca gcctggccaa gatgatgaaa ccccgtctct attaaaaata    3840
caaaaattag ctgggcgtgg tggcaggcac ctgtaatccc agcttcctgg gaggctgagg    3900
caggagaatc acttgaaccc ggggggcaga ggttgcagtg agccgagatc acgccactga    3960
actccagcct gggcaacaga gtgagactct gtctcaaaaa aaaaaaaaaa acaaaaacaa    4020
aaaagcaaga tcatccacta cacatgaaca tgaatcacag tattatttgc aca           4073

SEQ ID NO: 10           moltype = AA   length = 465
FEATURE                 Location/Qualifiers
source                  1..465
                        mol_type = protein
                        organism = Homo sapiens
SEQUENCE: 10
MIVFVRFNSS HGFPVEVDSD TSIFQLKEVV AKRQGVPADQ LRVIFAGKEL RNDWTVQNCD    60
LDQQSIVHIV QRPWRKGQEM NATGGDDPRN AAGGCEREPQ SLTRVDLSSS VLPGDSVGLA    120
VILHTDSRKD SPPAGSPAGR SIYNSFYVYC KGPCQRVQPG KLRVQCSTCR QATLTLTQGP    180
SCWDDVLIPN RMSGECQSPH CPGTSAEFFF KCGAHPTSDK ETSVALHLIA TNSRNITCIT    240
CTDVRSPVLV FQCNSRHVIC LDCFHLYCVT RLNDRQFVHD PQLGYSLPCV AGCPNSLIKE    300
LHHFRILGEE QYNRYQQYGA EECVLQMGGV LCPRPGCGAG LLPEPDQRKV TCEGGNGLGC    360
GFAFCRECKE AYHEGECSAV FEASGTTTQA YRVDERAAEQ ARWEAASKET IKKTTKPCPR    420
CHVPVEKNGG CMHMKCPQPQ CRLEWCWNCG CEWNRVCMGD HWFDV                    465

SEQ ID NO: 11           moltype = DNA   length = 4654
FEATURE                 Location/Qualifiers
source                  1..4654
                        mol_type = unassigned DNA
                        organism = Homo sapiens
SEQUENCE: 11
ggcggcggct ggaggagagc gcggtggaga gccgagcggg cggcggcgg gtgcggagcg     60
ggcgagggag cgcgcgcggc cgccacaaag ctcgggcgcg atgcggcgta                120
cctggcccgg cgcggcgact gctctccggg ctgcgggggg ccggccgcga gcccgggg      180
ccccgaggcc gcagcttgcc tgcgcgctct gagccttcgc aactcgcgag caaagtttgg    240
tggaggcaac gccaagcctg agtcctttct tcctctcgtt cccaaatcc gagggcagcc     300
cgcgggcgtc atgcccgcgc tcctccgcag cctggggtac gcgtgaagcc cgggaggctt    360
ggcgccggcg aagacccaag gaccactctt ctgcgtttgg agttgctccc cgcaaccccg    420
ggctcgtcgc tttctccatc ccgacccacg cggggcgcgg gacaacaca ggtcgcggag     480
gagcgttgcc attcaagtga ctgcagcagc agcggcagcg cctcggttcc tgagcccacc    540
gcaggctgaa ggcattgcgc gtagtccatg cccgtagagg aagtgtgcag atgggattaa    600
cgtccacatg gagatatgga agaggaccgg ggattggtac cgtaaccatg gtcagctggg    660
gtcgtttcat ctgcctggtc gtggtcacca tggcaacctt gtcccctgcc cggccctcct    720
tcagtttagt tgaggatacc acattagagc cagaagagcc accaaccaaa taccaaatct    780
ctcaaccaga agtgtacgtg gctgcgccag gggagtcgct agaggtgcgc tgcctgttaa    840
aagatgccgc cgtgatcagt tggactaagg atggggtgca cttggggccc aacaatagga    900
cagtgcttat tggggagtac ttgcagataa agggcgccac gcctagagac tccggcctct    960
atgcttgtac tgccagtagg actgtagaca gtgaaacttg gtacttcatg gtgaatgtca    1020
cagatgccat ctcatccgga gatgatgagg atgacaccga tggtgcggaa gatttttgtca   1080
gtgagaacaa taacaacaag agagcaccat actggaccaa cacagaaaag atggaaaagc    1140
ggctccatgc tgtgcctgcg gccaacactg tcaagtttcg ctgcccagcc gggggggaacc   1200
caatgccaac catgcgtggg ctgaaaaacg ggaaggagtt taagcaggag catcgcattg    1260
gaggctacaa ggtacgaaac cagcactgga gcctcattat ggaaagtgtg gtcccatctg    1320
acaagggaaa ttatacctgt gtagtgggaa atgatggcg gtccatcaat cacacgtacc    1380
acctggatgt tgtggagcga tcgcctcacc ggcccatcct ccaagccgga ctgcgggcaa    1440
atgcctccac agtggtcgga ggagacgtag agtttgtctg caaggtttac agtgatgccc    1500
agccccacat ccagtggatc aagcacgtgg aaaagaacgg cagtaaatac gggcccgacg    1560
ggctgccta cctcaaggtt ctcaaggccg ccggtgttaa caccacggac aaagagattg    1620
aggttctcta tattcggaat gtaacttttg aggacgctgg ggaatatacg tgcttggcgg    1680
gtaattctat tgggatatcc tttcactctg catggttgac agttctgcca gcgcctggaa    1740
gagaaaagga gattacagct tccccagact acctggagat agcatttac tgcataggg     1800
tcttcttaat cgcctgtatg gtggtaacag tcatcctgtg ccgaatgaag aacacgacca    1860
agaagccaga cttcagcagc cagccggctg tgcacaagct gaccaaacgt atccccctgc    1920
ggacacaggt aacagtttcg gctgagtcca gtcctccat gaactccaac ccgtcctgtg     1980
tgaggataac aacacgcctc tcttcaacg cagacacccc catgctggca gggtctccg      2040
agtatgaact tccagaggac ccaaaatggg agttttcaag agataagctg acactgggca    2100
agccctgggg agaggttgc tttgggcaag tggtcatggc ggaagcagtg ggaattgaca    2160
aagacaagcc caaggaggcg gtcaccgtgg ccgtgaagat gttgaaagat gatgccacag    2220
agaaagacct ttctgatctg gtgtcagaga tggagatgat gaagatgatt gggaaacaca    2280
```

-continued

```
agaatatcat aaatcttctt ggagcctgca cacaggatgg gcctctctat gtcatagttg    2340
agtatgcctc taaaggcaac ctccgagaat acctccgagc ccggaggcca cccgggatgg    2400
agtactccta tgacattaac cgtgttcctg aggagcagat gaccttcaag gacttggtgt    2460
catgcaccta ccagctggcc agaggcatgg agtacttggc ttcccaaaaa tgtattcatc    2520
gagatttagc agccagaaat gttttggtaa cagaaaacaa tgtgatgaaa atagcagact    2580
ttggactcgc cagagatatc aacaatatag actattacaa aaagaccacc aatgggcggc    2640
ttccagtcaa gtggatggct ccagaagccc tgtttgatag agtatacact catcagagtg    2700
atgtctggtc cttcggggtg ttaatgtggg agatcttcac tttaggggc tcgccctacc     2760
cagggattcc cgtggaggaa cttttttaagc tgctgaagga aggacacaga atggataagc    2820
cagccaactg caccaacgaa ctgtacatga tgatgaggac ctgttggcat gcagtgccct    2880
cccagagacc aacgttcaag cagttggtag aagacttgga tcgaattctc actctcacaa    2940
ccaatgagga atacttggac ctcagccaac ctctcgaaca gtattccct agttaccctg      3000
acacaagaag ttcttgttct tcaggagatg attctgtttt ttctccagac cccatgcctt    3060
acgaaccatg ccttcctcag tatccacaca taaacgggca tgttaaaaca tgaatgactg    3120
tgtctgcctg tccccaaaca ggacagcact gggaacctag ctacactgag cagggagacc    3180
atgcctccca gagcttgttg tctccacttg tatatatgga tcagaggagt aaataattgg    3240
aaaagtaatc agcatatgtg taaagattta tacagttgaa aacttgtaat cttccccagg    3300
aggagaagaa ggtttctgga gcagtggact gccacaagcc accatgtaac ccctctcaac    3360
tgccgtgcgt actggctgtg gaccagtagg actcaaggtg gacgtgcgtt ctgccttcct    3420
tgttaatttt gtaataattg gagaagattt atgtcagcac acacttacag agcacaaatg    3480
cagtatatag gtgctggatg tatgtaaata tattcaaatt atgtataaat atatattata    3540
tatttacaag gagttatttt ttgtattgat tttaaatgga tgtcccaatg cacctagaaa    3600
attggtctct cttttttaa tagctatttg ctaaatgctg ttcttacaca taatttctta     3660
attttcaccg agcagaggtg gaaaatact tttgctttca gggaaaatgg tataacgtta     3720
atttattaat aaattggtaa tatacaaaac aattaatcat ttatagtttt tttgtaatt    3780
taagtggcat ttctatgcag gcagcacagc agactagtta atctattgct tggacttaac    3840
tagttatcag atcctttgaa agaagaatat ttacaatata tgactaattt ggggaaaatg    3900
aagttttgat ttatttgtgt ttaaatgctg ctgtcagacg attgttctta gacctcctaa    3960
atgccccata ttaaaagaac tcattcatag gaaggtgttt cattttggtg tgcaaccctg    4020
tcattacgtc aacgcaacgt ctaactggac ttcccaagat aaatggtacg agcgtcctcn    4080
taaaagatgc cttaatccat tccttgagga cagaccttag ttgaaatgat agcagaatgt    4140
gcttctctct ggcagctggc cttctgcttc tgagttgcac attaatcaga ttagcctgta    4200
ttctcttcag tgaattttga taatggcttc cagactcttt ggcgttggag acgcctgtta    4260
ggatcttcaa gtcccatcat agaaaattga aacacagagt tgttctgctg atagttttgg    4320
ggatacgtcc atcttttta gggattgctt tcatctaatt ctggcaggac ctcaccaaaa    4380
gatccagcct catacctaca tcagacaaaa tatcgccgtt gttccttctg tactaaagta    4440
ttgtgtttg ctttggaaac acccactcac tttgcaatag ccgtgcaaga tgaatgcaga    4500
ttacactgat cttatgtgtt acaaaattgg agaaagtatt taataaaacc tgttaatttt    4560
tatactgaca ataaaaatgt ttctacagat attaatgtta acaagacaaa ataaatgtca    4620
cgcaacttat ttttttaata aaaaaaaaaa aaaa                                4654

SEQ ID NO: 12           moltype = AA  length = 821
FEATURE                 Location/Qualifiers
source                  1..821
                        mol_type = protein
                        organism = Homo sapiens
SEQUENCE: 12
MVSWGRFICL VVVTMATLSL ARPSFSLVED TTLEPEEPPT KYQISQPEVY VAAPGESLEV     60
RCLLKDAAVI SWTKDGVHLG PNNRTVLIGE YLQIKGATPR DSGLYACTAS RTVDSETWYF   120
MVNVTDAISS GDDEDDTDGA EDFVSENSNN KRAPYWTNTE KMEKRLHAVP AANTVKFRCP   180
AGGNPMPTMR WLKNGKEFKQ EHRIGGYKVR NQHWSLIMES VVPSDKGNYT CVVENEYGSI   240
NHTYHLDVVE RSPHRPILQA GLPANASTVV GGDVEFVCKV YSDAQPHIQW IKHVEKNGSK   300
YGPDGLPYLK VLKAAGVNTT DKEIEVLYIR NVTFEDAGEY TCLAGNSIGI SFHSAWLTVL   360
PAPGREKEIT ASPDYLEIAI YCIGVFLIAC MVVTVILCRM KNTTKKPDFS SQPAVHKLTK   420
RIPLRRQVTV SAESSSSMNS NTPLVRITTR LSSTADTPML RLRGVTYELP DPKWEFPRDK   480
LTLGKPLGEG CFGQVVMAEA VGIDKDKPKE AVTVAVKMLK DDATEKDLSD LVSEMEMMKM   540
IGKHKNIINL LGACTQDGPL YVIVEYASKG NLREYLRARR PPGMEYSYDI NRVPEEQMTF   600
KDLVSCTYQL ARGMEYLASQ KCIHRDLAAR NVLVTENNVM KIADFGLARD INNIDYYKKT   660
TNGRLPVKWM APEALFDRVY THQSDVWSFG VLMWEIFTLG GSPYPGIPVE ELFKLLKEGH   720
RMDKPANCTN ELYMMMRDCW HAVPSQRPTF KQLVEDLDRI LTLTTNEEYL DLSQPLEQYS   780
PSYPDTRSSC SSGDDSVFSP DPMPYEPCLP QYPHINGSVK T                      821

SEQ ID NO: 13           moltype = DNA  length = 3968
FEATURE                 Location/Qualifiers
source                  1..3968
                        mol_type = unassigned DNA
                        organism = Homo sapiens
SEQUENCE: 13
ggatggtcct ggtcacaaaa tattaaagag accgaccgct aagggaacag gaaaaacgtc      60
cgagacagcc gttgcaatta cgaatgacc agacttggta gcacggggca ttgattgctg     120
gtgcccaacc ggaccctcct cccctcttcc catcccttcc cccacccaaa gcaggctccc    180
gctgcggccg ggacctcgca tccctgcaac gtggccgggg ctgcattttt catgagccta    240
gggtgaacag gtgcgaagtg cgctgggagc atccggccag cggccgagcg cggggaacat    300
ggagagcgag cgcgacatgt accgccagtt ccaggactgg tgcctcagga cttacgggga   360
ctcaggcaag accaagacgg tgacccgtaa aaaatacgaa cggatcgtcc agctcctcaa    420
tggctccgag tcgagctcca cggacaacgc caaatttaaa ttctgggtca aatcgaaggg    480
cttccagctg ggccagccgg acgaggtccg cgggggaggc ggcggcgcca agcaagtgct    540
ctacgtgcct gtcaagacca cggatggcgt aggggtagat gagaagctat ctttacgacg    600
ggtagctgtg gttgaagatt ctttgacat tatttattcg atgcatgtgg aaacgggggcc     660
```

```
aaatggagaa caaattcgga aacacgctgg acaaaagaga acttacaaag caatttcaga  720
gagctatgcc ttcctaccaa gagaagcggt gacacgattt ctaatgagct gctcagagtg  780
ccagaaaaga atgcatttaa acccagatgg aacagatcat aaagataatg aaaaacctcc  840
cactttggtg accagcatga ttgactacaa catgccaatt accatggcct acatgaaaca  900
catgaagctg cagctgctaa actcacagca agatgaggat gaaagttcaa tagaaagtga  960
tgaatttgac atgagtgatt caacacggat gtcagctgtg aactctgatc ttagctccaa 1020
tcttgaagaa agaatgcaaa gtccccgaaa tcttcatggc cagcaagatg atgattctgc 1080
tgcagagagc tttaatggca atgagactct ggggcacagt tcaattgctt caggggaac  1140
acacagcagg gagatgggag actccaacag tgatggcaaa actgggctgg agcaagatga 1200
acagccactg aacctgagtg acagtcccct ctctgcgcag ctaacttcgg aatacagaat 1260
agatgatcac aacagtaatg ggaaaaacaa gtataagaat cttctaattt ctgacctcaa 1320
gatggaacga gaggcgagag aaaatggaag caagtctcct gcacatagtt actccagcta 1380
tgactctggc aaaaatgaga gtgtagaccg aggagctgag gacctctcac taaacagggg 1440
agatgaggac gaagatgacc acgaggacca tgacgattcg gagaaagtta atgagacaga 1500
cggcgttgaa gccgagcggc tgaaagcttt taatatgttt gtcaggctgt ttgtagatga 1560
aaacttggac cgaatggtcc caatctctaa gcagcccaaa gaaaagatcc aggctatcat 1620
tgactcatgc aggcgacaat tccctgagta tcaagagcgt gccagaaaac gtacgctac  1680
ttacctcaag tcctgcaggc ggatgaaaag aagtggtttc tgagatgtctc gacctattcc 1740
ttcccacctt acttcagcag ttgcagagag tatcttggct tcagcttgtg agagtgagag 1800
tagaaatgcc gccaagagga tgcgtctgga gagacagcag gatgagtctg ctccagctga 1860
caaacagtgt aaaccagagg cgacccaggc cacttactca acatcagctg ttccaggctc 1920
acaggacgtg ctgtacatca atgggaatgg gacctatagt taccatagtt acagagggct 1980
aggagggggt ctgctaaatc tgaatgatgc ttccagcagt ggacccactg atctcagcat 2040
gaaagagacaa ttggcgacta gctcaggatc ctccagcagc tcaaactcca gaccccagct 2100
gagtccaact gaaatcaatg ccgtgagaca gcttgttgca ggatatcgag aatcagctgc 2160
atttttattg cgatctgcag atgaactgga aaatctcatt ttacaacaga actgagacag 2220
acgaccacca tattcactga ggtctaaatt tgcagttttcc actaatgaca ttttgatttc 2280
ccaacagaga tacttctggt cttactgcac agtctttaa gagaaatact tccattatgc 2340
cacattgtcc ttgatccgta agtgatgtgt taaggtgctt caaggaact ctgacctctg 2400
aagtacttga gtactttag tatgtccagc ctattgctttt ttgttttagt gtgtcaccat 2460
aaatatcagg ggcataaaag gctatctatt cttaattcaa ggataaaaca gaagaagctt 2520
gtggtataaa acaatagttc aagatccagc tgaaatatta gtggaatttg ctactgactc 2580
attggactga aagctgaagt acctggcaaa aaaaaaaaaa agaaaaaaa aagccaaatt 2640
tcttgttgct acaggatata acaacaatga aaaggatctc gtattttaaa aaaatatga  2700
atttttataa aaagaaaact tgtttttcat tcaaacttgt cattttttact ttggtaactt 2760
tttcataggt cctaaaagaa aactgttttg agaaactact gtaagtacct tttccacatc 2820
cctttgcctt ctcctctttc caaattcttt ctacaaaaat aacacttgat gctggaaaaa 2880
cccttgccta cgttctttca atcgtcacat caggaactac ttccaagaga agcctgcatt 2940
tctgctctca tgctgatctc aaaaaccca ctcaacactg caactttatc atagcagttt 3000
tcatcccaga atttttttt taataatgac aagacatgtt gttgaaaaaa aatcacacct 3060
tggtttctta gagctgctcg ttcctgattg ccgctgctgt ctccaggcat ccctctagca 3120
gcacctggat gtagatgact gaatgttaag aggttgcaag tgacaatctg aaaatttgca 3180
ctcttgtgtg tagttttctt ttcattttctt tcagaaatag tttccaaaaa gaccattaca 3240
tctcctgata tgatttgtat aattttcagt tctagctaaa aataatgtaa ggaactctca 3300
gcggatgcag ctgcaactta caatgaactg tgccctccta tccccccatac tttaccctc  3360
tttcttattt tatagtgtgg gatacacatg agtgatgttt ctttgtgca ctgagacaag 3420
cctattttt aaatatttag ggagaagtac tttagttcat gcttcttata caactttttt 3480
ctgttgttta gctttggttg gattacaaat tctttgtgca ttcctgaatt tgccttattt 3540
catgtaaaat ttatgtcatt cagttttga caatgagttt gaggcatcag tgatatttct 3600
tatctacttg ttacatatag ttttttcaagt aatgactgtg attgtgaccg agtaatgtgc 3660
acttttctt gtaactgtgg acattgctat gcttttttct tctagtgttt ctagaattac 3720
tgttccttac aattatgtaa acaaaaaaca aaaaaaaaac ttttgtgata ctgttggtga 3780
atataatgtg aaaaatctta ttgaaatatg agtattttgg aaatacatag ctgcacaaac 3840
atcttttaag atgtggattt agagtttgct tatttaaatg aaaattcaaa aattgagggc 3900
tggtataatt ttctctgttt tgtttggttt aataaacaga tttctgtgtt aaagaaaaa  3960
aaaaaaaa                                                         3968

SEQ ID NO: 14          moltype = AA   length = 638
FEATURE                Location/Qualifiers
source                 1..638
                       mol_type = protein
                       organism = Homo sapiens
SEQUENCE: 14
MESERDMYRQ FQDWCLRTYG DSGKTKTVTR KKYERIVQLL NGSESSSTDN AKFKFWVKSK   60
GFQLGQPDEV RGGGGGAKQV LYVPVKTTDG VGVDEKLSLR RVAVVEDFFD IIYSMHVETG  120
PNGEQIRKHA GQKRTYKAIS ESYAFLPREA VTRFLMSCSE CQKRMHLNPD GTDHKDNGKP  180
PTLVTSMIDY NMPITMAYMK HMKLQLLNSQ QDEDESSIES DEFDMSDSTR MSAVNSDLSS  240
NLEERMQSPQ NLHGQQDDDS AAESFNGNET LGHSSIASGS THSREMGDSN SDGKTGLEQD  300
EQPLNLSDSP LSAQLTSEYR IDDHNSNGKN KYKNLLISDL KMEREARENG SKSPAHSYSS  360
YDSGKNESVD RGAEDLSLNR GDEDEDDHED HDDSEKVNET DGVEAERLKA FNMFVRLFVD  420
ENLDRMVPIS KQPKEKIQAI IDSCRRQFPE YQERARKRIR TYLKSCRRMK RSGFEMSRPI  480
PSHLTSAVAE SILASACESE SRNAAKRMRL ERQQDESAPA DKQCKPEATQ ATYSTSAVPG  540
SQDVLYINGN GTYSYHSYRG LGGGLLNLND ASSSGPTDLS MKRQLATSSG SSSSSNSRPQ  600
LSPTEINAVR QLVAGYRESA AFLLRSADEL ENLILQQN                          638

SEQ ID NO: 15          moltype = DNA   length = 2187
FEATURE                Location/Qualifiers
source                 1..2187
                       mol_type = unassigned DNA
```

```
                        organism = Homo sapiens
SEQUENCE: 15
agagtcctgg cgagggcgct ggccgagagg tgctcggctt gtagcaggtc ccgcactcca    60
gcctctcgct gccagggttt gctctctgct tgtcctgggc tgaggtgtcc atgacggagt   120
catccaagga ggaaaaaatc tgttccgggt gagcccaggc cgccccggat atgcgatggc   180
tgaggagcag acaccaggga ccacactgag gttgggtttc agaccaagac actggattct   240
cctagttaag ataaagagct ttgggtgcct gacagtgaaa atggtgtaat ctgcgttaac   300
agttcacagc ttgaaggcat gacaattaaa gaacacacat ggacttgtgg cacatggaaa   360
tgtgcgcaca gaaaaggaa atctataatt cttttaaagt aggaaggcat tcttccttgc    420
caaaatgggt acgttctgtt cggttatcaa gtttgaaaat ctacaagaat taaagagact   480
gtgtcactgg ggtcccatca tagcccttgg tgttatagca atatgttcta ccatggccat   540
gattgactct gtgttgtggt attggcccct acatacaact ggaggaagtg tgaatttcat   600
catgttgata aattggactg tcatgattct ttataattac ttcaatgcca tgtttgtcgg   660
tccggccttt gtccctctgg ggtggaaacc ggaaatttct caggatacca tctatctcca   720
gtattgtaaa gtctgccaag catacaaggc accacgttca catcactgca gaaagtgtaa   780
cagatgtgtg atgaagatgg accatcactg tccttggatc aacaactgtt gtggttacca   840
aaatcatgct tcgttcacac tgtttctcct tttagcacca ctgggttgta tccatgctgc   900
tttcatttt gtgatgacta tgtacacaca gcttatcat cgcctctcct ttgggtggaa     960
cacagtgaag atcgacatga gtgcagcccg agagatcct cttccaattg ttccatttgg    1020
attagctgca tttgctacca ccttgtttgc cttgggatta gctttaggaa caaccatagc   1080
tgttgggatg ttgtttttta tccagatgaa aataattctc agaaacaaaa cttctattga   1140
gtcatggatt gaagagaagg ctaaagatcg aattcagtat atcaactag atgaagtctt    1200
tgttttccca tatgatatgg gaagtagatg gaggaacttt aaacaggtat ttacgtggtc   1260
aggggtccct gaaggagatg gacttgagtg gccagtaaga gaaggctgtc accaatacag   1320
cttaacaata gaacagttga aacaaaaagc agataagaga gtcagaagtg ttcgctataa   1380
agtaatagaa gattatagtg gtgcctgctg ccctctgaaa aaggaatca aaccttctt     1440
cacaagtccc tgcaccgaag agcctcgaat acagctgcaa aaaggggaat tcattttagc   1500
cacaagaggt ttacgatact ggttatatgg agacaaaatt cttgatgatt cctttataga   1560
aggtgtttca agaataaggg gttggttccc tagaaatgt gtggaaaagt gtccctgtga    1620
tgctgaaaca gatcaagccc cagaggggga gaagaaaaat agatagctgc tgttaaaaca   1680
aaattatcct ttaagtctgc ttaattactt gaaaattgta catattacta aagaattatg   1740
caatgagcct actctggtta agatgttctt ttcctcaaag gtgccctagt gccatgattt   1800
aaatattttt attaccattt tgaaatggag aagccattct gcatatgcct ttgaattcct   1860
gcccttcttt accacctctt cctccccctc aaaggaaaaa catttcatcc aagtaagtta   1920
acggcatttt ctgtaggatt ttcttatgca ctgcacactc tggacctcac ctgcagatac   1980
agttcccccc ttgccaggag catctgcatg tggtacttct cttttccctc agttgatatt   2040
tcttatatga tattctagat actatagaac tcaatttgtc agattcagta aaccctcaga   2100
ttttgttacc tgtcttttaa aaatgcagat tttgtcaaat caaataaaga tcaatggatg   2160
ttgggtataa aaaaaaaaa aaaaaaa                                        2187

SEQ ID NO: 16           moltype = AA  length = 413
FEATURE                 Location/Qualifiers
source                  1..413
                        mol_type = protein
                        organism = Homo sapiens
SEQUENCE: 16
MGTFCSVIKF ENLQELKRLC HWGPIIALGV IAICSTMAMI DSVLWYWPLH TTGGSVNFIM    60
LINWTVMILY NYFNAMFVGP GFVPLGWKPE ISQDTMYLQY CKVCQAYKAP RSHHCRKCNR   120
CVMKMDHHCP WINNCCGYQN HASFTLFLLL APLGCIHAAF IFVMTYTQL YHRLSFGWNT    180
VKIDMSAARR DPLPIVPFGL AAFATTLFAL GLALGTTIAV GMLFFIQMKI ILRNKTSIES   240
WIEEKAKDRI QYYQLDEVFV FPYDMGSRWR NFKQVFTWSG VPEGDGLEWP VREGCHQYSL   300
TIEQLKQKAD KRVRSVRYKV IEDYSGACCP LNKGIKTFFT SPCTEEPRIQ LQKGEFILAT   360
RGLRYWLYGD KILDDSFIEG VSRIRGWFPR KCVEKCPCDA ETDQAPEGEK KNR          413

SEQ ID NO: 17           moltype = AA  length = 790
FEATURE                 Location/Qualifiers
source                  1..790
                        mol_type = protein
                        organism = Homo sapiens
SEQUENCE: 17
MLRGGRRGQL GWHSWAAGPG SLLAWLILAS AGAAPCPDAC CPHGSSGLRC TRDGALDSLH    60
HLPGAENLTE LYIENQQHLQ HLELRDLRGL GELRNLTIVK SGLRFVAPDA FHFTPRLSRL   120
NLSFNALESL SWKTVQGLSL QELVLSGNPL HCSCALRWLQ RWEEEGLGGV PEQKLQCHGQ   180
GPLAHMPNAS CGVPTLKVQV PNASVDVGDD VLLRCQVEGR GLEQAGWILT ELEQSATVMK   240
SGGLPSLGLT LANVTSDLNR KNVTCWAEND VGRAEVSVQV NVSFPASVQL HTAVEMHHWC   300
IPFSVDGQPA PSLRWLFNGS VLNETSFIFT EFLEPAANET VRHGCLRLNQ PTHVNNGNYT   360
LLAANPFGQA SASIMAAFMD NPFEFNPEDP IPDTNSTSGD PVEKKDETPF GVSVAVGLAV   420
FACLFLSTLL LVLNKCGRRN KFGINRPAVL APEDGLAMSL HFMTLGGSSL SPTEGKGSGL   480
QGHIIENPQY FSDACVHHIK RRDIVLKWEL GEGAFGKVFL AECHNLLPEQ DKMLVAVKAL   540
KEASESARQD FQREAELLTM LQHQHIVRFF GVCTEGRPLL MVFEYMRHGD LNRFLRSHGP   600
DAKLLAGGED VAPGPLGLGQ LLAVASQVAA GMVYLAGLHF VHRDLATRNC LVGQGLVVKI   660
GDFGMSRDIY STDYYRVGGR TMLPIRWMPP ESILYRKFTT ESDVWSFGVV LWEIFTYGKQ   720
PWYQLSNTEA IDCITQGREL ERPRACPPEV YAIMRGCWQR EPQQRHSIKD VHARLQALAQ   780
APPVYLDVLG                                                          790

SEQ ID NO: 18           moltype = DNA  length = 2647
FEATURE                 Location/Qualifiers
source                  1..2647
                        mol_type = unassigned DNA
```

```
organism = Homo sapiens
SEQUENCE: 18
tgcagctggg agcgcacaga cggctgcccc gcctgagcga ggcgggcgcc gccgcgatgc    60
tgcgaggcgg acggcgcggg cagcttggct ggcacagctg ggctgcgggg ccgggcagcc   120
tgctggcttg gctgatactg gcatctgcgg gcgccgcacc ctgccccgat gcctgctgcc   180
cccacggctc ctcgggactg cgatgcaccc gggatggggc cctggatagc ctccaccacc   240
tgcccggcgc agagaacctg actgagctct acatcgagaa ccagcagcat ctgcagcatc   300
tggagctccg tgatctgagg ggcctggggg agctgagaaa cctcaccatc gtgaagagtg   360
gtctccgttt cgtggcgcca gatgccttcc atttcactcc tcggctcagt cgcctgaatc   420
tctccttcaa cgctctggag tctctctcct ggaaaactgt gcagggcctc tccttacagg   480
aactggtcct gtcggggaac cctctgcact gttcttgtgc cctgcgctgg ctacagcgct   540
gggaggagga gggactgggc ggagtgcctg aacagaagct gcagtgtcat gggcaagggc   600
ccctggccca catgcccaat gccagctgtg gtgtgcccac gctgaaggtc caggtgccca   660
atgcctcggt ggatgtgggg gacgacgtgc tgctgcggtg ccaggtggag gggcggggcc   720
tggagcaggc cggctggatc ctcacagagc tggagcagtc agccacggtg atgaaatctg   780
ggggtctgcc atccctgggg ctgaccctgg ccaatgtcac cagtgacctc aacaggaaga   840
acgtgacgtg ctgggcagag aacgatgtgg gccgggcaga ggtctctgtt caggtcaacg   900
tctccttccc ggccagtgtg cagctgcaca cggcggtgga gatgcaccac tggtgcatcc   960
cctttctctgt ggatgggcag ccggcaccgt ctctgcgctg gctcttcaat ggctccgtgc  1020
tcaatgagac cagcttcatc ttcactgagt tcctggagcc ggcagccaat gagaccgtgc  1080
ggcacgggtg tctgcgcctc aaccagccca cccacgtcaa caacggcaac tacacgctgc  1140
tggctgccaa cccttcggc caggcctccg cctccatcat ggctgccttc atggacaacc  1200
ctttcgagtt caaccccgag gaccccatcc ctgacactaa cagcacatct ggagacccgg  1260
tggagaagaa ggacgaaaca ccttttgggg tctcggtggc tgtgggcctg gccgtctttg  1320
cctgcctctt cctttctacg ctgctccttg tgctcaacaa atgtggacgg agaaacaagt  1380
ttgggatcaa ccgcccggct gtgctggctc cagaggatgg gctggccatg tccctgcatt  1440
tcatgacatt gggtggcagc tccctgtccc ccaccgaggg caaaggctct gggctccaag  1500
gccacatcat cgagaaccca caatacttca gtgatgcctg tgttcaccac atcaagcgcc  1560
gggacatcgt gctcaagtgg gagctggggg agggcgcctt tgggaaggtc ttccttgctg  1620
agtgccacaa cctcctgcct gagcagacaa agatgctggt ggctgtcaag gcactgaagg  1680
aggcgtccga gagtgctcgg caggacttcc agcgtgaggc tgagctgctc accatgctgc  1740
agcaccagca catcgtgcgc ttcttcggcg tctgcaccga gggccgcccc ctgctcatgg  1800
tctttgagta tatgcggcac ggggacctca accgcttcct ccgatcccat ggacctgatg  1860
ccaagctgct ggctggtggg gaggatgtgg ctccaggccc cctgggtctg gggcagctgc  1920
tggccgtggc tagccaggtc gctgcgggga tggtgtacct ggcgggtctg catttttgtgc  1980
accgggacct ggccacacgc aactgtctag tgggccaggg actggtggtc aagattggtg  2040
attttggcat gagcagggat atctacagca ccgactatta ccgtgtggga ggccgcacca  2100
tgctgcccat tcgctggatg ccgccgaga gcatcctgta ccgtaagttc accaccgaga  2160
gcgacgtgtg gagcttcggc gtggtgctct gggagatctt cacctacggc aagcagccct  2220
ggtaccagct ctccaacacg gaggcaatcg actgcatcac gcagggacgt gagttggagc  2280
ggccacgtgc ctgcccacca gaggtctacg ccatcatgcg gggctgctgg cagcgggagc  2340
cccagcaacg ccacagcatc aaggatgtgc acgcccggct gcaagccctg gcccaggcac  2400
ctcctgtcta cctggatgtc ctgggctagg gggccgccc aggggctggg agtggttagc  2460
cggaatactg gggcctgccc tcagcatccc ccatagctcc cagcagcccc agggtgatct  2520
caaagtatct aattcaccct cagcatgtgg gaagggacag gtgggggctg ggagtagagg  2580
atgttcctgc ttctctaggc aaggtcccgt catagcaatt atatttatta tcccttgaaa  2640
aaaaaaa                                                             2647
```